United States Patent
Hackenberger et al.

(10) Patent No.: US 12,171,837 B2
(45) Date of Patent: Dec. 24, 2024

(54) CHEMOSELECTIVE THIOL-CONJUGATION WITH ALKENE OR ALKYNE-PHOSPHONAMIDATES

(71) Applicants: FORSCHUNGSVERBUND BERLIN E.V., Berlin (DE); LUDWIG-MAXIMILIANS-UNIVERSITÄT MÜNCHEN, Munich (DE)

(72) Inventors: Christian Hackenberger, Berlin (DE); Marc André Kasper, Berlin (DE); Maria Glanz, Berlin (DE); Tom Sauer, Rudolstadt (DE); Dominik Schumacher, Munich (DE); Jonas Helma-Smets, Munich (DE); Heinrich Leonhardt, Munich (DE); Andreas Stengl, Munich (DE)

(73) Assignees: FORSCHUNGSVERBUND BERLIN E.V., Berlin (DE); LUDWIG-MAXIMILIANS-UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 18/349,727

(22) Filed: Jul. 10, 2023

(65) Prior Publication Data
US 2023/0348529 A1    Nov. 2, 2023

Related U.S. Application Data

(60) Continuation of application No. 17/460,791, filed on Aug. 30, 2021, now Pat. No. 11,746,124, which is a
(Continued)

(30) Foreign Application Priority Data
Sep. 1, 2016 (EP) .................................... 16001917

(51) Int. Cl.
*A61K 47/64* (2017.01)
*A61K 38/07* (2006.01)
(Continued)

(52) U.S. Cl.
CPC .............. *A61K 47/64* (2017.08); *A61K 38/07* (2013.01); *A61K 47/68031* (2023.08);
(Continued)

(58) Field of Classification Search
None
See application file for complete search history.

(56) References Cited

U.S. PATENT DOCUMENTS

2010/0120719 A1    5/2010    Yen et al.
2015/0284713 A1    10/2015    Fischer et al.

FOREIGN PATENT DOCUMENTS

CN    102058547 A    5/2011
CN    105814213 A    7/2016
(Continued)

OTHER PUBLICATIONS

English language translation of Pudovik ("On the reaction of dialkyl arylphosphoramidites with chloroacetone", Zhurnal Obshchei Khimii, 1976, 46, p. 227-229), obtained May 6, 2024 (Year: 2024).*
(Continued)

*Primary Examiner* — Amy C Bonaparte
(74) *Attorney, Agent, or Firm* — Seed IP Law Group LLP

(57) ABSTRACT

Disclosed are novel conjugates and processes for the preparation thereof. A process for the preparation of alkene- or alkyne-phosphonamidates comprises the steps of
(Continued)

(I) reacting a compound of formula (III)

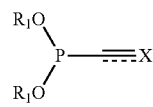

(III)

with an azide of formula (IV)

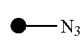

(IV)

to prepare a compound of formula (V)

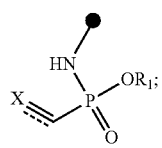

(V)

(II) reacting a compound of formula (V) with a thiol-containing molecule of formula (VI)

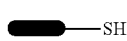

(VI)

resulting in a compound of formula (VII)

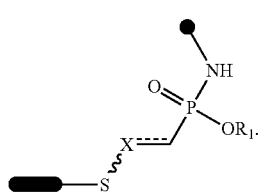

(VII)

20 Claims, 28 Drawing Sheets

Specification includes a Sequence Listing.

Related U.S. Application Data division of application No. 16/328,199, filed as application No. PCT/EP2017/071937 on Sep. 1, 2017, now Pat. No. 11,161,873.

(51) Int. Cl.
A61K 47/68 (2017.01)
C07F 9/44 (2006.01)
C07K 1/107 (2006.01)

(52) U.S. Cl.
CPC ...... *A61K 47/6849* (2017.08); *A61K 47/6855* (2017.08); *A61K 47/6889* (2017.08); *C07F 9/4461* (2013.01); *C07F 9/4473* (2013.01); *C07F 9/448* (2013.01); *C07K 1/1077* (2013.01)

(56) References Cited

FOREIGN PATENT DOCUMENTS

DE 2024250 12/1971
WO 2015/057063 A1 4/2015

OTHER PUBLICATIONS

Ariyakumaran et al., "Direct Staudinger-Phosphonite Reaction Provides Methylphosphonamidates as Inhibitors of CE4 De-N-acetylases," *ChemBioChem* 16:1350-1356 (2015).
Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs," *Mol. Pharmaceutics* 12:3986-3998 (2015).
Chinese Office Action for CN Application No. 201780053946.6 with English translation, 28 pages, dated Mar. 22, 2022.
Gao et al., "Synthesis of a Phosphonate-Linked Aminoglycoside-Coenzyme A Bisubstrate and Use in Mechanistic Studies of an Enzyme Involved in Aminoglycoside Resistance," *Chem. Eur. J.* 15:2064-2070 (2009).
Gubnitskaya et al., "Esters of N-substituted P-aminoethylphosphonic acid," *Zhurnal Obshchei Khimii* 59(3):556-564 (with machine translation) (1989).
Javed et al., Modular Synthesis of Novel Macrocycles Bearing α,β-Unsaturated Chemotypes through a Series of One-Pot, Sequential Protocols, *Chem. Eur. J.* 22:6755-6758 (2016).
Kobayashi et al., "Hydrogen-Transfer Alternating Copolymerization of P-Ethenyl-N-n-proplyphosphonamidic Acid Ethyl Ester with Cyclic Phosphonites Involving Oxidation-Reduction Process," *Polymer Journal* 23(9):1099-1104 (1991).
Pudovik et al., "On the reaction of dialkyl arylphosphoramidites with chloroacetone," *Zhurnal Obshchei Khimii* 46(2):227-229 (1976).
Rouvière et al., "Synthesis of potent and broad genotypically active NS5B Hcv non-nucleoside inhibitors binding to the thumb domain allosteric site 2 of the viral polymerase," *Bioorganic & Medicinal Chemistry Letters* 26:4536-4541 (2016).
Vallée et al., "Alkyne Phosphonites for Sequential Azide-Azide Couplings," *Angew. Chem. Int. Ed.* 52:9504-9508 (2013).
Zimmerman et al., "Production of Site-Specific Antibody-Drug Conjugates Using Optimized Non-Natural Amino Acids in a Cell-Free Expression System," *Bioconjugate Chem.* 25:351-361 (2014).

* cited by examiner

Figure 6: Crude Bisethoxyalkyne-phosphonite synthesis
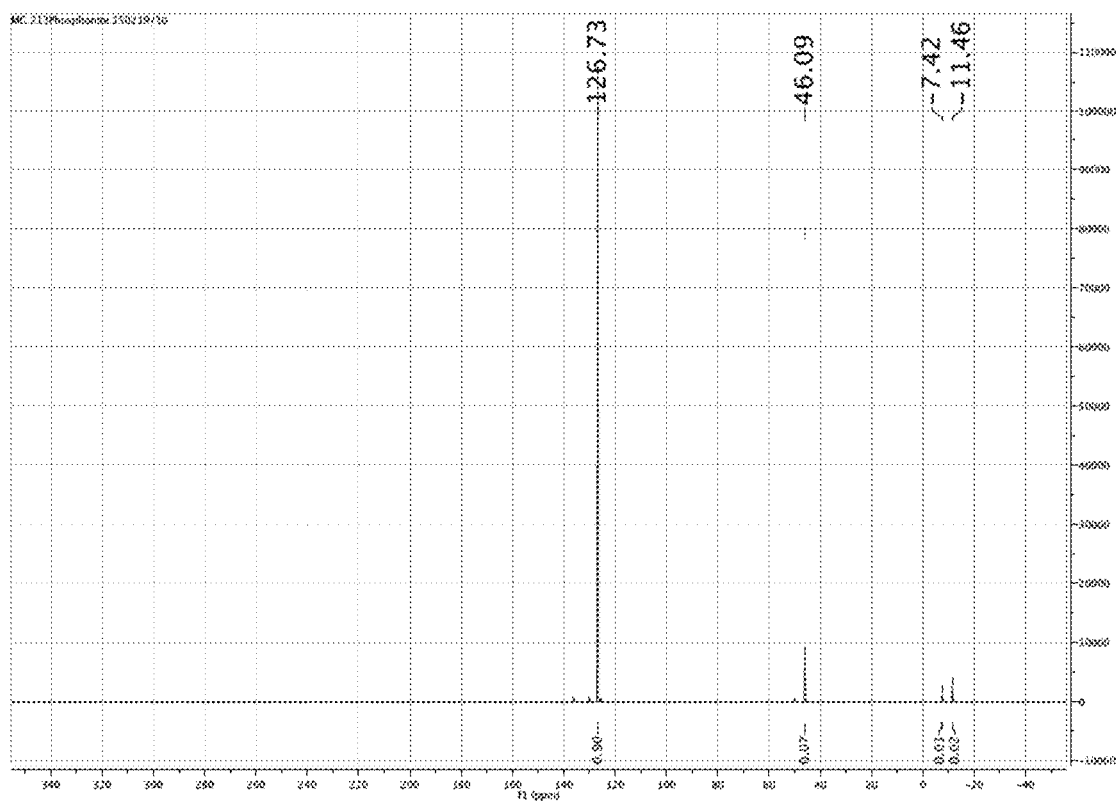
Figure 7: c(RGDfK)-azide
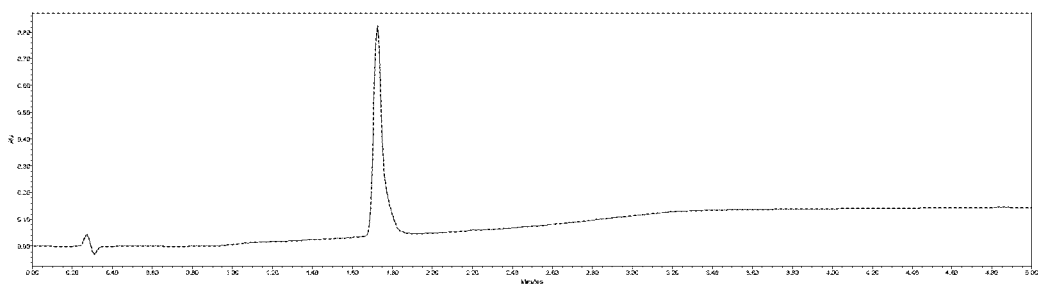
Figure 8: c(RGDfK)-alkyne
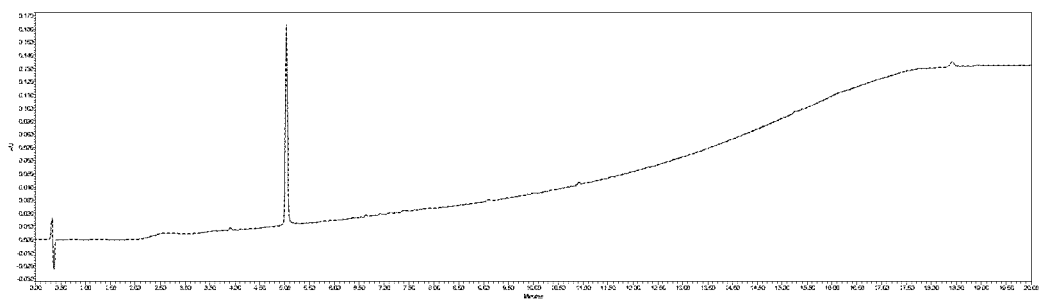

Figure 9 c(RGDfK)-glutathion
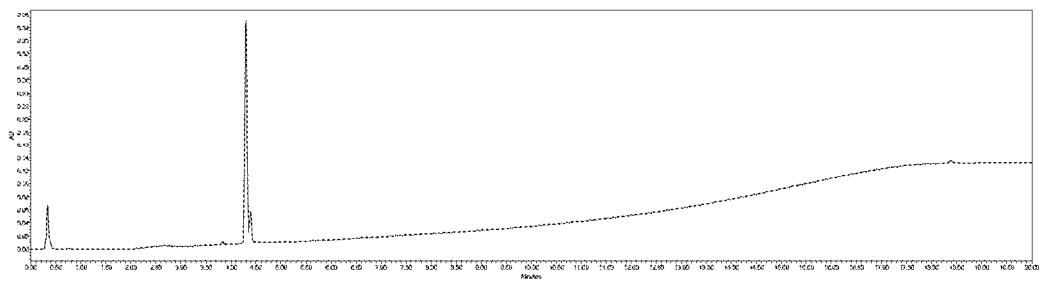
Figure 10
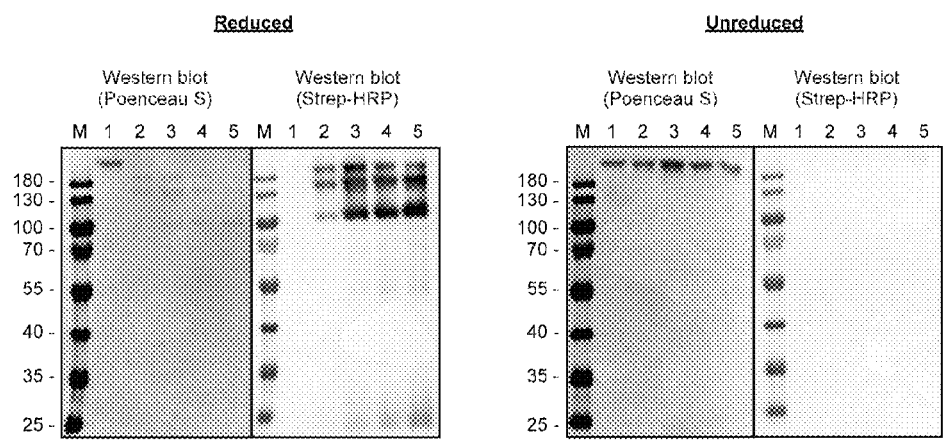
Figure 11
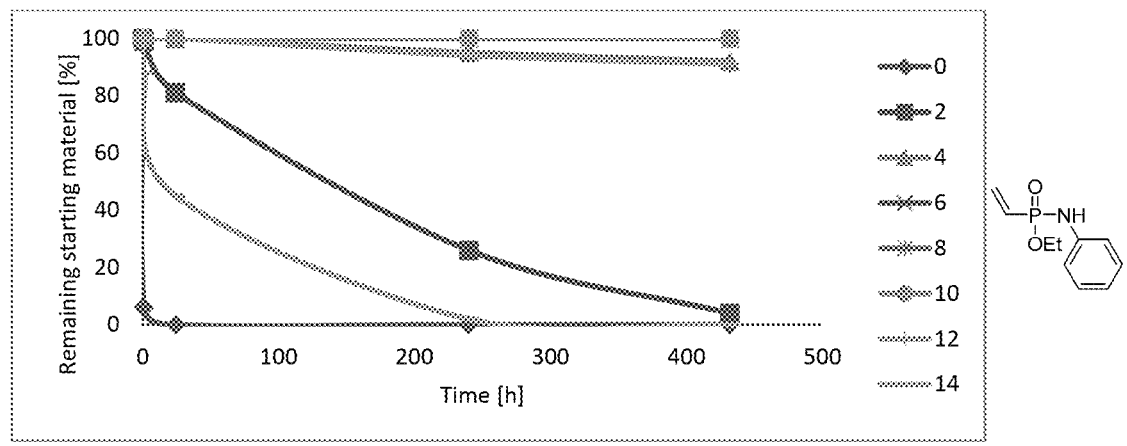

Figure 14

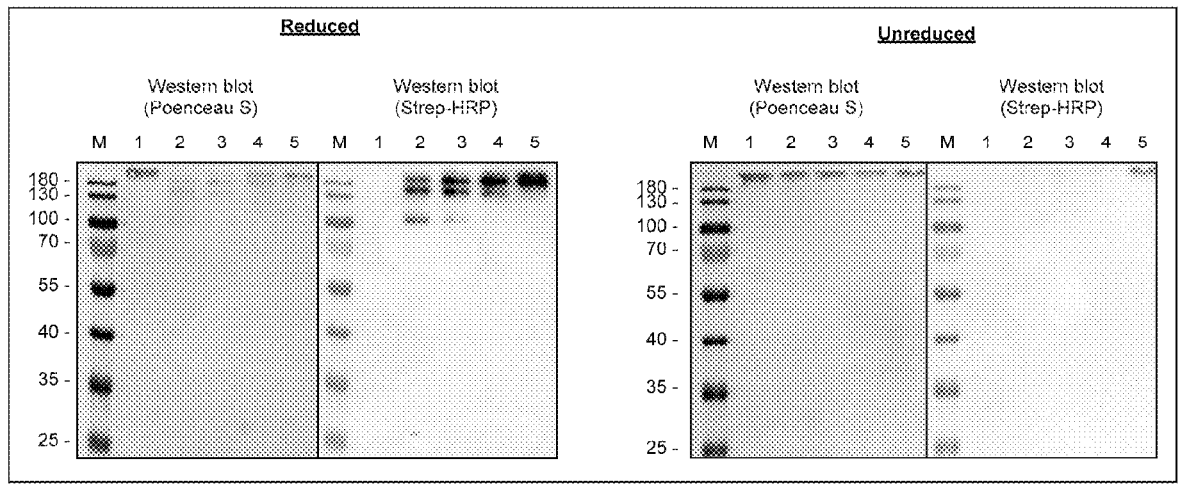

Figure 15

GLNDIFEAQKIEWHE (SEQ ID NO: 1)

KRRWKKNFIAVSAANRFKKISSSGAL (SEQ ID NO: 2)

EEEEEE (SEQ ID NO: 3)

GAPVPYPDPLEPR (SEQ ID NO: 4)

DYKDDDDK (SEQ ID NO: 5)

YPYDVPDYA ((SEQ ID NO: 6)

HHHHHH (SEQ ID NO: 7)

EQKLISEEDL (SEQ ID NO: 8)

TKENPRSNQEESYDDNES (SEQ ID NO: 9)

KETAAAKFERQHMDS (SEQ ID NO: 10)

MDEKTTGWRGGHVVEGLAGELEQLRARLEHHPQGQREP (SEQ ID NO: 11)

(SLAELLNAGLGGS (SEQ ID NO: 12)

TQDPSRVG (SEQ ID NO: 13)

WSHPQFEK (SEQ ID NO: 14)

CCPGCC (SEQ ID NO: 15)

GKPIPNPLLGLDST (SEQ ID NO: 16)

YTDIEMNRLGK (SEQ ID NO: 17)

DLYDDDDK (SEQ ID NO: 18)

TDKDMTITFTNKKDAE (SEQ ID NO: 19)

AHIVMVDAYKPTK (SEQ ID NO: 20)

KLGDIEFIKVNK (SEQ ID NO: 21)

Fig. 16A
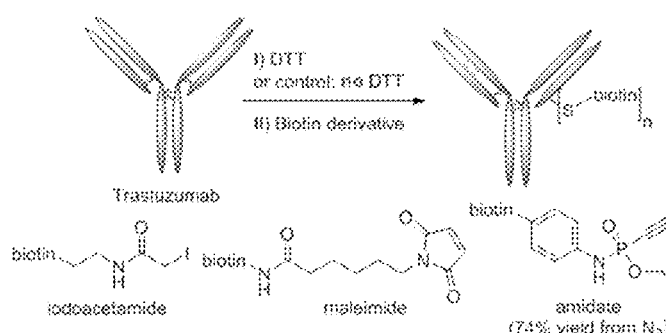
Fig. 16B
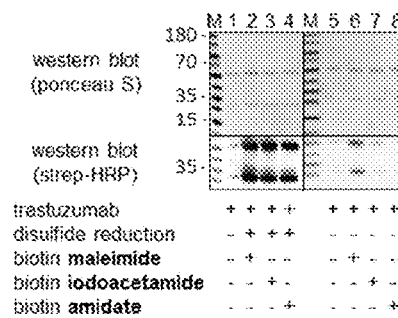
Fig. 17A
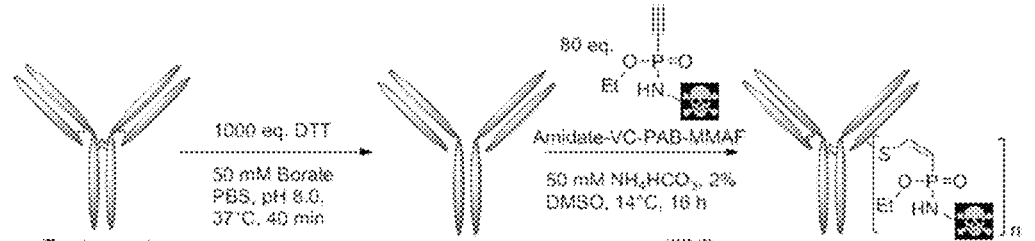
Fig. 17B
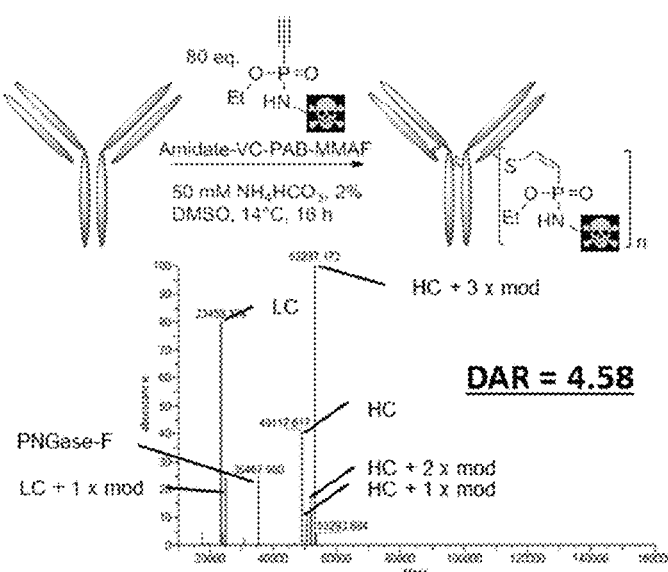
Fig. 17C Fig. 21A
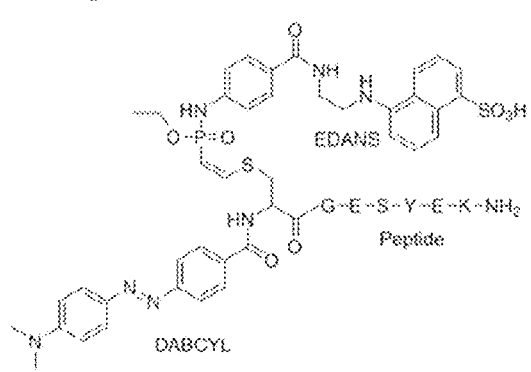
Fig. 21B
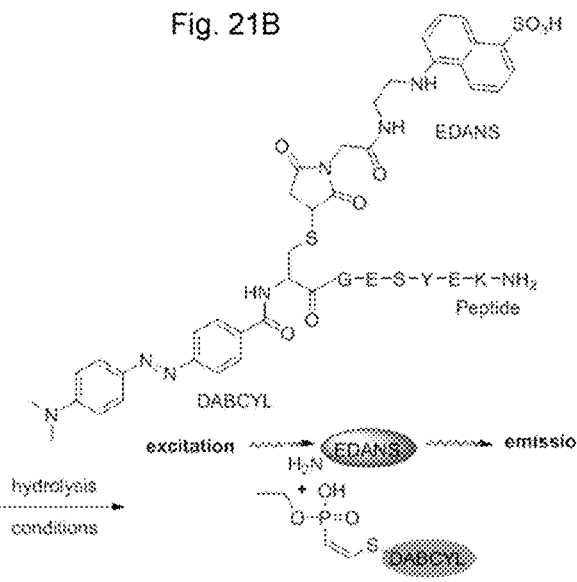
Fig. 21C
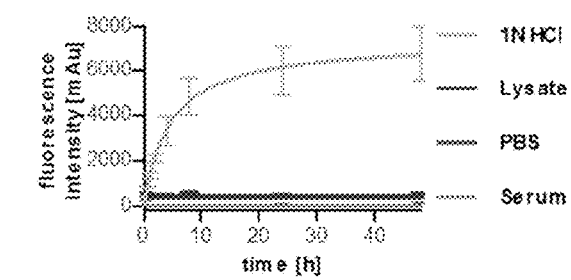
Fig. 21D
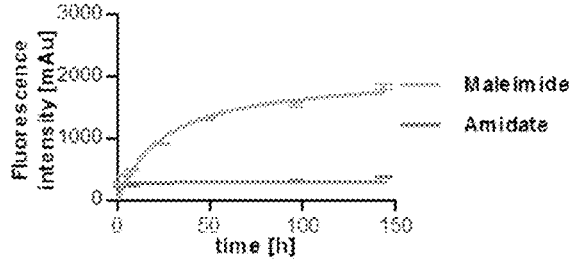
Fig. 21E Trastuzumab-biotin conjugate western blot
(strep-HRP)

| | BSA |
| | HC |
| | LC |

Trastuzumab-Mal-Biotin    + + + + +  - - - - -
Trastuzumab-P5-Biotin     - - - - -  + + + + +
BSA                       - + + + +  - + + + +
Incubation Time (days)    - 0 1 2 5  - 0 1 2 5

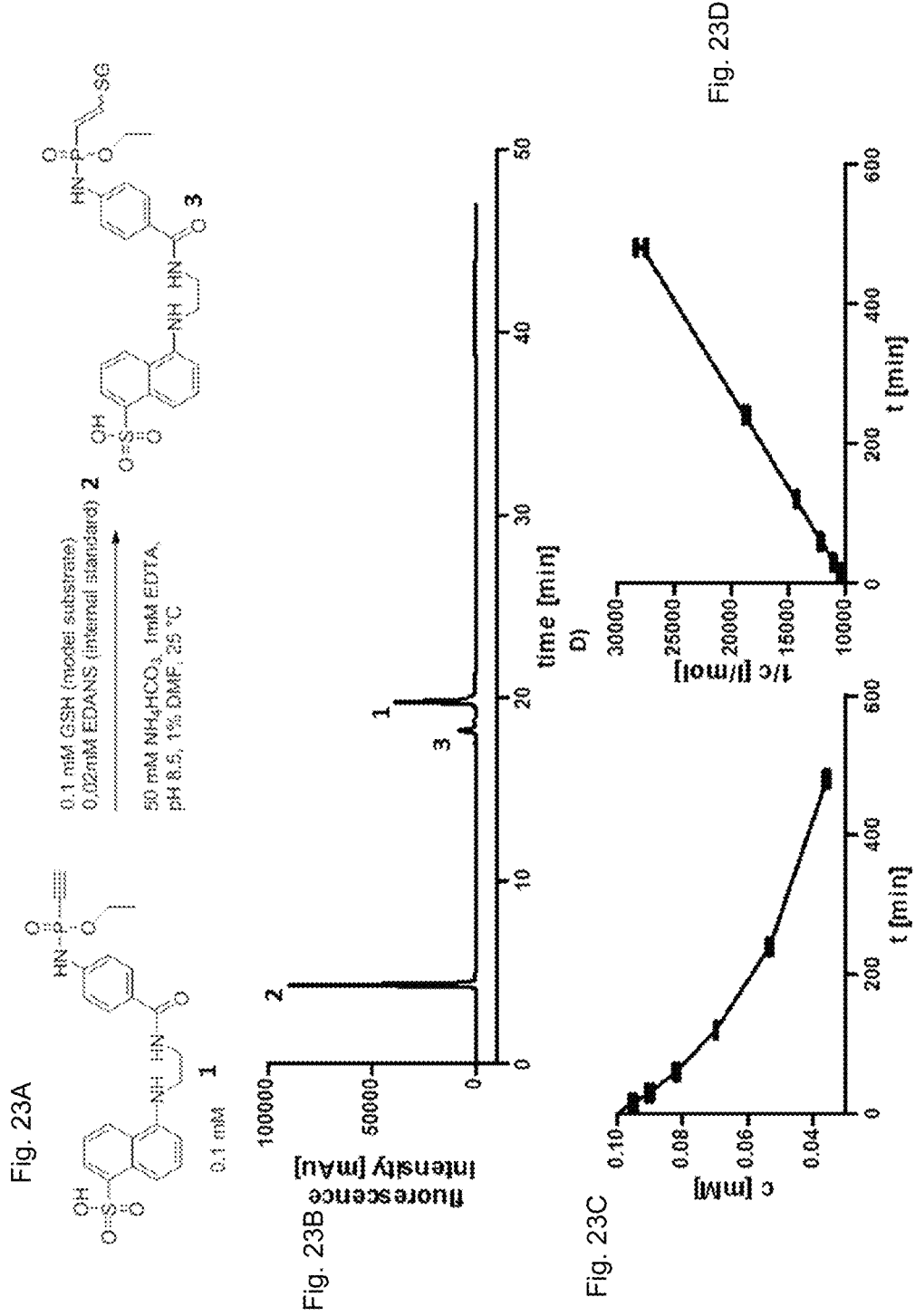

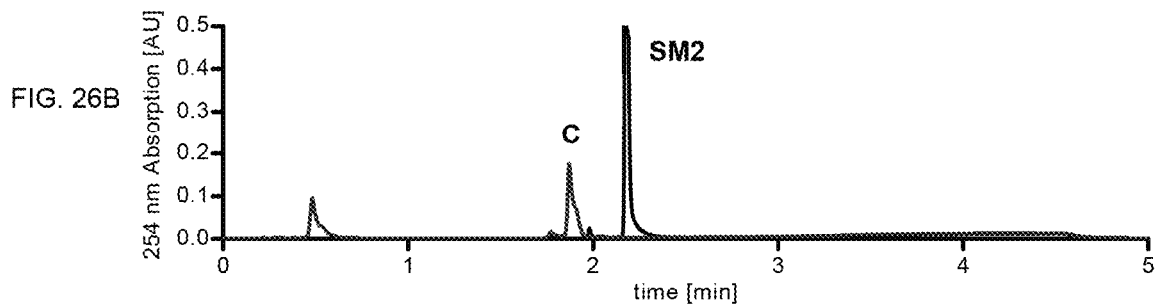
FIG. 26B
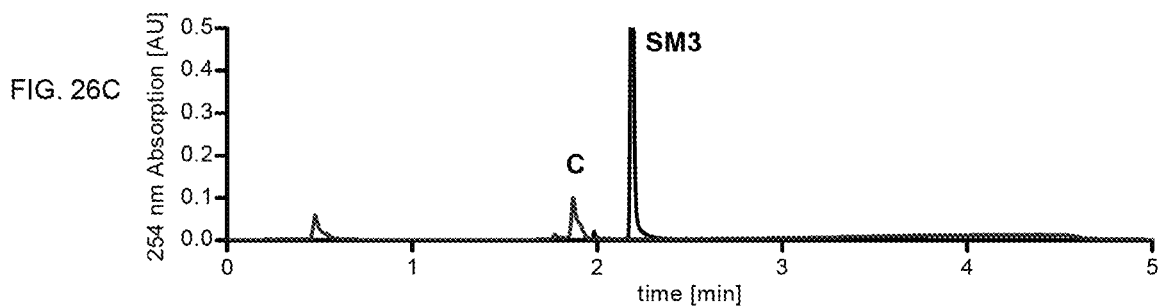
FIG. 26C
Fig. 27
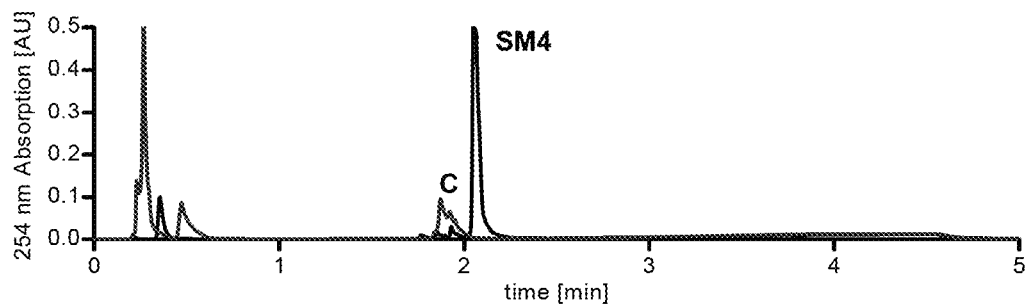
Fig. 28
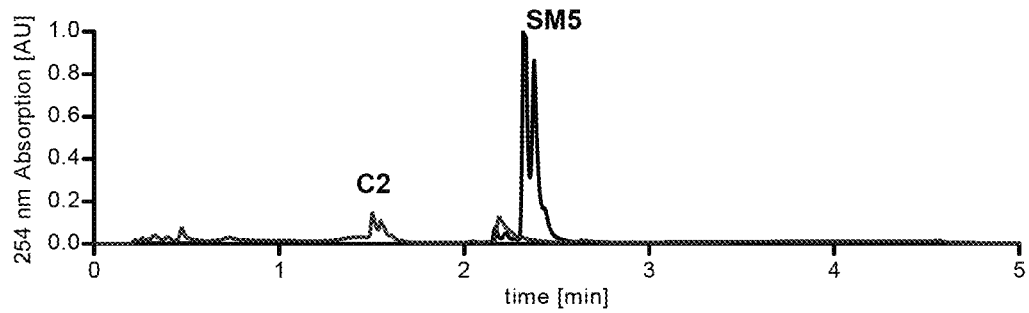

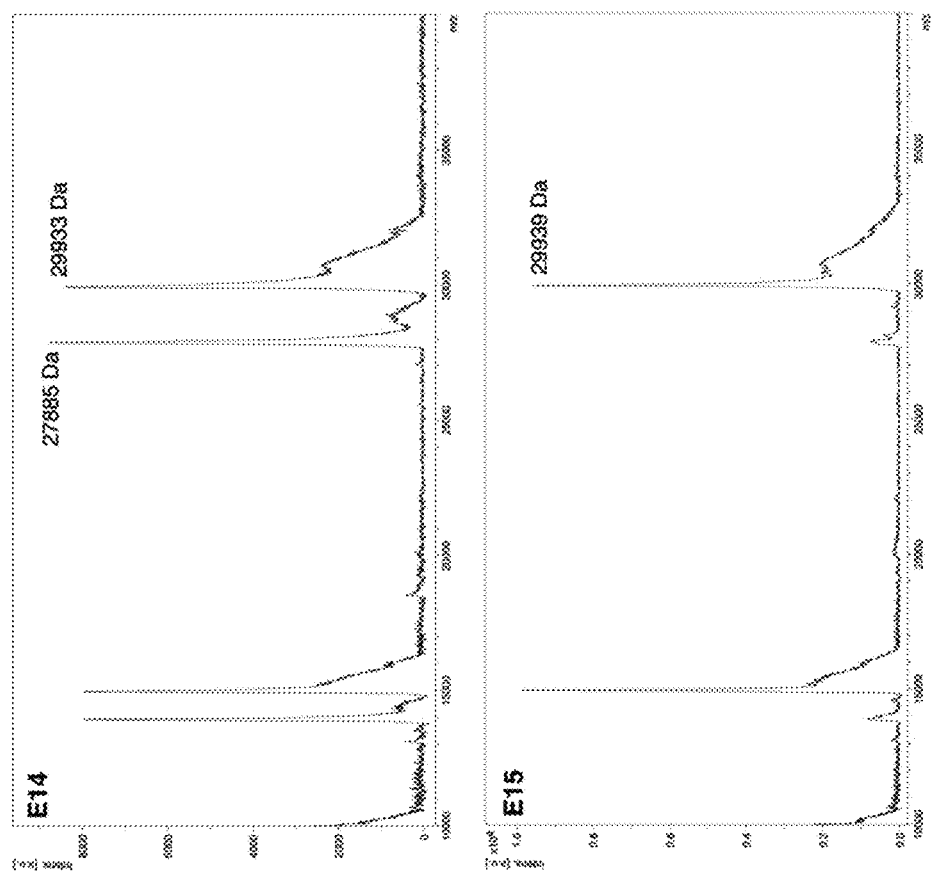
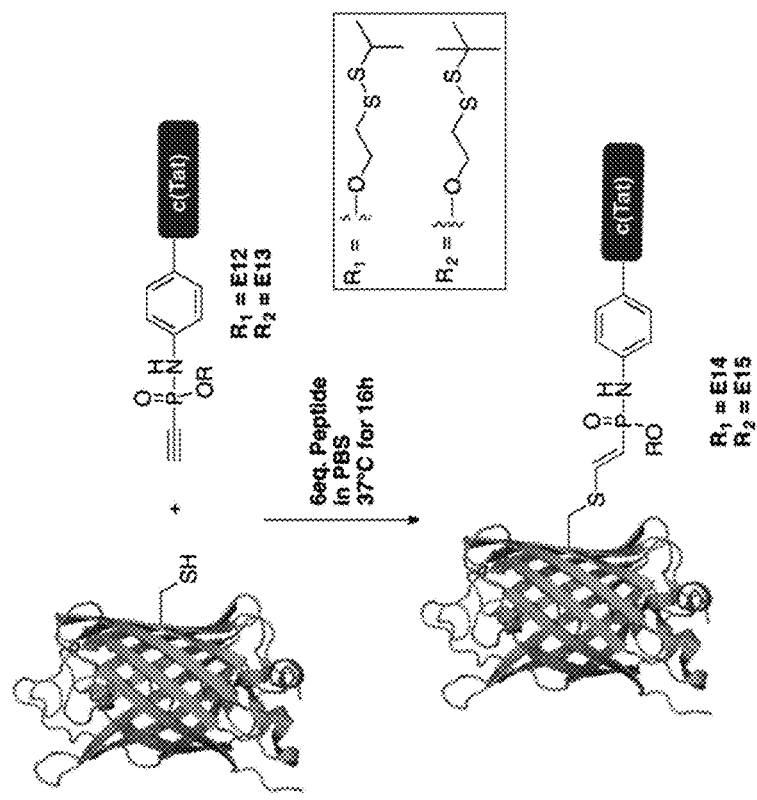
Figure 29

[Fig. 41]
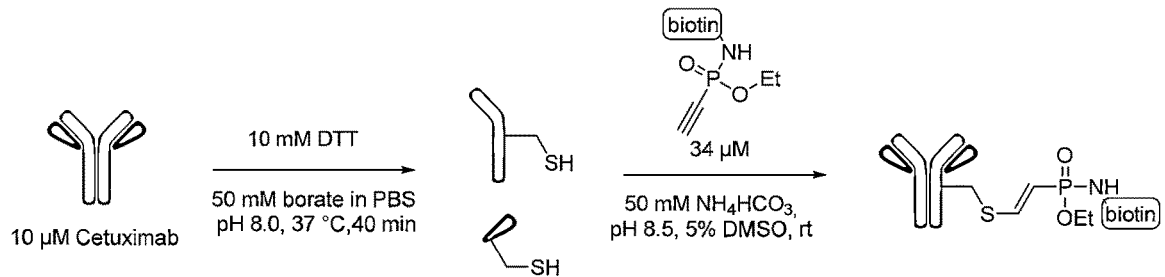
[Fig. 42]
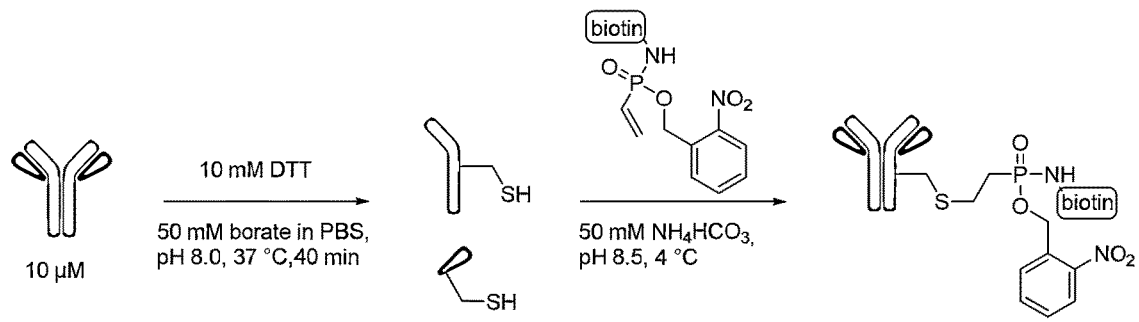
[Fig. 43]
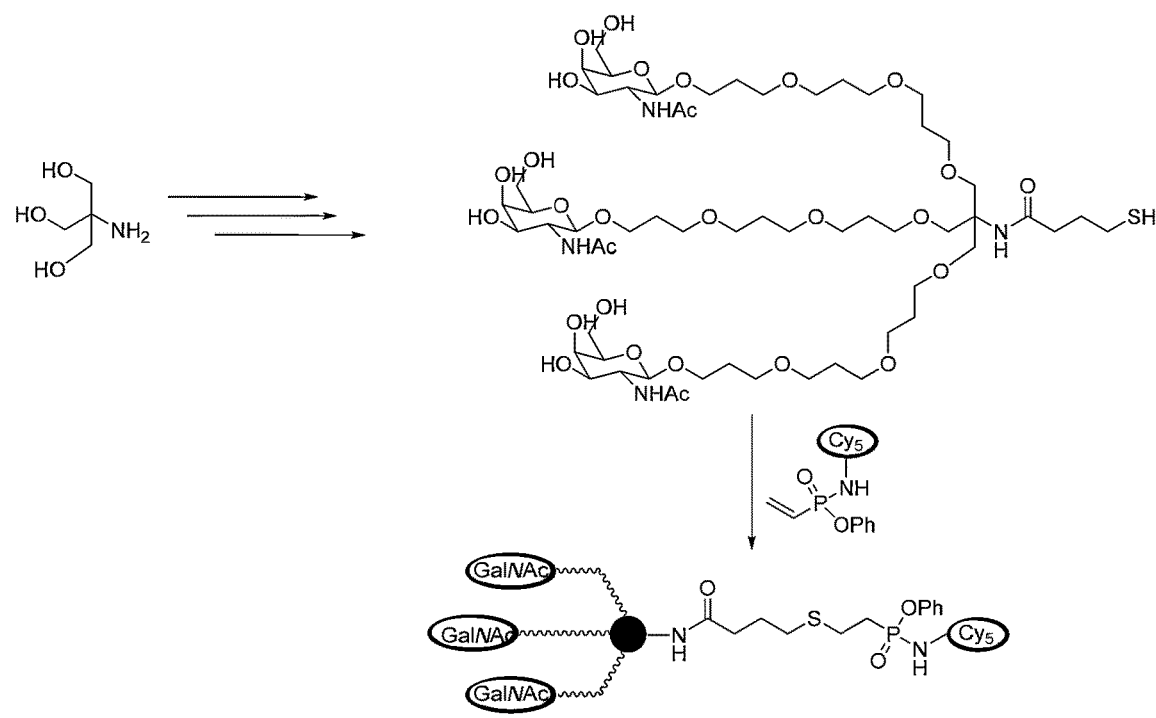

R1=H; R2= iPr: SM1
R1=H; R2=tBu: SM2
R1=Me; R2= iPr: SM3

CHEMOSELECTIVE THIOL-CONJUGATION WITH ALKENE OR ALKYNE-PHOSPHONAMIDATES

CROSS REFERENCE TO RELATED APPLICATIONS

The present application is a continuation of U.S. patent application Ser. No. 17/460,791, filed Aug. 30, 2021, which is a divisional of U.S. patent application Ser. No. 16/328,199, filed Feb. 25, 2019, now U.S. Pat. No. 11,161,873, which is a U.S. national phase application of International Application No. PCT/EP2017/071937, filed Sep. 1, 2017, which claims priority to European Patent Application No. 16001917.0, filed Sep. 1, 2016. U.S. patent application Ser. Nos. 17/460,791 and 16/328,199 are hereby incorporated in their entirety.

REFERENCE TO AN ELECTRONIC SEQUENCE LISTING

The contents of the electronic sequence listing (350066_401C1_SEQUENCE_LISTING.xml; Size: 27005 bytes; and Date of Creation: Jul. 10, 2023) is herein incorporated by reference in its entirety.

BACKGROUND

Chemoselective and bioorthogonal reactions have emerged as powerful tools for the site-specific modification of proteins (1, 2). With these reactions, various protein- and antibody-conjugates became accessible, which carried functional modules like fluorophores and other spectroscopic labels, polymers, toxins as well as small molecules and proteins that resemble posttranslational protein modifications. Thereby, chemoselective protein modification techniques have greatly contributed to fundamental studies ranging from the investigation of biological functions of proteins and the development of new imaging techniques to promising new medicinal approaches in diagnostics, the design of protein-based pharmaceuticals and the targeted-delivery of drugs.

Over the last years, researchers have mainly concentrated on two different aspects in the engineering of bioorthogonal reactions for the modification of proteins (3). On the one hand, many efforts have been devoted to fast reactions requiring highly reactive starting materials for the transformation of unique functionalities present in protein side-chains (4,5). This approach is complimented by advanced amber suppression techniques to achieve a site-specific labeling, which resulted in a number of genetically encoded, highly reactive bioorthogonal reporters to undergo various types of cycloaddition reactions, including strain-promoted alkyne-azide cycloaddition or inverse-demand Diels-Alder reactions (6,7). On the other hand, researchers have focused on developing and applying high-yielding protein modification reactions, especially if high amounts of functional protein-conjugates and ideally quantitative conversions are desired to avoid tedious if not impossible purification steps (1). To achieve this, high yields in protein expression are of particular importance. Since amber suppression can result in low amounts of expressed protein, standard and auxotrophic expression systems are often preferred. A common scenario to achieve site-specific labeling in combination with standard protein expression is the placement of a unique Cys residue in a protein of choice by site-directed mutagenesis, followed by Cys-modification strategies (8). Alternatively, azide- or alkyne-containing amino acids can be incorporated using auxotrophic expression systems (9), which can be modified using Staudinger ligations and Cu-catalyzed azide-alkyne cycloaddition (CuAAC) (10,11).

While both of these aspects have seen significant advancements in recent years, a general and modular accessibility of highly reactive and complex functional modules for a metal-free chemoselective modification reaction remains often challenging. This is due to the requirement of additional protecting group manipulations in the synthesis of reactive bioorthogonal building blocks, which can be problematic in light of the high reactivity and lability of the employed bioorthogonal functions. For example, the synthesis of a highly reactive cyclooctyne-containing fluorescent peptide carrying a Xe-cryptophane for molecular imaging, required a sophisticated yet low yielding use of orthogonal protecting groups (12).

In 2013, a modular chemoselective method for the step-wise coupling of two azide-building blocks by combining a CuAAC with the Staudinger-phosphonite reaction (SPhR) was developed (13). Introduction of SPhR for the chemoselective labeling of azido-containing peptides and proteins in aqueous systems to form protein-phosphonamidate-conjugates via boran protected bisethoxyalkylene-phosphonite is known from (14).

Previous techniques for the conjugation of Cys residues rely mainly on maleimide conjugation, which often tend to hydrolyze and are prone to thiol exchange under high thiol concentrations. For a recent comprehensive overview on Cys-conjugation techniques (22). WO 2015/169784 discloses a process for the preparation of C2-disulfide-bridged peptides and proteins, wherein the bridging is achieved by a thiol-yn-reaction with alkynes. U.S. Pat. No. 2,535,174 describes the alkaline catalyzed addition of saturated aliphatic mercaptans to esters of ethenephosphonic acids. However, the thiol-conjugates of alkyne and alkene-phosphonamidates as disclosed herein have neither been reported nor are they anticipated by the prior art.

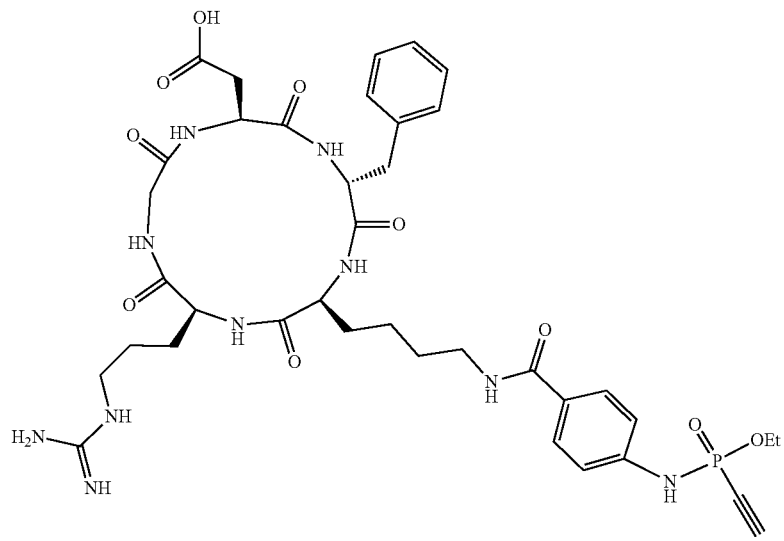 [SMILES: C#CP(=O)(Nc1ccc(C(=O)NCCCC[C@@H]2NC(=O)[C@@H](Cc3ccccc3)NC(=O)[C@H](CC(=O)O)NC(=O)CNC(=O)[C@H](CCCNC(=N)N)NC2=O)cc1)OCC]

to give

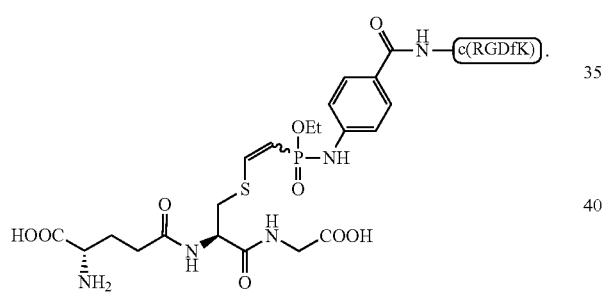

Figure 4:
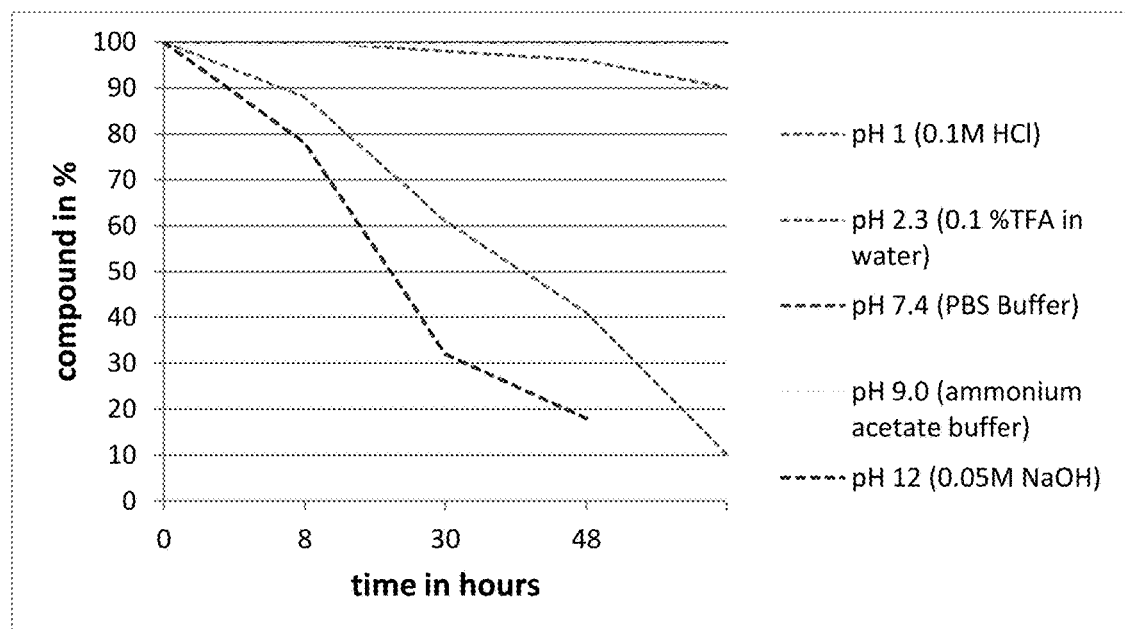

FIG. 4 shows the pH-dependent stability of c(RGDfK)-Glutathion

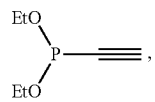

where the full consumption of the starting material was confirmed (product at 126.73 ppm).

FIG. 7 shows the UPLC chromatogram of purified c(RGDfK)-azide

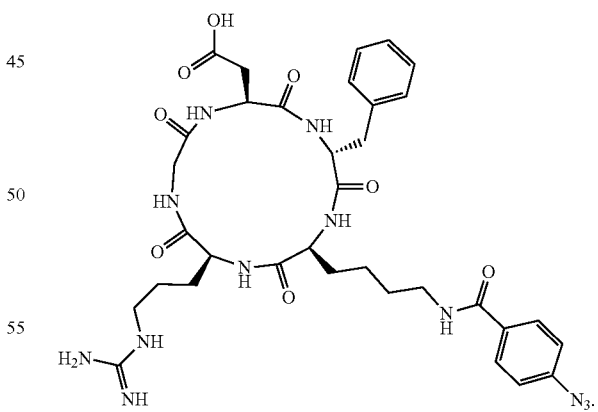

Figure 5:
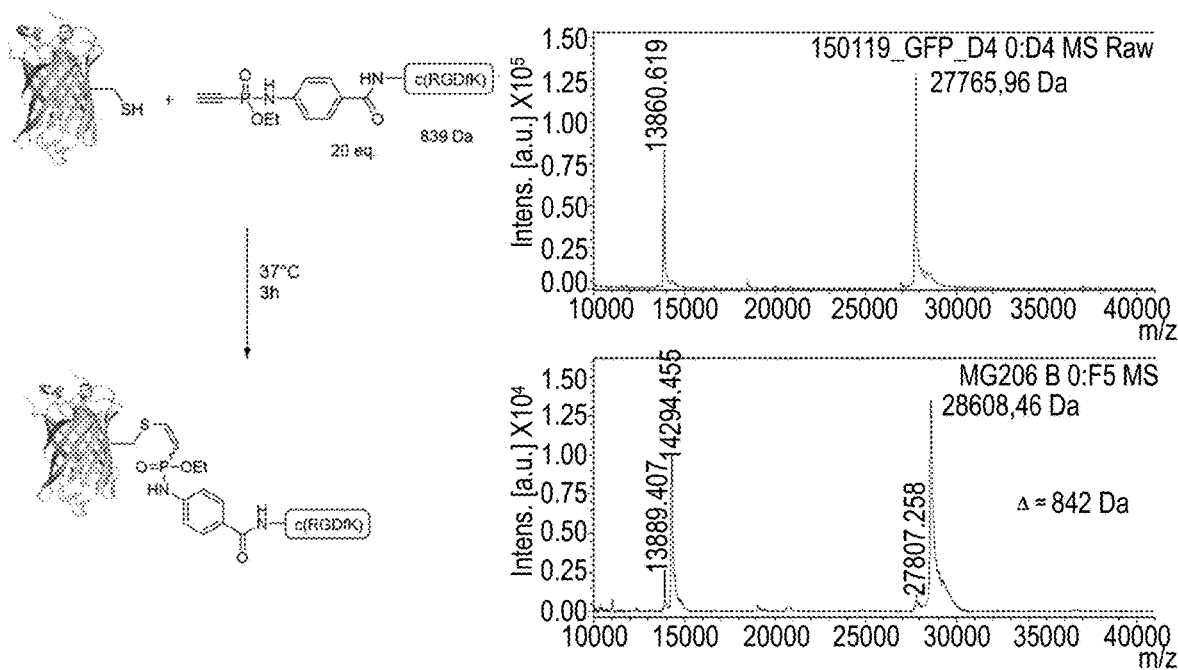

FIG. 5 shows the Staudinger-induced thiol-addition to a single addressable Cys-containing eGFP, in which the conjugate depicted in FIG. 30 was formed again in quantitative conversion after 3 h incubation at 37° C.

FIG. 6 shows a $^{31}$P NMR-NMR from the crude synthesis of bisethoxyalkyne-phosphonite FIG. 8 shows the LC-UV chromatogram of purified c(RGDfK)-alkyne

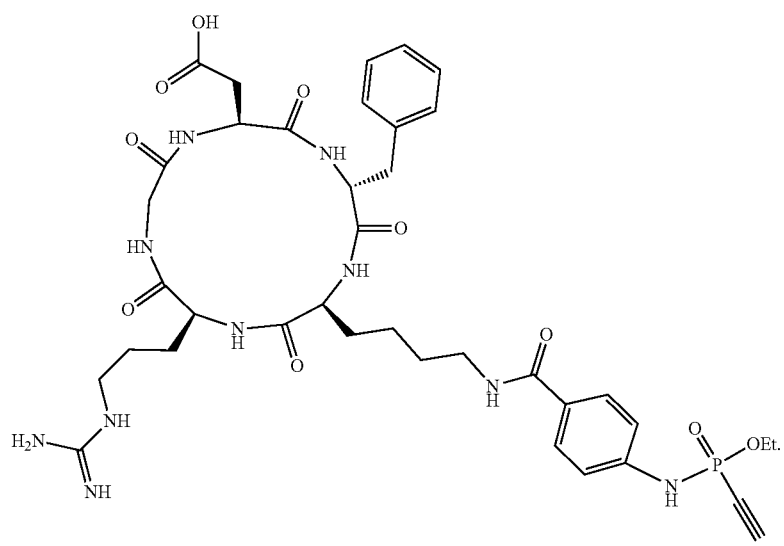 [SMILES: C#CP(=O)(Nc1ccc(C(=O)NCCCC[C@@H]2NC(=O)[C@@H](Cc3ccccc3)NC(=O)[C@H](CC(=O)O)NC(=O)CNC(=O)[C@H](CCCNC(=N)N)NC2=O)cc1)OCC]

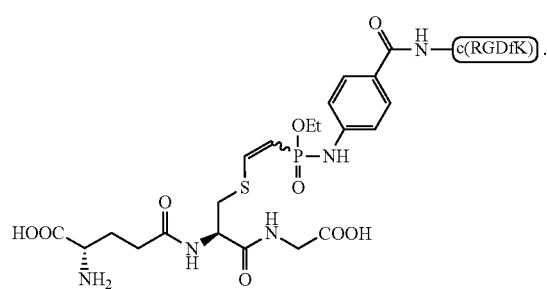 [SMILES: CCOP(=O)(C=CSC[C@H](NC(=O)CC[C@H](N)C(=O)O)C(=O)NCC(=O)O)Nc1ccc(C(=O)NC)cc1]

FIG. 9 shows the LC-UV chromatogram of purified c(RGDfK)-glutathion

FIG. 10 shows a western blot analysis after non reducing SDS-PAGE. 1: Cetuximab starting material. 2: 5 min, 3: 1 h, 4: 2 h, 5: 20 h incubation with a biotin modified phosphonamidate. Reaction with (left) and without (right) prior reduction of the disulfides.

FIG. 11 shows the stability of ethyl-N-phenyl-P-vinyl-phosphonamidate to different pHs over time. Stability of the phosphonamidate to different pHs was proven by $^{31}$P-NMR in aqueous buffers at room temperature.

Figure 12:
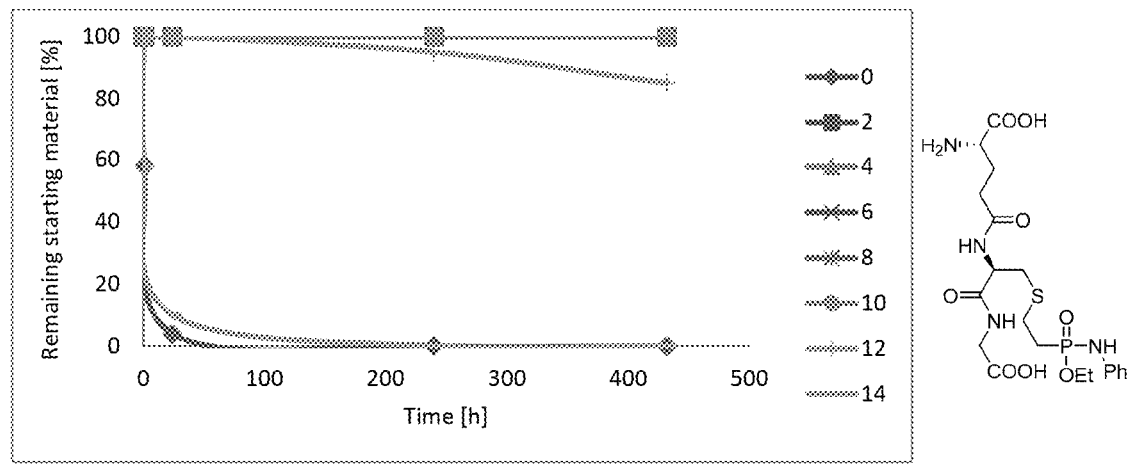

FIG. 12 shows the stability of a glutathione phosphonamidate adduct to different pHs over time. Stability of a thiol-adduct to different pHs was proven by $^{31}$P-NMR in aqueous buffers at room temperature.

Figure 13:
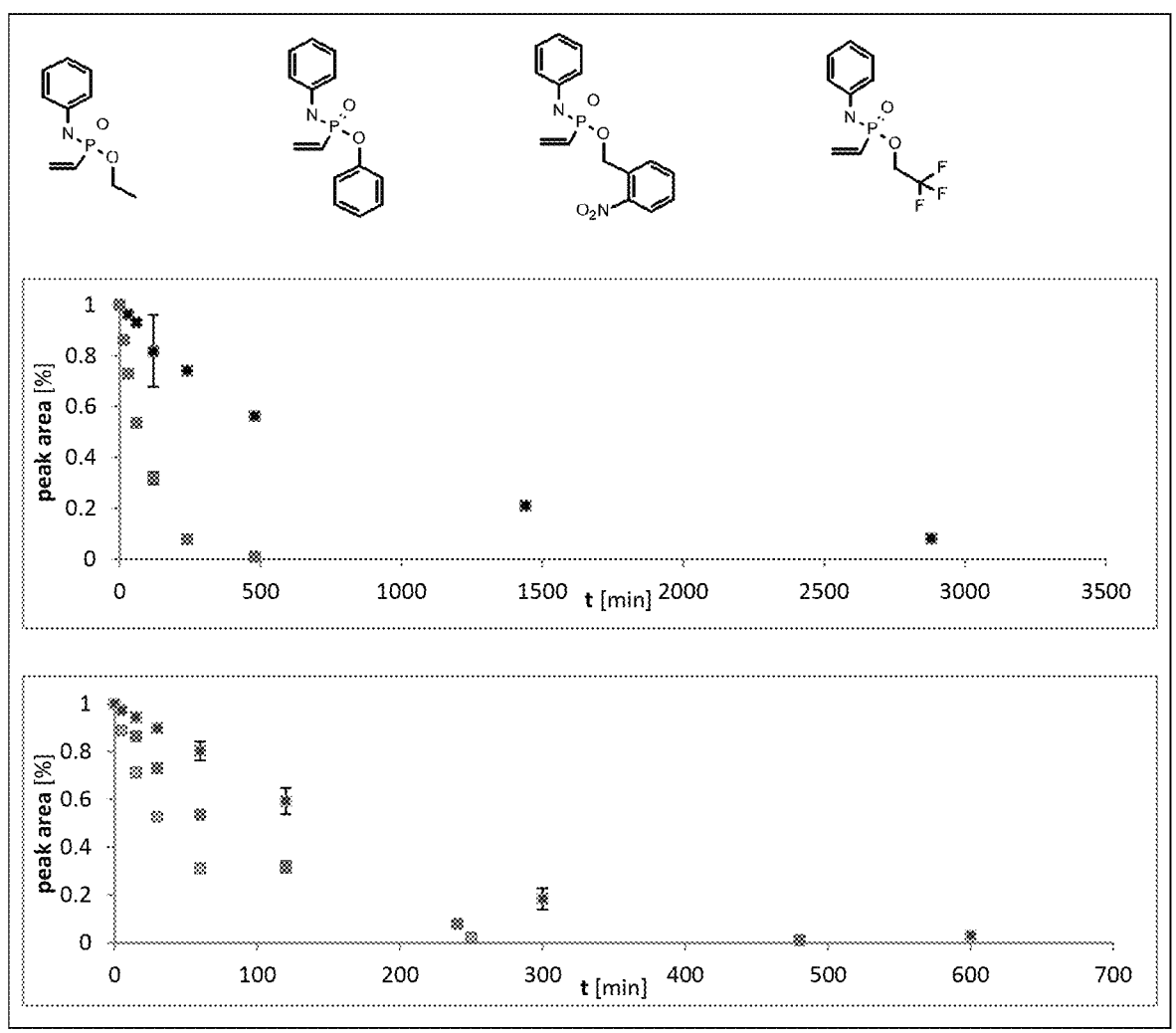

FIG. 13 shows the consumption of various N-phenyl vinyl phosphonamidates in the reaction with glutathione at pH 8.5. HPLC UV traces were taken at different time points. Experiments were performed in triplicates.

FIG. 14 shows a western blot analysis after non reducing SDS-PAGE. 1: Cetuximab starting material. 2: 5 min, 3: 1 h, 4: 2 h, 5: 20 h incubation with a biotin modified phosphonamidate. Reaction with (left) and without (right) prior reduction of the disulfides.

FIG. 15 shows the sequences mentioned throughout the specification.

FIG. 16A shows trastuzumab modification with three different Cys-reactive biotin derivatives.

FIG. 16B shows the western blot analysis. Lanes 1 and 5: untreated antibody. Lanes 2-4: reactions with prior DTT treatment. Lanes 6-8: Control reactions without prior DTT treatment.

FIGS. 17A to 17C show trastuzumab modification with phosphonamidate modified, cathepsin cleavable MMAF (Amidate-VC-PAB-MMAF). FIG. 17A shows the reaction scheme comprising reduction and alkylation of interchain disulfides. FIG. 17B shows SDS-PAGE analysis of the reaction. FIG. 17C shows the deconvoluted MS spectra of the antibody fragments after deglycosylation with PNGase F and reduction with DTT. LC: Light chain; HC: Heavy chain; mod: Amidate-VC-PAB-MMAF.

Figure 18:
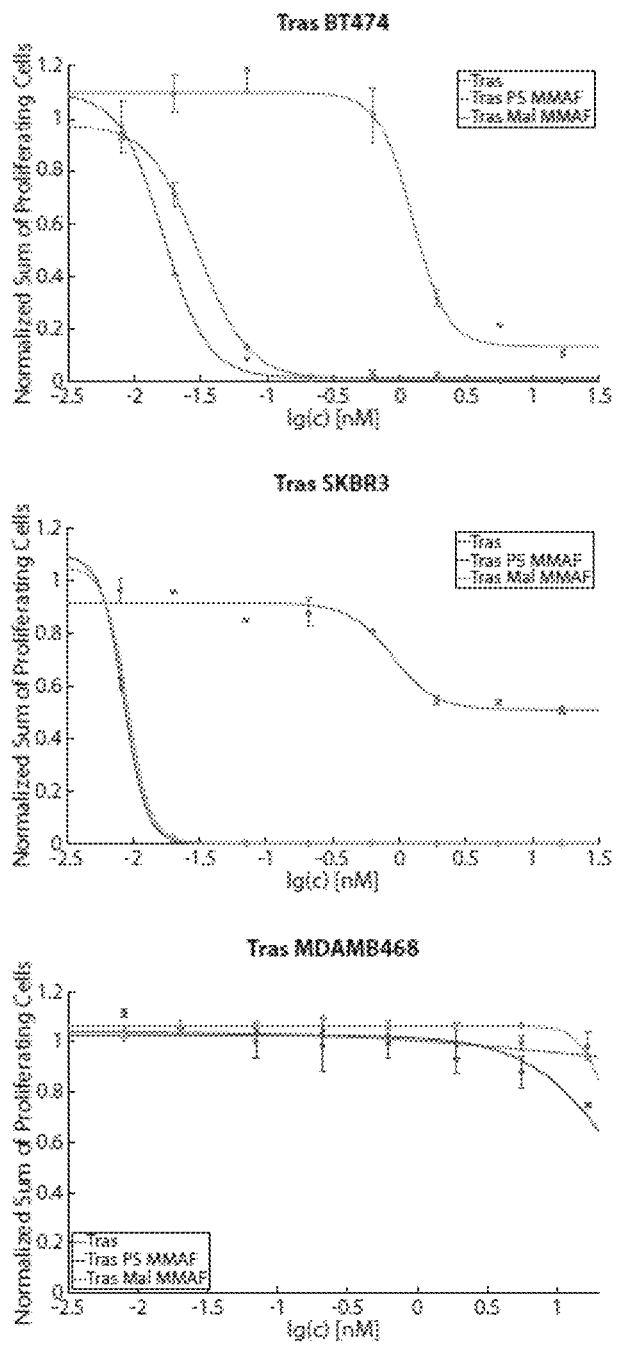

FIG. 18 shows the increased antiproliferative potency of MMAF linked trastuzumab on two different Her2 overexpressing cell lines (BT474 and SKBR3) and one control (MDAMB468). Plots depict the number of proliferating cells after 4 days of antibody treatment in dependency of the antibody concentration. Trastuzumab alone, trastuzumab-phosphonamidate-MMAF and trastuzumab-maleimide-MMAF were tested.

Figure 19:
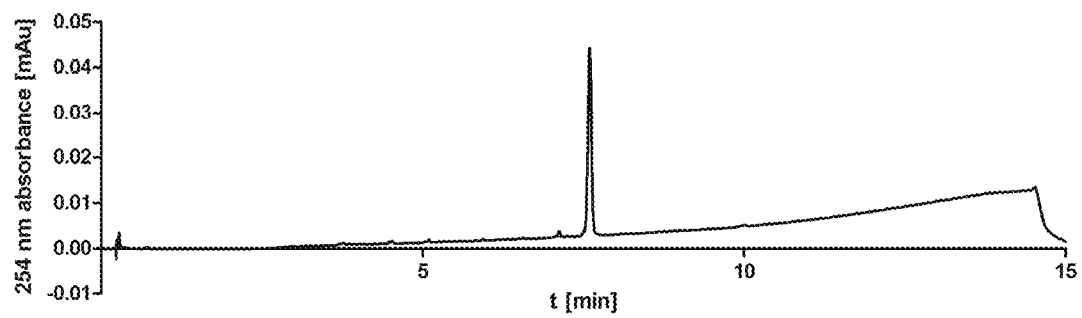

FIG. 19 shows the UPLC-UV chromatogram of purified phosphonamidate-Val-Cit-Pab-MMAF

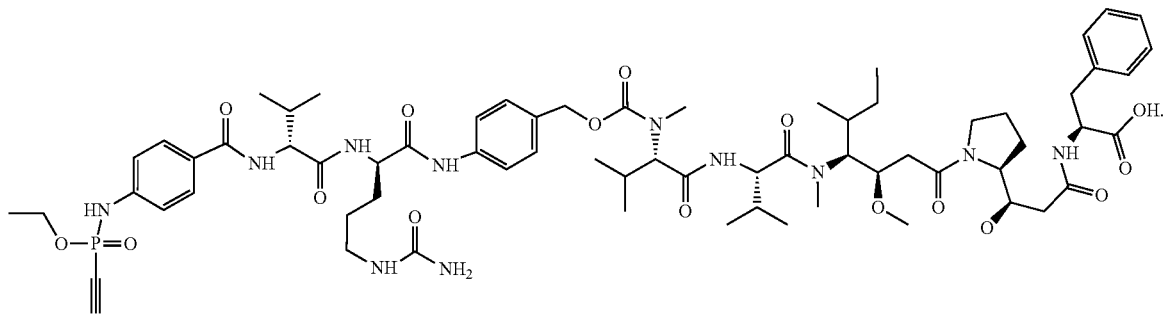

Figure 20:
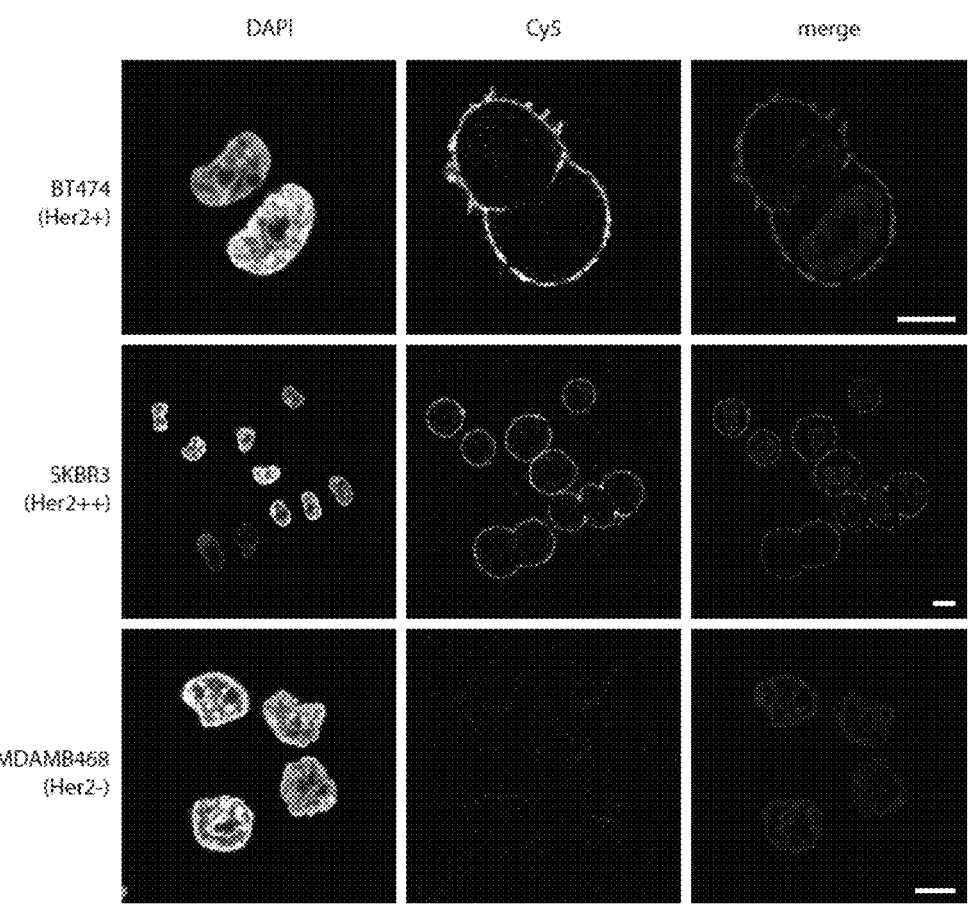

FIG. 20 shows immunostainings of fixed cells over expressing the cell surface receptor Her2 (BT474 and SKBR3) or exhibiting low Her2 expression levels (MDAMB468).

FIG. 21A shows the structure of a phosphonamidate linked FRET conjugate. FIG. 21B shows the structure of a maleimide linked FRET conjugate. FIG. 21C shows the principle of the fluorescence-quencher based readout. FIG. 21D shows monitoring of the fluorescence increase over time. FIG. 21E shows the comparison of a phosphonamidate- and a maleimide-linked dye-quencher pair during exposure to 1000 eq. glutathion in PBS.

Figure 22A:
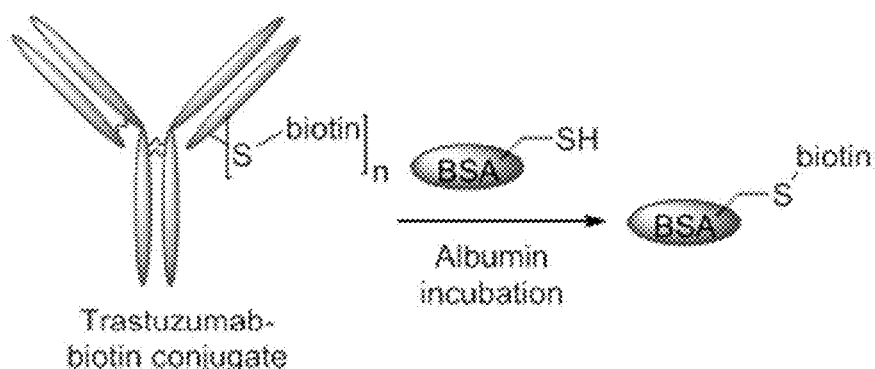
Figure 22B:
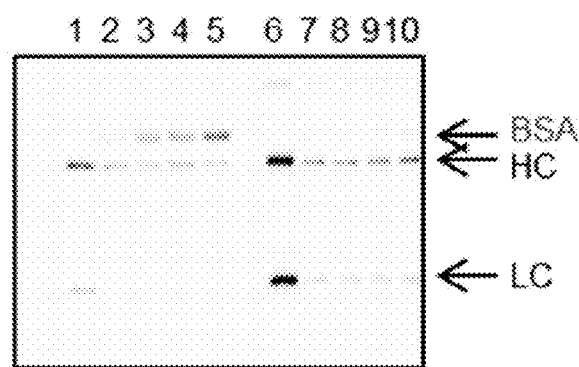

FIGS. 22A and 22B show the transfer of the antibody modification to serum proteins. FIG. 22A shows incubation of Tratuzumab-biotin conjugates. FIG. 22B shows monitoring of the biotin transfer to albumin by western blot analysis. Lane 1: Untreated maleimide conjugate. Lanes 2-5: Analysis of the BSA exposed maleimide adduct after 0, 1, 2 and 5 days. Lane 6: Untreated amidate conjugate. Lanes 7-10: Analysis of the BSA exposed amidate adduct after 0, 1, 2 and 5 days.

FIGS. 23A to 23D show the determination of the second order rate constant of the thiol addition. FIG. 23A shows the reaction of the EDANS phosphonamidate with glutathione. FIG. 23B shows the fluorescence HPLC trace after 30 min reaction time. FIG. 23C shows the monitoring of the phosphonamidate decrease over time. FIG. 23D shows the plot of the inverse concentration against reaction time. Error bars represent the mean of three replicates (n=3).

Figure 24:
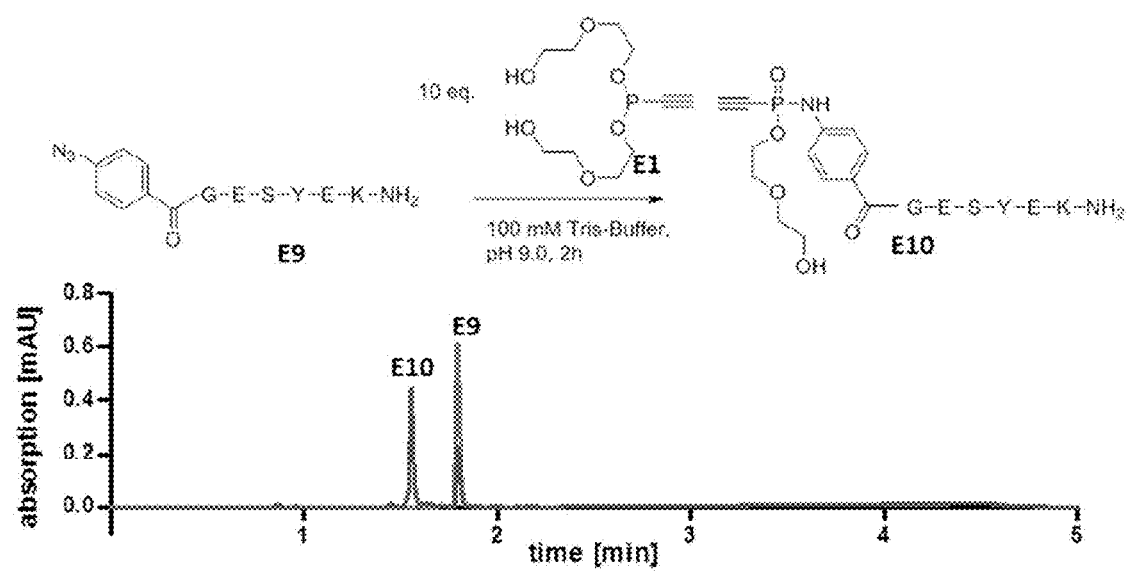

FIG. 24 shows the reaction of an azido modified peptide with the water soluble phosphonite E1 in Tris buffer. The upper portion shows the reaction scheme. The lower portion shows the HPLC-trace, starting material and reaction after 2 h were tested.

Figure 25A:
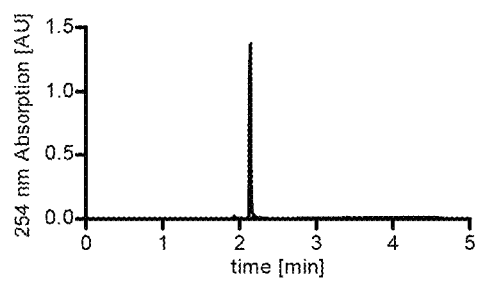
Figure 25B:
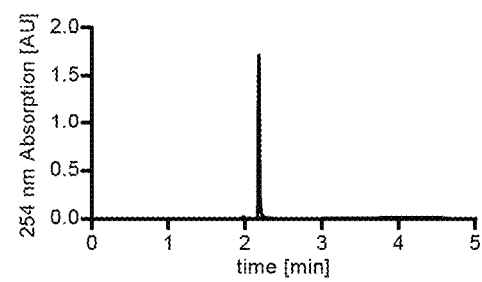
Figure 25C:
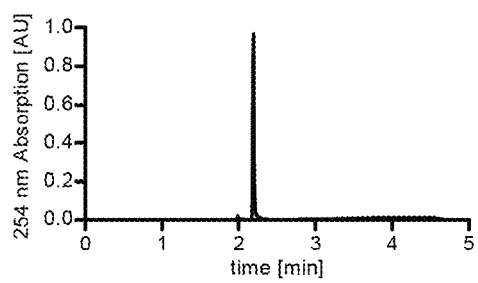
Figure 25D:
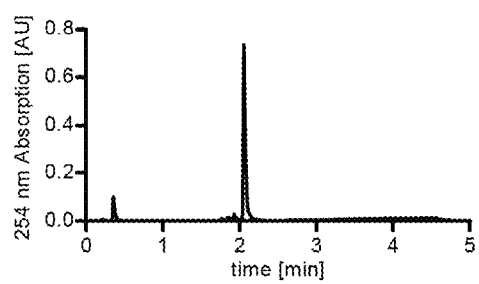
Figure 25E:
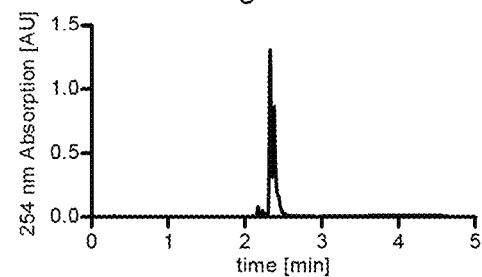

FIG. 25A shows a HPLC trace of the first conjugate according to Table 5. FIG. 25B shows a HPLC trace of the second conjugate according to Table 5. FIG. 25C shows a HPLC trace of the third conjugate according to Table 5. FIG. 25D shows a HPLC trace of the fourth conjugate according to Table 5. FIG. 25E shows a HPLC trace of the fifth conjugate according to Table 5.

Figure 26A:
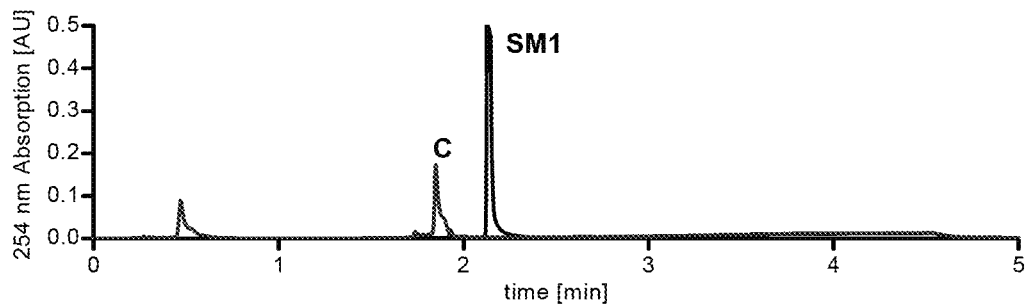

FIG. 26A to 26C show the UPLC-MS analysis of the cleavage of disulfide containing amidate-adducts SM1, SM2 and SM3 with TCEP. Incubation with TCEP, and with PBS only were tested. Peaks were identified by MS. FIG. 26A shows the UPLC-MS analysis for SM1. FIG. 26B shows the UPLC-MS analysis for SM2. FIG. 26C shows the UPLC-MS analysis for SM3.

FIG. 27 shows the UPLC-MS analysis of the cleavage of the ester-containing amidate-adduct SM4 with cell lysate. Incubation with cell lysate and with PBS only were tested. Peaks were identified by MS.

FIG. 28 shows the cleavage of the diazo-containing amidate-adduct SM5 with sodium dithionite. Incubation with TCEP and with PBS only were tested. Peaks were identified by MS.

FIG. 29 shows the thiol addition of alkyne-c(Tat) to eGFP C70M S147C.

Figure 30:
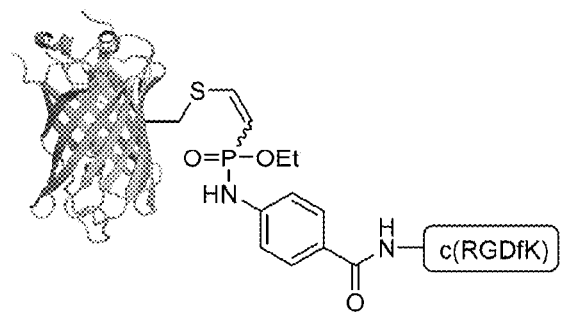

FIG. 30 shows a conjugate of formula (VII), which comprises a GFP protein, preferably an eGFP protein, on the left side and a cyclid RGD peptide on the right side.

Figure 31:
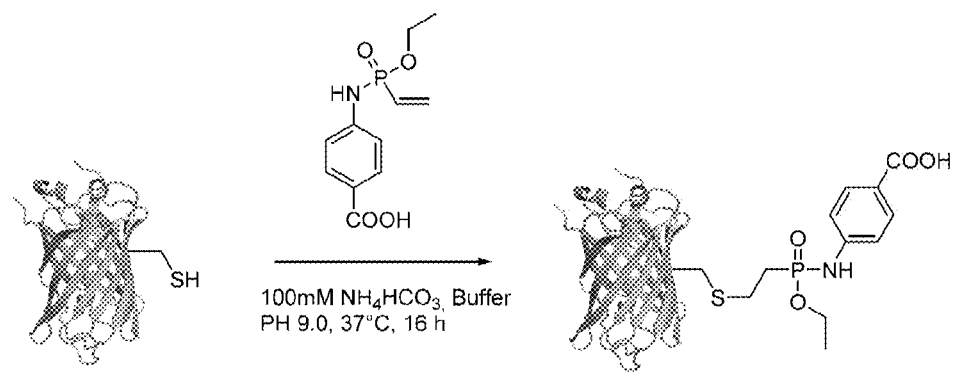

FIG. 31 shows an addition of a water-soluble vinyl phosphonamidate to eGFP with one addressable cysteine to form a conjugate of formula (VII).

Figure 32:
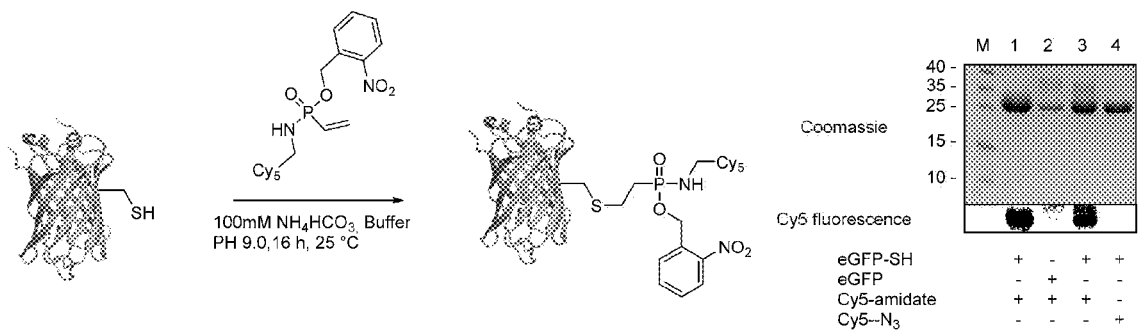

FIG. 32 shows a Cy5 phosphonamidate labeling of eGFP with one addressable cysteine to form a conjugate of formula (VII). In gel fluorescence read out after SDS Page confirms selective Cy5 labeling.

Figure 33:
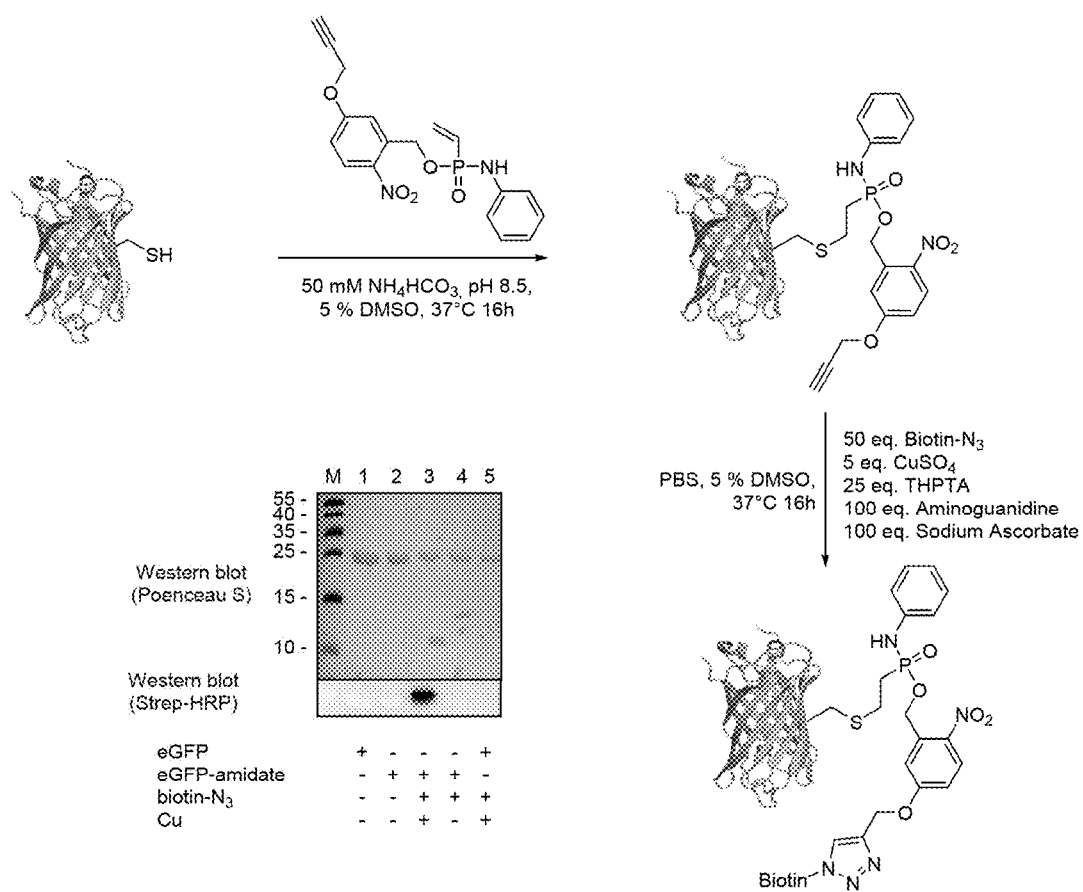

FIG. 33 shows a photocleavable alkyne labeling of eGFP with one addressable cysteine to form a conjugate of formula (VII), subsequent biotin labeling via CuACC, and western blot analysis.

Figure 34:
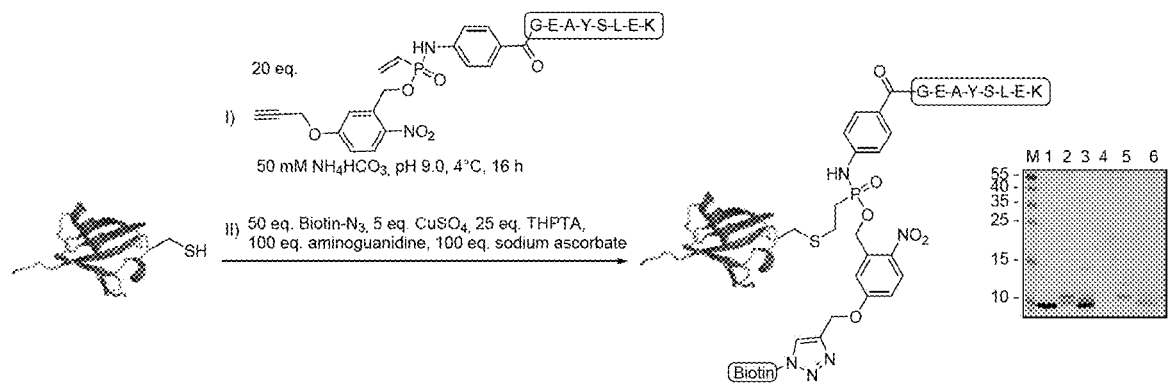

FIG. 34 shows a photocleavable alkyne labeling of ubiquitin with one addressable cysteine to form a conjugate of formula (VII), and subsequent biotin labeling via CuACC. Western blot analysis after immobilization on streptavidin beads. 1: ubiquitin starting material, 2: reaction mixture after CuACC, 3: supernatant after incubation of the reaction mixture with streptavidin agarose, 4: flow through after wash of streptavidin agarose, 5: boiled beads, 6: irradiated beads.

Figure 35:
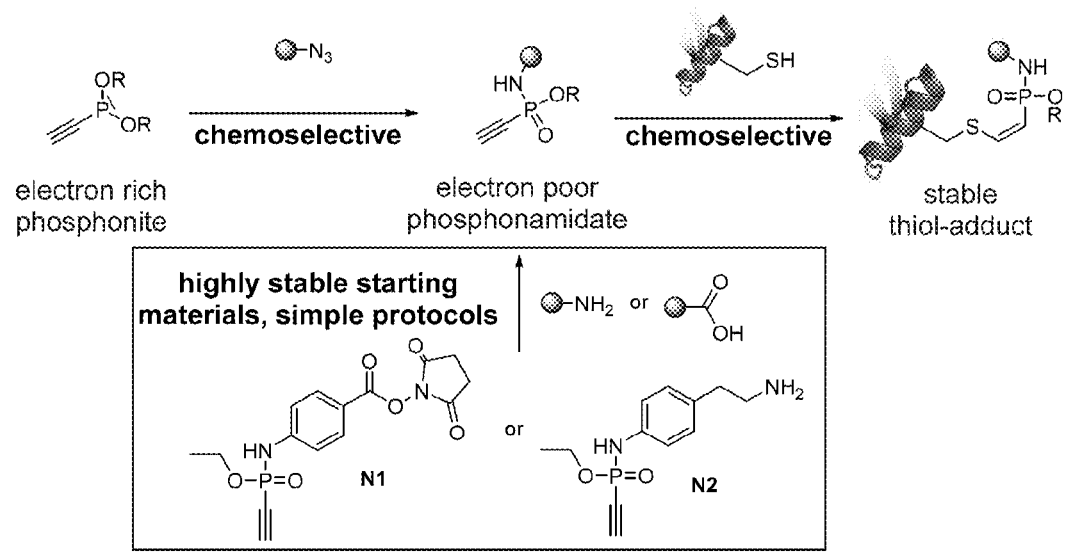

FIG. 35 shows the principle of alkyne-phosphonamidate-synthesis and subsequent chemoselective modification of Cys-residues.

Figure 36:
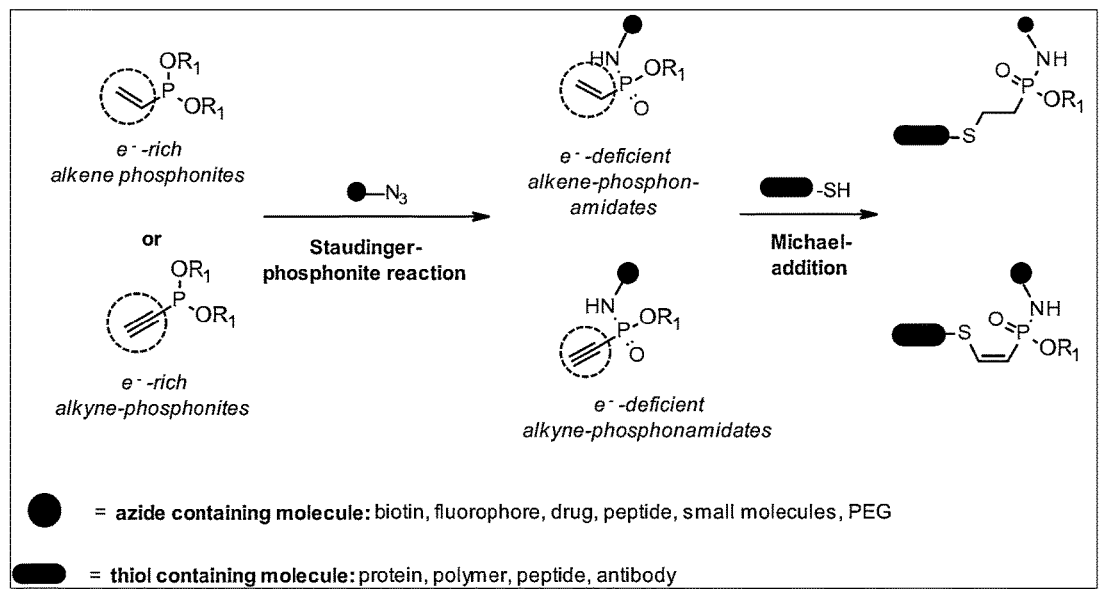

FIG. 36 describes the general strategy for a synthesis according to the present invention at the example of ethenyl or ethynyl phosphonites. R1 represents an optionally substituted aliphatic or aromatic residue.

Figure 37A:
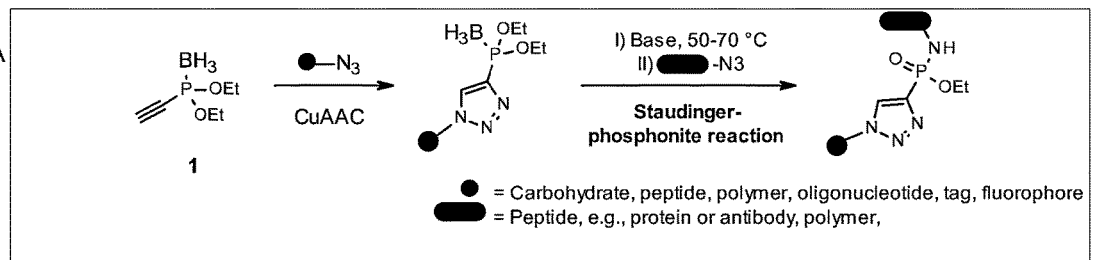
Figure 37B:
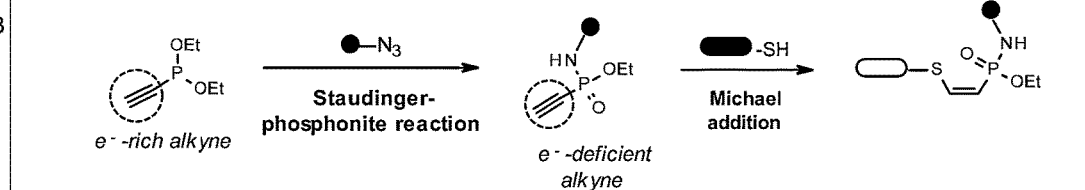

FIGS. 37A-B show the difference between a process known in the art (e.g., 15) and a process according to the present invention. FIG. 37A shows sequential azide-azide couplings using alkyne phosphonites. FIG. 37B shows a Staudinger-induced thiol-addition (the thiol addition may be also denoted as "Michael addition") for the modification of Cys residues according to the invention. Merely as examples, ethenyl and ethynyl (diethyl)phosphonite were used.

Figure 38:
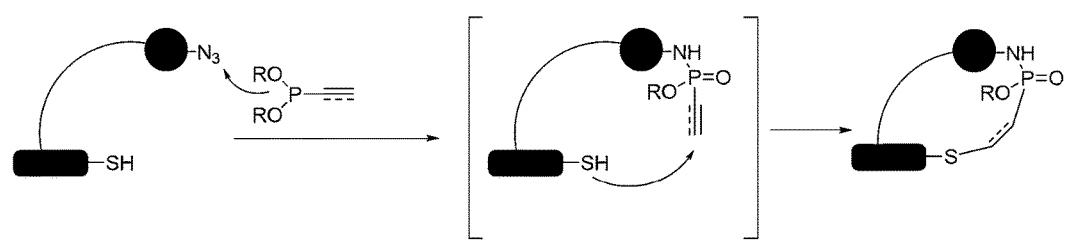

FIG. 38 shows that the incorporation of both an azide and a thiol into the same molecule provides for an intramolecular Staudinger-induced thiol addition that can realize an intramolecular cyclization.

Figure 39:
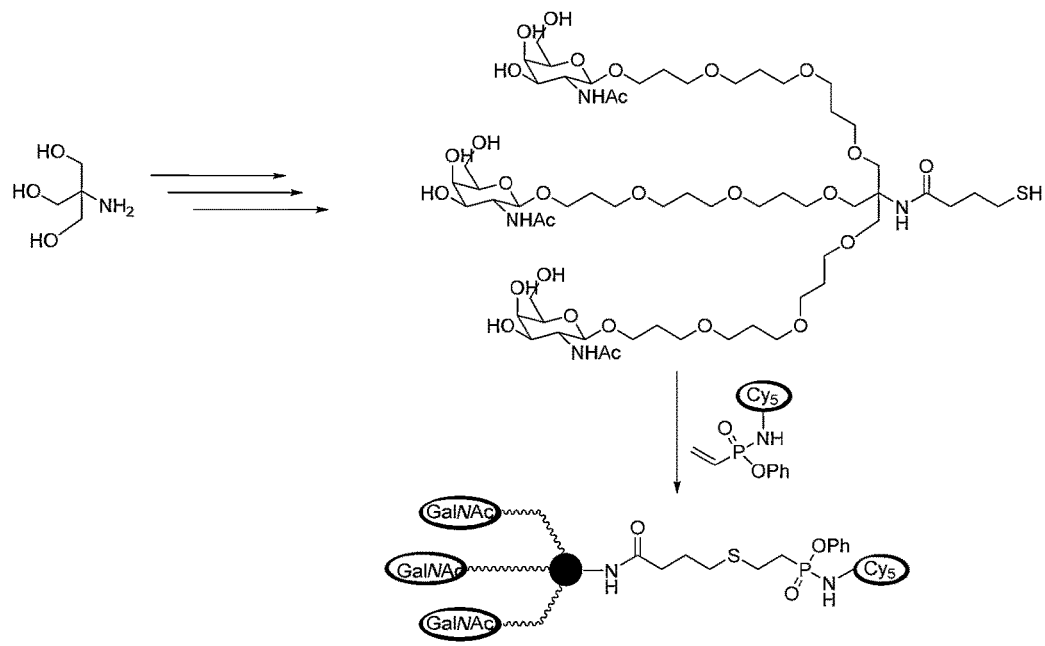

FIG. 39 shows a fluorescently labeled ASGP-R addressing Cy5 conjugate of formula (X) which can be produced via the modular addition to vinyl phosphonamidates.

Figure 40:
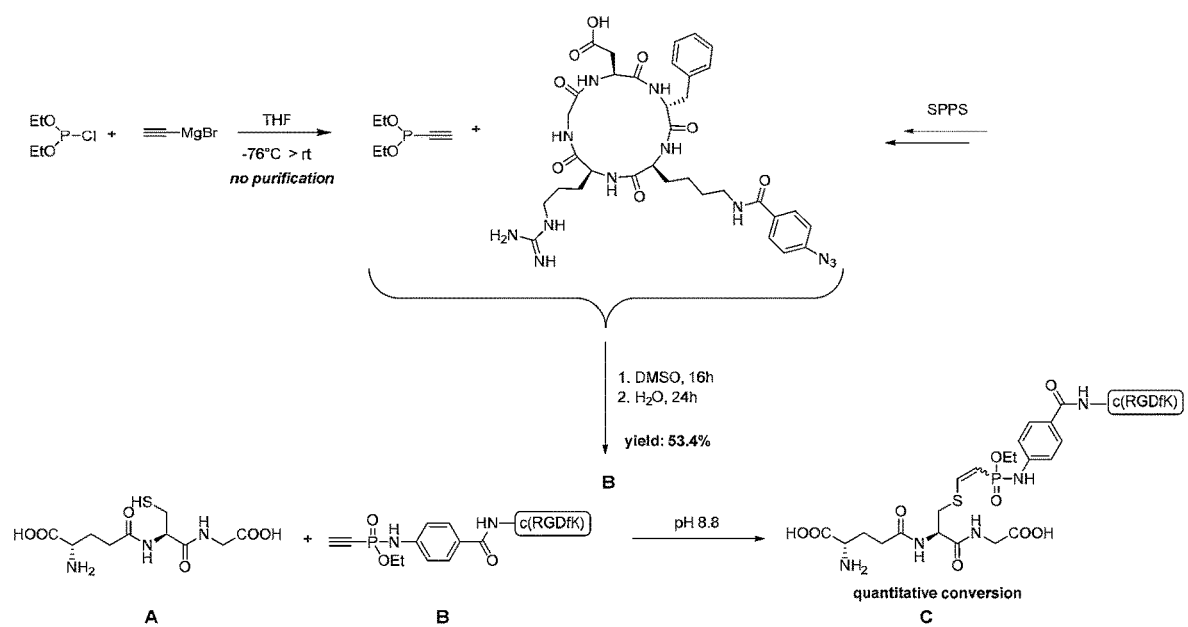

FIG. 40 shows the Staudinger-induced thiol-addition of cyclic azido-RGD-peptides to GSH.

FIG. 41 shows the two-step reduction and alkylation approach for cysteine selective antibody modification with a biotin modified alkynyl phosphonamidate.

FIG. 42 shows the reduction of antibody disulfides and subsequent modification with a biotin vinyl phosphonamidate.

FIG. 43 shows the synthesis of a fluorescently labeled ASGP-R addressing Cy5 conjugate via the modular addition to vinyl phosphonamidates.

Figure 44:
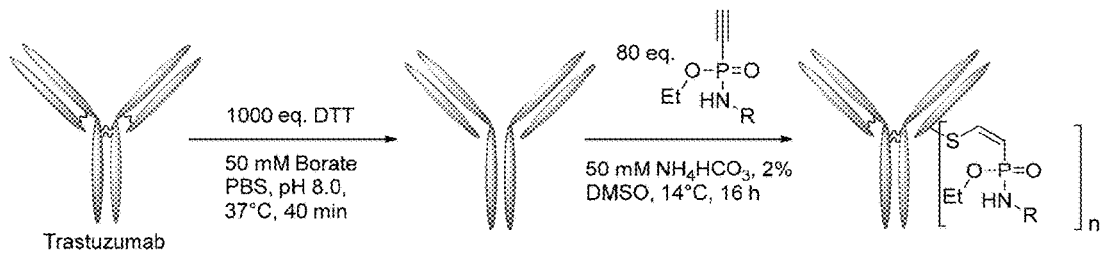

FIG. 44 shows the general procedure for the modification of Trastuzumab via the reduction/alkylation protocol.

Figure 45:
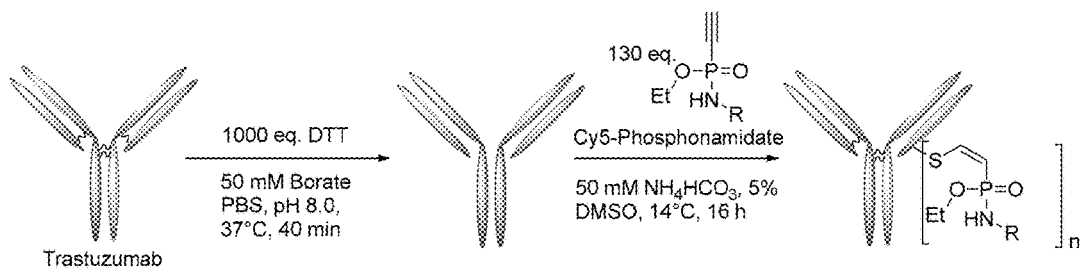

FIG. 45 shows procedures for the Staudinger-induced thiol addition with alkynyl-phosphonites for the generation of Antibody Fluorophore Conjugates (AFCs).

Figure 46:
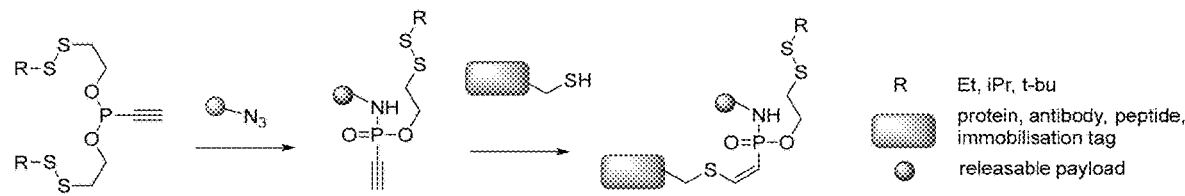

FIG. 46 shows the synthesis of a conjugate having a cleavable disulfide-comprising O-substituent via the Staudinger phosphonite reaction, followed by the addition of a thiol-containing molecule to the unsaturated phosphonamidate.

Figure 47:
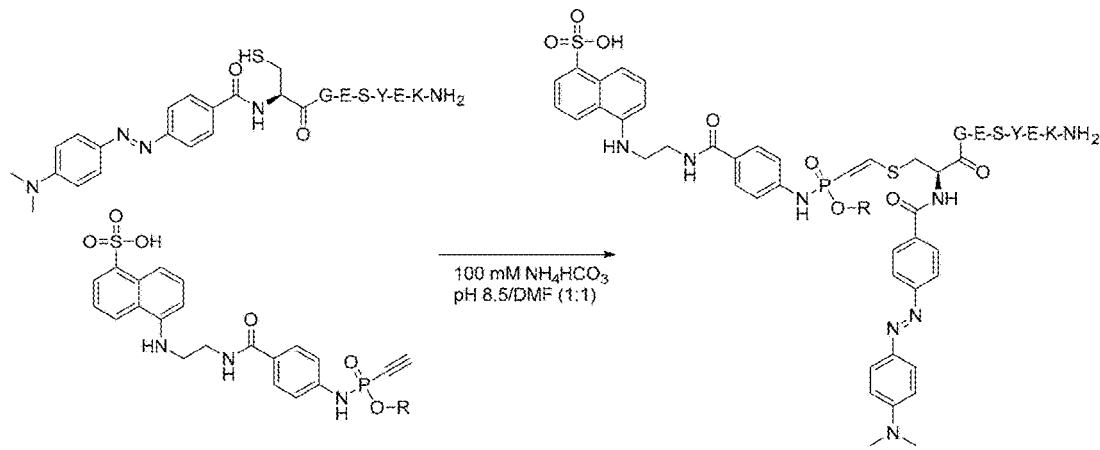

FIG. 47 shows the general procedure 5 for the addition of a Cys-model peptide to different 0-Substituted EDANS phosphonamidates.

Figure 48:
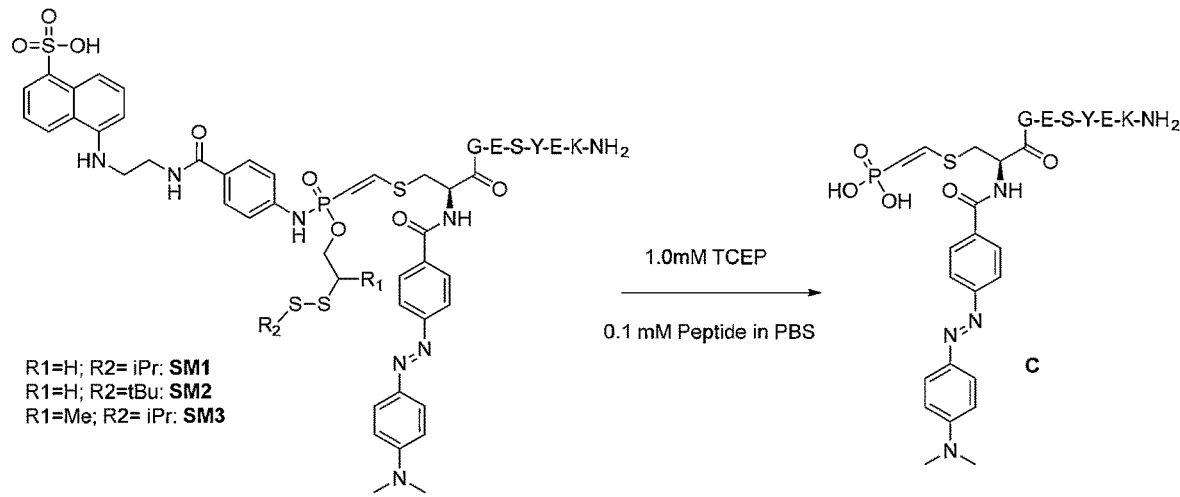

FIG. 48 shows the procedure for the cleavage of the disulfide containing amidate-adducts with TCEP.

Figure 49:
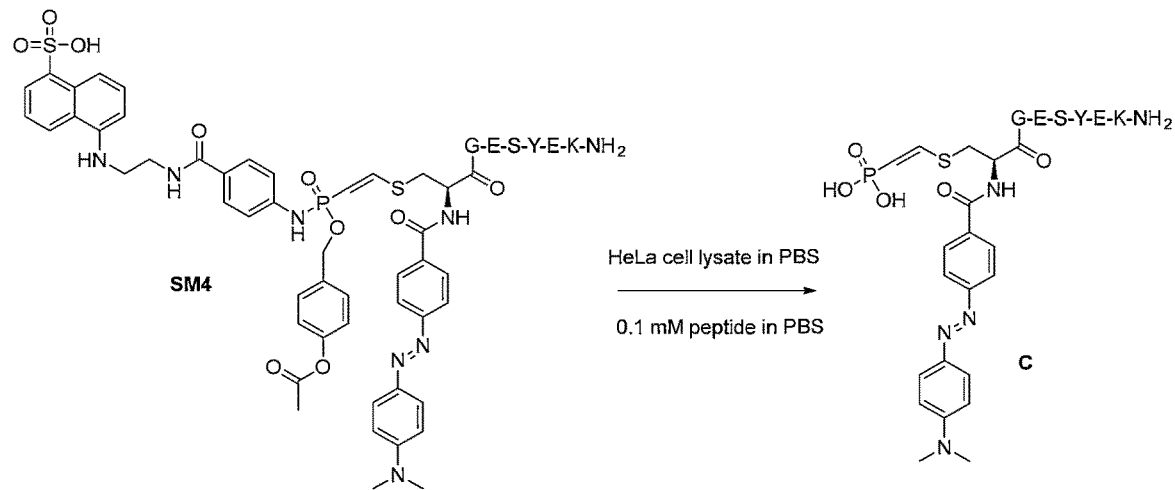

FIG. 49 shows the procedure for the cleavage of the ester-containing amidate-adducts with cell lysate.

Figure 50:
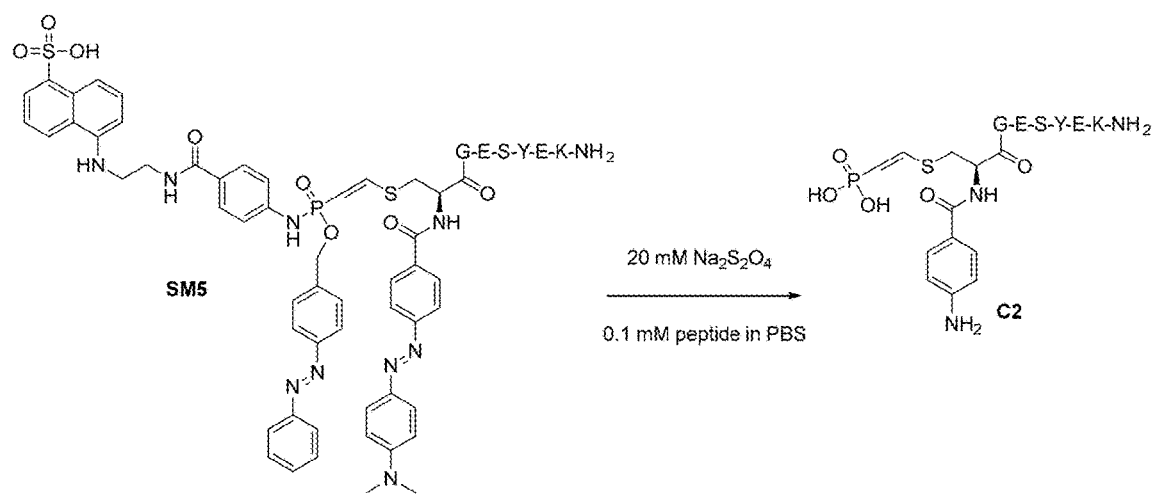

FIG. 50 shows the procedure for the diazo-containing amidate-adducts with sodium dithionite.

Figure 51:
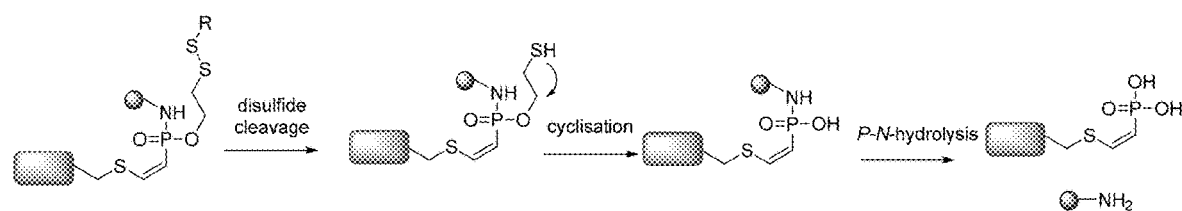

FIG. 51 shows the reductive cleavage and elimination mechanism.

Figure 52:
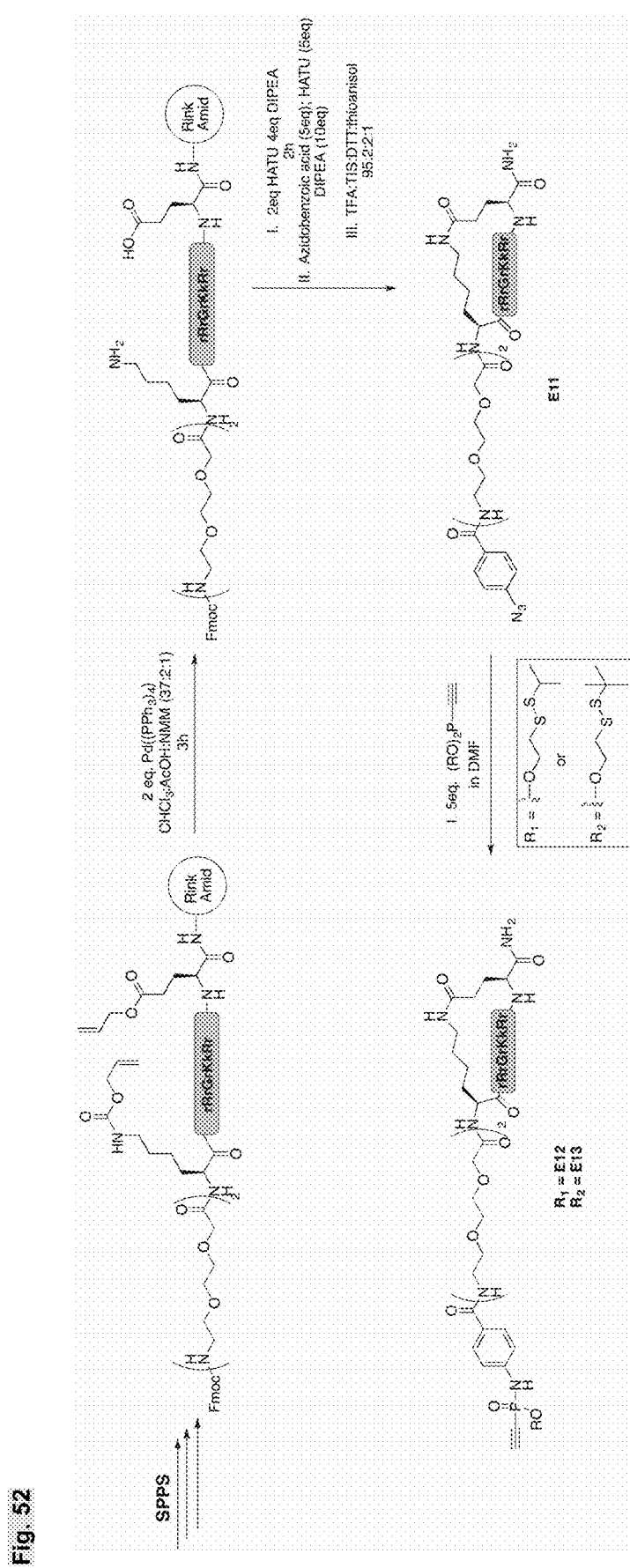

FIG. 52 shows the SPPS of alkyne functionalized cyclic Tat.

Figure 53:
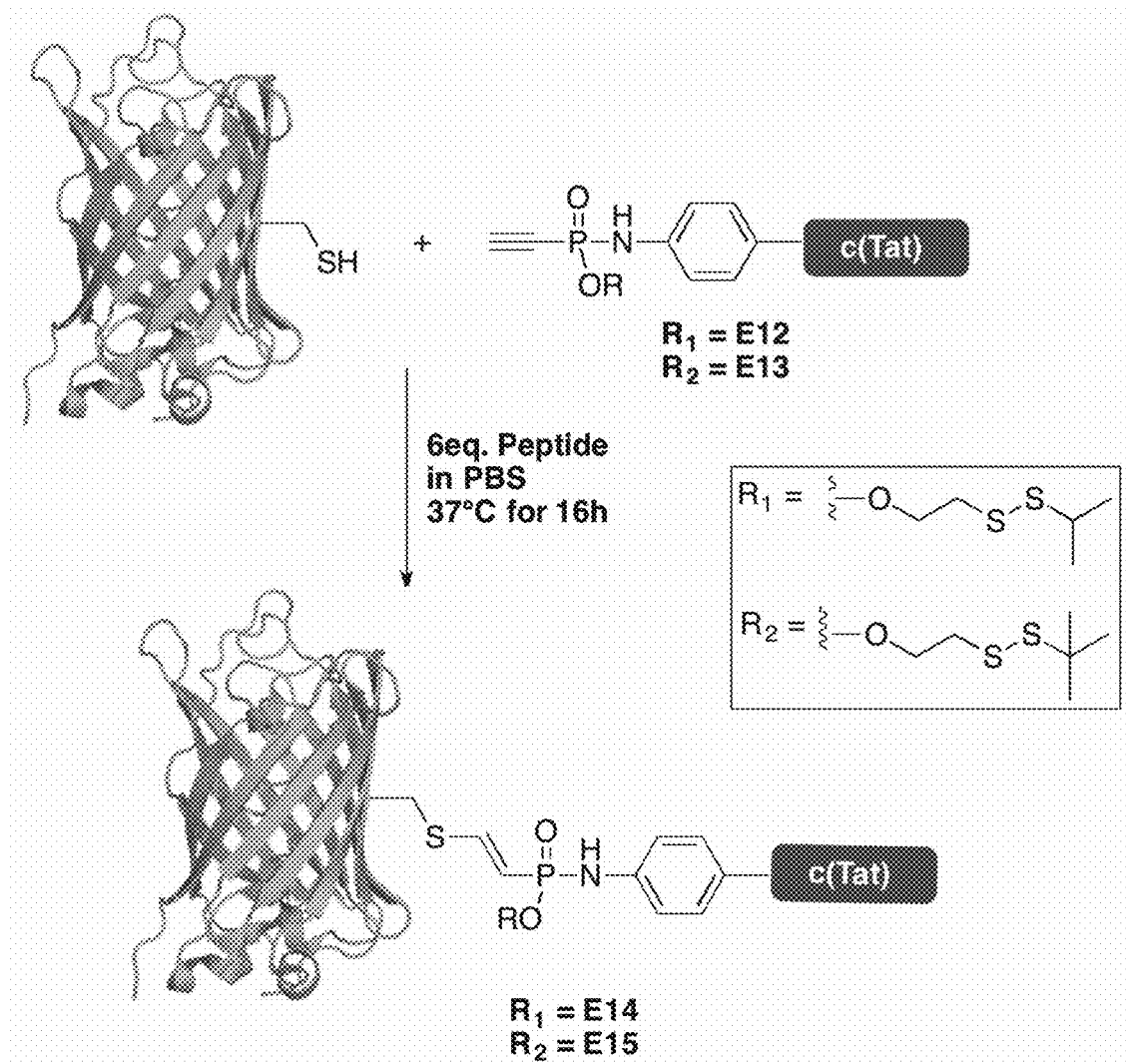

FIG. 53 shows the hydrothiolation reaction of an electron-deficient c(Tat)-phosphonamidate alkyne with GFP C70M S147C.

Figure 54:
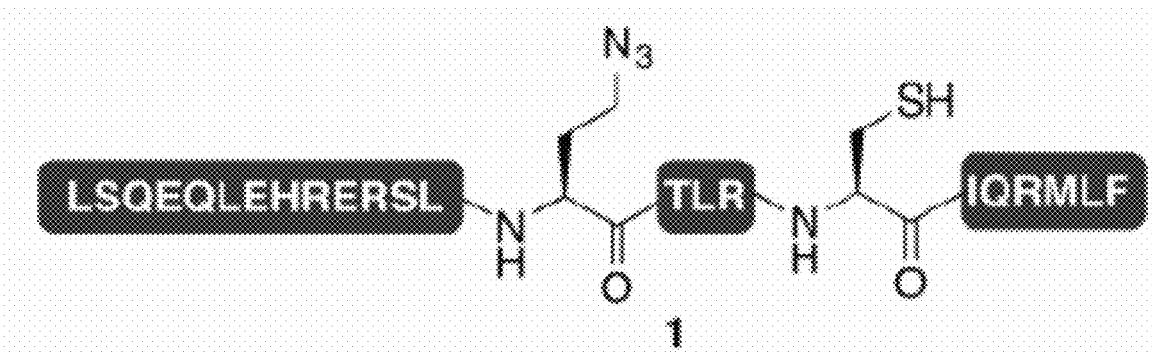

FIG. 54 shows the BCL9-azide.

Figure 55:
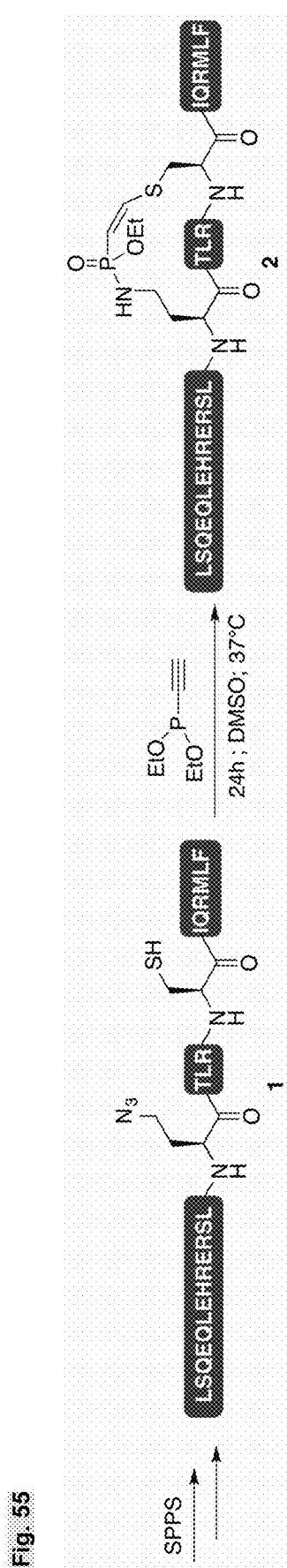

FIG. 55 shows the Staudinger Reaction on BCL9-azide with alkyne-phosphonamidate.

Figure 56:
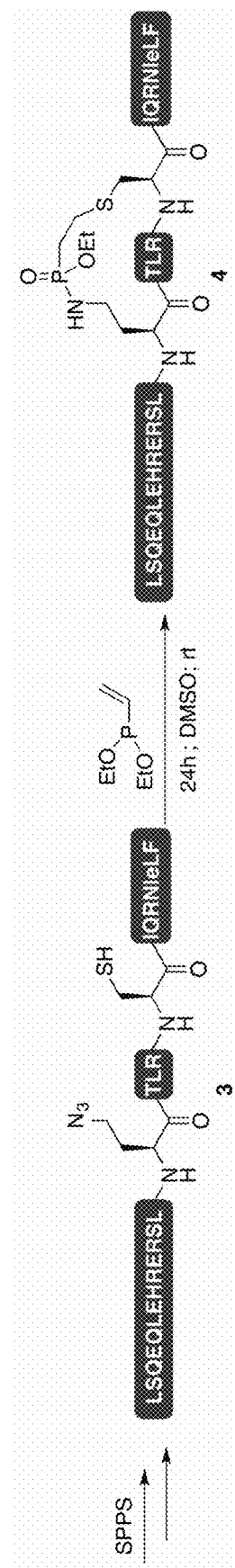

FIG. 56 shows the Staudinger Reaction on BCL9-azide with alkene-phosphonamidate.

DEFINITIONS

The person skilled in the art is aware that the terms "a" or "an", as used in the present application, may, depending on the situation, mean "one (1)" "one (1) or more" or "at least one (1)".

Halogen, unless defined otherwise: elements of the 7$^{th}$ main group, preferably fluorine, chlorine, bromine and iodine, more preferably fluorine, chlorine and bromine and, in combination with Mg even more preferably bromine.

alkyl, unless defined otherwise elsewhere: saturated straight-chain or branched hydrocarbon radicals having preferably $(C_1-C_8)$—, $(C_1-C_6)$- or $(C_1-C_4)$-carbon atoms. Examples: methyl, ethyl, propyl, 1-methylethyl, butyl, etc.

Alkenyl, unless defined otherwise elsewhere: unsaturated straight-chain or branched hydrocarbon radicals having a double bond. Alkenyl is preferably $(C_2-C_8)$—, $(C_2-C_6)$- or $(C_2-C_4)$-alkenyl. Examples: ethenyl, 1-propenyl, 3-butenyl, etc.

Alkynyl, unless defined otherwise elsewhere: unsaturated straight-chain or branched hydrocarbon radicals having a triple bond. Alkynyl is preferably $(C_2-C_8)$—, $(C_2-C_6)$- or $(C_2-C_4)$-alkynyl. Examples: ethynyl, 1-propynyl, etc.

Alkoxy (alkyl radical —O—), unless defined otherwise elsewhere: an alkyl radical which is attached via an oxygen atom (—O—) to the basic structure. Alkoxy is preferably $(C_1-C_8)$—, $(C_1-C_6)$- or $(C_1-C_4)$-alkoxy. Examples: methoxy, ethoxy, propoxy, 1-methylethoxy, etc.

Analogously, alkenoxy and alkynoxy, unless defined otherwise elsewhere, are alkenyl radicals and alkynyl radicals, respectively, which are attached via —O— to the basic structure. Alkenoxy is preferably $(C_2-C_8)$—, $(C_2-C_6)$- or $(C_2-C_4)$-alkenoxy. Alkynoxy is preferably $(C_3-C_{10})$—, $(C_3-C_6)$— or $(C_3-C_4)$-alkynoxy.

alkylcarbonyl (alkyl radical —C(=O)—), unless defined otherwise: alkylcarbonyl is preferably $(C_1-C_8)$—, $(C_1-C_6)$— or $(C_1-C_4)$-alkylcarbonyl. Here, the number of carbon atoms refers to the alkyl radical in the alkylcarbonyl group.

Analogously, alkenylcarbonyl and alkynylcarbonyl, are, unless defined otherwise elsewhere: alkenyl radicals and alkynyl radicals, respectively, which are attached via —C(=O)— to the basic structure. Alkenylcarbonyl is preferably $(C_2-C_8)$—, $(C_2-C_6)$- or $(C_2-C_4)$-alkenylcarbonyl. Alkynylcarbonyl is preferably $(C_2-C_8)$—, $(C_2-C_6)$- or $(C_2-C_4)$-alkynylcarbonyl.

Alkoxycarbonyl (alkyl radical —O—C(=O)—), unless defined otherwise elsewhere: alkoxycarbonyl is preferably $(C_1-C_8)$—, $(C_1-C_6)$- or $(C_1-C_4)$-alkoxycarbonyl. Here, the number of carbon atoms refers to the alkyl radical in the alkoxycarbonyl group.

Analogously, alkenoxycarbonyl and alkynoxycarbonyl, unless defined otherwise elsewhere, are: alkenyl radicals and alkynyl radicals, respectively, which are attached via —O—C(=O)— to the basic structure. Alkenoxycarbonyl is preferably $(C_2-C_8)$—, $(C_2-C_6)$- or $(C_2-C_4)$-alkenoxycarbonyl. Alkynoxycarbonyl is preferably $(C_3-C_8)$—, $(C_3-C_6)$- or $(C_3-C_4)$-alkynoxycarbonyl. alkylcarbonyloxy (alkyl radical —C(=O)—O—), unless defined otherwise elsewhere: an alkyl radical which is attached via a carbonyloxy group (—C(=O)—O—) by the oxygen to the basic structure. alkylcarbonyloxy is preferably $(C_1-C_8)$—, $(C_1-C_6)$— or $(C_1-C_4)$-alkylcarbonyloxy.

Analogously, alkenylcarbonyloxy and alkynylcarbonyloxy, unless defined otherwise elsewhere, are: alkenyl radicals and alkynyl radicals, respectively, which are attached via (—C(=O)—O—) to the basic structure. Alkenylcarbonyloxy is preferably $(C_2-C_8)$—, $(C_2-C_6)$— or $(C_2-C_4)$-alkenylcarbonyloxy. Alkynylcarbonyloxy is preferably $(C_2-C_8)$—, $(C_2-C_6)$— or $(C_2-C_4)$-alkynylcarbonyloxy.

alkylthio, unless defined otherwise elsewhere: an alkyl radical which is attached via —S— to the basic structure. alkylthio is preferably $(C_1-C_8)$—, $(C_1-C_6)$— or $(C_1-C_4)$-alkylthio.

Analogously, alkenylthio and alkynylthio, unless defined otherwise elsewhere, are: alkenyl radicals and alkynyl radicals, respectively, which are attached via —S— to the basic structure.

Alkenylthio is preferably $(C_2-C_8)$—, $(C_2-C_6)$— or $(C_2-C_4)$-alkenylthio. Alkynylthio is preferably $(C_3-C_8)$—, $(C_3-C_6)$— or $(C_3-C_4)$-alkynylthio.

The term "substituted" as used unless defined otherwise elsewhere, refers to a very broad substitution pattern. As can be seen from the disclosure of this invention, especially position $R_1$,  and  allow the substitution with numerous organic (macro)molecules. It is submitted that the structure of these molecules is not relevant for the presently disclosed process and the resulting conjugates. Thus, it would represent an undue limitation to limit the principle of this new and innovative concept to only some molecules. Nevertheless, it is submitted that the term refers to organic substituents or salts thereof, respectively, which may again be substituted several times by further organic substituents or salts thereof, respectively. Examples for such complex substituents were produced and are presented in this application (see, e.g. Schemes 5, 6, 7, 11, 13, 15, 19, 20, 21, 22, 23, and 24). Preferably, the term substituted refers to groups which are substituted with one or more substituents selected from nitro, cyano, Cl, F, Cl, Br, —NH—R, NR$_2$, COOH, —COOR, —OC(O)R—NH$_2$, —OH, —CONH$_2$CONHR, CON(R)$_2$, —S—R, —SH, —C(O)H, —C(O)R, (C$_1$-C$_{20}$)-alkyl, (C$_1$-C$_{20}$)-alkoxy, (C$_2$-C$_{20}$)-allyl, (hetero)cyclic rings of 3 to 8 ring-members wherein, if present, the heteroatom or atoms are independently selected from N, O and S, (hetero)aromatic systems with 5 to 12 ring atoms (e.g., phenyl, pyridyl, naphtyl etc.), wherein R again can represent any of these substituents and the substitution can be repeated several times, for example, substitution can be repeated for 1, 2, 3, 4, 5, 6, 7, 8, 9 or 10 times; see, e.g. the ● substituent in Scheme 11:

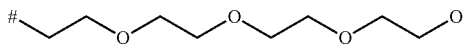

wherein #represents the position of N$_3$ or N if ● is already part of a compound of formula (VII). However, the skilled person will agree that an alkyl-chain which is substituted with a polysaccharide of 40 units cannot be simply described by general substitution pattern.

The terms "peptide" as used herein refers to an organic compound comprising two or more amino acids covalently joined by peptide bonds (amide bond). Peptides may be referred to with respect to the number of constituent amino acids, i.e., a dipeptide contains two amino acid residues, a tripeptide contains three, etc. Peptides containing ten or fewer amino acids may be referred to as oligopeptides, while those with more than ten amino acid residues are polypeptides. The amino acids can form at least one circle or a branched or unbranched chain or mixtures thereof. Proteins and antibodies are peptides and, thus, encompassed by the term, but may be named separately, due to their importance.

The term "amino acid" as used herein refers to an organic compound having a —CH(NH$_3$)—COOH group. In one embodiment, the term "amino acid" refers to a natural occurring amino acid arginine, lysine, aspartic acid, glutamic acid, glutamine, asparagine, histidine, serine, threonine, tyrosine, cysteine, methionine, tryptophan, alanine, isoleucine, leucine, phenylalanine, valine, proline and glycine. However, the term in its broader meaning also encompasses non-natural occurring amino acids.

Amino acids and peptides according to the invention can also be modified at functional groups. Non limiting examples are saccharides, e.g., N-Acetylgalactosamine (GalNAc), or protecting groups, e.g., Fluorenylmethoxycarbonyl (Fmoc)-modifications or esters.

The term "protein" refers to peptides which comprise one or more long chains of amino acid residues. Proteins perform a vast array of functions in vivo and in vitro including catalysing metabolic reactions, DNA replication, responding to stimuli, and transporting molecules, catalysing reactions. Proteins are folded into a specific three-dimensional structure. The residues in a protein are often chemically modified, e.g., by post-translational modification, which alters the physical and chemical properties, folding, stability, activity, and ultimately, the function of the proteins. Sometimes proteins have non-peptide groups attached, which can be called prosthetic groups or cofactors. Proteins, including enzymes and coenzymes, can also work together to achieve a particular function, and they often associate to form stable protein complexes. All these forms are encompassed by the term "protein".

The term "protein tags" as used herein refers to peptide sequences which can be attached to proteins or other thiol-comprising compounds via the linker according to the present invention for various purposes. Non limiting examples for protein tags are affinity tags, solubilization tags, chromatography tags epitope tags and reporter enzymes.

Affinity tags are appended to proteins and other thiol-comprising compounds via the linker according to the present invention so that they can be, e.g., purified using an affinity technique.

These include for example chitin binding protein (CBP), maltose binding protein (MBP), and glutathione-S-transferase (GST) or the poly(His) tag.

Solubilization tags can be used to assist in the proper folding in proteins and keep them from precipitating. These include thioredoxin (TRX) and poly(NANP). Some affinity tags have a dual role as a solubilization agent, such as MBP, and GST.

Chromatography tags are used to alter chromatographic properties of the protein to afford different resolution across a particular separation technique. Often, these consist of polyanionic amino acids, such as FLAG-tag.

Epitope tags are short peptide sequences which are chosen because high-affinity antibodies can be reliably produced in many different species. These are usually derived from viral genes. Epitope tags include V5-tag, Myc-tag, HA-tag and NE-tag. These tags are particularly useful for western blotting, immunofluorescence and immunoprecipitation experiments, and antibody purification.

The term "reporter enzymes" as used herein refer to any known enzyme which allows an increase of a signal in a biochemical detection. Non limiting examples are, colorant forming enzymes such as alkaline phosphatase (AP), horseradish peroxidase (HRP) or glucose oxidase (GOX); fluorescent proteins, such as green fluorescence protein (GFP), redox sensitive GFP (RoGFP), Azurite or Emerald; luciferase, i.e. a class of oxidative enzymes that produce bioluminescence (e.g. firefly luciferase (EC 1.13.12.7)); chloramphenicol acetyl transferase (CAT); β-galactosidase; or β-glucuronidase.

Non-limiting examples of protein tags are: AviTag, a peptide allowing biotinylation by the enzyme BirA and so the protein can be isolated by streptavidin (GLNDIFEAQK-IEWHE), Calmodulin-tag, a peptide bound by the protein calmodulin (KRRWKKNFIAVSAANRFKKISSSGAL), polyglutamate tag, a peptide binding efficiently to anion-exchange resin such as Mono-Q (EEEEEE), E-tag, a peptide recognized by an antibody (GAPVPYPDPLEPR), FLAG-tag, a peptide recognized by an antibody (DYKDDDDK), HA-tag, a peptide from hemagglutinin recognized by an antibody (YPYDVPDYA)His-tag, 5-10 histidines bound by a nickel or cobalt chelate (HHHHHH), Myc-tag, a peptide derived from c-myc recognized by an antibody (EQKLI-SEEDL), NE-tag, a novel 18-amino-acid synthetic peptide (TKENPRSNQEESYDDNES) recognized by a monoclonal IgG1 antibody, which is useful in a wide spectrum of applications including Western blotting, ELISA, flow cytometry, immunocytochemistry, immunoprecipitation, and affinity purification of recombinant proteins, S-tag, a peptide derived from Ribonuclease A (KETAAAKFER- QHMDS), SBP-tag, a peptide which binds to streptavidin (MDEKTTGWRGGHVVEGLAGELEQLRAR-LEHHPQGQREP), Softag 1, for mammalian expression (SLAELLNAGLGGS), Softag 3, for prokaryotic expression (TQDPSRVG), Strep-tag, a peptide which binds to streptavidin or the modified streptavidin called streptactin (Strep-tag II: WSHPQFEK), TC tag, a tetracysteine tag that is recognized by FlAsH and ReAsH biarsenical compounds (CCPGCC), V5 tag, a peptide recognized by an antibody (GKPIPNPLLGLDST), VSV-tag, a peptide recognized by an antibody (YTDIEMNRLGK), Xpress tag (DLYDDDDK), Isopeptag, a peptide which binds covalently to pilin-C protein (TDKDMTITFTNKKDAE), SpyTag, a peptide which binds covalently to SpyCatcher protein (AHIVMVDAYKPTK), SnoopTag, a peptide which binds covalently to SnoopCatcher protein (KLGDIEFIKVNK), BCCP (Biotin Carboxyl Carrier Protein), a protein domain biotinylated by BirA enabling recognition by streptavidin, Glutathione-S-transferase-tag, a protein which binds to immobilized glutathione, Green fluorescent protein-tag, a protein which is spontaneously fluorescent and can be bound by nanobodies, Halo-tag, a mutated hydrolase that covalently attaches to the HaloLink™ Resin (Promega), Maltose binding protein-tag, a protein which binds to amylose agarose, Nus-tag, Thioredoxin-tag, Fc-tag, derived from immunoglobulin Fc domain, allow dimerization and solubilization. Can be used for purification on Protein-A Sepharose, Designed Intrinsically Disordered tags containing disorder promoting amino acids (P,E,S,T,A,Q,G, . . . ), alkaline phosphatase (AP), horseradish peroxidase (HRP) glucose oxidase (GOX), green fluorescent protein (GFP), redox sensitive GFP (RoGFP), Azurite, Emerald, firefly luciferase (EC 1.13.12.7)), chloramphenicol acetyl transferase (CAT), β-galactosidase, β-glucuronidase, tubulin-tyrosine ligase (TTL).

The term "antibody", as used herein, is intended to refer to immunoglobulin molecules, preferably comprised of four polypeptide chains, two heavy (H) chains and two light (L) chains which are typically inter-connected by disulfide bonds. Each heavy chain is comprised of a heavy chain variable region (abbreviated herein as VH) and a heavy chain constant region. The heavy chain constant region can comprise e.g. three domains CH1, CH2 and CH3. Each light chain is comprised of a light chain variable region (abbreviated herein as VL) and a light chain constant region. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and up to four FRs arranged from amino-terminus to carboxy-terminus e.g. in the following order: FR1, CDR1, FR2, CDR2, FR3, CDR3, FR4.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (e.g. about residues 24-34 (L1), 50-56 (L2) and 89-97 (L3) in the light chain variable domain and 31-35 (H1), 50-65 (H2) and 95-102 (H3) in the heavy chain variable domain; and/or those residues from a "hypervariable loop" (e.g. about residues 26-32 (L1), 50-52 (L2) and 91-96 (L3) in the light chain variable domain and 26-32 (H1), 53-55 (H2) and 96-101 (H3) in the heavy chain variable domain). In some instances, a complementarity determining region can include amino acids from both a CDR region defined according to Kabat and a hypervariable loop.

Depending on the amino acid sequence of the constant domain of their heavy chains, intact antibodies can be assigned to different "classes". There are five major classes of intact antibodies: IgA, IgD, IgE, IgG, and IgM, and several of these maybe further divided into "subclasses" (isotypes), e.g., IgG1, IgG2, IgG3, IgG4, IgA1, and IgA2. A preferred class of immunoglobulins for use in the present invention is IgG.

The heavy-chain constant domains that correspond to the different classes of antibodies are called [alpha], [delta], [epsilon], [gamma], and [mu], respectively. The subunit structures and three-dimensional configurations of different classes of immunoglobulins are well known. As used herein antibodies are conventionally known antibodies and functional fragments thereof.

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hyper variable region(s) of an antibody, e.g., the CDR1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320).

"Functional fragments", "antigen-binding antibody fragments", or "antibody fragments" of the invention include but are not limited to Fab, Fab', Fab'-SH, F(ab')$_2$, and Fv fragments; diabodies; single domain antibodies (DAbs), linear antibodies; single-chain antibody molecules (scFv); and multispecific, such as bi- and tri-specific, antibodies formed from antibody fragments. An antibody other than a "multi-specific" or "multi-functional" antibody is understood to have each of its binding sites identical. The F(ab')$_2$ or Fab may be engineered to minimize or completely remove the intermolecular disulfide interactions that occur between the CH1 and CL domains.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index.

Variants of the antibodies or antigen-binding antibody fragments contemplated in the invention are molecules in which the binding activity of the antibody or antigen-binding antibody fragment is maintained.

"Binding proteins" contemplated in the invention are for example antibody mimetics, such as Affibodies, Adnectins, Anticalins, DARPins, Avimers, Nanobodies.

A "human" antibody or antigen-binding fragment thereof is hereby defined as one that is not chimeric (e.g., not "humanized") and not from (either in whole or in part) a non-human species. A human antibody or antigen-binding fragment thereof can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained there from. Another example of a human antibody or antigen-binding fragment thereof is one that is encoded by a nucleic acid isolated from a library of antibody sequences of human origin (e.g., such library being based on antibodies taken from a human natural source).

A "humanized antibody" or humanized antigen-binding fragment thereof is defined herein as one that is (i) derived from a non-human source (e.g., a transgenic mouse which bears a heterologous immune system), which antibody is based on a human germline sequence; (ii) where amino acids of the framework regions of a non-human antibody are partially exchanged to human amino acid sequences by genetic engineering or (iii) CDR-grafted, wherein the CDRs of the variable domain are from a non-human origin, while one or more frameworks of the variable domain are of human origin and the constant domain (if any) is of human origin.

A "chimeric antibody" or antigen-binding fragment thereof is defined herein as one, wherein the variable domains are derived from a non-human origin and some or all constant domains are derived from a human origin.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. The term monoclonal antibody specifically includes chimeric, humanized and human antibodies.

An "isolated" antibody is one that has been identified and separated from a component of the cell that expressed it. Contaminant components of the cell are materials that would interfere with diagnostic or therapeutic uses of the antibody, and may include enzymes, hormones, and other proteinaceous or nonproteinaceous solutes.

As used herein, an antibody "binds specifically to", is "specific to/for" or "specifically recognizes" an antigen of interest, e.g. a tumor-associated polypeptide antigen target, is one that binds the antigen with sufficient affinity such that the antibody is useful as a therapeutic agent in targeting a cell or tissue expressing the antigen, and does not significantly cross-react with other proteins or does not significantly cross-react with proteins other than orthologs and variants (e.g. mutant forms, splice variants, or proteolytically truncated forms) of the aforementioned antigen target. The term "specifically recognizes" or "binds specifically to" or is "specific to/for" a particular polypeptide or an epitope on a particular polypeptide target as used herein can be exhibited, for example, by an antibody, or antigen-binding fragment thereof, having a monovalent $K_D$ for the antigen of less than about $10^{-4}$ M, alternatively less than about $10^{-5}$ M, alternatively less than about $10^{-6}$ M, alternatively less than about $10^{-7}$ M, alternatively less than about $10^{-8}$ M, alternatively less than about $10^{-9}$ M, alternatively less than about $10^{-10}$ M, alternatively less than about $10^{-11}$ M, alternatively less than about $10^{-12}$ M, or less. An antibody "binds specifically to," is "specific to/for" or "specifically recognizes" an antigen if such antibody is able to discriminate between such antigen and one or more reference antigen(s). In its most general form, "specific binding", "binds specifically to", is "specific to/for" or "specifically recognizes" is referring to the ability of the antibody to discriminate between the antigen of interest and an unrelated antigen, as determined, for example, in accordance with one of the following methods. Such methods comprise, but are not limited to surface plasmon resonance (SPR), Western blots, ELISA-, RIA-, ECL-, IRMA-tests and peptide scans. For example, a standard ELISA assay can be carried out. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative is more than 5-fold, 10-fold, 50-fold, and preferably more than 100-fold. Typically, determination of binding specificity is performed by using not a single reference antigen, but a set of about three to five unrelated antigens, such as milk powder, BSA, transferrin or the like.

"Binding affinity" or "affinity" refers to the strength of the total sum of non-covalent interactions between a single binding site of a molecule and its binding partner. Unless indicated otherwise, as used herein, "binding affinity" refers to intrinsic binding affinity which reflects a 1:1 interaction between members of a binding pair (e.g. an antibody and an antigen). The dissociation constant "$K_D$" is commonly used to describe the affinity between a molecule (such as an antibody) and its binding partner (such as an antigen) i.e. how tightly a ligand binds to a particular protein. Ligand-protein affinities are influenced by non-covalent intermolecular interactions between the two molecules. Affinity can be measured by common methods known in the art, including those described herein. In one embodiment, the "$K_D$" or "$K_D$ value" according to this invention is measured by using surface plasmon resonance assays using suitable devices including but not limited to Biacore instruments like Biacore T100, Biacore T200, Biacore 2000, Biacore 4000, a Biacore 3000 (GE Healthcare Biacore, Inc.), or a ProteOn XPR36 instrument (Bio-Rad Laboratories, Inc.).

The terms "nucleoside" and "nucleoside moiety" as use herein reference a nucleic acid subunit including a sugar group and a heterocyclic base, as well as analogs of such sub-units, such as a modified or naturally occurring deoxyribonucleoside or ribonucleoside or any chemical modifications thereof. Other groups (e.g., protecting groups) can be attached to any component(s) of a nucleoside. Modifications of the nucleosides include, but are not limited to, 2'-, 3'- and 5'-position sugar modifications, 5- and 6-position pyrimidine modifications, 2-, 6- and 8-position purine modifications, modifications at exocyclic amines, substitution of 5-bromo-uracil, and the like. Nucleosides can be suitably protected and derivatized to enable oligonucleotide synthesis by methods known in the field, such as solid phase automated synthesis using nucleoside phosphoramidite monomers, H-phosphonate coupling or phosphate triester coupling.

A "nucleotide" or "nucleotide moiety" refers to a sub-unit of a nucleic acid which includes a phosphate group, a sugar group and a heterocyclic base, as well as analogs of such sub-units. Other groups (e.g., protecting groups) can be attached to any component(s) of a nucleotide. The term "nucleotide", may refer to a modified or naturally occurring deoxyribonucleotide or ribonucleotide. Nucleotides in some cases include purines and pyrimidines, which include thymidine, cytidine, guanosine, adenine and uridine. The term "nucleotide" is intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, dimethylacetamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The term "oligonucleotide", as used herein, refers to a polynucleotide formed from a plurality of linked nucleotide units as defined above. The nucleotide units each include a nucleoside unit linked together via a phosphate linking group, or an analog thereof. The term oligonucleotide also refers to a plurality of nucleotides that are linked together via linkages other than phosphate linkages such as phosphorothioate linkages or squaramide linkages. The oligonucleotide may be naturally occurring or non-naturally occurring. In some cases, the oligonucleotides may include ribonucleotide monomers (i.e., may be oligoribonucleotides) and/or deoxyribonucleotide monomers.

The term "monosaccharide" as use herein refers to an open chained or cyclic compound of general formula $C_m(H_2O)_n$ wherein m is 3, 4, 5, 6, 7 or 8 and n is 2, 3, 4, 5 6, 7 or 8. However, the term also encompasses derivatives of these basic compounds wherein a OH group is replaced by an $NH_2$ group (such as glucosamine), desoxysaccharides, wherein at least one OH group is replaced by H (e.g. desoxiribose). Preferred examples for monosaccharides are D-(+)-Glycerolaldehyde; D-(−)-Erythrose; D-(−)-Threose; D-(−)-Ribose; D-(−)-Arabinose; D-(+)-Xylose; D-(−)-Lyxose; D-(+)-Allose; D-(+)-Altrose; D-(+)-Glucose; D-(+)-Mannose; D-(−)-Gulose; D-(−)-Idose; D-(+)-Galactose; D-(+)-Talose; Dihydroxyacetone;

D-Erythrulose; D-Ribulose; D-Xylulose; D-Psicose; D-Fructose; D-Sorbose; D-Tagatose. The term monosaccharide also encompasses monosaccharides which one, two, three or four hydroxyl-groups are substituted.

The term "polysaccharides" refers to molecules comprising at least 2 (two), preferably at least 5 (five), more preferably at least 10 (ten) monosaccharides which are connected via a glycosidic bond.

A carbohydrate as used herein encompasses a monosaccharide and a polysaccharide and derivatives thereof.

A polymer as used herein refers to macromolecules composed of many repeated organic subunits, however, which are no polysaccharides, oligonucleotides or peptides. Examples for polymers are Polyethylenglycole (PEG), polyoxyethylene (PEO) or polyglycerol (e.g. polyglycerolpolyricinoleate (PGPR).

The term "fluorophore" is well-known to the skilled person and refers to chemical compounds that re-emit light upon light excitation. Non limiting examples are $CY_5$, EDANS, Xanthene derivatives (e.g. fluorescein, Rhodamine, Oregon green, eosin, Texas red), Cyanine derivatives (e.g., indocarbocyanine, oxacarbocyanine, merocyanine), Squaraine derivatives (e.g., Seta, Se Tau, Square dyes), Naphthalene derivatives (e.g., dansyl or prodan derivatives), Coumarin derivatives, Oxadiazole derivatives, Anthracene derivatives (e.g., Anthraquinones such as DRAQ5, DRAQ7, CyTRAK Orange), Pyrene derivatives (e.g., cascade blue), Oxazine derivatives (e.g., Nile red, Nile blue, Cresyl violet), Acridine derivatives (e.g., Proflavin, Acridine Orange, Acridine Yellow), Arylmethine derivatives (e.g., Auramine, Crystal Violet, Malachite Green), or Tetrapyrrole derivatives (e.g., Parphin, Phthal ocyanine, Bilirubin).

The term "aliphatic or aromatic residue" as used herein refers to an aliphatic substituent, e.g. an alkyl residue which, however, can be substituted by further aliphatic and/or aromatic substituents, e.g. an aliphatic residue can be a nucleic acid, a peptide, a protein, an enzyme, a co-enzyme, an antibody, a nucleotide, an oligonucleotide, a monosaccharide, a polysaccharide, a polymer, a fluorophore, optionally substituted benzene, etc. as long as the direct link of such a molecule to the core structure (in case of $R_1$, e.g., to the respective oxygen of a compound of formula (III) or (V)) is aliphatic. An aromatic residue is a substitute, which direct link to the core structure is part of an aromatic system, e.g., an optionally substituted phenyl or pyridyl or peptide, if the direct link of the peptide to the core structure is for example via a phenyl-residue.

The term "antibody drug conjugate" or abbreviated ADC is well known to a person skilled in the art, and, as used herein, refers to the linkage of an antibody or an antigen binding fragment thereof with a drug, such as a chemotherapeutic agent, a toxin, an immunotherapeutic agent, an imaging probe, and the like. As used herein, a "linker" is any chemical moiety that links an antibody or an antigen binding fragment thereof covalently to the drug. As used herein, the term "linker drug conjugate" refers to a molecule or chemical group comprising or consisting of a linker as defined herein before, and a drug. In this regard, the term "linker drug conjugate" in general refers to that part of an antibody drug conjugate which is not the antibody or an antigen binding fragment thereof. In general, in a linker drug conjugate the linker is covalently linked to the drug.

Also described herein are "antibody fluorophore conjugates" or abbreviated AFC, which refers to the linkage of an antibody or an antigen binding fragment thereof with a fluorophore, such as, for example, Cy5. The fluorophore may be linked to the antibody or antigen-binding fragment thereof through a linker, for example a linker as described above in the context of an antibody drug conjugate. The antibody fluorophore conjugate may comprise a "linker fluorophore conjugate". As used herein, the term "linker fluorophore conjugate" refers to a molecule or chemical group comprising or consisting of a linker as defined herein before, and a fluorophore. In this regard, the term "linker fluorophore conjugate" in general refers to that part of an antibody drug conjugate which is not the antibody or an antigen binding fragment thereof. In general, in a linker fluorophore conjugate the linker is covalently linked to the fluorophore.

DETAILED DESCRIPTION

The invention provides a new chemoselective reaction of Cys residues in (unprotected) peptides, proteins, such as enzymes and co-enzymes (e.g. coenzyme A), antibodies or other thiol-comprising compounds with alkene- or alkyne-phosphonamidates. In one embodiment, the peptides, proteins, antibodies or other thiol-comprising compounds are unprotected. In another embodiment, the alkene- or alkyne-phosphonamidates are electron deficient alkene- or alkyne-phosphonamidates. The resulting conjugates have not been described in the literature previously.

Scheme 1, which is depicted in FIG. 36, describes the general strategy for a synthesis according to the present invention at the example of ethenyl or ethynyl phosphonites. R1 represents an optionally substituted aliphatic or aromatic residue.

Scheme 2, which is depicted in FIG. 37, shows the difference between a process known in the art (e.g., 15) and a process according to the present invention A) Sequential azide-azide couplings using alkyne phosphonites; B) Staudinger-induced thiol-addition (the thiol addition may be also denoted as "Michael addition", as e.g. in FIG. 37B) for the modification of Cys residues according to the invention. Merely as examples, ethenyl and ethynyl (diethyl)phosphonite were used.

It is submitted that the processes described herein allow to combine a huge amount of different organic compounds in position $R_1$  and .

Furthermore, the invention refers to a method for bioconjugation of two complex molecules: a chemoselective reaction, which induces a second chemoselective reaction for the conjugation to proteins. This concept is based on the unique reactivity of an azide-building block with an unprotected alkyne or alkene phosphonite via the Staudinger-phosphonite reaction (SPhR) resulting in the generation of a, preferably, electron-deficient double or triple bond (Scheme 1 and 2B). The resulting electrophilic system can subsequently be employed for the reaction with thiol-containing proteins and antibodies or further thiol-comprising compounds to deliver functional conjugates such as antibody or protein conjugates.

It is demonstrated with the attached results:
The synthesis of different alkene and alkyne phosphonites
(Chemoselective) Staudinger reactions with alkene and alkyne phosphonites
Conjugation reactions of alkene- or alkyne-phosphonamidates with thiol-containing molecules, including small molecules, peptides, proteins and antibodies
Thiol addition to alkyne-phosphonamidates in aqueous systems showed a high diastereoselectivity for the formation of the Z-Product
Stability of these conjugates under physiologically relevant conditions
Synthesis of conjugates comprising a cleavable group
This invention features several innovative aspects, which further ease the accessibility of conjugates such as antibody or protein conjugates, in particular with complex payloads and labels containing several functional groups, with novel conjugation chemistry:
A new reaction for modifying thiols in small molecules, polymers, proteins and antibodies, therefore
Unprecedented chemical structure at Cys-moiety
Two complex molecule (e.g. peptide and proteins or peptide and antibody) can be connected by straightforward step-wise chemoselective conjugations
No need of final protecting group manipulations after installation of chemoselective handle (i.e., preferably electron-deficient, alkene or alkyne-phosphonamidate) or after the chemoselective conjugation
Linker with great variability (P-substituents can be varied, various O-substituents at the phosphorus center, O-substituents comprising a cleavable group)
High stability of conjugates as opposed to usual Maleimide reagents; fast conjugation reactions
High stereoselectivity of the thiol addition to alkyne-phosphonamidates Generally, the process according to the present invention can be carried out to conjugate different compounds such as small molecules (e.g. optionally substituted alkyl, phenyl or heterocycles), proteins, antibodies, oligonucleotides or polysaccharides with tags, proteins oligonucleotides etc. To achieve this coupling, the present invention refers in a first aspect to a process for the preparation of conjugates of formula (VII) comprising the steps of
(I) Reacting a compound of formula (III)

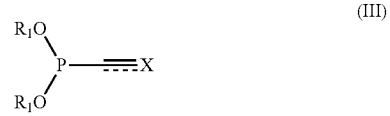

(III)

wherein

 represents a double or triple bond;

X represents $R_3$—C when  is a triple bond (thus, the structure is

);

X represents $(R_3R_4)C$ when 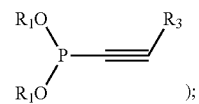 is a double bond (thus, the structure is

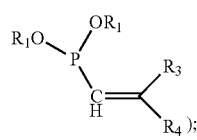

$R_1$ independently represents an optionally substituted aliphatic or aromatic residue, such as phenyl; with $(C_1\text{-}C_8\text{-alkoxy})_n$, wherein n is 1, 2, 3, 4, 5 or 6 with F, with Cl, with Br, with I, with —$NO_2$, with —$N(C_1\text{-}C_8\text{-alkyl})H$, with —$NH_2$, with —$N(C_1\text{-}C_8\text{-alkyl})_2$, with =O, with $C_3\text{-}C_8$-cycloalkyl, with optionally substituted phenyl substituted $C_1\text{-}C_8$-alkyl such as

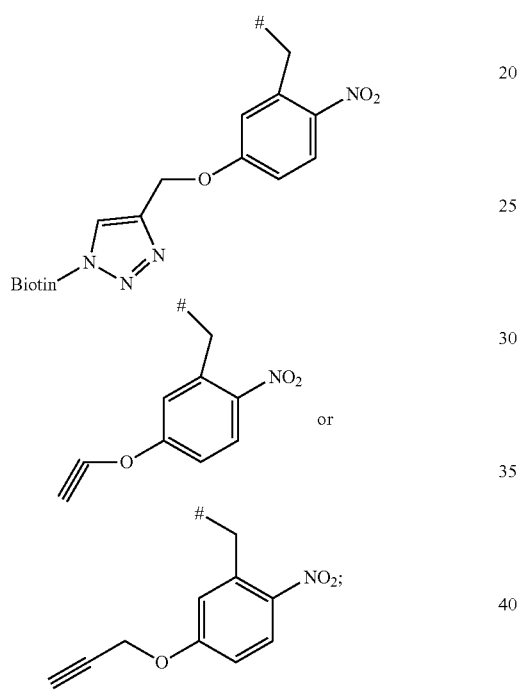

or optionally independently with $C_1\text{-}C_8$-alkyl, $(C_1\text{-}C_8\text{-alkoxy})_n$, F, Cl, I, Br, —$NO_2$, —$N(C_1\text{-}C_8\text{-alkyl})H$, —$NH_2$, —$N(C_1\text{-}C_8\text{-alkyl})_2$, substituted phenyl; or 5- or 6-membered heteroaromatic system such as pyridyl; preferably $C_1\text{-}C_8$-alkyl, $C_1\text{-}C_8$-alkyl substituted with $(C_1\text{-}C_8\text{-alkoxy})_n$, phenyl or phenyl substituted with —$NO_2$;

or
which may be again substituted at one of the Nitrogen-ring-atoms with biotin or any other peptide, protein, such as an enzyme or co-enzyme (e.g. coenzyme A), antibody, protein tag, fluorophore, oligonucleotide, or polysaccharide and wherein #represents the position of O;

$R_3$ represents H or $C_1\text{-}C_8$-alkyl;
$R_4$ represents H or $C_1\text{-}C_8$-alkyl; and
with an azide of formula (IV)

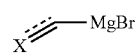 (IV)

wherein
● represents an aliphatic or aromatic residue;
to prepare a compound of formula (V)

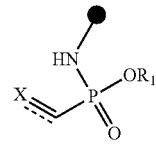 (V)

wherein ●, ⫽, $R_1$, and X are as defined above.
(II) Reacting a compound of formula (V) with a thiol-containing molecule of formula (VI)

 (VI)

wherein ▬ represents an optionally substituted $C_1\text{-}C_8$-alkyl, an optionally substituted Phenyl, an optionally substituted aromatic 5- or 6-membered heterocyclic system, an amino acid, a peptide, a protein, an antibody, a saccharide, a polysaccharide, a nucleotide, a oligonucleotide or a polymer;
resulting in a compound of formula (VII)

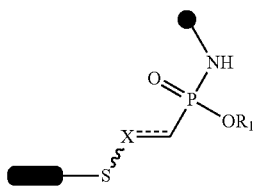 (VII)

wherein
⫽ represents a bond if ⫽ in a compound of formula (V) represents a double bond; or
⫽ represents a double bond if ⫽ in a compound of formula (V) represents a triple bond; and
▬, ●, $R_1$ and X are as defined above.

The invention also refers to a process comprising a step (a) prior to step (1) of the process described above. Thus, such a process comprises the steps of
a) Reacting a compound of formula (I)

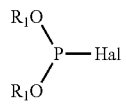 (I)

wherein $R_1$ and Hal are defined as above;
with an alpha unsaturated compound of formula (II) comprising a double or triple bond in alpha-position

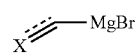 (II)

wherein

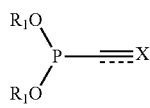 represents a double or triple bond;

X represents R₃—C when 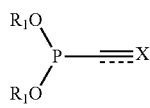 is a triple bond; or

X represents (R₃R₄)C when 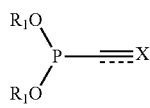 is a double bond;

$R_3$ represents H or $C_1$-$C_8$-alkyl; and $R_4$ represents H or $C_1$-$C_8$-alkyl;

to form a compound of formula (III)

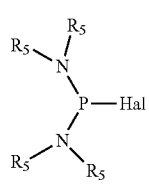

(III)

wherein

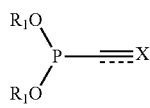, X and $R_1$ are as defined above;

alternatively, reacting a compound of formula (I')

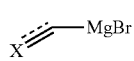

(I')

wherein $R_5$ independently represents $C_1$-$C_8$-alkyl;

Hal represents a halogen selected from the group consisting of Cl, Br, I, preferably Cl;

with an alpha unsaturated compound of formula (II) comprising a double or triple bond in alpha-position

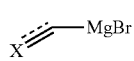

(II)

wherein

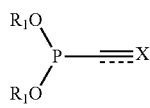 represents a double or triple bond;

X represents R₃—C when 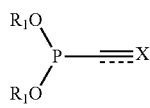 is a triple bond or

X represents (R₃R₄)C when 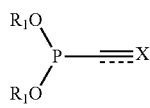 is a double bond;

$R_3$ represents H or $C_1$-$C_8$-alkyl; and $R_4$ represents H or $C_1$-$C_8$-alkyl;

to form a compound of formula (III')

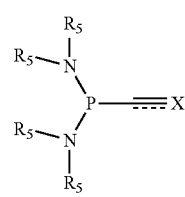

(III')

and reacting said compound of formula (III') with $R_1$—OH to form a compound of formula (III)

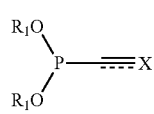

(III)

wherein

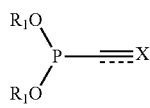 and X are defined as above and $R_1$ is as defined above but not individually selected;

(I) Reacting a compound of formula (III) with an azide of formula (IV)

(IV)

wherein

● represents an aliphatic or aromatic residue;

to prepare a compound of formula (V)

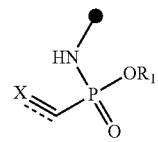

(V)

wherein

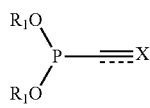, $R_1$ and X are as defined above;

(II) Reacting a compound of formula (V) with a thiol-containing molecule of formula (VI)

(VI)

wherein ■ represents an optionally substituted $C_1$-$C_8$-alkyl, an optionally substituted Phenyl, an optionally substituted aromatic 5- or 6-membered heterocyclic system, an amino acid, a peptide, a protein, an antibody, a saccharide, a polysaccharide, a nucleotide, a oligonucleotide or a polymer;

resulting in a compound of formula (VII)

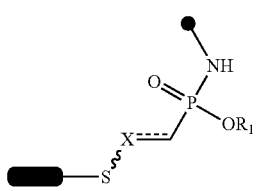

(VII)

wherein

// represents a bond if 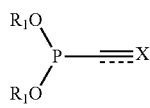 in a compound of formula (V) represents a double bond; or // represents a double bond if 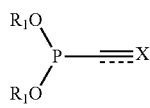 in a compound of formula (V) represents a triple bond; and ■, ●, $R_1$ and X are as defined above.

Preferably, in this process 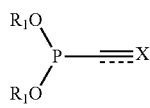 represents a triple bond.

In one embodiment, the P-atom of compounds of formula (III), preferably wherein ⌿ represents a double bond, can be protected by $BH_3$ prior to the Staudinger reaction (e.g. for purification purposes) and can easily be deprotected before the Staudinger reaction:

b) reacting a compound of formula (III)
to form a compound of formula (III)

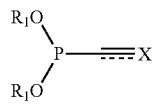
(III)

wherein X and R, are as defined above;
with $BH_3$ to form a compound of formula (III')

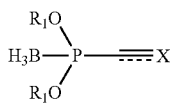
(III')

wherein X and R, are as defined above.

Deprotection of boran protected phosphonites of formula (III') to form the reactive P(III) species can be easily achieved by the addition of a weak base such as DABCO (1,4-Diazabicyclo[2.2.2]octan=Triethylendiamin (TEDA)).

Compounds of formula (III) can also be synthesized starting from $PCl_3$:

wherein $R_1$ is as defined herein.

The processes described herein can also be carried out with a compound of formula (III*) instead of a compound (III)

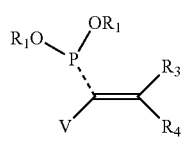
(III*)

Wherein V represents $C_1$-$C_8$-alkyl, preferably methyl, ethyl or propyl, more preferably methyl; and $R_1$, $R_2$ and $R_3$ are as defined for compound (III) above. For the preparation of compounds of formula (III*), compounds of formula (II*) can be used

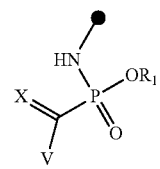
(II*)

wherein V, $R_3$ and $R_4$ are defined herein.

A process according to the invention with compound (III*) results in compounds of formula (V*)

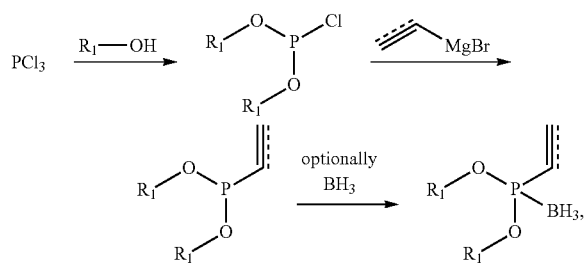
(V*)

wherein V represents $C_1$-$C_8$-alkyl, preferably methyl, ethyl or propyl, more preferably methyl; ● and $R_1$ are as defined for compound (V);
and compounds of formula (VII*)

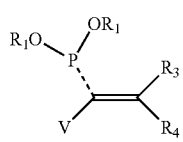
(VII*)

wherein V represents $C_1$-$C_8$-alkyl, preferably methyl, ethyl or propyl, more preferably methyl; ●, ⬛ and $R_1$ are as defined for compound (VII). All steps for the processes described herein for compounds of formula (V) and (VII) can be performed analogously for compounds of formula (V*) and (VII*).

Accordingly, the present invention also relates to a process for the preparation of alkene-phosphonamidates comprising the steps of:
(I) Reacting a compound of formula (III)

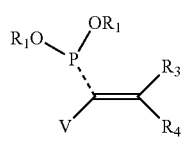
(III*)

wherein
V represents $C_1$-$C_8$-alkyl, preferably methyl, ethyl or propyl, more preferably methyl;
$R_1$ independently represents an optionally substituted aliphatic or aromatic residue, such as phenyl; with $(C_1$-$C_8$-alkoxy$)_n$, wherein n is 1, 2, 3, 4, 5 or 6, with F, with Cl, with Br, with I, with —$NO_2$, with —N($C_1$-$C_8$-alkyl)H, with —$NH_2$, with —N($C_1$-$C_8$-alkyl)$_2$, with =O, with $C_3$-$C_8$-cycloalkyl, with optionally substituted phenyl substituted $C_1$-$C_8$-alkyl such as

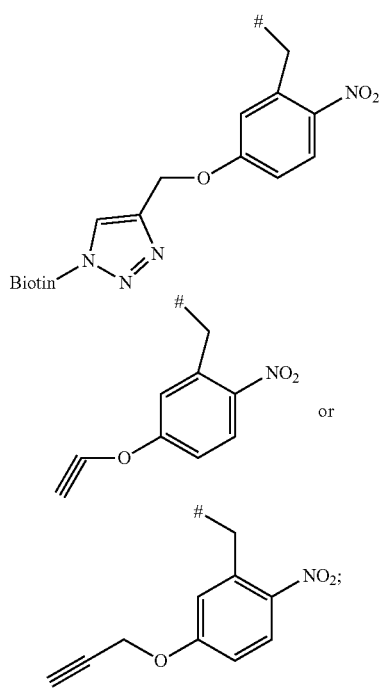

or optionally independently with $C_1$-$C_8$-alkyl, $(C_1$-$C_8$-alkoxy$)_n$, F, Cl, I, Br, —$NO_2$, —$N(C_1$-$C_8$-alkyl)H, —$NH_2$, —$N(C_1$-$C_8$-alkyl$)_2$, substituted phenyl; or 5- or 6-membered heteroaromatic system such as pyridyl; preferably $C_1$-$C_8$-alkyl, $C_1$-$C_8$-alkyl substituted with $(C_1$-$C_8$-alkoxy$)_n$, phenyl or phenyl substituted with —$NO_2$;

or which may be again substituted at one of the Nitrogen-ring-atoms with biotin or any other peptide, protein, such as an enzyme or co-enzyme (e.g. coenzyme A), antibody, protein tag, fluorophore, oligonucleotide, or polysaccharide and wherein #represents the position of O;

$R_3$ represents H or $C_1$-$C_8$-alkyl;
$R_4$ represents H or $C_1$-$C_8$-alkyl; and
with an azide of formula (IV)

 (IV)

wherein
● represents an aliphatic or aromatic residue;
to prepare a compound of formula (V*)

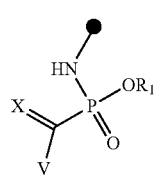 (V*)

Wherein ●, V, and $R_1$ are as defined above;
X is $(R_3R_4)C$; and
$R_3$ and $R_4$ are as defined above;

(II) Reacting a compound of formula (V*) with a thiol-containing molecule of formula (VI)

 (VI)

wherein ● represents an optionally substituted $C_1$-$C_8$-alkyl, an optionally substituted Phenyl, an optionally substituted aromatic 5- or 6-membered heterocyclic system, an amino acid, a peptide, a protein, an antibody, a saccharide, a polysaccharide, a nucleotide, a oligonucleotide or a polymer;

resulting in a compound of formula (VII*)

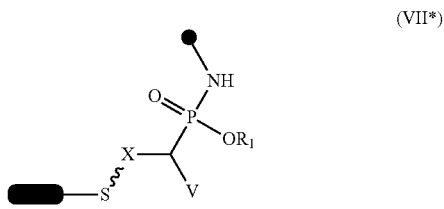 (VII*)

wherein
■, ●, V, $R_1$ and X are as defined above.

One embodiment of the present invention also refers to compounds of formula (V*) and (VII*).

In the processes of the invention described herein it is not required that the compound (V) or (V*) obtained in step (I) has exactly the same structure as the compound (V) or (V*) used for reacting with the thiol-containing molecule of formula (VI) in step (II). In this respect, the ●, R1 and/or X moieties of the compound (V) or (V*) may be modified before the compound (V) or (V*) is used for reacting with the thiol-containing molecule of formula (VI) in step (II). Such modification may be carried out as long as the ●, R1 and/or X moieties after modification are still covered by the definitions disclosed herein above. As a merely illustrative example, as shown in the following reaction scheme, the ● moiety of a compound A of formula (V) obtained in step (I) may be modified to give the compound B of formula (V), which is then used for reacting with the thiol-containing molecule of formula (VI) in step (II):

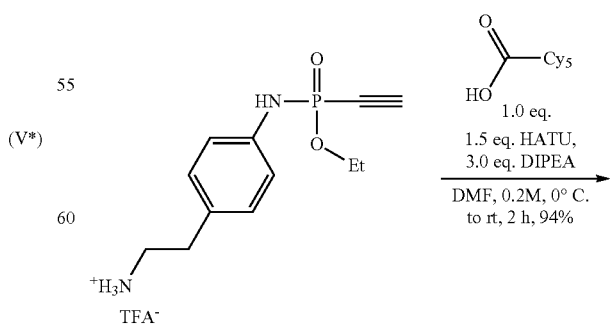

A

-continued

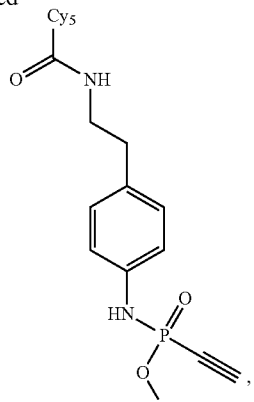

B wherein TFA⁻ is trifluoroacetate, Cy5 is the fluorescence dye Cy5, HATU is (1-[Bis(dimethylamino)methylene]-1H-1,2,3-triazolo[4,5-b]pyridinium 3-oxid hexafluorophosphate), DIPEA is N,N-diisopropylethylamine and DMF is N,N-dimethylformamide.

In one preferred embodiment of a process according to the invention, $R_1$ independently represents methyl, ethyl, propyl, butyl, phenyl, nitro-substituted phenyl, $(C_1\text{-}C_2\text{-alkoxy})_n$ wherein n is 1, 2, 3, 4, 5 or 6, more preferably 2-(2-methoxyethoxy)ethyl, phenyl, benzyl or nitro-substituted benzyl, methyl or ethyl, even more preferably methyl or ethyl. In an even more preferred embodiment $R_1$ is the same.

In another preferred embodiment, $R_1$ can even be modified after the thiol-addition (step (II), for example, the substituent $R_1$ can comprise a triple bond as in

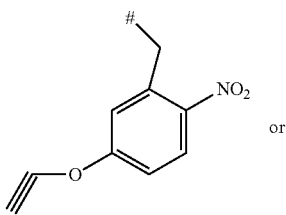 or

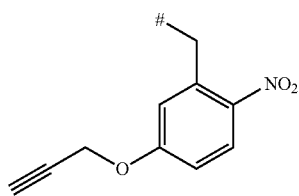

Which can be reacted with any desired organic compound-$N_3$ (such as peptide-$N_3$, protein-$N_3$, such as an enzyme-$N_3$ or co-enzyme-$N_3$ (e.g. coenzyme A-$N_3$), antibody-$N_3$, protein tag-$N_3$, fluorophore-$N_3$, oligonucleotide-$N_3$, or polysaccharide-$N_3$ e.g. Biotin-$N_3$) to form a triazole-bridged complex, for example

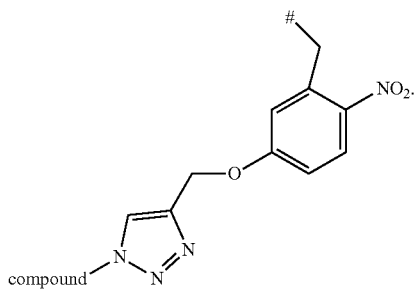

Accordingly, $R_1$ may represent

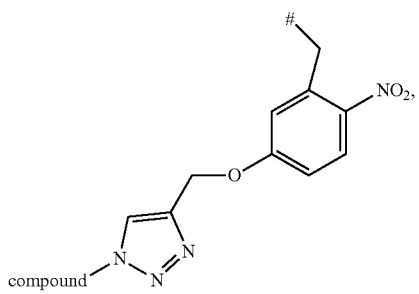

wherein "compound" may represent a peptide, a protein, an enzyme, a co-enzyme (e.g. co-enzyme A), an antibody, a protein tag, a fluorophore, an oligonucleotide, a polysaccharide, or biotin; wherein #represents the position of O.

In another preferred embodiment, $R_1$ is an optionally substituted aliphatic or aromatic residue, such as phenyl; with $(C_1\text{-}C_8\text{-alkoxy})_n$, wherein n is 1, 2, 3, 4, 5 or 6 with F, with Cl, with Br, with I, with —$NO_2$, with —$N(C_1\text{-}C_8\text{-alkyl})$H, with —$NH_2$, with —$N(C_1\text{-}C_8\text{-alkyl})_2$, with =O, with $C_3\text{-}C_8$-cycloalkyl, with optionally substituted phenyl substituted $C_1\text{-}C_8$-alkyl such as

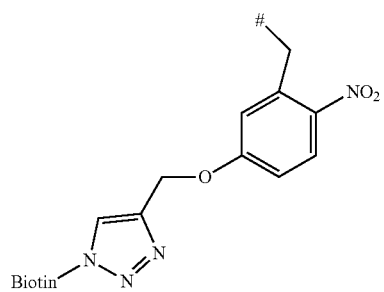

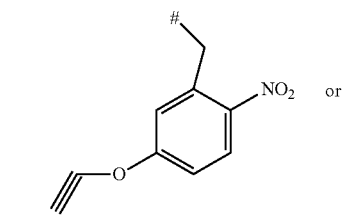 or

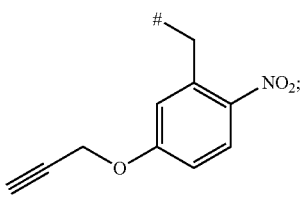

or optionally independently with $C_1$-$C_8$-alkyl, $(C_1$-$C_8$-alkoxy$)_n$, F, Cl, I, Br, —$NO_2$, —$N(C_1$-$C_8$-alkyl)H, —$NH_2$, —$N(C_1$-$C_8$-alkyl)_2$, substituted phenyl; or 5- or 6-membered heteroaromatic system such as pyridyl; preferably $C_1$-$C_8$-alkyl, $C_1$-$C_8$-alkyl substituted with $(C_1$-$C_8$-alkoxy$)_n$, phenyl or phenyl substituted with —$NO_2$.

Accordingly, R, may independently represent an optionally substituted aliphatic or aromatic residue, such as phenyl. "Optionally substituted" in the "optionally substituted aliphatic or aromatic residue" refers to optional substitution of the aliphatic or aromatic residue independently with any possible residue.

$R_1$ may represent $C_1$-$C_8$-alkyl optionally substituted with at least one of $(C_1$-$C_8$-alkoxy$)_n$ wherein n is 1, 2, 3, 4, 5 or 6, F, Cl, Br, I, —$NO_2$, —$N(C_1$-$C_8$-alkyl)H, —$NH_2$, —$N(C_1$-$C_8$-alkyl)_2$, =O, $C_3$-$C_8$-cycloalkyl, —S—S—$(C_1$-$C_8$-alkyl), hydroxy-$(C_1$-$C_8$-alkoxy$)_n$ wherein n is 1, 2, 3, 4, 5 or 6, $C_2$-$C_8$-alkynyl or optionally substituted phenyl such as

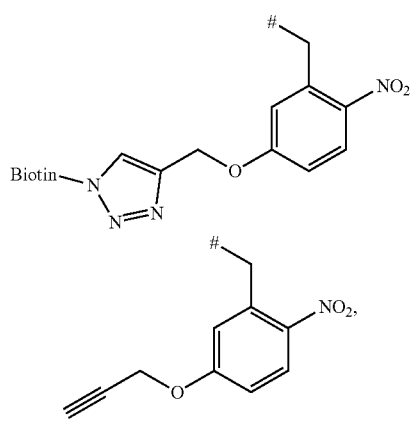

wherein #represents the position of O in formula (III) or formula (III*).

$R_1$ may represent phenyl optionally independently substituted with at least one of $C_1$-$C_8$-alkyl, $(C_1$-$C_8$-alkoxy$)_n$ wherein n is 1, 2, 3, 4, 5 or 6, F, Cl, I, Br, —$NO_2$, —$N(C_1$-$C_8$-alkyl)H, —$NH_2$ or —$N(C_1$-$C_8$-alkyl)_2$.

$R_1$ may represent a 5- or 6-membered heteroaromatic system such as pyridyl.

$R_1$ may represent $C_1$-$C_8$-alkyl, $C_1$-$C_8$-alkyl substituted with —S—S—$(C_1$-$C_8$-alkyl), $C_1$-$C_8$-alkyl substituted with $(C_1$-$C_8$-alkoxy$)_n$ wherein n is 1, 2, 3, 4, 5 or 6, $C_1$-$C_8$-alkyl substituted with optionally substituted phenyl, phenyl or phenyl substituted with —$NO_2$.

In some embodiments $R_1$ represents an aliphatic or aromatic residue which is optionally substituted with —S—S—$(C_1$-$C_8$-alkyl). In a preferred embodiment, $R_1$ represents

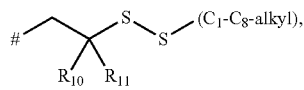

wherein $R_{10}$ and $R_{11}$ independently represent hydrogen or $C_1$-$C_8$-alkyl; and #represents the position of O. In a more preferred embodiment $R_{10}$ and $R_{11}$ independently represent hydrogen, methyl or ethyl. In a still more preferred embodiment, $R_1$ represents

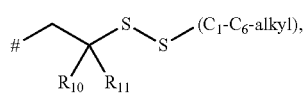

wherein $R_{10}$ and $R_{11}$ independently represent hydrogen, methyl or ethyl; and #represents the position of O. In some of these embodiments $R_{10}$ and $R_{11}$ are both hydrogen. In some of these embodiments $R_{10}$ is hydrogen and $R_{11}$ is $C_1$-$C_6$-alkyl. In some of these embodiments $R_{10}$ is hydrogen and $R_{11}$ is methyl or ethyl. Preferably, in these embodiments both $R_1$ are the same.

In some embodiments $R_1$ represents $C_1$-$C_8$-alkyl substituted with phenyl, said phenyl being further substituted with

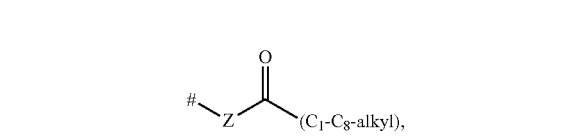

wherein Z is O or NH, and wherein #represents the position of said phenyl. In some embodiments Z is O. In some embodiments Z is NH. The $C_1$-$C_8$-alkyl in the

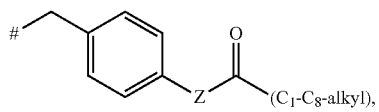

may be, for example, methyl, ethyl, propyl or butyl; preferably methyl, ethyl or propyl; more preferably methyl or ethyl; most preferably methy. In a preferred embodiment $R_1$ represents

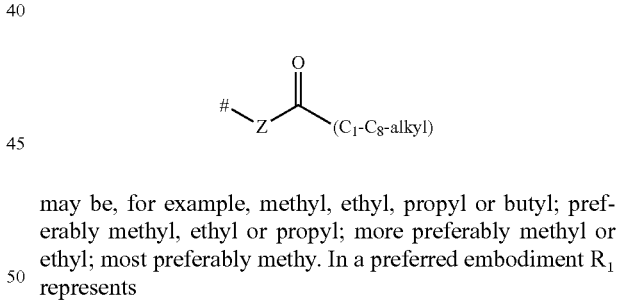

wherein the $C_1$-$C_8$-alkyl may be, for example, methyl, ethyl, propyl or butyl; preferably methyl, ethyl or propyl; more preferably methyl or ethyl; most preferably methyl; wherein Z is O or NH, and wherein #represents the position of O. In another preferred embodiment $R_1$ represents

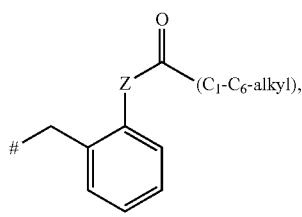

wherein the $C_1$-$C_8$-alkyl may be, for example, methyl, ethyl, propyl or butyl; preferably methyl, ethyl or propyl; more preferably methyl or ethyl; most preferably methyl; wherein Z is O or NH, and wherein #represents the position of O. Preferably, in these embodiments both $R_1$ are the same.

In some embodiments $R_1$ represents $C_1$-$C_8$-alkyl substituted with phenyl, said phenyl being further substituted with

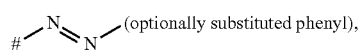

and wherein #represents the position of said phenyl. In some embodiments $R_1$ represents $C_1$-$C_8$-alkyl substituted with phenyl, said phenyl being further substituted with

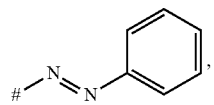

wherein #represents the position of said phenyl. In a preferred embodiment $R_1$ represents

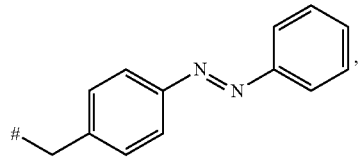

wherein #represents the position of O. In another preferred embodiment $R_1$ represents

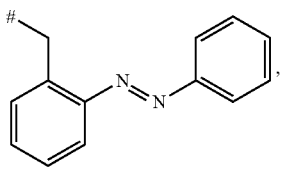

wherein #represents the position of O. Preferably, in these embodiments both R, are the same.

In some embodiments $R_1$ represents an aliphatic or aromatic residue which is optionally substituted with hydroxy-$(C_1$-$C_8$-alkoxy$)_n$ wherein n is 1, 2, 3, 4, 5 or 6. In a preferred embodiment $R_1$ is hydroxyethoxyethyl, more preferably —$(CH_2)_2$—O—$(CH_2)_2$—OH.

In some embodiments $R_1$ represents an aliphatic or aromatic residue which is optionally substituted with $C_2$-$C_8$-alkynyl. In a preferred embodiment $R_1$ is homopropargyl.

In another preferred embodiment of a process according to the invention, ⫽ represents a double bond, X represents $(R_3R_4)C$, $R_3$ and $R_4$ independently represent H or $C_1$-$C_8$-alkyl and ⫽ represents a bond. In another preferred embodiment, $R_3$ and $R_4$ each represent H.

In another preferred embodiment of a process according to the invention ⫽ represents a triple bond, X represents $R_3$—C, $R_3$ represents H or $C_1$-$C_8$-alkyl, more preferably H, and ⫽ represents a double bond.

In another preferred embodiment of a process according to the invention ● represents an optionally substituted $C_1$-$C_8$-alkyl such as

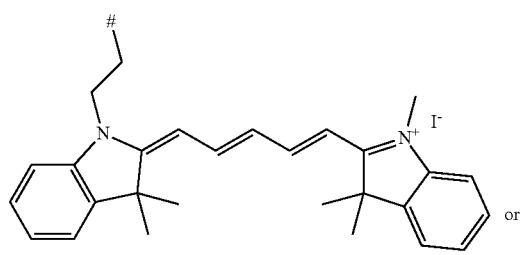

or

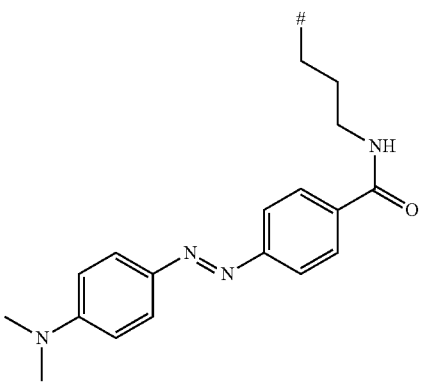

or
or an optionally substituted phenyl such as

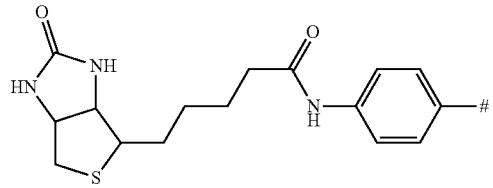

wherein #represents the position of the —$N_3$ group of compounds of formula (IV), a radioactive or non-radioactive nuclide, biotin, a nucleotide, an oligonucleotide, a polymer, a carbohydrate, an amino acid, a peptide, an optionally substituted 5- or 6-membered heteroaromatic system, a protein tag, or a fluorophore such as $CY_5$ or EDANS.

In another preferred embodiment of a process according to the invention ● represents a cyclic RGD peptide of structure (VIII) (c(RGDfK)

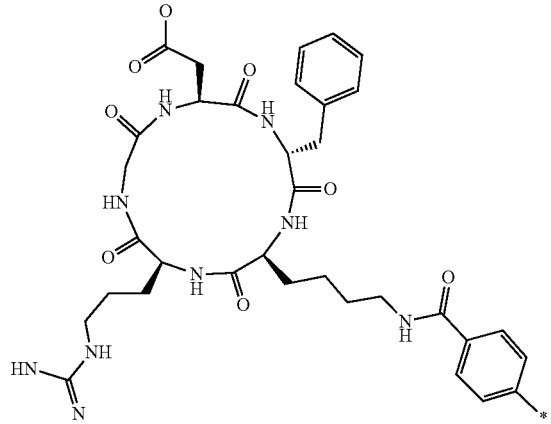

(VIII)

wherein
* represents the position of the $N_3$ group;
Biotin;
$CY_5$ or EDANS;
phenyl, optionally substituted with one, two, three, four or five substituents independently selected from the group consisting of $C_1$-$C_8$-alkyl, $C_1$-$C_8$-alkoxy, halogen, —ON, —$NO_2$, —$NH_2$, —N($C_1$-$C_8$-alkyl), —N($C_1$-$C_8$-alkyl)$_2$-COOH, —COO($C_1$-$C_8$-alkyl), —O—C(O)—($C_1$-$C_8$-alkyl), —C(O)N—($C_1$-$C_8$-alkyl), —N(H)—C(O)—($C_1$-$C_8$-alkyl) preferably optionally substituted with one substituent selected from the group consisting of $C_1$-$C_8$-alkoxy, —COOH, —COO($C_1$-$C_8$-alkyl and $NO_2$.
$C_1$-$C_8$-alkyl optionally substituted with at least one substituent selected from the group consisting of $C_3$-$C_8$-cycloalkyl; heterocyclyl with 3 to 8 ring members wherein the heteroatom(s) are selected from N, O, S; $C_1$-$C_8$-alkoxy; halogen; —CN; —$NO_2$; —$NH_2$; —N($C_1$-$C_8$-alkyl); —N($C_1$-$C_8$-alkyl)$_2$; —COOH; —COO($C_1$-$C_8$-alkyl); —O—C(O)—($C_1$-$C_8$-alkyl); —$CONH_2$; —C(O)N($C_1$-$C_5$-alkyl)$_2$; —C(O)NH—($C_1$-$C_5$-alkyl); —N(H)—C(O)—($C_1$-$C_5$-alkyl), preferably $C_1$-$C_8$-alkoxy, —COOH, —COO($C_1$-$C_8$-alkyl and $NO_2$, phenyl or a heteroaromatic system, a monosaccharide, a polysaccharide, a peptide, a nucleotide, an oligonucleotide, a polymer, an amino acid, a fluorophor, a protein tag (substituent 1$^{st}$ generation), wherein a substituent 1$^{st}$ generation may again optionally be substituted with $C_3$-$C_8$-cycloalkyl; heterocyclyl with 3 to 8 ring members wherein the heteroatom(s) are selected from N, O, S; $C_1$-$C_8$-alkoxy; halogen; —ON; —$NO_2$; —$NH_2$; —N($C_1$-$C_8$-alkyl); —N($C_1$-$C_5$-alkyl)$_2$; —COOH; —COO($C_1$-$C_8$-alkyl); —O—C(O)—($C_1$-$C_8$-alkyl); —$CONH_2$; —C(O)N($C_1$-$C_8$-alkyl)$_2$; —C(O)NH—($C_1$-$C_8$-alkyl); —N(H)—C(O)—($C_1$-$C_8$-alkyl), preferably $C_1$-$C_8$-alkoxy, —COOH, —COO($C_1$-$C_8$-alkyl and $NO_2$, phenyl or a heteroaromatic system (substituents 2$^{nd}$ generation) and wherein a substituent 2$^{nd}$ generation may be substituted again by at least one substituent selected from the same group and wherein such substitution may go until generation 3, 4, 5, 6, 7, 8, 9 or 10.

In another preferred embodiment of a process according to the invention ● represents a cyclic RGD peptide of structure (VIII) (c(RGDfK)

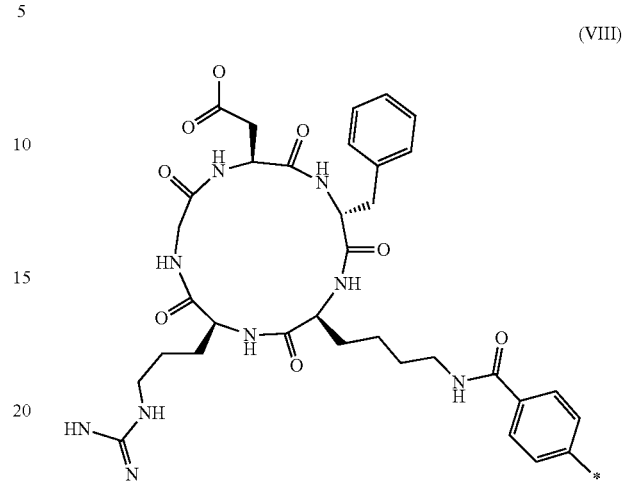

(VIII)

wherein
* represents the position of the $N_3$ group;
Biotin;
$CY_5$ or EDANS;
phenyl, optionally substituted with one, two, three, four or five substituents independently selected from the group consisting of $C_1$-$C_8$-alkyl, $C_1$-$C_8$-alkoxy, halogen, —CN, —$NO_2$, —$NH_2$, —N($C_1$-$C_8$-alkyl), —N($C_1$-$C_8$-alkyl)$_2$-COOH, —COO($C_1$-$C_8$-alkyl), —O—C(O)—($C_1$-$C_8$-alkyl), —C(O)N—($C_1$-$C_8$-alkyl), —N(H)—C(O)—($C_1$-$C_8$-alkyl) preferably optionally substituted with one substituent selected from the group consisting of $C_1$-$C_8$-alkoxy, —COOH, —COO($C_1$-$C_8$-alkyl and $NO_2$.
$C_1$-$C_8$-alkyl optionally substituted with one, two, three, four or five substituents independently selected from the group consisting of phenyl which may be optionally substituted with one, two, three, four or five substituents independently selected from the group consisting of $C_1$-$C_8$-alkyl, $C_1$-$C_8$-alkoxy, halogen, —CN, —$NO_2$, —$NH_2$, —N($C_1$-$C_8$-alkyl), —N($C_1$-$C_8$-alkyl)$_2$-COOH, —COO($C_1$-$C_8$-alkyl), —O—C(O)—($C_1$-$C_8$-alkyl), —C(O)N—($C_1$-$C_8$-alkyl), —N(H)—C(O)—($C_1$-$C_8$-alkyl), preferably optionally substituted with one substituent selected from the group consisting of $C_1$-$C_8$-alkoxy, —COOH, —COO($C_1$-$C_8$-alkyl and $NO_2$, $C_1$-$C_8$-alkoxy; halogen; —CN; —$NO_2$; —$NH_2$; —N($C_1$-$C_8$-alkyl); —N($C_1$-$C_8$-alkyl)$_2$; —COOH; —COO($C_1$-$C_8$-alkyl); —O—C(O)—($C_1$-$C_8$-alkyl); —C(O)N—($C_1$-$C_8$-alkyl); —N(H)—C(O)—($C_1$-$C_8$-alkyl), preferably $C_1$-$C_8$-alkoxy, —COOH, —COO($C_1$-$C_8$-alkyl, —$NO_2$;

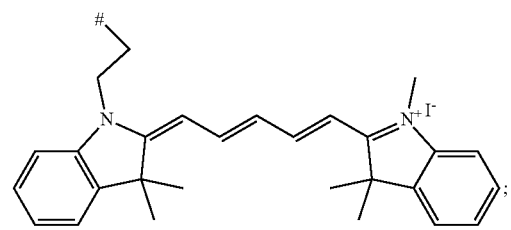

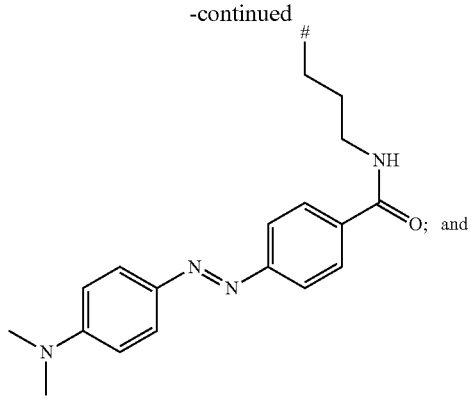

wherein #represents the position of the —N₃ group. TFA⁻ is trifluoroacetate.

In another preferred embodiment of a process according to the invention ● represents an optionally substituted $C_1$-$C_8$-alkyl such as a linker, a drug, or a linker-drug conjugate.

In another preferred embodiment of a process according to the invention ● represents an optionally substituted phenyl such as a linker, a drug, or a linker-drug conjugate.

In another preferred embodiment of a process according to the invention ⬛ represents an antibody, preferably a IgG-antibody, such as Cetuximab or Trastuzumab; a peptide, such as GFP protein, eGFP-protein, a tripeptide, e.g., a peptide of formula (IX)

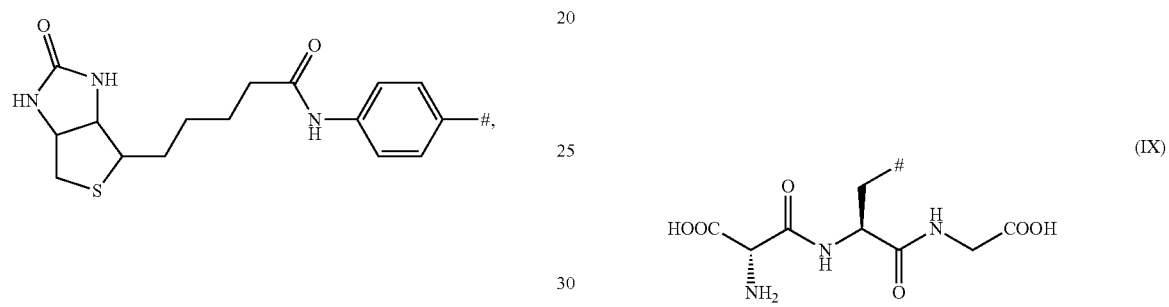

(IX)

wherein #represents the N-position.

In another preferred embodiment of a process according to the invention ● represents an optionally substituted phenyl such as

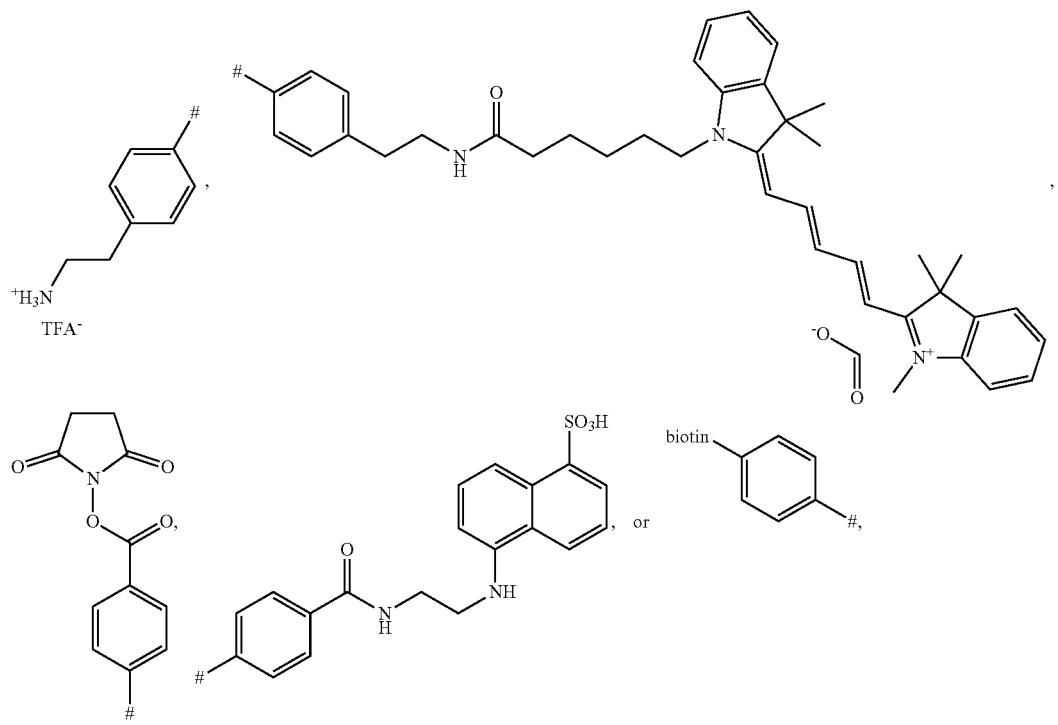

Wherein #represents the position of S; or optionally substituted $C_1$-$C_8$-alkyl such as

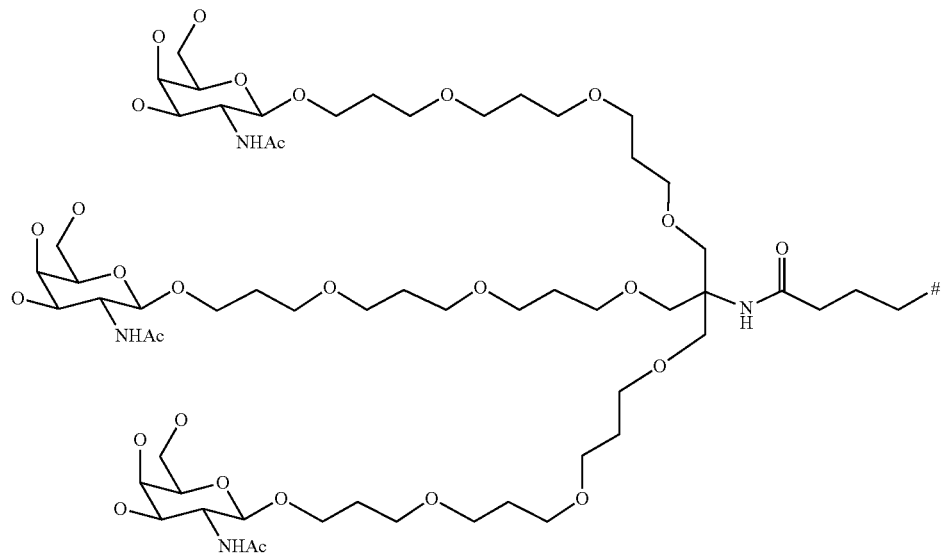

Wherein #marks the S-position.

In another preferred embodiment of a process according to the invention  represents

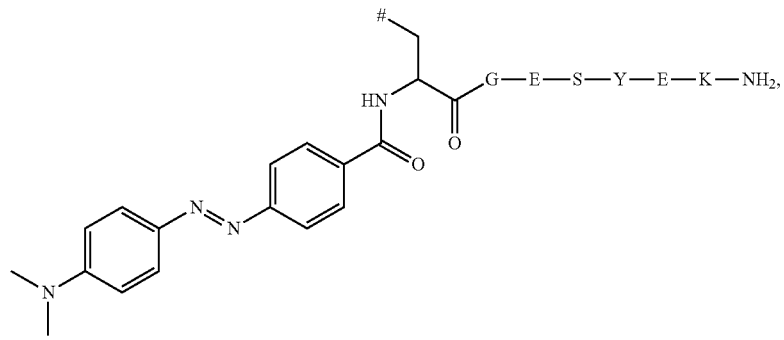

wherein #represents the position of S.

In an embodiment of a process according to the invention the

—$N_3$ and the

—SH are in the same molecule.

Accordingly, the present invention also relates to a process wherein a compound of formula (XX)

(XX)

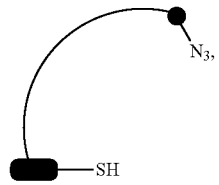

wherein the

—$N_3$ and the

are in the same molecule as indicated by the arc connecting the ● and the ⬛,
is reacted with a compound of formula (III) as defined herein to give a compound of formula (VIIa):

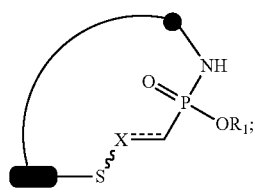

(VIIa)

wherein ⫽ represents a bond if ⫽ in a compound of formula (III) represents a double bond; or ⫽ represents a double bond if ⫽ in a compound of formula (III) represents a triple bond; and
⬛, ●, R₁ and X are as defined herein.

Accordingly, the present invention also relates to a process wherein a compound of formula (XX)

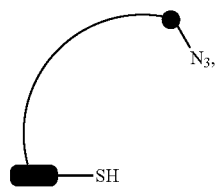

(XX)

wherein the

and the

are in the same molecule as indicated by the arc connecting the ● and the ⬛,
is reacted with a compound of formula (III*) as defined herein to give a compound of formula (VII*a):

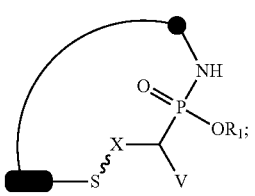

(VII*a)

wherein ⬛, ●, V, R₁ and X are as defined herein.

In some embodiments the compound (XX) having the

and the

in the same molecule is a peptide, such as for example the BCL9 peptide. Accordingly, the compound of formula (VIIa) or (VII*a) obtained by the process may be a cyclic peptide, such as for example a cyclic peptide derived from the BCL9 peptide.

All steps for the processes described herein for compounds of formula (V), (V*), (VII) and (VII*) can be performed analogously for compounds of formula (VIIa) and (VII*a).

The incorporation of both an azide and a thiol into the same molecule provides for an intramolecular Staudinger-induced thiol addition that can realize an intramolecular cyclization as exemplarily shown in the FIG. 38.

Without wishing to be bound by any theory, it is assumed that first the azide is reacting with the electron-rich alkyne/alkene-phosphonite upon which the phosphonamidate is formed and an electron-poor alkyne/alkene-phosphonamidate is formed that undergoes a fast intramolecular thiol addition with the SH moiety.

One embodiment of the present invention also refers to compounds of formula (VIIa) and (VII*a).

Compounds

The invention also refers to compounds of formula (V)

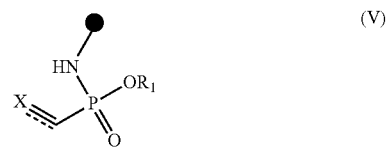

(V)

Wherein R₁ and X and ● are as defined above.

The invention also refers to compounds of formula (V*)

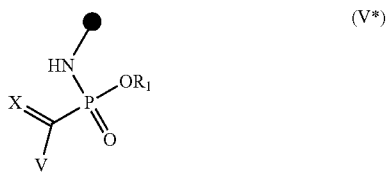

(V*)

wherein ●, V, R₁, and X are as defined above.

Preferably, in the compounds of formula (V) or (V*) ● represents an optionally substituted $C_1$-$C_8$-alkyl such as

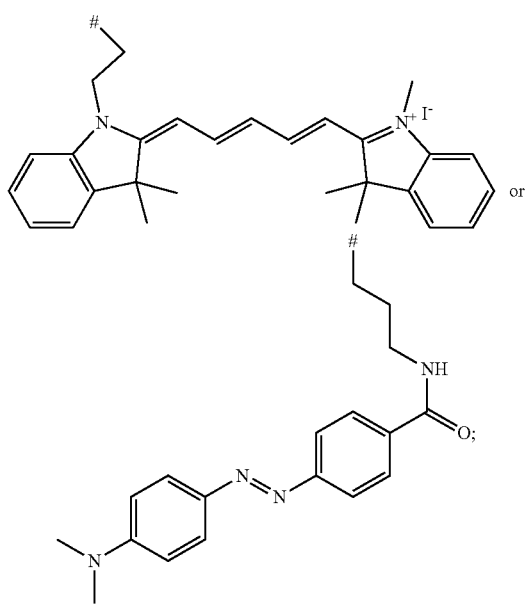

or

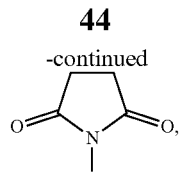

-continued

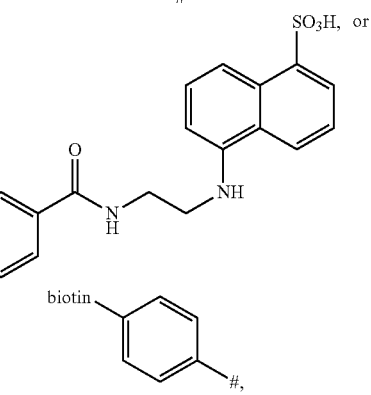

wherein #represents the position of N. TFA⁻ is trifluoroacetate.

Preferably, in the compounds of formula (V) or (V*) ● represents an optionally substituted $C_1$-$C_8$-alkyl such as a linker, a drug, or a linker-drug conjugate.

Preferably, in the compounds of formula (V) or (V*) ● represents an optionally substituted phenyl such as a linker, a drug, or a linker-drug conjugate.

The invention also refers to compounds of formula (VII)

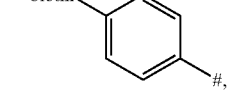

(VII)

wherein

⫽ represents a bond and X represents ($R_3R_4$)C; or

⫽ represents a double bond and X represents $R_3$—C;

$R_3$ represents H or $C_1$-$C_8$-alkyl;

$R_4$ represents H or $C_1$-$C_8$-alkyl;

■ represents an optionally substituted $C_1$-$C_8$-alkyl, an optionally substituted Phenyl, an optionally substituted aromatic 5- or 6-membered heterocyclic system, an amino acid, a peptide, a protein, an antibody, a saccharide, a polysaccharide, a nucleotide, a oligonucleotide or a polymer;

● represents an aliphatic or aromatic residue;

$R_1$ independently represents an optionally substituted aliphatic or aromatic residue, such as phenyl; with ($C_1$-$C_8$-alkoxy)$_n$, wherein n is 1, 2, 3, 4, 5 or 6 with F, with Cl, with Br, with I, with —$NO_2$, with —N($C_1$-$C_8$-alkyl)H, with —$NH_2$, with —N($C_1$-$C_8$- an optionally substituted phenyl such as

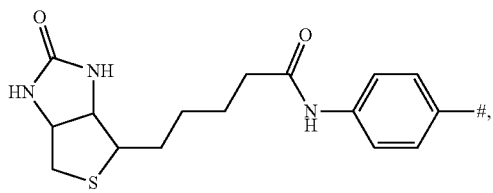

wherein #represents the N-position; a radioactive or non-radioactive nuclide, biotin, a nucleotide, an oligonucleotide, a polymer, a carbohydrate, an amino acid, a peptide, an optionally substituted phenyl, an optionally substituted 5- or 6-membered heteroaromatic system, an optionally substituted $C_1$-$C_8$-alkyl, a protein tag or a fluorophore such as $CY_5$.

Preferably, in the compounds of formula (V) or (V*) ● represents an optionally substituted phenyl such as

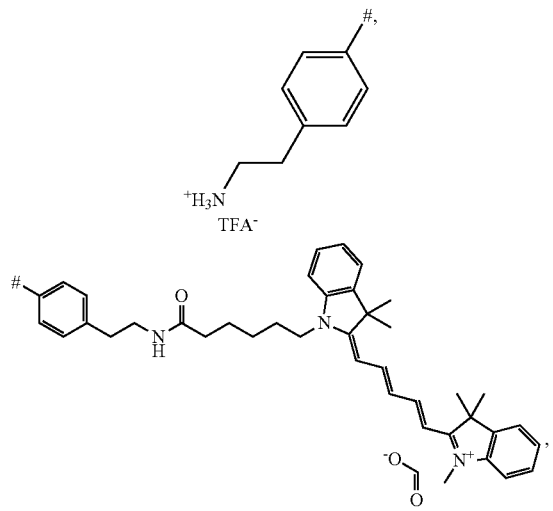

alkyl)$_2$, with =O, with C$_3$-C$_8$-cycloalkyl, with optionally substituted phenyl substituted C$_1$-C$_8$-alkyl such as

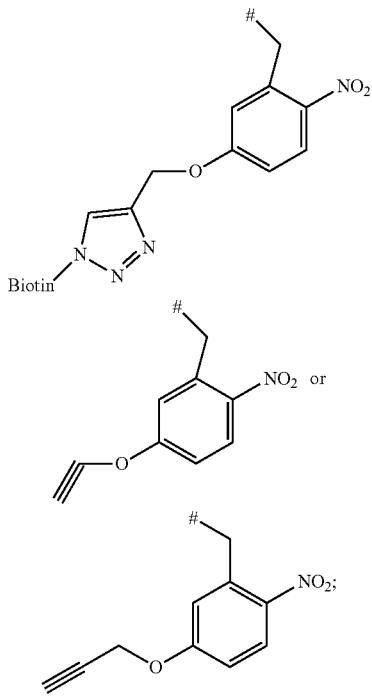

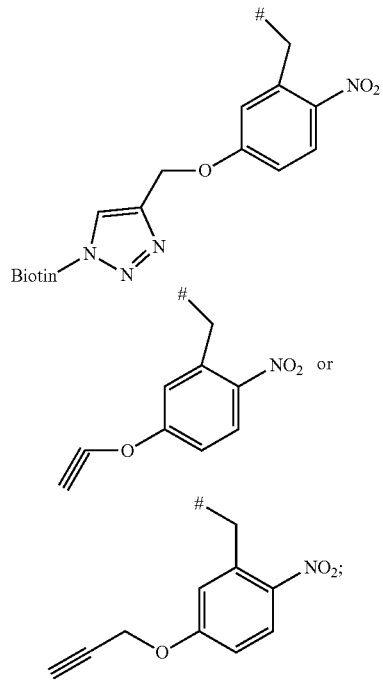

or optionally independently with C$_1$-C$_8$-alkyl, (C$_1$-C$_8$-alkoxy)$_n$, F, Cl, I, Br, —NO$_2$, —N(C$_1$-C$_8$-alkyl)H, —NH$_2$, —N(C$_1$-C$_8$-alkyl)$_2$, substituted phenyl; or 5- or 6-membered heteroaromatic system such as pyridyl; preferably C$_1$-C$_8$-alkyl, C$_1$-C$_8$-alkyl substituted with (C$_1$-C$_8$-alkoxy)$_n$, phenyl or phenyl substituted with —NO$_2$;

The invention also refers to compounds of formula (VII*)

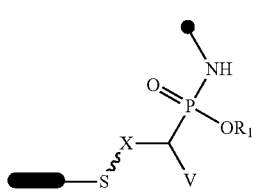

(VII*)

wherein

● represents an optionally substituted C$_1$-C$_8$-alkyl, an optionally substituted Phenyl, an optionally substituted aromatic 5- or 6-membered heterocyclic system, an amino acid, a peptide, a protein, an antibody, a saccharide, a polysaccharide, a nucleotide, a oligonucleotide or a polymer;

● represents an aliphatic or aromatic residue;

R$_1$ independently represents an optionally substituted aliphatic or aromatic residue, such as phenyl; with (C$_1$-C$_8$-alkoxy)$_n$, wherein n is 1, 2, 3, 4, 5 or 6 with F, with Cl, with Br, with I, with —NO$_2$, with —N(C$_1$-C$_8$-alkyl)H, with —NH$_2$, with —N(C$_1$-C$_8$-alkyl)$_2$, with =O, with C$_3$-C$_8$-cycloalkyl, with optionally substituted phenyl substituted C$_1$-C$_8$-alkyl such as or optionally independently with C$_1$-C$_8$-alkyl, (C$_1$-C$_8$-alkoxy)$_n$, F, Cl, I, Br, —NO$_2$, —N(C$_1$-C$_8$-alkyl)H, —NH$_2$, —N(C$_1$-C$_8$-alkyl)$_2$, substituted phenyl; or 5- or 6-membered heteroaromatic system such as pyridyl; preferably C$_1$-C$_8$-alkyl, C$_1$-C$_8$-alkyl substituted with (C$_1$-C$_8$-alkoxy)$_n$, phenyl or phenyl substituted with —NO$_2$;

V represents C$_1$-C$_8$-alkyl, preferably methyl, ethyl or propyl, more preferably methyl;

X represents (R$_3$R$_4$)C

R$_3$ represents H or C$_1$-C$_8$-alkyl; and

R$_4$ represents H or C$_1$-C$_8$-alkyl.

Preferably, in the compounds of formula (VII) or (VII*) ● represents an optionally substituted C$_1$-C$_8$-alkyl such as

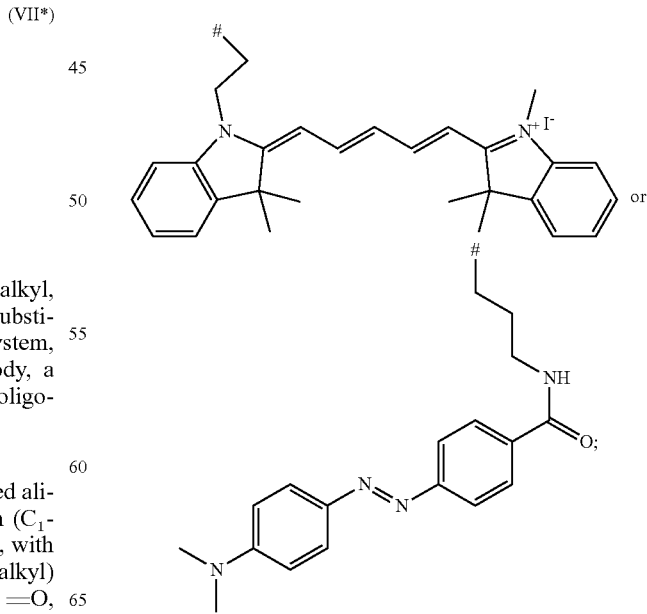

an optionally substituted phenyl such as

[structure: biotin-phenyl group with #]

a radioactive or non-radioactive nuclide, biotin, a nucleotide, an oligonucleotide, a polymer, a carbohydrate, an amino acid, a peptide, an optionally substituted phenyl, an optionally substituted 5- or 6-membered heteroaromatic system, an optionally substituted $C_1$-$C_8$-alkyl, a protein tag or a fluorophore such as $CY_5$ or EDANS.

Preferably, in the compounds of formula (VII) or (VII*) ● represents an optionally substituted phenyl such as

[structure: phenethylammonium TFA⁻]

[structure: CY5-linker-phenyl]

[structure: NHS ester of benzoic acid with #]

[structure: dansyl-ethylamide benzamide with SO₃H], or

[structure: biotin-phenyl-#]

wherein # represents the
position of N. TFA⁻ is trifluoroacetate.

Preferably, in the compounds of formula (VII) or (VII*) ● represents an optionally substituted $C_1$-$C_8$-alkyl such as a linker, a drug, or a linker-drug conjugate.

Preferably, in the compounds of formula (VII) or (VII*) ● represents an optionally substituted phenyl such as a linker, a drug, or a linker-drug conjugate.

Preferably, in the compounds of formula (VII) or (VII*) ⬛ represents an antibody, preferably a IgG-antibody, more preferably a Cetuximab or a Trastuzumab; a peptide, preferably GFP protein or eGFP-protein or a tripeptide, more preferably a peptide of formula (IX) or $C_1$-$C_8$-alkyl.

Preferably, in the compounds of formula (VII) or (VII*) ⬛ represents

[structure: dabcyl-peptide G-E-S-Y-E-K-NH₂]

wherein # represents the position of S.

Preferred conjugates of formula (VII) or formula (VII*) are conjugates wherein
  ⬛ represents an antibody and
  ● represents a protein tag or a fluorophore such as $CY_5$ or EDANS, or a protein.

Further preferred conjugates of formula (VII) are conjugates wherein
  ⬛ represents a protein and
  ● represents a protein tag or a fluorophore such as $CY_5$ or EDANS, an antibody or a protein.

One preferred embodiment are conjugates of formula (VII) wherein
  ⬛ represents a protein and
  ● represents a protein.

Further, preferred conjugates of formula (VII) or formula (VII*) are conjugates wherein
  ⬛ represents an antibody and
  ● represents a linker, a drug, or a linker-drug conjugate.

The invention also refers to compounds of formula (VIIa)

(VIIa)

[structure of formula VIIa with P(=O)(OR₁), X, S, NH linking ● and ⬛]

wherein ● and ⬛ are in the same molecule as indicated by the arc connecting the ● and the ⬛, and wherein ●, ⬛, ∕∕, X and R₁ are as defined herein, in particular as defined with regard to compound (VII). Preferably, the compound (VIIa) is a cyclic peptide, such as for example a cyclic peptide derived from the BCL9 peptide.

The invention also refers to compounds of formula (VII*a)

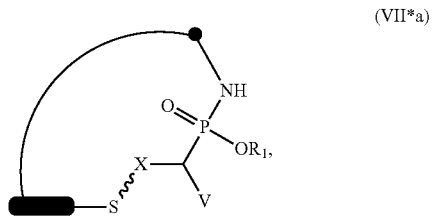

(VII*a)

wherein ● and ⬛ are in the same molecule as indicated by the arc connecting the ● and the ⬛, and wherein ●, ⬛, V, X and R₁ are as defined herein, in particular as defined with regard to compound (VII*). Preferably, the compound (VII*a) is a cyclic peptide, such as for example a cyclic peptide derived from the BCL9 peptide.

The following compounds of formula (VII) are also preferred:

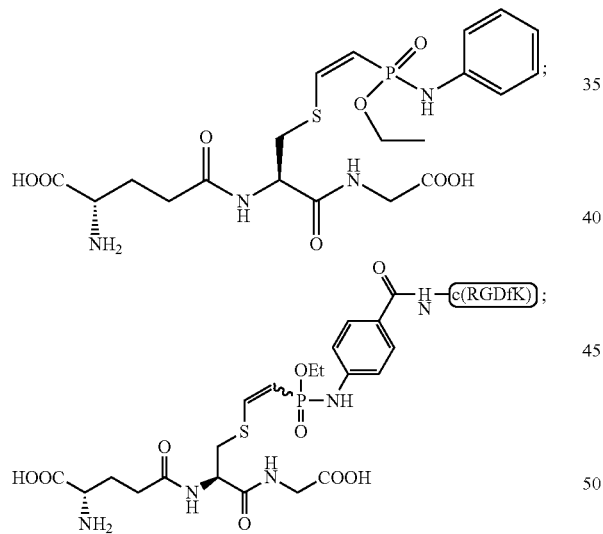

the compound depicted in FIG. 30;

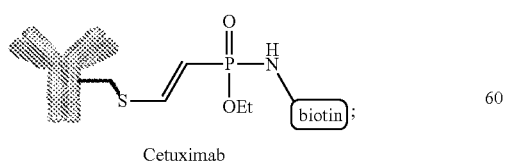

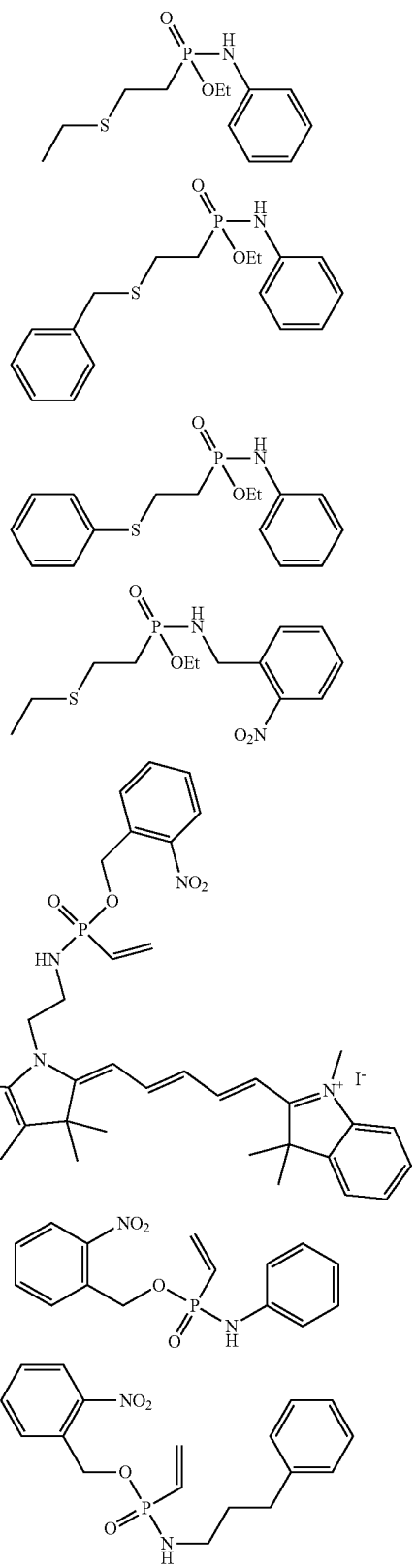

A fluorescently labeled ASGP-R addressing Cy₅ conjugate of formula (X) which can be produced via the modular addition to vinyl phosphonamidates is depicted in FIG. 39.

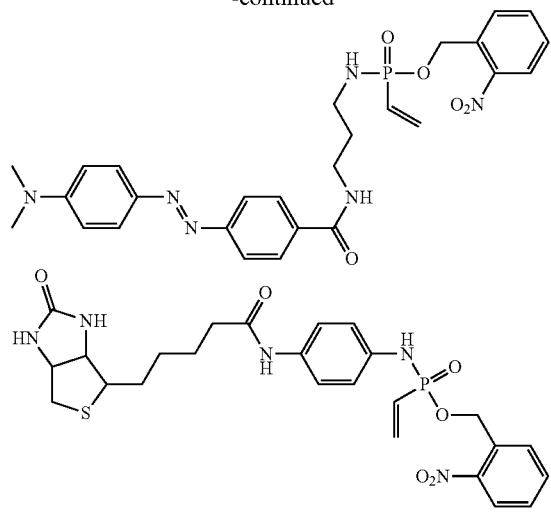

The following compounds of formula (VII) are also preferred:

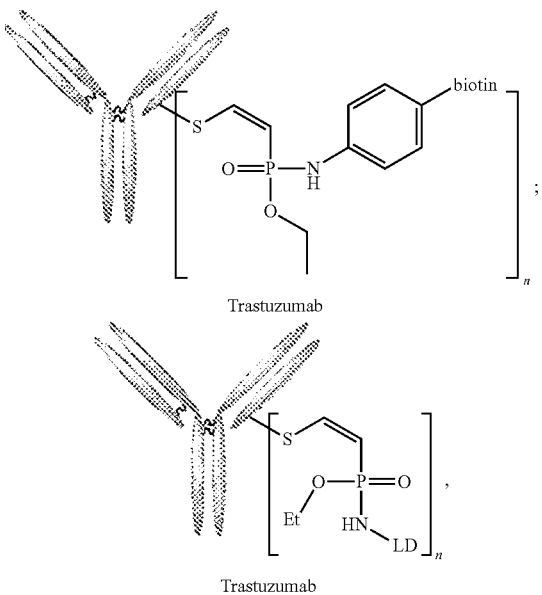

wherein LD represents a linker drug conjugate having the structure

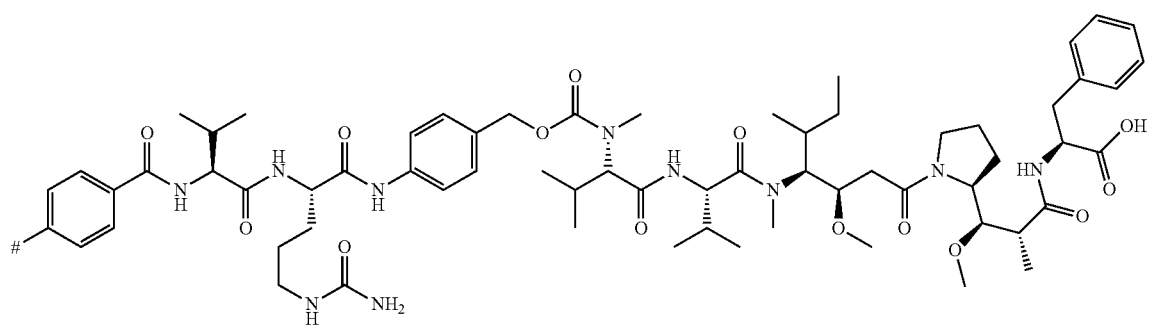

and #represents the position of the N; and

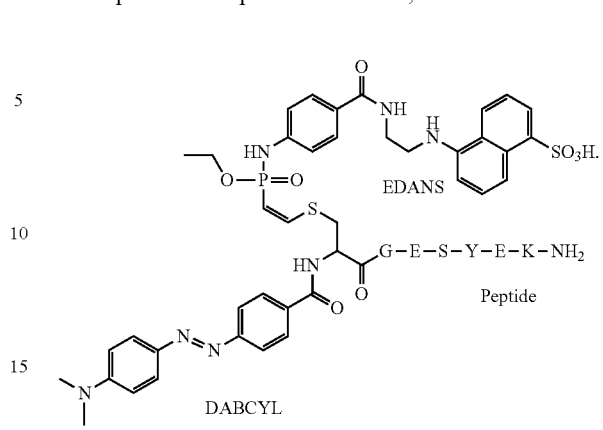

Moreover, also compounds provided herein as examples in the example section for compounds of formula (VII) are preferred.

The skilled person understands that embodiments according to the invention can be combined with each other with the proviso that a combination which would contravene any natural law is excluded.

Synthesis of Phosphonamidate of Formula (V)

Step a)

General procedure for the preparation of alkenyl or alkynyl phosphonamidates by Staudinger phosphonite reaction requires the reaction of an alkenyl- or alkynylmagnesiumbromide of formula (II) with a dialkyl halogenchlorophosphite of formula (I), preferably a chlorophosphonite, below −20° C., e.g. between −100° C. and −40° C., preferably between −90° C. and −50° C. (e.g. around 87° C.). Preferably, the reaction is carried out under inert gas such as argon. "Inert" in this situation refers to a gas which will not react with any of the educts or products of this reaction under the given reaction conditions. Of course, the reaction time depends on the reaction volume and amount of substance. However, as a guideline, the reaction time should be in a range from 2 min to 4 h. The amounts of compound of formula (I) and (II) should be in a range from 5:1 to 1:5 such as 2:1 to 1:2, e.g., around 1:1.

Step (I)

The reaction of a compound of formula (III) with an azide of formula (IV) can be performed at room temperature, i.e. around 25° C. However, the reaction can also be carried out at temperatures in a range from 0° C. to 50° C. The reaction time depends on the reaction volume and the amount of substance. However, as a guideline, the reaction should be carried out in a time frame from 1 h to 72 h. The amounts of compound of formula (III) and (IV) should be in a range from 5:1 to 1:5 such as 2:1 to 1:2, e.g., around 1:1.

Preferred solvents for step (1) described herein is carried out in a polar aprotic solvent system such as tetrahydrofurane (THF), dimethylformamide (DMF), acetonitrile (MeCN), acetone, dimethyl sulfoxide (DMSO), ethyl acetate (EtOAc), N-methylpyrrolidone or mixtures thereof, preferably THF, DMF, MeCN, THF/DMF, THF/MeCN; or a mixture of a polar unprotic solvent and a non-polar solvent such as hexane, toluene, benzene, 1,4-dioxane, chloroform, diethylether or dichloromethane (DCM), preferably THF/toluene. Step (1) may be also carried out in an aqueous medium, for example in water or in an aqueous buffer, such as for example phosphate-buffered saline (PBS), tris(hydroxymethyl)-aminomethane (TRIS) or bicarbonate.

Procedure for Base Mediated Hydrothiolations of Electron-Deficient Phosphonamidate Alkynes Step (II)

Phosphonamidate of formula (V) and a base (and additive where required) can be suspended in a respective solvent. Then a thiol of formula (VI) can be added, e.g., via a microliter syringe and the mixture is allowed to react at room temperature, i.e. around 25° C. However, the reaction can also be carried out at temperatures in a range from 0° C. to 50° C. The reaction time depends on the reaction volume and the amount of substance. However, as a guideline, the reaction should be carried out in a time frame from 0.1 h (hours) to 10 h, e.g., in a time frame from 0.1 h to 3 h or even within a time frame between 0.1 h and 1 h.

In a preferred embodiment, step (II) described herein is carried out in the presence of a weak base. Preferred weak bases are carbonates such as ammonium $(NH_4)_2CO_3$, $Na_2CO_3$, $Rb_2CO_3$, $K_2CO_3$, or $Cs_2CO_3$ or correlating hydrogencarbonates thereof (e.g. $NaHCO_3$ etc.); and weak Nitrogen containing bases such as triethylamine $Et_3N$ ($pK_a$ 10.76 at 25° C.). Preferably, a base with a $pK_a$ value within the range of 7.5 to 11.5 is used.

The solvent (system) can be chosen from a wide range of solvents. The solvent can be a polar aprotic solvent system such as tetrahydrofurane (THF), dimethylformamide (DMF), acetonitrile (MeCN), acetone, dimethyl sulfoxide (DMSO), ethyl acetate (EtOAc), N-methylpyrrolidone or mixtures thereof, preferably THF, DMF, DMSO; non-polar solvents such as hexane, toluene, benzene, 1,4-dioxane, chloroform, diethylether or dichloromethane (DCM), preferably DCM; polar protic solvents such as water, ethanol, isopropanol, methanol, n-butanol, preferably ethanol; or mixtures thereof, e.g., DMF/water. The solvent may be also an aqueous medium, such as for example water or an aqueous buffer, such as for example phosphate-buffered saline (PBS), tris(hydroxymethyl)-aminomethane (TRIS) or bicarbonate.

EXAMPLES

General Procedure for the Preparation of Alkynyl Phosphonamidates

In a flame dried Schlenk flask under an atmosphere of argon a solution of ethynyl magnesiumbromide (0.5 M in THF, 2 mL, 1 mmol) was cooled to −78° C. in a bath of dry ice/acetone. The diethyl chlorophosphite (157 mg, 144 µL, 1 mmol) was added dropwise via a syringe. The solution was stirred at −78° C. for 30 minutes, then warmed up to room temperature and subsequently stirred for another 1.5 hours. Afterwards 3 mL of dry THF and azide (1 mmol) was added and the solution was stirred at room temperature for 24 hours. Then $H_2O$ (5 mL) was added and the solution was stirred for another 24 hours open to air. After removal of the solvent under reduced pressure the crude mixture was analyzed by $^{31}P$ NMR.

Synthesis of Vinyl Phosphonites

General Procedure a for the Synthesis of Vinyl Phosphonites from Phosphorous Trichloride.

A flame-dried Schlenkflask was charged with 1.50 mmol (1.0 eq.) of phosphorous trichloride in 20 ml of dry toluene and cooled to −78° C. 3.3 mmol of pyridine (2.2 eq.) and a solution of 3.3 mmol of the alcohol (2.2 eq.) in 5 ml $Et_2O$ were added drop wise. The resulting suspension was allowed to warm to room temperature, stirred for another 30 min and cooled again to −78° C. 1.65 mmol (1.1 eq.) of Vinylgrignard (1.0 M in THF) was added and the reaction was stirred at room temperature for two hours. Finally 2.25 mmol (1.5 eq.) of borane (1.0 M in THF) were added at 0° C. and stirred for another hour. The crude product was dry packed on a silica column for purification.

General Procedure B for the Synthesis of Vinyl Phosphonites from Bis(Diisopropylamino)Chlorophosphine A flame-dried Schlenkflask was charged with 1.5 mmol (1.0 eq.) Bis(diisopropylamino)chlorophosphine, dissolved in 200 µl of dry THF and cooled to −78° C. 1.65 mmol (1.1 eq.) of Vinylgrignard (1.0 M in THF) was added and the reaction was stirred at room temperature for 30 minutes. A solution of 3.3 mmol vacuum dried alcohol (2.2 eq.) in 1 ml of dry THF or MeCN and 3.3 mmol (2.2 eq.) Tetrazole (0.45 M in MeCN) was added. The resulting suspension was stirred at room temperature overnight. Finally 2.25 mmol (1.5 eq.) of borane (1.0 M in THF) were added at 0° C. and stirred for another hour. The crude product was dry packed on a silica column for purification.

General Procedure C for the Synthesis of Vinyl Phosphonamidates from Diethylchloro Phosphite, Vinyl Grignard Reagent and Different Azides A 25-ml Schlenk flask was charged with 1.71 ml vinyl-magnesium bromide (0.7 M in THF, 1.20 mmol, 1.2 eq.) under an argon atmosphere, cooled to −78° C. and 140 µl diethyl chlorophosphite (1.00 mmol, 1.0 eq.) were added drop wise. The yellowish solution was allowed to warm to 0° C., stirred for another two hours and 1.00 mmol of azide (1.0 eq.) dissolved in 3.2 ml of THF was added and stirred over night at room temperature. 5 ml of water were added and stirred for another 24 h. The solvents were removed under reduced pressure and the crude product was purified by flash column chromatography on silica gel.

Ethyl-N-phenyl-P-ethynyl-phosphonamidate

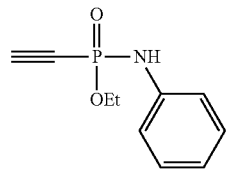

Ethyl N-phenyl-P-ethynyl-phosphonamidate was prepared after "general procedure for the preparation of alkenyl or alkynyl phosphonamidates" on 5 mmol scale from phenyl azide (595 mg, 5 mmol). The crude mixture was purified by silica gel column chromatography eluting with hexane/ethyl acetate. The product was obtained as colourless solid in a yield of 430 mg (2.1 mmol, 42%). $^1H$ NMR (300 MHz, Chloroform-d): δ=7.28 (t, J=7.7 Hz, 2H, ArH), 7.11 (d, J=8.0 Hz, 2H, ArH), 7.02 (t, J=7.3 Hz, 1H, ArH), 6.74 (d, J=7.6 Hz, 1H, NH), 4.55-3.93 (m, 2H, CH$_2$), 2.89 (d, J=12.8 Hz, 1H, CH), 1.39 (t, J=7.0 Hz, 3H, CH$_3$) ppm. $^{13}$C NMR (75 MHz, Chloroform-d): δ=138.99, 129.39, 122.42, 118.23, 118.13, 88.10, 87.45, 76.34 (d, J=273.3 Hz), 62.26 (d, J=5.2 Hz), 16.23 (d, J=7.4 Hz) ppm. $^{31}$P NMR (122 MHz, Chloroform-d): δ=−9.17 ppm. HRMS ESI-TOF m/z [M+H]$^+$=210.0678 (calcd.). 210.0687 (found).

Ethyl-N-benzyl-P-ethynyl-phosphonamidate

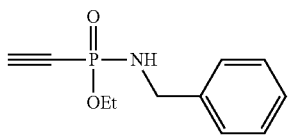

Ethyl N-benzyl-P-ethynyl-phosphonamidate was prepared after "general procedure for the preparation of alkenyl or alkynyl phosphonamidates" from benzyl azide (133 mg, 125 μL, 1 mmol). The crude mixture was purified by silica gel column chromatography eluting with hexane/ethyl acetate. The product was obtained as colourless solid in a yield of 37 mg (0.17 mmol, 17%). $^1$H NMR (300 MHz, Chloroform-d): δ=7.51-7.18 (m, 5H, ArH), 4.26-4.04 (m, 4H, 2×CH$_2$), 3.34 (s, 1H, CH), 2.91 (d, J=12.7 Hz, 1H, NH), 1.34 (t, J=7.1 Hz, 3H, CH$_3$) ppm. $^{13}$C NMR (75 MHz, Chloroform-d): δ=138.99, 138.90, 128.71, 127.62, 127.54, 87.77, 87.16, 76.83 (d, J=260.0 Hz), 62.03 (d, J=5.1 Hz), 44.86, 16.25 (d, J=7.3 Hz) ppm. $^{31}$P NMR (122 MHz, Chloroform-d): 5=−2.76 ppm. HRMS ESI-TOF m/z [M+H]$^+$=224.0835 (calcd.). 224.0835 (found).

Ethyl-N-phenyl-P-vinyl-phosphonamidate

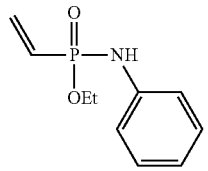

The compound was synthesized according to the general procedure C from 1.15 ml diethyl chlorophosphite (8 mmol). The pure phosphonamidate was purified by flash column chromatography (EtOAc) and obtained as a white solid. (675 mg, 3.20 mmol, 40.0%)

$^1$H NMR (600 MHz, Chloroform-d) δ=7.24 (dd, J=8.5, 7.3, 2H), 7.05-7.01 (m, 2H), 6.99 (d, J=5.8, 1H), 6.94 (tt, J=7.3, 1.1, 1H), 6.33-6.23 (m, 2H), 6.10 (ddd, J=50.3, 9.6, 5.1, 1H), 4.29-4.04 (m, 2H), 1.35 (t, J=7.1, 3H). $^{13}$C NMR (151 MHz, Chloroform-d) δ=140.43, 134.44, 129.28, 127.51 (d, J=172.7), 121.26, 117.31 (d, J=6.6), 60.44 (d, J=6.2), 16.22 (d, J=7.0). $^{31}$P NMR (122 MHz, Chloroform-d) δ=15.68. HRMS for C$_{10}$H$_{15}$NO$_2$P$^-$ [M+H]$^+$ calcd: 212.0835. found: 212.0839.

Ethyl-N-(4-carboxy-phenyl)-P-vinyl-phosphonamidate

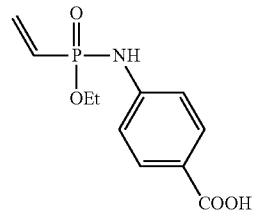 [SMILES: C=CP(=O)(Nc1ccc(C(=O)O)cc1)OCC]

The compound was synthesized according to the general procedure C from 288 μl diethyl chlorophosphite (2 mmol). The pure phosphonamidate was purified by flash column chromatography (CH$_2$Cl$_2$/MeOH, 9:1 to 4:1) and obtained as a white solid. (173 mg, 0.68 mmol, 34.0%) $^1$H NMR (600 MHz, DMSO-d$_6$) δ=8.37 (d, J=7.9, 1H), 7.80 (d, J=8.7, 2H), 7.12 (d, J=8.7, 2H), 6.42-6.04 (m, 3H), 4.11-3.94 (m, 2H), 1.26 (t, J=7.0, 3H). $^{13}$C NMR (151 MHz, DMSO-d$_6$) δ=167.56, 146.36, 135.00, 131.21, 129.04 (d, J=165.8), 123.06, 117.00 (d, J=6.9), 60.84 (d, J=5.7), 16.61 (d, J=6.3). $^{31}$P NMR (122 MHz, DMSO-d$_6$) δ=14.36. HRMS for C$_{11}$H$_{15}$NO$_4$P$^+$ [M+H]$^+$ calcd: 256.0733. found: 256.0723.

Ethyl-N-benzyl-P-vinyl-phosphonamidate

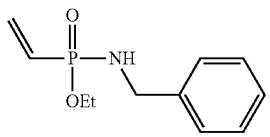

The compound was synthesized according to the general procedure C from 290 μl diethyl chlorophosphite (2 mmol). The pure phosphonamidate was purified by flash column chromatography (EtOAc) and obtained as a colourless oil. (155 mg, 0.69 mmol, 34.3%)

$^1$H NMR (300 MHz, Chloroform-d) δ=7.36-7.21 (m, 5H), 6.33-5.88 (m, 3H), 4.16-3.90 (m, 4H), 3.21 (d, J=8.5, 1H), 1.28 (t, J=7.1, 3H). $^{13}$C NMR (75 MHz, Chloroform-d) δ=139.65 (d, J=5.9), 133.21 (d, J=1.5), 129.45, 128.46, 127.20, 127.17, 60.11 (d, J=5.7), 44.58, 16.27 (d, J=6.7). $^{31}$P NMR (122 MHz, Chloroform-d) δ=20.52. HRMS for C$_{11}$H$_{17}$NO$_2$P$^+$ calcd: 226.0991. found: 226.1003.

Ethyl-N-(2-nitro-Benzyl)-P-vinyl-phosphonamidate

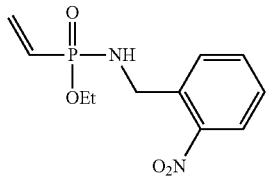 [SMILES: C=CP(=O)(NCc1ccccc1[N+](=O)[O-])OCC]

The compound was synthesized according to the general procedure C from 120 μl diethyl chlorophosphite (0.83 mmol). The pure phosphonamidate was purified by flash column chromatography (2% MeOH in CH$_2$Cl$_2$) and obtained as a brown oil. (125 mg, 0.46 mmol, 55.4%) $^1$H NMR (300 MHz, Chloroform-d) δ=8.03 (d, J=8.1, 1H), 7.73-7.57 (m, 2H), 7.45 (t, J=7.6, 1H), 6.31-5.83 (m, 3H), 4.39 (dd, J=11.2, 7.7, 2H), 4.12-3.85 (m, 2H), 3.65 (q, J=8.6, 1H), 1.26 (t, J=7.1, 3H). $^{13}$C NMR (75 MHz, Chloroform-d) δ=148.09, 135.45 (d, J=4.2), 133.83, 133.52 (d, J=1.6), 131.10, 128.41, 128.26 (d, J=169.7), 124.95, 60.35 (d, J=5.7), 42.42 (d, J=1.3), 16.22 (d, J=6.7). $^{31}$P NMR (122 MHz, Chloroform-d)=20.63. HRMS for $C_{11}H_{16}N_2O_4P^+$ calcd: 271.0842. found: 271.0851.

Ethyl-N-(3-phenyl-propyl)-P-vinyl-phosphonamidate

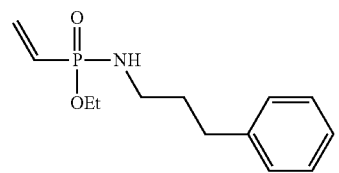 [SMILES: C=CP(=O)(NCCCc1ccccc1)OCC]

The compound was synthesized according to the general procedure C from 290 μl diethyl chlorophosphite (2 mmol). The pure phosphonamidate was purified by flash column chromatography (EtOAc) and obtained as a colourless oil. (165 mg, 0.65 mmol, 32.5%)

$^1$H NMR (300 MHz, Chloroform-d) δ=7.28 (dd, J=8.1, 6.2, 2H), 7.23-7.11 (m, 3H), 6.28-5.89 (m, 3H), 4.04 (qt, J=10.2, 7.2, 2H), 2.92 (dq, J=9.1, 7.0, 2H), 2.84-2.70 (m, 1H), 2.70-2.60 (m, 2H), 1.82 (p, J=7.3, 2H), 1.31 (t, J=7.1, 3H). $^{13}$C NMR (75 MHz, Chloroform-d) δ=141.28, 132.98 (d, J=1.5), 128.42 (d, J=169.0), 128.34, 128.24, 125.88, 59.95 (d, J=5.7), 40.23, 33.53 (d, J=5.6), 32.86, 16.32 (d, J=6.7). $^{31}$P NMR (122 MHz, Chloroform-d) δ=20.82. HRMS for $C_{11}H_{16}N_2O_4P^+$ calcd: 271.0842. found: 271.0851. HRMS for $C_{13}H_{21}NO_2P^+$ calcd: 254.1304. found: 254.1312.

Ethyl-N-cyclohexyl-P-vinyl-phosphonamidate

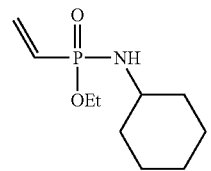

The compound was synthesized according to the general procedure C from 140 μl diethyl chlorophosphite (1 mmol). The pure phosphonamidate was purified by flash column chromatography (1.5% MeOH in $CH_2Cl_2$) and obtained as a colourless oil. (70 mg, 0.32 mmol, 32.2%)

$^1$H NMR (600 MHz, Chloroform-d) δ=6.25-5.93 (m, 3H), 4.14-3.97 (m, 2H), 2.96 (dqd, J=13.8, 9.6, 8.1, 4.2, 1H), 2.51 (t, J=9.6, 2H), 1.97-1.84 (m, 2H), 1.74-1.65 (m, 1H), 1.57 (dt, J=13.0, 3.9, 1H), 1.32 (t, J=7.1, 3H), 1.30-1.09 (m, 5H). $^{13}$C NMR (75 MHz, Chloroform-d) δ=132.56 (d, J=1.8), 129.30 (d, J=168.8), 59.80 (d, J=5.9), 49.71, 36.03, 25.24, 24.96, 16.32 (d, J=6.8). $^{31}$P NMR (122 MHz, Chloroform-d) δ=19.34. HRMS for $C_{10}H_{21}NO_2P^+$ calcd: 218.1304. found: 218.1302.

Staudinger-Induced Thiol-Additions with Alkynyl-Phosphonites:

Synthesis of Diethyl-Alkynyl-Phosphonite and Reaction with Different Azides (Step b)

Diethyl-alkynyl-phosphonite was synthesized according to published protocols (13) and reacted with different aliphatic and aromatic azides (Scheme 3). The formation of the desired alkynyl-phosphonamidates was monitored by $^{31}$P-NMR (see Table 1 for conversions for different azide substrates).

Scheme 3 Staudinger-phosphonite reaction of diethyl-alkynyl phosphonites with R—N$_3$ (R see Table 1)

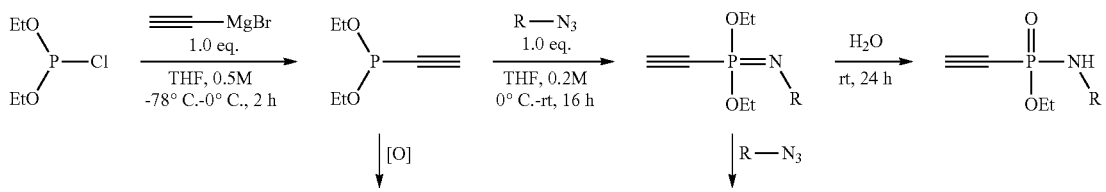

TABLE 1

Substrate scope for the Staudinger phosphonite reaction of diethyl-alkynyl-phosphonite (values in %)

| Entry | R = | alkyne-P(O)(OEt)(NHR) | triazole-P(O)(OEt)(NHR) | EtO-P(O)(OEt)-alkyne |
|---|---|---|---|---|
| 1 | phenyl | 94 | n. d. | n. d. |
| 2 | 4-methoxyphenyl | 91 | n. d. | n. d. |
| 3 | 4-carboxyphenyl | 70 | n. d. | 25 |
| 4 | 4-(methoxycarbonyl)phenyl | 44 | n. d. | n. d. |
| 5 | 3-phenylpropyl | 70 | 4 | 25 |
| 6 | benzyl | 73 | 10 | 14 |
| 7 | 2-nitrobenzyl | 76 | 5 | 18 |
| 8 | 3-methoxybenzyl | 45 | 17 | 28 | n.d. = not detected); determined by $^{31}$P-NMR.

N-phenyl- and N-benzyl-phosphonamidates were isolated by column chromatography in yields of 41% and 17% respectively. The highest conversions were obtained in THF (Table 2).

TABLE 2

Influence of the solvent on the Staudinger phosphonite reaction between diethyl-alkynyl-phosphonite and phenylazide.

| Entry | Solvent | Conversion |
|---|---|---|
| 1 | THF | 94 |
| 2 | THF/DMF | 86 |
| 3 | THF/Acetonitrile | 91 |
| 4 | THF/Toluene | 88 |

General Procedure for Base Mediated Hydrothiolations of Phosphonamidate Alkynes or Alkenes To a capped vial Ethyl N-phenyl-P-ethynyl-phosphonamidate (10 mg, 0.05 mmol) and the respective base (and additive where required) was added. The mixture was suspended in 200 μL of respective solvent. Then ethanethiol (3.1 mg, 3.6 μL, 0.05 mmol) was added via a microliter syringe and the mixture was stirred at room temperature for 3 hours. Afterwards the mixture was diluted with $CH_2Cl_2$ (5 mL) and $H_2O$ (5 mL) was added. After extraction the phases were separated and the aqeuous layer was extracted three times with $CH_2Cl_2$ (5 mL). The combined organic layers were washed two times with $H_2O$ (5 mL) and with brine (5 mL). After removal of the solvent the crude mixture was analyzed by $^1$H NMR and $^{31}$P NMR. The preparation of alkene phosphonamidates is analogous to the preparation of alkyne phosphonamidates.

Ethyl-N-phenyl-P-(2-ethylsulfanyl)-ethenyl-phosphonamidate

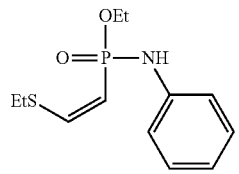

To a capped vial Ethyl N-phenyl-P-ethynyl-phosphonamidate (10 mg, 0.05 mmol) and potassium carbonate (2.8 mg, 0.02 mmol) was added. The mixture was suspended in a 1 to 1 mixture of DMF/H$_2$O (200 µL). Then ethanethiol (3.1 mg, 3.6 µL, 0.05 mmol) was added via a microliter syringe and the mixture was stirred at room temperature for 3 hours. Afterwards the mixture was diluted with CH$_2$Cl$_2$ (5 mL) and H$_2$O (5 mL) was added. After extraction the phases were separated and the aqeuous layer was extracted three times with CH$_2$Cl$_2$ (5 mL). The combined organic layers were washed two times with H$_2$O (5 mL) and with brine (5 mL). After removal of the solvent under reduced pressure the product was obtained in a yield of 12 mg (0.044 mmol, 89%). $^1$H NMR (300 MHz, Chloroform-d): δ=7.45 (dd, J=21.7, 16.7 Hz, 1H, P—CH, E), 7.30-7.17 (m, 3H, ArH), 7.06 (d, J=12.5 Hz, 1H, S—CH, Z), 7.01-6.90 (m, 2H, ArH), 5.75 (dd, J=16.7, 12.5 Hz, 1H, P—CH, Z), 4.35-4.00 (m, 2H, OCH$_2$), 2.75 (q, J=7.5 Hz, 2H, SCH$_2$), 1.36 (t, J=7.0 Hz, 3H, OCH$_2$CH$_3$), 1.28 (t, J=7.5 Hz, 3H, SCH$_2$CH$_3$) ppm. $^{13}$C NMR (75 MHz, Chloroform-d): δ=150.40, 140.11, 129.31, 121.50, 117.47 (d, J=6.4 Hz), 60.61 (d, J=6.0 Hz), 29.59, 25.90, 16.42 (d, J=6.9 Hz), 15.53, 13.75 ppm. $^{31}$P NMR (122 MHz, Chloroform-d) δ 15.13, 14.35 ppm. HRMS ESI-TOF m/z [M+H]$^+$=272.0869 (calcd.). 272.0855 (found).

(Ethyl-N-phenyl-P-ethenyl-phosphonamidate)-S-glutathion Conjugate

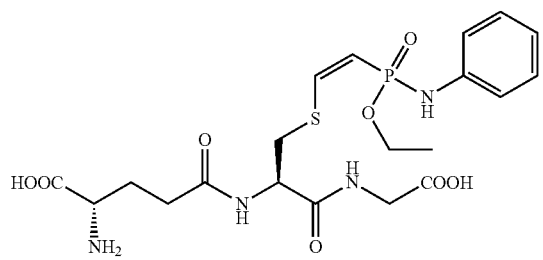 [SMILES: CCOP(=O)(/C=C\SC[C@H](NC(=O)CC[C@H](N)C(=O)O)C(=O)NCC(=O)O)Nc1ccccc1]

To a capped vial Ethyl N-phenyl-P-ethynyl-phosphonamidate (31 mg, 0.15 mmol) and potassium carbonate (7 mg, 0.05 mmol) was added. The mixture was suspended in a 1 to 1 mixture of DMF/H$_2$O (500 µL). Then (2S)-2-amino-4-{[(1R)-1-[(carboxymethyl)carbamoyl]-2-sulfanylethyl]carbamoyl}-butanoic acid (31 mg, 0.1 mmol) was added and the mixture was stirred at room temperature for 3 hours. Afterwards the mixture was diluted with H$_2$O (5 mL) and CH$_2$Cl$_2$ (5 mL) was added. After extraction the phases were separated and the organic layer was extracted three times with H$_2$O (5 mL). The aqueous layers were washed three times with CH$_2$Cl$_2$ (5 mL). Afterwards the solvent was removed under reduced pressure. The crude mixture was purified by preparative HPLC eluting with acetonitrile and ammonium acetate buffer. The product was obtained as ammonium acetate salt in a yield of 35.5 mg (0.061 mmol, 61%). $^1$H NMR (300 MHz, Deuterium Oxide): δ=7.37 (d, J=12.6 Hz, 1H, S—CH, Z), 7.21 (t, J=7.9 Hz, 2H, ArH), 6.94 (dd, J=7.8, 5.3 Hz, 3H, ArH), 5.77 (dd, J=17.5, 12.2 Hz, 1H, PCH, Z), 4.45 (ddd, J=12.8, 8.3, 5.2 Hz, 1H), 4.01 (q, J=7.4 Hz, 2H, CH$_2$), 3.84-3.52 (m, 2H, CH$_2$), 3.21 (dd, J=14.7, 5.1 Hz, 1H, CH), 3.02 (dd, J=14.6, 8.5 Hz, 1H, CH), 2.45-2.20 (m, 2H, CH$_2$), 1.96 (q, J=7.2 Hz, 2H, CH$_2$), 1.19 (t, J=7.1 Hz, 3H, CH$_3$) ppm. $^{13}$C NMR: (75 MHz, Deuterium Oxide) δ=174.66, 174.45, 173.59, 171.25, 171.19, 151.73, 139.17, 129.38, 122.06, 117.75 (d, J=6.8 Hz), 86.89, 86.83, 86.72, 62.14, 53.76 (d, J=12.1 Hz), 42.35, 35.94, 31.18, 25.92, 15.41 ppm. $^{31}$P NMR: (122 MHz, Deuterium Oxide) δ=18.96, 18.11 (d, J=4.2 Hz) ppm. HRMS ESI-TOF m/z [M+H]$^+$=517.1516 (calcd.). 517.1526 (found).

Thiol-Addition of Ethanethiol and Glutathione to Alkynyl-Phosphonamidate

Ethanethiol was chosen as aliphatic model substrate. All experiments were conducted for 3 hours at room temperature in 0.1 mmol scale using 400 µL of the solvent. Conversions and diastereoselectivities were determined by $^{31}$P-NMR and $^1$H-NMR (Scheme 4).

Scheme 4 Model reaction for the screening of reaction conditions

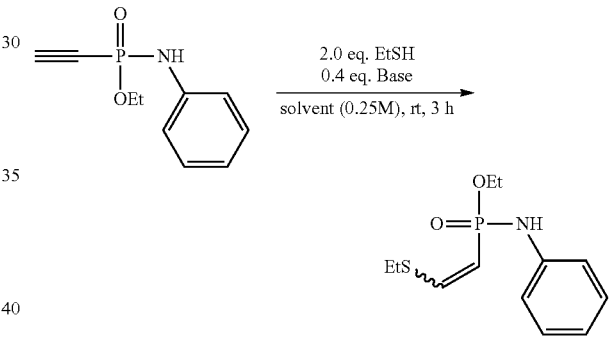

First experiments confirmed the formation of both the E- and the Z-conformational isomer. The vicinal H—H coupling constant of 12.5 Hz of the major diastereomer and 21.7 Hz of the minor diastereomer in the $^1$H NMR of the diastereomeric mixture indicates that the Z-isomer is the major product for all the reaction conditions (see Table 3).

TABLE 3

Screening of solvents for the base mediated hydrothiolation of electron-deficient alkynyl phosphonamidates.

| Entry | Solvent | Base | Conversion | E/Z |
|---|---|---|---|---|
| 1 | CH$_2$Cl$_2$ | K$_2$CO$_3$ | 100% | 1:99 |
| 2 | EtOH | K$_2$CO$_3$ | 100% | 2:98 |
| 3 | DMF/H$_2$O (1:1) | K$_2$CO$_3$ | 100% | 2:98 |
| 4 | THF | K$_2$CO$_3$ | 100% | 2:98 |
| 5 | DMF | K$_2$CO$_3$ | 100% | 5:95 |
| 6 | DMSO | K$_2$CO$_3$ | 100% | 12:88 |

The influence of the solvent to the thiol-addition was then further investigated revealing quantitative formation of the thiol adduct for every tested solvent. Full conversion was achieved in all of the tested solvents. DMSO showed the lowest diastereoselectivity (12% E-product). Therefore the influence of the base was than further investigated in DMSO and in DMF/H$_2$O (1:1) (Table 4).

TABLE 4

Screening of bases for the hydrothiolation of electron-deficient alkynyl phosphonamidates in DMSO and DMF/H$_2$O (1:1).

| Entry | Base | DMSO | | DMF/H$_2$O | |
|---|---|---|---|---|---|
| | | Conversion | E/Z | Conversion | E/Z |
| 1 | Et$_3$N | 5% | —/— | 36% | 3:97 |
| 2 | (NH$_4$)$_2$CO$_3$ | 100% | 4:96 | 100% | 2:98 |
| 3 | Na$_2$CO$_3$ | 100% | 6:94 | 100% | 1:99 |
| 4 | Rb$_2$CO$_3$ | 100% | 8:92 | 100% | 2:98 |
| 5 | K$_2$CO$_3$ | 100% | 12:88 | 100% | 2:98 |
| 6 | Cs$_2$CO$_3$ | 100% | 17:83 | 100% | 2:98 |

It turned out that the diastereoselectivity of the reaction in DMSO is dependent of the applied base. In contrast to this, reactions in aqueous systems always delivered the Z-alkene as the major product.

In conclusion it was possible to optimize the reaction conditions of the model reactions. The reaction can be applied in aqueous solvent systems and quantitative conversions can be achieved at room temperature after 3 hours using mild carbonate bases. No side reactions were observed.

In the next step these optimized reaction conditions were now applied to synthesize a water soluble glutathion phosphonamidate conjugate (Scheme 5).

Scheme 5 Synthesis of glutathion-phosphonamidate conjugate

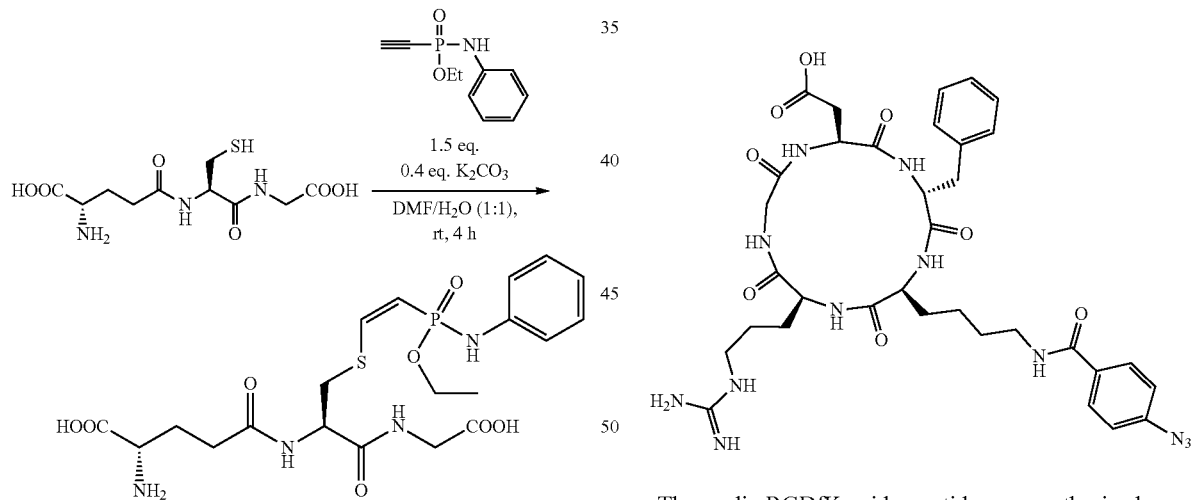

Figure 1:
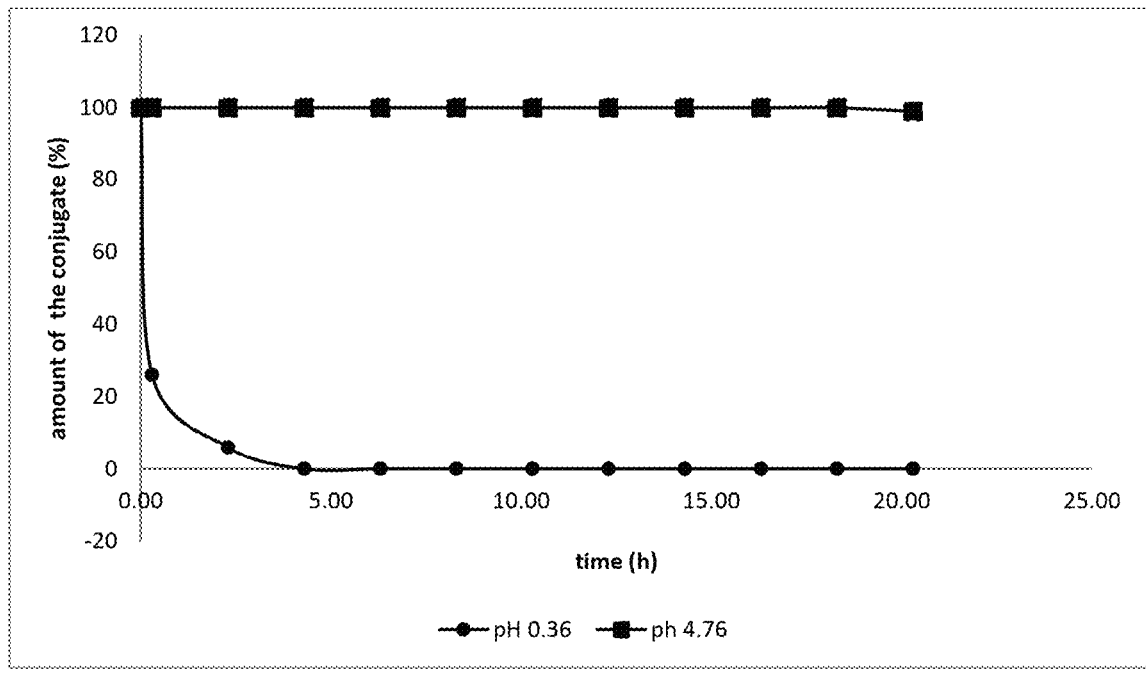
FIG. 1 shows the hydrolytic decay of a glutathion-phosphonamidate conjugate according to Scheme 5 under acidic conditions.

The conjugate could be isolated by semipreparative HPLC under basic conditions as a diastereomeric mixture in a yield of 61%. Having reasonable quantities of this water soluble phosphonamidate-conjugate in hand, studies could be performed in order to determine the hydrolytic properties of the phosphorus-nitrogen bond. For these studies a 3 µM solution of conjugate and the standard tetramethylphosphonium bromide (1.2 µM) in aqeuous buffer was prepared and the hydrolysis of the phosphonamidate was characterized by monitoring the decay of the conjugate against the standard by means of $^{31}$P NMR over 24 hours. The results are shown in FIG. 1 which shows the hydrolytic decay of the GSH-phosphonamidate conjugate under acidic conditions.

Under strong acidic conditions (1 M HCL, pH 0.36) the phosphonamidate showed rapid decomposition, which is represented by the lower curve (circles). For slight acidic conditions (150 mM NH$_4$OAc-buffer, pH=4.76), as depicted in the blue curve the compound was stable over the duration of the measurement (squares).

Figure 2:
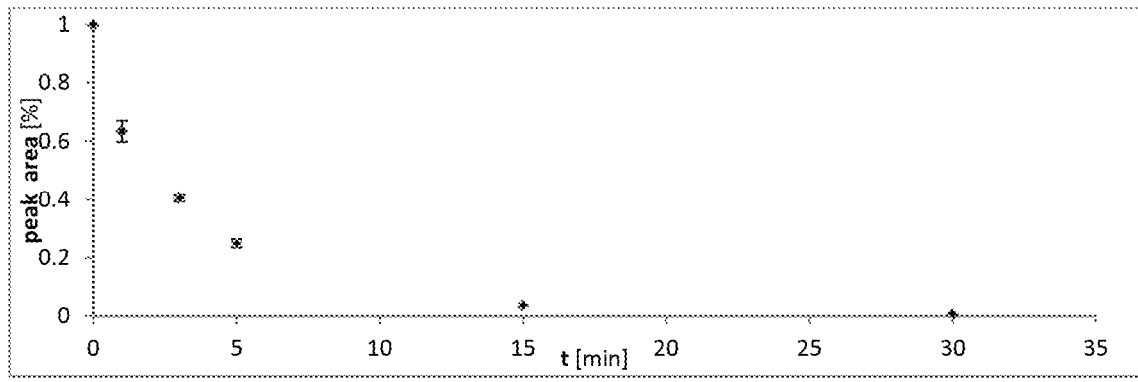
FIG. 2 shows the conversion of an alkynylphosphonamidate to the thiol adduct, determined by HPLC.

The rate of the reaction was determined by HPLC. Glutathione was added to a solution of ethyl-N-phenyl alkynyl phosphonamidate in aqueous buffer at slightly basic pH. The reaction was stopped after several time points by the addition of an acidic buffer and analyzed by HPLC-UV, referring to inosine as an internal standard. FIG. 2 refers to the consumption of ethyl-N-phenyl alkynyl phosphonamidate in the reaction with glutathione at pH 8.5. HPLC UV traces were taken at different time points. Experiment was performed in triplicate.

As FIG. 2 shows, we achieve a very fast conversion of more than 95% of the alkynyl phosphonamidate starting material after 15 min at pH 8.5.

Staudinger-Induced Thiol-Addition of RGD Peptides to GFP

In a next proof of principle study we synthesized an azido-containing cyclic RGD peptide (c(RGDfK)), which is known to bind to overexpressed integrins in cancer cells. This cyclic azido-peptide was reacted with the bisethoxy-alkyne-phosphonite to form the highly reactive phosphonamidate in 53% isolated yield after HPLC with no observed by-product formation (Scheme 6, which is depicted in FIG. 40).

Scheme 6, which is depicted in FIG. 40, shows the Staudinger-induced thiol-addition of cyclic azido-RGD-peptides to GSH.

Synthesis of c(RGDfK)-Azide

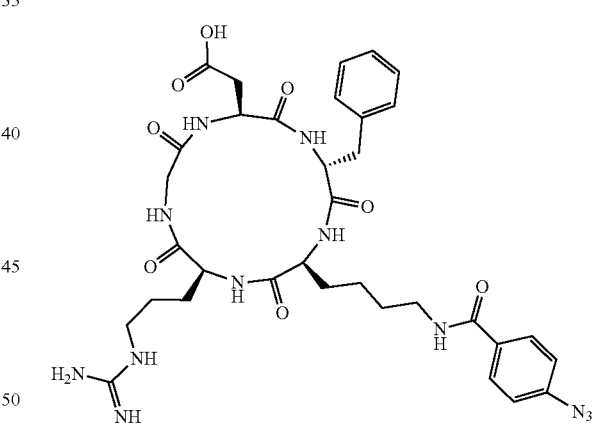

The cyclic RGDfK-azido peptide was synthesized manually on a NovaSynTGT alcohol resin with a loading of 0.26 mmol/g. First the resin was activated by stirring 480.7 mg resin in 2.5 ml toluene and 480 µl acetylchloride at 60° C. for three hours. Double coupling of Fmoc-Asp(OAII)—OH (123.56 mg, 0.3125 mmol, 2.5 eq) was performed in DCM using DIPEA (212.6 µl, 1.25 mmol, 10 eq.) as activating base each for one hour. Further amino acid couplings were performed by mixing amino acid (0.25 mmol, 2 eq.), HATU (0.25 mmol, 2 eq.) and DIPEA (0.5 mmol, 4 eq.) in DMF and coupling once for 30 minutes and once for one hour. Fmoc deprotection was accomplished with 20% piperidine in DMF. After the final amino acid coupling the alloc deprotection was achieved by treating the resin with Pd(P(Ph$_3$)$_4$) (433 mg, 0.375 mmol, 3 eq.) in chloroform/acetic acid/

NMM (37:2:1;v:v:v) for two hours in an argon atmosphere, followed by Fmoc deprotection and cyclisation with HATU (0.25 mmol, 2 eq.) and DIPEA (0.5 mmol, 4 eq.) in DMF for 16 hours. To be abled to install the aromatic azide on the lysine residue Fmoc-Lys(dde)-OH was used in the solid phase synthesis and was orthogonally deprotected on resin using 2% hydrazine in DMF three times for three minutes, followed by coupling of 4-azidobenzoic acid (81.65 mg, 0.5 mmol, 4 eq.) with HATU (190 mg, 0.5 mmol, 4 eq.) and DIPEA (1 mmol, 8 eq.) in DMF for two hours. Cleavage from the resin was performed using TFA/DCM (75:25; v:v) for 2.5 hours. Precipitation was carried out in cold and dry ether. The crude was analyzed by UPLC-MS and either used as crude in the following staudinger reaction or purified by preparative reverse phase C18 HPLC (0-5 min 95/5, water (0.1% TFA)/MeCN (0.1% TFA); 5-60 min 10/90, water (0.1% TFA)/MeCN (0.1% TFA)). The product was gained as white powder (8.0 mg, 11.0 μmol, 8.5% yield) and was analyzed by analytical UPLC (5 to 95% of acetonitrile in water containing 0.1% TFA on a RP-C18 column). The UPLC chromatogram of the c(RGDfK)-azide is shown in FIG. 7. LRMS: m/z: 749.67 [M+H]$^+$ (calcd. m/z: 749.3485).

Synthesis of c(RGDfK)-Phosphonamidate Alkyne

Bisethoxyalkyne-Phosphonite Synthesis

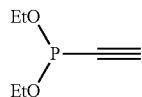

Ethynyl magnesium bromide in THF (5 M, 2 ml, 1 mmol, 1 eq.) was cooled to −78° C. in a flame dried schlenk flask and diethylchlorophosphite (0.143 ml, 1 mmol, 1 eq.) was added. The solution was stirred for 10 minutes at −78° C. and let warm to room temperature and stirred for another 90 minutes. The full consumption of starting material was checked by $^{31}$P-NMR (product at 126.73 ppm; see FIG. 6: Crude Bisethoxyalkyne-phosphonite synthesis to FIG. 9) and used as crude in the following staudinger reaction with azido-c(RGDfK).

Staudinger Reaction on c(RGDfK)-Azide

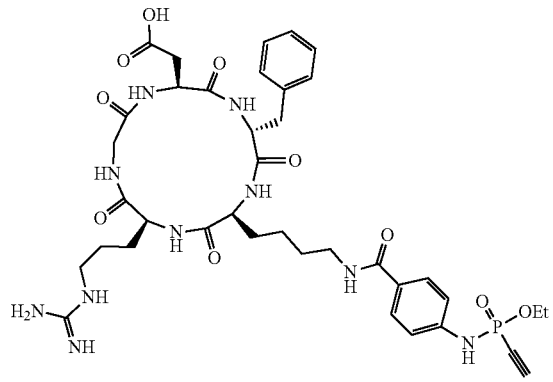 [SMILES: C#CP(=O)(Nc1ccc(C(=O)NCCCC[C@@H]2NC(=O)[C@@H](Cc3ccccc3)NC(=O)[C@H](CC(=O)O)NC(=O)CNC(=O)[C@H](CCCNC(=N)N)NC2=O)cc1)OCC]

When crude peptide was used it (66 mg, 88.2 μmol, 1 eq.) was dissolved in DMSO (4 ml, 22 mM) and dried in a flame dried flask for one hour prior to adding bisethoxyalkyne-phosphonite (volume according to percentage of product determined by NMR, 132.3 μmol, 1.5 eq.). After the reaction mixture was stirred over night at room temperature 4 ml of water were added and stirred for 6 hours, before lyophiliza-tion. The crude product was purified by semi-preparative reverse phase C18 HPLC (0-5 min 95/5, water (0.1% TFA)/MeCN (0.1% TFA); 5-60 min 10/90, water (0.1% TFA)/MeCN (0.1% TFA)) and gave the product as a white powder (6.2 mg, 6.64 μmol, 5.3% overall yield).

Using the purified c(RGDfK)-azido peptide (6.9 mg, 9.14 μmol, 1 eq.) it was dissolved in DMSO (1.5 ml, 6 mM) and dried in a flame dried flask for one hour prior to adding bisethoxyalkyne-phosphonite (volume according to percentage of product determined by NMR, 36.56 μmol, 4 eq.). After the reaction mixture was stirred over night at room temperature 1.5 ml water was added and stirred again for six hours before lyophilization. The crude product was purified by semi-preparative reverse phase C18 HPLC (0-5 min 95/5, water (0.1% TFA)/MeCN (0.1% TFA); 5-60 min 10/90, water (0.1% TFA)/MeCN (0.1% TFA)) and gave the product as a white powder (4.1 mg, 4.89 μmol, 53.5% yield).

The final product was analyzed by LC-UV: rt. 5.0 min (0-1 min 95/5, water (0.1% TFA)/MeCN (0.1% TFA); 1-16.5 min 5/95, water (0.1% TFA)/MeCN (0.1% TFA) on RP-C18 column) and mass. The chromatogram of the c(RGDfK)-alkyne is shown in FIG. 8. HRMS: m/z: 839.3636 [M+H]$^-$ (calcd. m/z: 839.3606).

Hydrothiolations of Electron-Deficient c(RGDfK)-Phosphonamidate Alkyne

Model Reaction with Glutathione

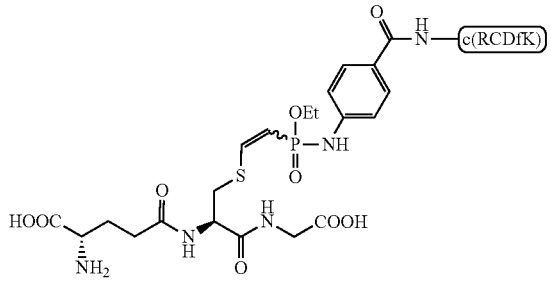

Glutathione (1 mg, 3.25 μmol, 1 eq.) and c(RGDfK)-phosphonamidate alkyne (1.24 mg, 3.25 μmol, 1 eq.) were mixed in 135 μl 10 mM ammoniumbicarbonate buffer pH 9.2 and 15 μl acetonitrile (c=21.6 mM). After 10 minutes of shaking quantitative conversion to the addition product was observed by LC-UV/MS.

The final product was analyzed by LC-UV: rt. 4.3/4.4 min (0-1 min 95/5, water (0.1% TFA)/MeCN (0.1% TFA); 1-16.5 min 5/95, water (0.1% TFA)/MeCN (0.1% TFA) on RP-C18 column) HRMS: m/z: 1146.4451 [M+H]$^+$ (calcd. m/z: 1146.4444), 573.7321 [M+2H]2+ (calcd. m/z: 573.7262).

Figure 3:
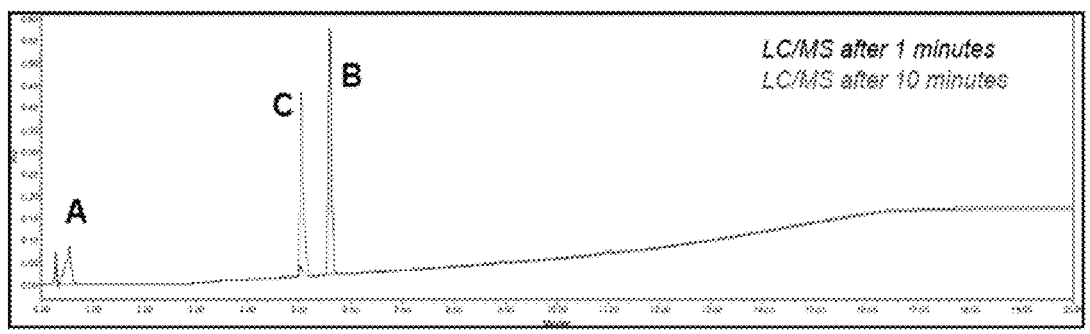
FIG. 3 shows a LC/MS analysis of the addition of glutathione (GSH) to cyclic c(RGDfK)-phosphonamidate alkyne

As a first test substrate for the reaction with thiols, we used glutathione (GSH) and found a fast and high yielding addition of the thiol to the phosphonamidate-alkyne in nearly quantitative conversions after 10 minutes under slightly basic conditions at pH 8.8 at room temperature (FIG. 3: Staudinger-induced thiol-addition of cyclic azido-RGD-peptides to GSH).

On this model addition product we conducted stability studies at different pH and under the addition of thiols like MesNa and DTT at neutral and basic pH. It could have been shown that the formed product is stable in a broad pH range from pH 2.3 until pH 9.0 (FIG. 4: pH stability of c(RGDfK)-Glutathion).

Also the product is stable towards high concentration (0.2 M, 100 eq.) of DTT and MesNa at physiological pH (PBS buffer; pH 7.4). At pH 9.0 MesNa is slowly adding to the formed double bond (10% addition product formed after four days). In contrast to that DTT is rapidly forming an addition product with (42% after 30 hours) and followed by degradation over time.

Staudinger-Induced Thiol-Addition of GFP Protein

In the next step we probed the Staudinger-induced conjugation reaction with a Cys-containing model protein. Here we used a mutated eGFP bearing only one addressable cysteine for the thiol conjugation to the cyclic RGD-phosphonamidate.

Reaction with GFP C70M S147C

GFP C70M S147C (3.13 nmol, 1 eq) was rebuffered to 100 μl 10 mM Ammoniumbicarbonte pH 8.4 and c(RGDfK)-phosphonamidate alkyne (0.08 mg, 93.9 nmol, 30 eq.) was added. The reaction mixture was shaken at 37° C. and 800 rpm for three hours. Finally the mixture was spin filtrated using Amicon Spin filters with a 10 kDa MWCO. After spin filtrating the sample ten times at 14000 rpm for 5 minutes and adding fresh 10 mM Ammoniumbicarbonate buffer MALDI-TOF analysis was conducted and verified total conversion of GFP C70M S147C to the desired product. The structure of the product is shown in FIG. 30.

MALDI TOF: expected (in Da): 28605.31 (M+H$^+$), 14303.16 (M+2H$^+$). found (in Da): 28608.46 (M+H$^+$), 14294.46 (M+2H$^+$).

With this approach we could validate the feasibility of this reaction on the protein level at a concentration of 31 μM, in which the conjugate was formed again in virtually quantitative conversions, as verified by MALDI-MS analysis and MS/MS analysis of the digested protein conjugate (FIG. 5: Staudinger-induced thiol-addition to thiol-containing eGFP.).

Stability Studies for c(RGDfK)-Glutathion c(RGDfK)-glutathion was solved at a concentration of 2 mM in different solvents (0.1 M HCl at pH 1; 30% acetonitrile in water containing 0.1% TFA with a pH of 2.3; PBS buffer rat pH 7.4; ammonium acetate buffer rat pH 9.0; 0.05 M NaOH at pH 12) and 0.5 mM of Inosine was added as internal standard. The stability of the starting material was then monitored over three days.

The stability studies in presence of a competing thiol c(RGDfK)-glutathion was solved in either PBS or 1 M Tris HCl pH 9.0 at a concentration of 2 mM and 10 eq. DTT or MesNa was added.

The Mixture was Monitored Over Several Days.

Antibody conjugation with alkyne phosphonamidates First experiments were conducted with Cetuximab, a monoclonal IgG1 antibody against human epidermal growth factor. The antibody was modified with a biotin phosphonamidate and analyzed by SDS-PAGE under non reducing conditions, followed by anti-biotin western blotting (Scheme 7, which is depicted in FIG. 41).

Scheme 7, which is depicted in FIG. 41, shows the two-step reduction and alkylation approach for cysteine selective antibody modification with a biotin modified alkynyl phosphonamidate.

The intact antibody was reduced by incubation with DTT in 50 mM borate containing PBS (pH 8.0) at 37° C. Excess of DTT was removed after the reaction by size exclusion columns and the reduced antibody fragments were incubated with a biotin phosphonamidate (1.1 equivalents per thiol) in 50 mM ammonium bicarbonate buffer (pH 8.5). EDTA (1 mM) was added to the reaction mixture to complex heavy metal ions that promote disulfide formation.

Western blot analysis confirmed modification of the antibody fragments, even though the intact antibody is not formed back by reoxidation of the remaining cysteines. This could be explained by a high degree of modification. No modification could be detected without prior reduction of the disulfide bonds. Thus further confirming the high selectivity of these compounds for free cysteine residues. Further experiments will include the determination of the degree of modification and experiments that prove the functionality of the modified antibody (see FIG. 10: Western blot analysis after non reducing SDS-PAGE. SM: Cetuximab starting material. 1: 5 min, 2: 1 h, 3: 2 h, 4: 20 h incubation with a biotin modified phosphonamidate. Reaction with (left) and without (right) prior reduction of the disulfides).

Cysteine selective modification was further confirmed by tryptic digest of the cetuximab phosphonamidate conjugates, followed by MS/MS analysis. To simplify the MS/MS spectra, the modification was conducted under previously described conditions with the structurally simpler ethyl-N-phenyl alkynyl phosphonamidate. Modification of Cys 263 of the heavy chain and Cys 214 of the light chain could be confirmed by MS/MS (HCD fragmentation) while no modification was detected without prior reduction of the disulfide bonds.

Staudinger-Induced Thiol-Additions with Vinyl Phosphonites:

a) Synthesis of Various Borane Protected Vinyl Phosphonites

Diethyl vinylphosphonite was synthesized based on previously published protocols by alkylation of diethyl chlorophosphite with vinylmagnesium bromide and subsequent borane addition (13) (Scheme 8). The desired phosphonite was isolated in 37% yield.

Scheme 8 Synthesis of borane protected diethyl vinyl phosphonite

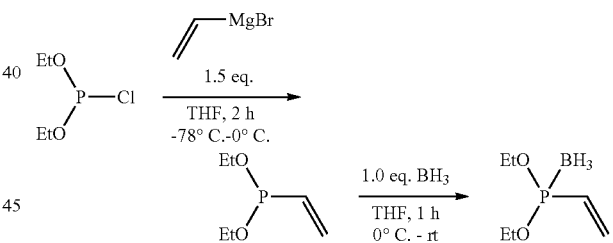

Vinylphosphonites with different O-substituents were synthesized starting from phosphorous trichloride by substitution of two chlorides with the corresponding alcohols in the presence of pyridine. The formed mono chloro phosphite was reacted with the vinyl Grignard reagent and protected with borane. All these steps were performed in a one-pot strategy.

Scheme 9
Synthesis of various borane protected diethyl vinyl phosphonites from PCl$_3$ with isolated yields.

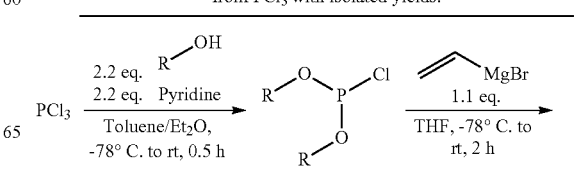

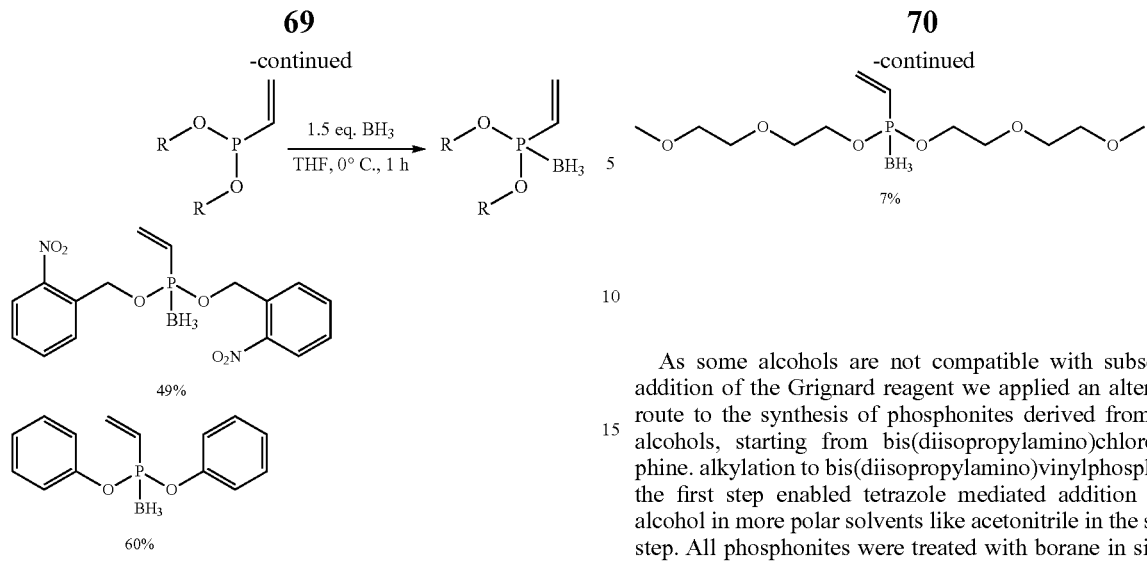

As some alcohols are not compatible with subsequent addition of the Grignard reagent we applied an alternative route to the synthesis of phosphonites derived from these alcohols, starting from bis(diisopropylamino)chlorophosphine. alkylation to bis(diisopropylamino)vinylphosphine in the first step enabled tetrazole mediated addition of the alcohol in more polar solvents like acetonitrile in the second step. All phosphonites were treated with borane in situ and isolated by flash chromatography.

Scheme 10
Synthesis of various borane protected vinyl phosphonites from bis(diisopropylamino) chloro phposphine with isolated yields.

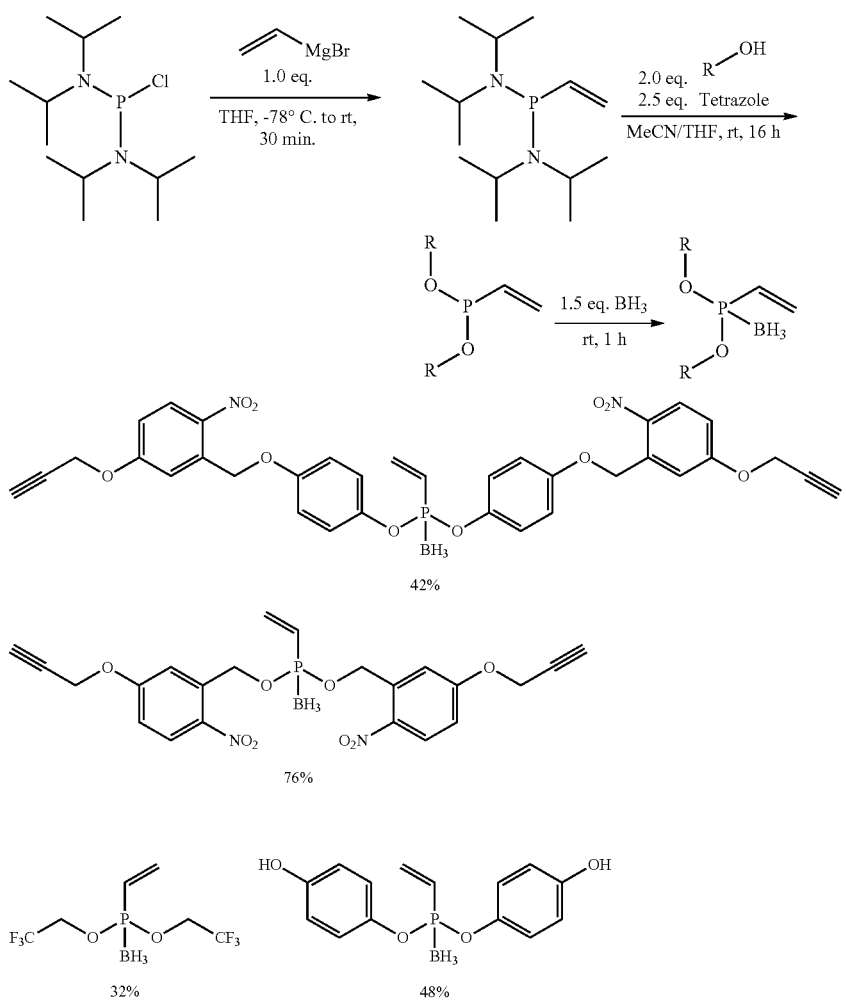

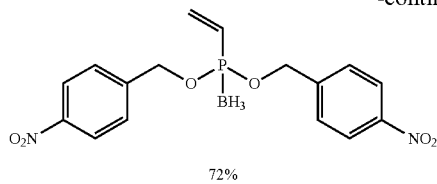

72%

Experimental Part for IIa)
Diethyl Vinylphosphonite Borane

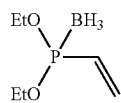

A 25-ml Schlenk flask was charged with 2.14 ml vinylmagnesium bromide (0.7 M in THF, 1.50 mmol, 1.5 eq.) under an argon atmosphere, cooled to −78° C. and 140 µl diethyl chlorophosphite (1.00 mmol, 1.0 eq.) were added drop wise. The yellowish solution was allowed to warm to 0° C., stirred for another two hours and 1.00 ml of Borane (1.0 M in THF, 1.00 mmol, 1.0 eq.) were added and stirred for one more hour at 0° C. The organic solvents were removed under reduced pressure and the crude product was purified by flash column chromatography on silica gel (Hexane/EtOAc, 9:1) to yield the desired compound as colourless oil. (60 mg, 0.37 mmol, 37.0%)

$^1$H NMR (300 MHz, Chloroform-d) δ=6.36-6.03 (m, 3H), 4.19-3.96 (m, 4H), 1.33 (t, J=7.1, 6H), 0.55 (ddd, J=190.3, 94.1, 16.6, 3H). $^{13}$C NMR (75 MHz, Chloroform-d) δ=134.62 (d, J=8.7), 130.12 (d, J=75.0), 63.16 (d, J=4.8), 16.59 (d, J=5.6). $^{31}$P NMR (122 MHz, Chloroform-d) δ=129.58 (dd, J=167.1, 82.6).

NMR data is in accordance with those reported in the literature.[18]

Di(2-Nitrobenzyl) vinylphosphonite borane

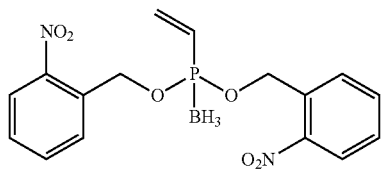

The compound was synthesized according to the general procedure A from PCl$_3$ (260 µl, 3.00 mmol). The pure borane protected phosphonite was purified by flash column chromatography (Hexane/EtOAc, 4:1) and obtained as a yellowish solid. (555 mg, 1.48 mmol, 49.2%)

$^1$H NMR (300 MHz, Chloroform-d) δ=8.10 (d, J=8.2, 2H), 7.77-7.63 (m, 4H), 7.57-7.44 (m, 2H), 6.51-6.18 (m, 3H), 5.45 (qd, J=14.8, 7.5, 4H), 1.42--0.02 (m, 3H). $^{13}$C NMR (75 MHz, Chloroform-d) δ=146.80, 136.84 (d, J=10.2), 132.52 (d, J=6.8), 129.10, 129.05, 128.67, 128.61 (d, J=74.3), 125.09, 65.56 (d, J=3.6). $^{31}$P NMR (122 MHz, Chloroform-d) δ=136.23 (dd, J=151.3, 56.0). HRMS for C$_{16}$H$_{18}$BN$_2$NaO$_6$P$^+$ [M+Na]$^+$ calcd: 399.0888. found: 399.0885.

Di(2-(2-methoxyethoxy)ethyl) vinylphosphonite borane

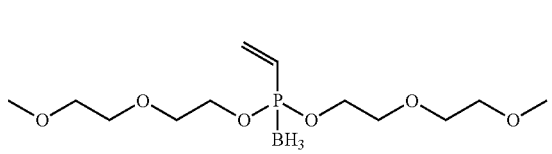

The compound was synthesized according to the general procedure A from PCl$_3$ (130 µl, 1.50 mmol). The pure borane protected phosphonite was purified by flash column chromatography (CH$_2$Cl$_2$/MeOH, 19:1 to 9:1) and obtained as a colourless oil. (34 mg, 0.11 mmol, 7.3%)

$^1$H NMR (300 MHz, Chloroform-d) δ=6.37-6.00 (m, 3H), 4.16 (dq, J=7.6, 4.9, 4H), 3.70 (t, J=4.8, 4H), 3.64 (dd, J=5.8, 3.3, 4H), 3.54 (dd, J=5.9, 3.3, 4H), 3.38 (s, 6H), 1.14--0.12 (m, 3H). $^{13}$C NMR (75 MHz, Chloroform-d) δ=135.00 (d, J=8.9), 129.51 (d, J=75.7), 71.79, 70.47, 70.21 (d, J=6.0), 65.92 (d, J=5.2), 58.95. $^{31}$P NMR (122 MHz, Chloroform-d) δ=133.77-130.56 (m).

Diphenyl Vinylphosphonite Borane

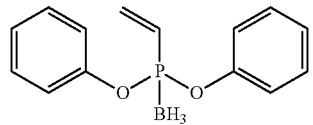

The compound was synthesized according to the general procedure A from PCl$_3$ (393 µl, 4.50 mmol). The pure borane protected phosphonite was purified by flash column chromatography (Hexane/EtOAc, 4:1) and obtained as a colourless oil. (700 mg, 2.71 mmol, 60.3%)

$^1$H NMR (300 MHz, Chloroform-d) δ=7.39 (td, J=7.7, 5.5, 4H), 7.30-7.17 (m, 6H), 6.67-6.18 (m, 3H), 1.48-0.01 (m, 3H). $^{13}$C NMR (75 MHz, Chloroform-d) δ=151.27 (d, J=8.7), 137.01 (d, J=12.5), 129.70 (d, J=1.0), 129.05 (d, J=71.1), 125.35 (d, J=1.3), 120.90 (d, J=4.2). $^{31}$P NMR (122 MHz, Chloroform-d) δ=134.08-130.87 (m). HRMS for C$_{14}$H$_{16}$BNaO$_2$P$^+$ [M+Na]$^+$ calcd: 281.0873. found: 281.0873.

Bis(4-(2-nitro-5-(oxypropargyl)benzyloxy)phenyl) vinyl phosphonite borane

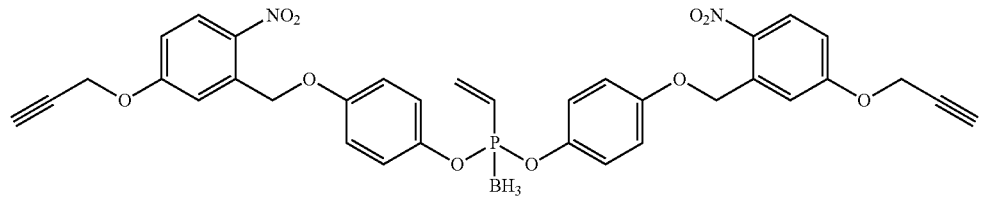

The compound was synthesized according to the general procedure B from Bis(diisopropylamino)chlorophosphine (71 mg, 0.27 mmol). The pure borane protected phosphonite was purified by flash column chromatography (Hexane/CH$_2$Cl$_2$, 1:1) and obtained as a yellowish solid. (75 mg, 0.11 mmol, 41.9%) $^1$H NMR (300 MHz, Chloroform-d) δ=8.25 (d, J=9.1, 2H), 7.47 (d, J=2.8, 2H), 7.17-6.87 (m, 1 OH), 6.62-6.14 (m, 3H), 5.48 (s, 4H), 4.78 (d, J=2.4, 4H), 2.55 (t, J=2.4, 2H), 1.51--0.24 (m, 3H). $^{13}$C NMR (75 MHz, Chloroform-d) δ=161.89, 155.27 (d, J=1.3), 145.34 (d, J=8.4), 140.04, 137.08 (d, J=12.6), 136.97, 129.06 (d, J=71.3), 127.77, 121.93 (d, J=4.0), 115.74 (d, J=1.1), 113.85, 113.79, 76.89, 76.89, 67.37, 56.24. $^{31}$P NMR (122 MHz, Chloroform-d) δ=136.36-131.69 (m). HRMS for C$_{34}$H$_{30}$BN$_2$NaO$_{10}$P$^+$ [M+Na]$^+$ calcd: 691.1623. found: 691.1629.

Bis(2-nitro-5-(oxypropargyl)benzyl) vinyl phosphonite borane

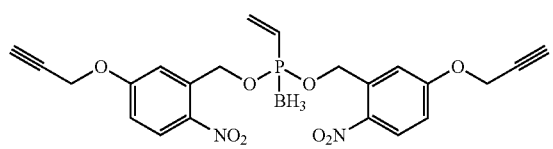

The compound was synthesized according to the general procedure B from Bis(diisopropylamino)chlorophosphine (513 mg, 1.92 mmol). The pure borane protected phosphonite was purified by flash column chromatography (Hexane/CH$_2$Cl$_2$, 4:1) and obtained as a yellowish solid. (704 mg, 1.45 mmol, 75.6%)

$^1$H NMR (300 MHz, Chloroform-d) δ=8.19 (d, J=9.1, 2H), 7.31 (d, J=2.8, 2H), 7.00 (dd, J=9.2, 2.8, 2H), 6.58-6.22 (m, 3H), 5.49 (qd, J=15.5, 7.4, 4H), 4.81 (d, J=2.4, 4H), 2.62 (t, J=2.4, 2H), 1.31-0.12 (m, 3H). $^{13}$C NMR (75 MHz, Chloroform-d) δ=161.86, 139.86, 136.92 (d, J=10.4), 135.78 (d, J=6.8), 128.43 (d, J=73.2), 127.79, 114.10, 113.92, 76.95, 76.89, 65.54 (d, J=3.6), 56.31. $^{31}$P NMR (122 MHz, Chloroform-d) δ=136.32 (d, J=107.0). HRMS for C$_{22}$H$_{22}$BN$_2$NaO$_8$P$^+$ calcd: 507.1099. found: 507.1111.

Bis(2,2,2-trifluoroethyl) vinyl phosphonite borane

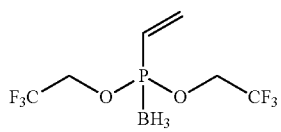

The compound was synthesized according to the general procedure B from Bis(diisopropylamino)chlorophosphine (266 mg, 1.00 mmol). The pure borane protected phosphonite was purified by flash column chromatography (Hexane/CH$_2$Cl$_2$, 9:1 to 4:1) and obtained as a colourless liquid. (87 mg, 0.32 mmol, 32.2%)

$^1$H NMR (300 MHz, Chloroform-d) δ=6.52-6.11 (m, 3H), 4.36 (p, J=8.1, 4H), 0.62 (ddd, J=203.0, 103.5, 15.0, 3H). $^{13}$C NMR (75 MHz, Chloroform-d) δ=137.57, 127.48 (d, J=79.1), 122.37 (qd, J=276.0, 7.5), 63.60 (qd, J=37.7, 2.5). $^{19}$F NMR (282 MHz, Chloroform-d) δ=2.13. $^{31}$P NMR (122 MHz, Chloroform-d) δ=145.49 (dd, J=135.6, 65.1).

Bis-(4-Hydroxyphenyl) vinyl phosphonite borane

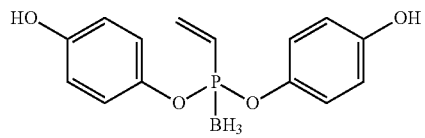

The compound was synthesized according to the general procedure B from Bis(diisopropylamino)chlorophosphine (534 mg, 2.00 mmol) and Hydrochinon (2.20 g, 10 eq.).

The pure borane protected phosphonite was purified by flash column chromatography (Hexane/EtOAc, 4:1 to 1:1) and obtained as a colourless solid. (280 mg, 0.96 mmol, 48.3%) $^1$H NMR (300 MHz, DMSO-d$_6$) δ=9.49 (s, 2H), 6.96 (d, J=8.5, 4H), 6.74 (d, J=8.9, 4H), 6.63-6.22 (m, 3H), 1.20--0.12 (m, 3H). $^{31}$P NMR (122 MHz, DMSO-d$_6$) δ=131.80. HRMS for C$_{14}$H$_{16}$BNaO$_4$P$^+$ calcd: 313.0771. found: 313.0774.

Di(4-nitrobenzyl) vinylphosphonite borane

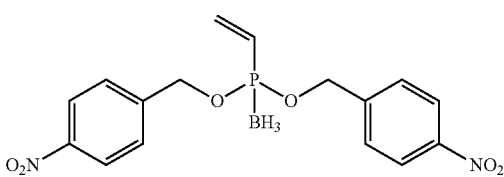

The compound was synthesized according to the general procedure B from Bis(diisopropylamino)chlorophosphine (533 mg, 2.00 mmol). The pure borane protected phosphonite was purified by flash column chromatography (Hexane/CH$_2$Cl$_2$, 9:1 to 4:1) and obtained as a white solid. (540 mg, 1.44 mmol, 71.8%)

$^1$H NMR (300 MHz, Chloroform-d) δ=8.17 (d, J=8.6, 4H), 7.49 (d, J=8.5, 4H), 6.47-6.16 (m, 3H), 5.12 (qd, J=13.2, 8.3, 4H), 1.40--0.00 (m, 3H). $^{13}$C NMR (75 MHz, Chloroform-d) δ=147.66, 143.09 (d, J=6.1), 136.50 (d, J=10.2), 128.80 (d, J=76.0), 127.78, 123.73, 67.30 (d, J=3.8). $^{31}$P NMR (122 MHz, Chloroform-d) δ=137.95 (d, J=95.6).

2-nitro-5-(oxypropargyl)benzyl Alcohol

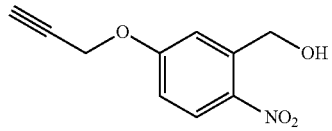

A 5 ml-microwave tube was charged with 200 mg of 5-Hydroxy-2-nitrobenzyl alcohol (1.18 mmol, 1.0 eq.), 245 mg K$_2$CO$_3$ (1.77 mmol, 1.5 eq.), 132 μl Propargyl bromide (80 wt. % solution in Toluene) and 4 ml DMF. The resulting suspension was irradiated for 1 h at 100° C. After cooling to room temperature, 5 ml of water were added. The resulting precipitate was filtered, washed three times with water and vacuum dried to give 179 mg of light brown solid. (0.87 mmol, 73.2%)

NMR data is in accordance with those reported in the literature.[19]

4-(2-nitro-5-(oxypropargyl)benzyloxy)phenol

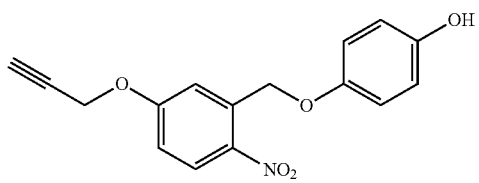 [SMILES: C#CCOc1ccc([N+](=O)[O-])c(COc2ccc(O)cc2)c1]

A flame dried Schlenk-tube, 400 mg of 2-nitro-5-(oxypropargyl)benzyl alcohol (1.93 mmol, 1.0 eq.), together with 850 mg hydrochinon (7.72 mmol, 4.0 eq.) and 750 mg of triphenylphosphine (2.90 mmol, 1.5 eq.) were dissolved in 10 ml of dry THF. The solution was cooled to 0° C. and 1.33 ml of diethyl azodicarboxylate (40% solution in Toluene) (2.90 mmol, 1.5 eq.) were added dropwise and the reaction was allowed to warm to room temperature overnight. The crude product was dry packed on a silica column for purification, eluting with Hexan/EtOAc (7:3 to 3:2), yielding 505 mg of a yellow solid. (1.68 mmon, 87.5%)

$^1$H NMR (300 MHz, Chloroform-d) δ=8.26 (d, J=9.1, 1H), 7.51 (d, J=2.8, 1H), 7.00 (dd, J=9.2, 2.9, 1H), 6.89 (d, J=9.0, 2H), 6.80 (d, J=9.0, 2H), 5.46 (s, 2H), 4.79 (d, J=2.4, 2H), 2.54 (t, J=2.4, 1H). $^{13}$C NMR (75 MHz, Chloroform-d) δ=161.86, 152.11, 150.03, 140.10, 137.71, 127.69, 116.11, 116.03, 113.88, 113.69, 76.95, 76.68, 67.66, 56.20. HRMS for C$_{16}$H$_{14}$NO$_5^+$ [M+H]$^+$ calcd: 300.0866. found: 300.0871.

Small Molecule Studies: Reaction of Unprotected Alkene Phosphonites with Different Azides The Staudinger phosphonite reaction with vinyl phosphonites was first investigated with rather simple diethyl derivatives. Those were synthesized by alkylation of commercial available diethyl chlorophosphite and reacted with different aliphatic and aromatic azides in situ. The desired phosphonamidates were isolated by column chromatography, after Hydrolysis of the Phosphonimidates.

Scheme 11 Staudinger phosphonite reaction of diethyl vinyl phosphonite with different azides with isolated yields.

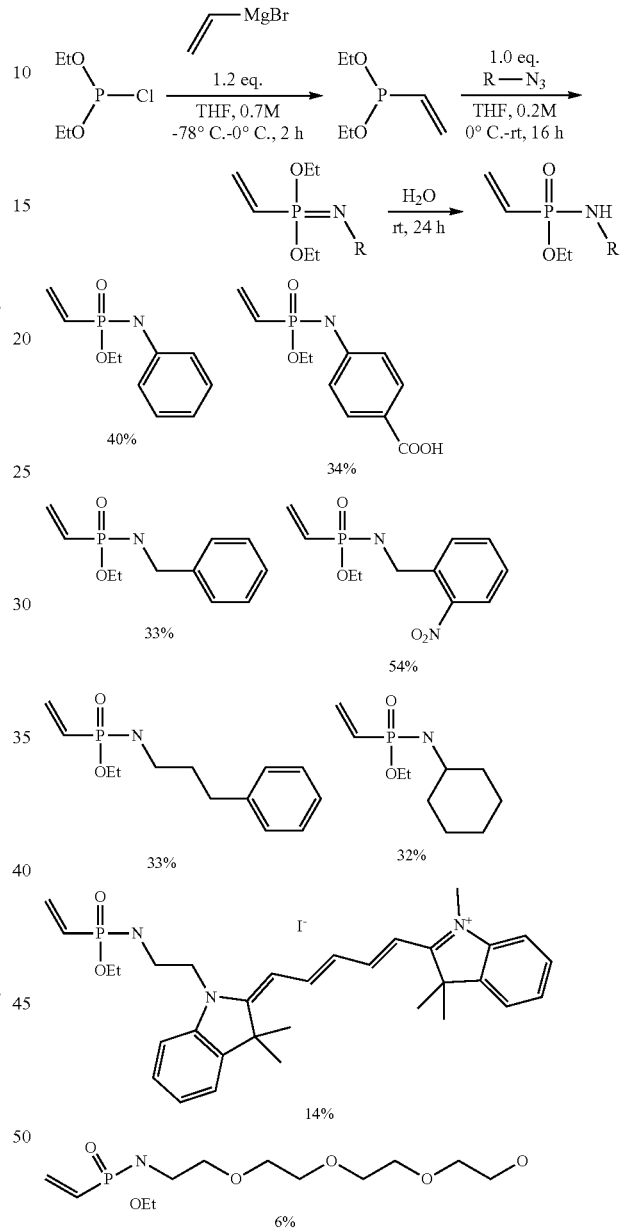

Varying the O-substituents of the Phosphonamidates allows the fine tuning of the reactivity in the thiol-addition as well as the installation of a third functionality to the system.

Phosphonamidates with substituents other than ethyl were synthesized by staudinger phosphonite reaction of the respective phosphonites. Isolated borane protected phosphonites were treated with DABCO to form the reactive P(III) species and reacted with an azide in situ to form the phosphonimidate. Subsequent Hydrolysis by water addition formed the desired phosphonamidates in moderate yields.

Scheme 12
In situ Staudinger phosphonite reaction after DABCO mediated deprotection of vinyl phosphonite borane aducts.

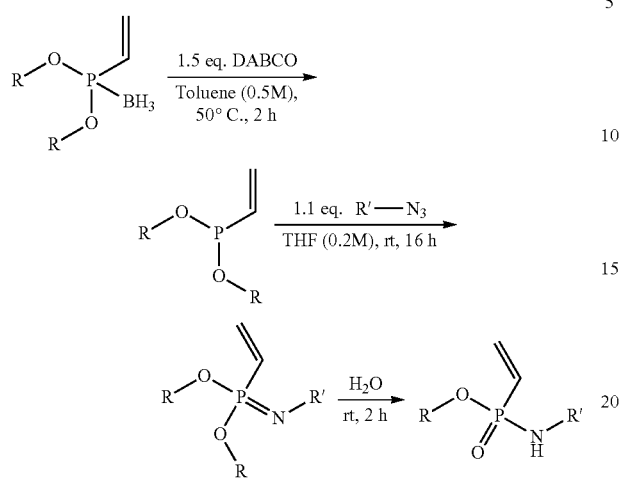

The 2-nitro-benzyl group is widely known as a photolabile substituent and has been shown to release attached molecules upon UV-irradiation.[20] From our expertise in phosphonamidate chemistry, we knew that the P—N-Bond of the phosphonamidate the very labile once the Phosphonamidate ester is cleaved. Therefore we wanted to synthesize 2-nitro-benzyl substituted Phosphonamidates that enable the controlled light mediated release of an amine from the thiol addition conjugates.

Scheme 13 Isolated Yields of the Staudinger phosphonite reaction between 2-nitro-benzyl vinyl phosphonite and various azides.

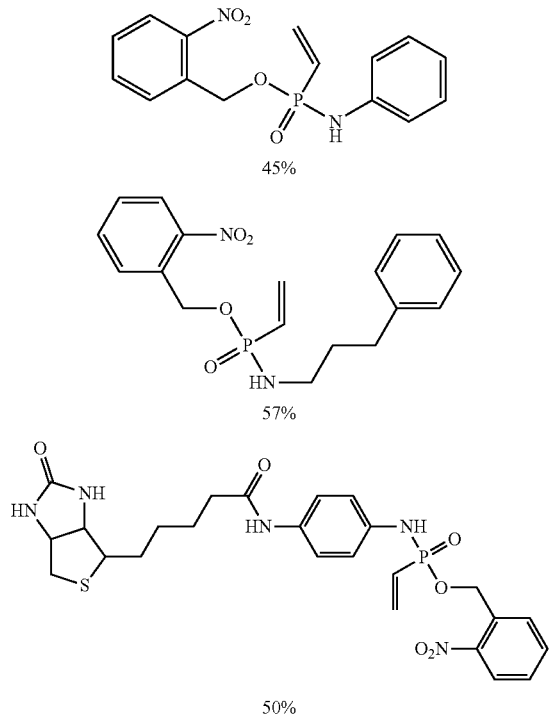

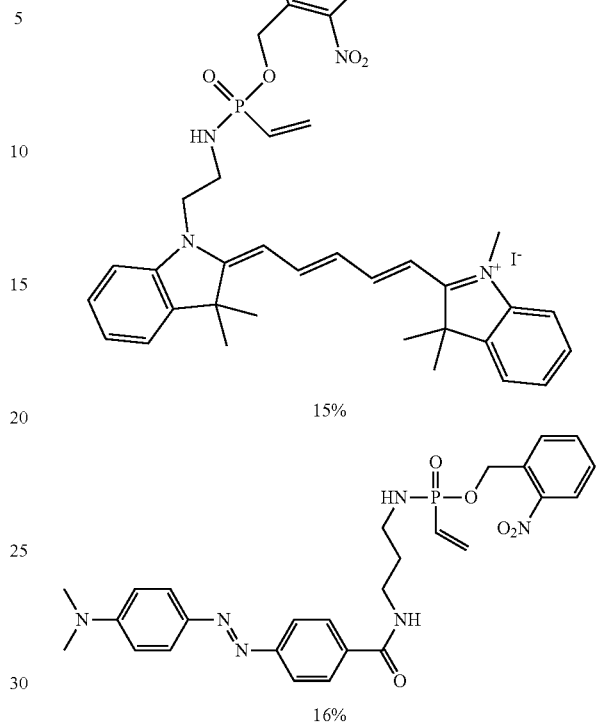

Several 2-nitro-benzyl substituted phosphonamidates could be synthesized, including a photo cleavable biotin as well as a Cy5-dye and a DABCYL quencher variant. An additional alkyne at the 2-nitro-benzyl group enables the installation of a third functionality to the system wire copper catalyzed click chemistry, which can be cleaved of again by photo irradiation.

Scheme 14
Isolated Yields of the staudinger phosphonite reaction between two different alkyne modified 2-nitro-benzyl vinyl phosphonites and phenyl azide.

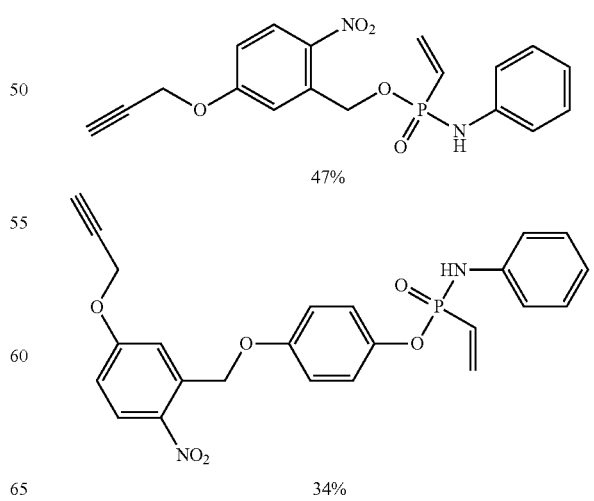

Further fine tuning of the reactivity of the subsequent thiol-addition was achieved by changing the electronic properties of the phosphonamidates. Therefore different phenyl- as well as trifuloroethyl derivatives were synthesized.

Scheme 15 Isolated Yields of the Staudinger phosphonite reaction between varirous vinyl phosphonites with different azides.

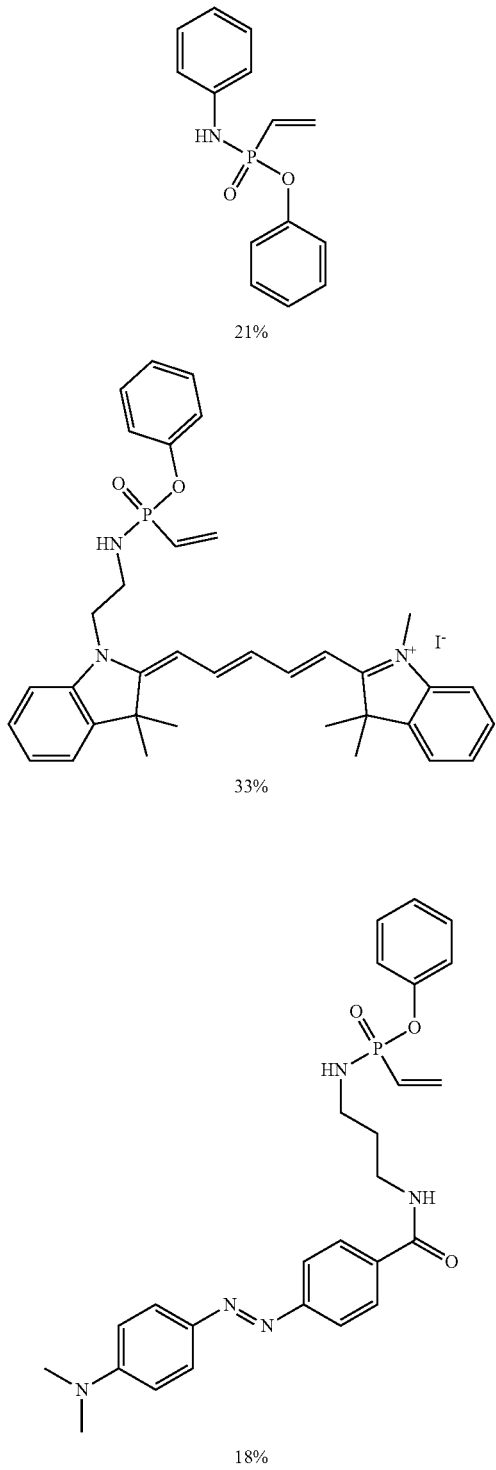

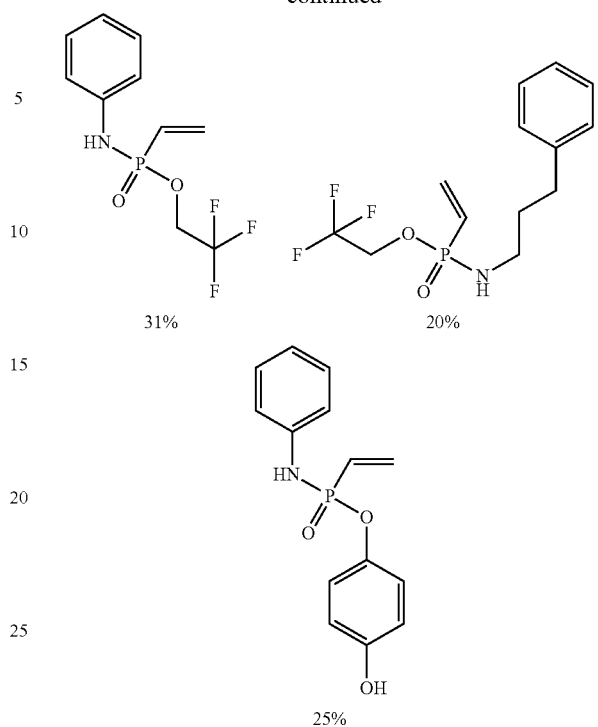

Some phosphonites could not be isolated with a borane protection group, as their corresponding alcohols are not compatible with borane addition. We were able to show that these phosphonites can be used in an in situ synthesis with an azide without isolation of the phosphonite as depicted in Scheme 16.

Scheme 16
One pot synthesis of a pyridyl phosphonite and subsequent staudinger phosphonite reaction with phenyl azide.

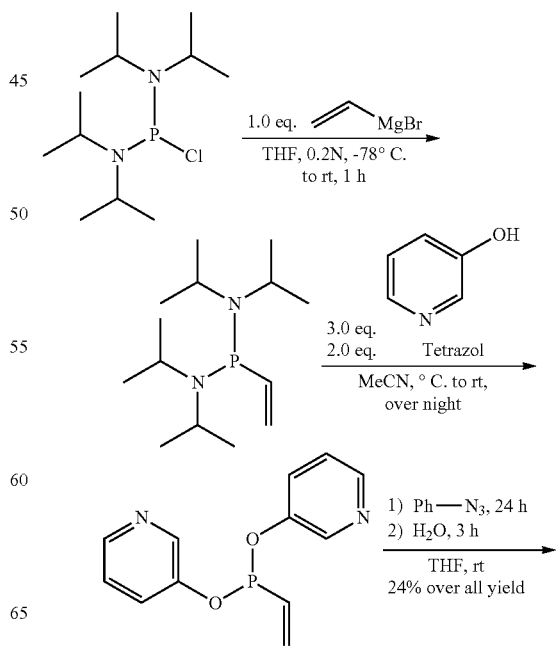

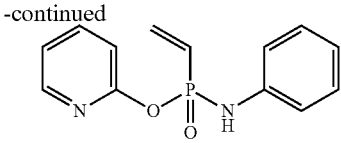

Stability of a phosphonamidate to different pHs was proven by $^{31}$P-NMR in aqueous buffers at room temperature. In a first experiment, Ethyl-N-phenyl-P-vinyl-phosphonamidate was chosen to measure stability. It turned out that the compound is stable over a broad pH range. P—N-bond cleavage occurred under strong acidic conditions (FIG. 11: Stability of Ethyl-N-phenyl-P-vinyl-phosphonamidate to different pHs over time).

Thiol-Addition of Small Molecule Thiols and Glutathione to Vinyl Phosphonamidates In a first study, vinyl phosphonamidates were reacted with different small molecule thiols under reaction conditions that previously worked well for alkynyl phosphonamidates. Full conversion of the Phosphonamidate starting material could be observed after 3 h treatment with one equivalent of a thiol in presence of potassium carbonate.

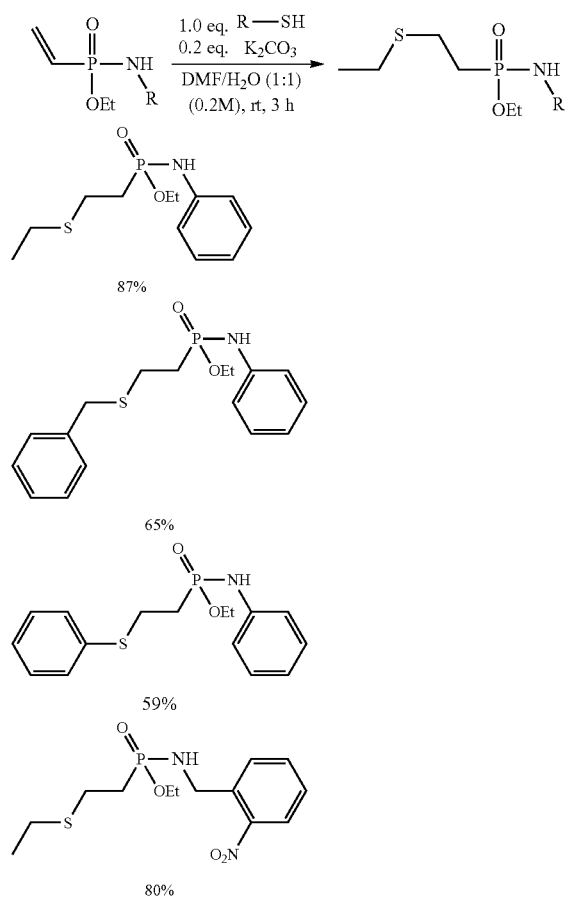

Scheme 17
Thiol addition of different small molecule thiols to ethyl vinyl phosphonamidates.

In the next step these reaction conditions were now applied to synthesize water soluble glutathione phosphonamidate conjugates. The reaction proceeded in case of the water soluble 4-carboxyphenyl-phosphonamidate without the addition of any organic solvent. The highly polar products were isolated by semi preparative HPLC with a slightly basic gradient.

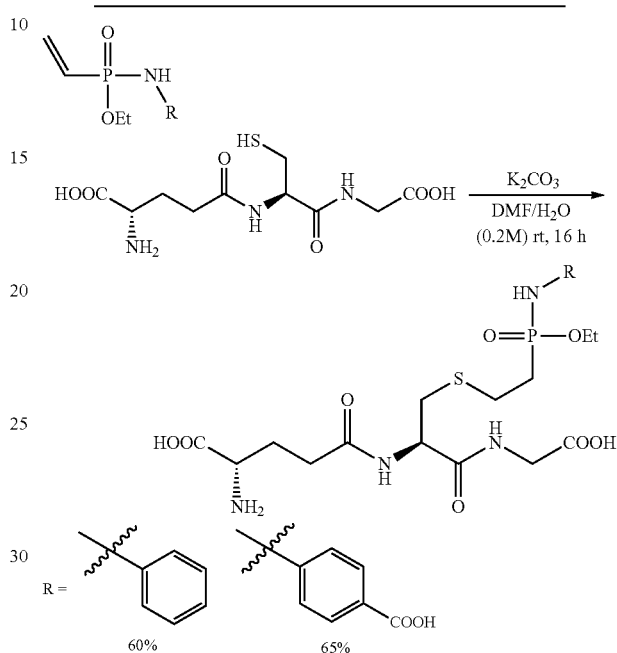

Scheme 18
Addition of glutathione to ethyl vinyl phosphonamidates with isolated yields (semi prep HPLC).

Stability of a thiol-adduct to different pHs was proven by $^{31}$P-NMR in aqueous buffers at room temperature. The conjugates showed excellent stability over a broad pH range. P—N-bond cleavage occurred under strong acidic conditions. An elimination of the thiol referred to as retro thiol-addition was not observed (FIG. 12: Stability of a glutathione phosphonamidate adduct to different pHs over time.).

The effect of the O-substituent on the reaction rate was investigated by the addition of glutathione to a solution of various N-phenyl alkynyl phosphonamidates in ammonium bicarbonate buffer at pH 8.5. Conversion of different phosphonamidates over time is shown in FIG. 11.

We found out that that vinyl phosphonamidates are much slower in the reaction with thiols than there corresponding alkynyl derivatives. We assumed that exchanging the electron donating ethyl group of the phosphonamidates to more electron withdrawing substituents should further increase the electrophilicity and therefore raise the rate of the thiol addition. Exchanging the ethyl to a phenyl group already reduces the half-life time $t_{1/2}$ of the staring material in the reaction from ten hours to one hour. Trifluoroethyl further reduces $t_{1/2}$ to thirty minutes while 2-nitro benzyl reacts to fifty percent in two hours (FIG. 13: Consumption of various N-phenyl vinyl phosphonamidates in the reaction with glutathione at pH 8.5. HPLC UV traces were taken at different time points. Experiments were performed in triplicates).

Thiol-Addition to Vinyl Phosphonamidates on Protein Level

First experiments with alkene phosphonamidates on protein level were conducted with the water soluble Ethyl-N-(4-carboxy-phenyl)-P-vinyl-phosphonamidate. As previous studies indicated that carbonate bases work very well in the promotion of the thiol-addition, ammonium bicarbonate buffer at pH 9.0 was chosen for the first experiments. A mutated eGFP variant bearing only one addressable cysteine was selected for the study.

Scheme 19, which is depicted in FIG. 31, shows an addition of a water soluble vinyl phosphonamidate to eGFP with one addressable cysteine.

The protein was incubated with 50 equivalents of the phosphonamidate at 37° C. Even though MALDI/MS analysis of the reaction mixture after 16 hours showed still unreacted protein, we were very pleased to observe formation of the desired protein conjugate.

Further eGFP conjugation experiments were conducted with a fluorescent Cy5-Phosphonamidate and observed by in-gel fluorescence measurements of the Cy5-channel.

Scheme 20, which is depicted in FIG. 32, shows a Cy5 phosphonamidate labeling of eGFP with one addressable cysteine. In gel fluorescence read out after SDS Page confirms selective Cy5 labeling.

The selectivity of the reaction for cysteine residues could be confirmed in this experiment. Neither an eGFP variant without any accessible cysteine incubated with the phosphonamidate nor addition of a Cy5 azide to the Cys containing eGFP showed fluorescent labeling. Addition of 5% DMSO (line 1) or acetonitrile (line 3) to the reaction mixture were both sufficient in solubilizing the dye without influencing the reaction itself.

Light Cleavable Triple Conjugation

We mentioned earlier that we were able to synthesize phosphonamidates with o-nitro benzyl substituents bearing an additional alkyne handle for CuAAC. One possible application for these compounds is the installation of a biotin to the alkyne to purify protein conjugates. We envision that the biotin binds to streptavidin beads, unbound material can be washed away and pure protein can be eluted by light irradiation.

In a first experiment on protein level, a simple N-phenyl Phosphonamidate with an O-substituted light cleavable Alkyne was reacted first with our single cysteine containing eGFP under previously optimized conditions. After the step, an azido modified biotin was attached to the construct via CuACC and the conjugates were analyzed by anti-biotin western blotting.

Scheme 21, which is depicted in FIG. 33, shows a photocleavable alkyne labeling of eGFP with one addressable cysteine with subsequent biotin labeling via CuACC and western blot analysis.

Western blot analysis confirmed successful conjugation of the biotin to the eGFP construct. When eGFP without attached phosphonamidate was used in the CuACC reaction no biotin was detected. The same is true in the absence of Copper.

Further immobilization experiments on Streptavidin beads were conducted with a phosphonamidate, Synthesized from an azido containing peptide and a single cystein containing Ubiquitin. The high molecular weight of the peptide induces a shift of the protein in the SDS gel, allowing the estimation of the conjugation yield.

Scheme 22, which is depicted in FIG. 34, shows a photocleavable alkyne labeling of ubiquitin with one addressable cysteine with subsequent biotin labeling via CuACC. Western blot analysis after immobilization on streptavidin beads. 1: Ubiquitin starting material, 2: reaction mixture after CuACC, 3: Supernatant after incubation of the reaction mixture with streptavidin agarose, 4: flow through after wash of streptavidin agarose, 5: boiled beads, 6: Irradiated beads.

The conjugation yield of the peptide to the protein could be estimated to 60%. The final construct was successfully immobilized on streptavidin beads. The constructs can be released by either boiling the beads in SDS buffer, which releases the intact protein peptide conjugate or irradiation by UV light. The latter method cleaves the phosphonamidate ester, leading to instability of the P—N-Bond and therefore release of the unconjugated protein. Further experiments will be conducted with phosphonamidates that form intact esters upon light irradiation to release the conjugated construct upon light irradiation.

b) Antibody Conjugation with Vinyl Phosphonamidates

Vinyl phosphonamidates were also applied to the modification of monoclonal antibodies. As we found out that 2-nitro-benzyl substituted vinyl phosphonamidates react faster in the thiol addition, we chose those phosphonamidate with a biotin modification.

Scheme 23, which is depicted in FIG. 42, shows the reduction of antibody disulfides and subsequent modification with a biotin vinyl phosphonamidate.

We chose the same reaction conditions for the reduction-alkylation procedure as described previously with the exception of 4° C. for the thiol-addition, because we found out that lower temperatures slow down disulfide formation and therefore lead to higher conjugation yield.

Western blot analysis confirmed cysteine selective modification of the antibody. High selectivity for free cysteine residues could be observed by the absence of a Signal in the anti-biotin western blot without prior reduction of the disulfide bonds. In contrast to the labeling experiments with alkynyl phosphonamidates, this time reformation of the antibody fragments could be observed (FIG. 14: Western blot analysis after non reducing SDS-PAGE. SM: Cetuximab starting material. 1: 5 min, 2: 1 h, 3: 2 h, 4: 4 h, 5: 20 h incubation with a biotin modified phosphonamidate. Reaction with (left) and without (right) prior reduction of the disulfides).

Cysteine selective modification was further confirmed by tryptic digest of the cetuximab phosphonamidate conjugates, followed by MS/MS analysis. To simplify the MS/MS spectra, the modification was conducted under previously described conditions with the structurally simpler phenyl-N-phenyl alkynyl phosphonamidate. Modification of Cys 264 and Cys 146 of the heavy chain could be confirmed by MS/MS (HCD fragmentation) while no modification was detected without prior reduction of the disulfide bonds.

Alkene Phosphonites in the Synthesis ASGP-R Addressing Drug Conjugates

We further want to apply our modular conjugation approach to the synthesis of targeted drug conjugates. Khorev et al described previously the synthesis of an ASGP-R addressing trivalent ligand with a terminal amino modification. Based on this route, we synthesized the same ligand with a terminal thiol modification (20).

Scheme 24, which is depicted in FIG. 43, shows the synthesis of a fluorescently labeled ASGP-R addressing Cy5 conjugate via the modular addition to vinyl phosphonamidates.

Having the thiol modified, fully deprotected ligand in hand we successfully conjugated the construct to our fluorescent Cy5-phosphonamidate. With this conjugate, we can now monitor the sufficient uptake into hepatocytes by FACS analysis and fluorescent microscopy.

FIG. 15 shows the sequences mentioned throughout this description.

Introduction of the Alkyne-Phosphonamidate Moiety by Generic Building Blocks Via an Amide Bond Generic building blocks as the amino-modified derivative $N_2$ or the NHS-ester $N_1$ shown in Scheme 25 can introduce an alkyne-phosphonamidate moiety into functional molecules via amide bond forming reactions.

Scheme 25, which is depicted in FIG. 35, shows alkyne-phosphonamidates for the chemoselective modification of Cys-residues. Introduction via chemoselective Staudinger-phosphonite reaction or amide coupling with the generic building blocks $N_1$ and $N_2$.

This approach can be advantageous as one does not have to handle labile P(III) compounds. Furthermore, it has been shown that high yields can be achieved by using those generic building blocks, which is of a particular interest for expensive starting materials.

Scheme 26
Two examples of high yielding attachment of the alkyne-phosphonamidate moiety to functional fluorescent dyes via amide bonds.

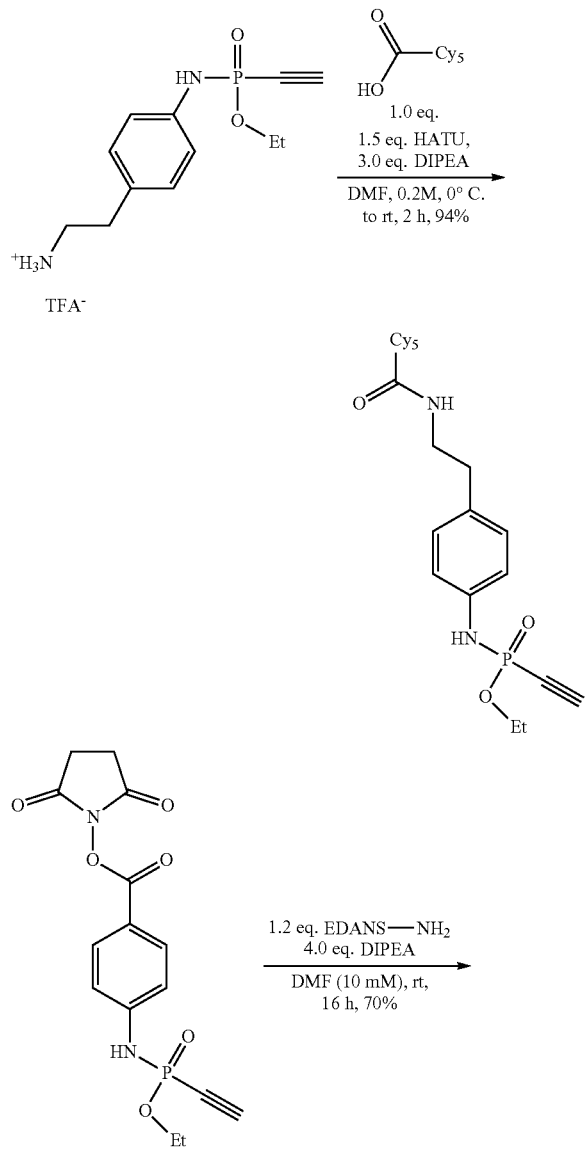

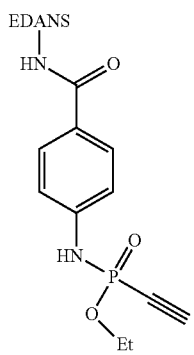

Procedures for the Introduction of the Alkyne-Phosphonamidate Moiety by Generic Building Blocks Via an Amide Bond Preparative HPLC Preparative HPLC was performed on a Gilson PLC 2020 system (Gilson Inc, WI, Middleton, USA) using a VP 250/32 Macherey-Nagel Nucleodur C18 HTec Spum column (Macherey-Nagel GmbH & Co. Kg, Germany). The following gradients were used throughout all sections of this disclosure: Method C: (A=$H_2O$+0.1% TFA (trifluoroacetic acid), B=MeCN (acetonitrile)++0.1% TFA, flow rate 30 ml/min, 5% B 0-5 min, 5-90% B 5-60 min, 90% B 60-65 min. Method D: (A=$H_2O$+0.1% TFA, B=MeCN++0.1% TFA), flow rate 30 ml/min, 5% B 0-5 min, 5-25% B 5-10 min, 25%-45% B 10-50 min, 45-90% 50-60 min, 90% B 60-65 min.

Semi-Preparative HPLC

Semi-Preparative HPLC was performed on a Shimadzu prominence HPLC system (Shimadzu Corp., Japan) with a CBM20A communication bus module, a FRC-10A fraction collector, 2 pumps LC-20AP, and a SPD-20A UV/VIS detector, using a VP250/21 Macherey-Nagel Nucleodur C18 HTec Spum column (Macherey-Nagel GmbH & Co. Kg, Germany). The following gradients were used throughout all sections of this disclosure: Method E: (A=$H_2O$+0.1% TFA, B=MeCN++0.1% TFA), flow rate 10 ml/min, 5% B 0-5 min, 5-99% B 5-65 min, 99% B 65-75 min.

General Procedure 1 for the Synthesis of Aromatic Azides

A 500-ml round-bottom flask was charged with 10 mmol aromatic amine, suspended in 15 ml water and cooled to 0° C. 5 ml of concentrated aqueous HCl were added, followed by drop-wise addition of 1.27 g sodium nitrite (15.00 mmol, 1.50 eq.) solution in 10 ml Water. The mixture was stirred for 20 min at 0° C., 100 ml EtOAc (ethyl acetate) were added and a solution of 0.98 g sodium azide (15.00 mmol, 1.5 eq.) in 5 ml water was added drop-wise. The solution was allowed to warm to room temperature and stirred for one more hour. Phases were separated, the aqueous phase was extracted two times with EtOAc, combined organic fractions were washed two times with water, dried ($MgSO_4$) and all volatiles were removed under reduced pressure.

General Procedure 2 for the Synthesis of O-Ethyl-Alkynyl Phosphonamidates from Diethyl Chlorophosphite A 25-ml Schlenk flask was charged with 173 µl diethyl chlorophosphite (1.20 mmol, 1.2 eq.) under an argon atmosphere, cooled to −78° C. and 2.40 ml ethynylmagnesium bromide solution (0.5 M in THF, 1.20 mmol, 1.2 eq.) was added drop wise. The yellowish solution was allowed to warm to room temperature and 1.00 mmol of azide (1.0 eq.) dissolved in 3.0 ml of THF or DMF was added and stirred over night at room temperature. 5 ml of water were added and stirred for another 2 h. The reaction mixture was extracted with EtOAc, the combined organic fractions dried (MgSO$_4$) and solvents were removed under reduced pressure. The crude product was purified by flash column chromatography on silica gel or preparative reversed phase HPLC.

4-azidobenzoic Acid

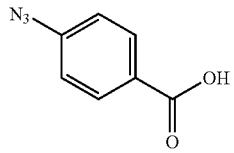 [SMILES: [N-]=[N+]=Nc1ccc(C(=O)O)cc1]

The compound was synthesized according to the general procedure 1 from 2.00 g 4-aminobenzoic acid (14.58 mmol) and obtained as a yellowish solid. (2.00 g, 12.26 mmol, 84.1%)

$^1$H NMR (300 MHz, Chloroform-d) δ=8.11 (d, J=8.4, 2H), 7.11 (d, J=8.4, 2H). NMR data was in accordance with literature values (23).

4-azidobenzoic-acid-N-hydroxysuccinimide ester

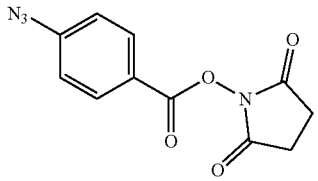 [SMILES: [N-]=[N+]=Nc1ccc(C(=O)ON2C(=O)CCC2=O)cc1]

In a 50-ml round-bottom-flask, 500 mg 4-azidobenzoic acid (3.056 mmol, 1.00 eq.), 705 mg N-hydroxysuccinimide (6.112 mmol, 2.00 eq.) and 20 mg 4-Dimethylaminopyridine (0.164 mmol, 0.05 eq.) were suspended in 10 ml of dry CH$_2$Cl$_2$. 1.172 g EDC*HCl (1-(3-dimethylaminopropyl)-3-ethylcarbodiimide hydrochloride, 6.112 mmol, 2.00 eq.) were added slowly at 0° C. and the reaction mixture was allowed to stir at room temperature for two hours. The solvent was removed under reduced pressure and the crude product purified by column chromatography on silicagel (50% EtOAc in hexane) and obtained as white solid (763 mg, 2.934 mmol, 96.0%)

$^1$H NMR (300 MHz, Chloroform-d) δ=8.14 (d, J=8.6, 2H), 7.15 (d, J=8.6, 2H), 2.92 (s, 4H). $^{13}$C NMR (75 MHz, CDCl$_3$) δ=169.15, 160.97, 146.85, 132.42, 121.19, 119.21, 25.59. NMR data was in accordance with literature values (24).

Ethyl-N-(4-(2,5-dioxo-1-pyrrolidinyl)oxy-carbonyl-phenyl)-P-ethynylphosphonamidate

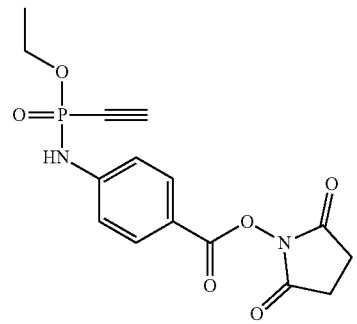 [SMILES: C#CP(=O)(Nc1ccc(C(=O)ON2C(=O)CCC2=O)cc1)OCC]

The compound was synthesized according to the general procedure 2 from 173 µl diethyl chlorophosphite (1.20 mmol, 1.20 eq.), 2.40 ml ethynylmagnesium bromide solution (0.5 M in THF (tetrahydrofuran), 1.20 mmol, 1.20 eq.) and 260 mg 4-azidobenzoic-acid-N-hydroxysuccinimide ester (1.00 mmol, 1.00 eq.). The crude phosphonamidate was purified by flash column chromatography on silicagel (100% EtOAc) and obtained as a yellowish solid. (225 mg, 0.643 mmol, 64.3%)

$^1$H NMR (300 MHz, Chloroform-d) δ=8.05 (d, J=8.6, 2H), 7.37 (d, J=7.4, 1H), 7.16 (d, J=8.6, 2H), 4.38-4.13 (m, 2H), 2.96 (d, J=13.2, 1H), 2.90 (s, 4H), 1.40 (t, J=7.1, 3H). $^{13}$C NMR (75 MHz, Chloroform-d) δ=169.59, 161.51, 145.64, 132.55, 118.38, 117.59 (d, J=8.0), 88.69 (d, J=50.2), 62.93 (d, J=5.2), 25.82, 16.24 (d, J=7.3). $^{31}$P NMR (122 MHz, Chloroform-d) δ=−10.65. HR-MS for C$_{15}$H$_{16}$N$_2$O$_6$P$^+$ [M+H]$^+$ calcd: 351.0740. found 351.0749.

2-(4-Azidophenyl)-ethanol

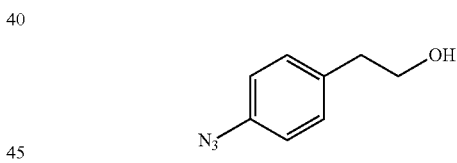

The compound was synthesized according to the general procedure 1 from 1.00 g of 2-(4-Aminophenyl)-ethanol (7.21 mmol) and obtained as brown oil (0.50 g, 3.06 mmol, 42.5%).

$^1$H NMR (300 MHz, Chloroform-d) δ=7.21 (d, J=8.3, 2H), 6.97 (d, J=8.3, 2H), 3.83 (t, J=6.5, 2H), 2.84 (t, J=6.5, 2H), 1.81 (s, 1H). $^{13}$C NMR (75 MHz, CDCl$_3$) δ=138.26, 135.41, 130.42, 119.18, 63.55, 38.50. NMR data was in accordance with literature values (25).

2-(4-Azidophenyl)-ethyl-4-toluenesulfonate

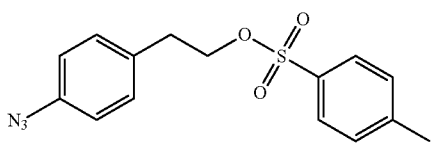 [SMILES: Cc1ccc(S(=O)(=O)OCCc2ccc(N=[N+]=[N-])cc2)cc1]

A 50-ml round-bottom flask was charged with 455 mg of 2-(4-Azidophenyl)-ethanol (2.79 mmol, 1.00 eq.), dissolved in 8 ml pyridine and cooled to 0° C. 787 mg of solid tosyl chloride (4.18 mmol, 1.50 mmol) was added portion-wise and the mixture was stirred for 4 h at room temperature, 10 ml of saturate NaCl-solution and 10 ml water were added and the yellow solution was extracted three times with EtOAc, combined organic fractions were washed two times with 1 N HCl, twice with saturate NaHCO$_3$-solution and once with water. The organic layer was dried (MgSO$_4$) and all volatiles were removed under reduced pressure. Product was obtained as yellow oil (0.72 g, 2.44 mmol, 87.4%).

$^1$H NMR (300 MHz, Chloroform-d) δ=7.69 (d, J=8.2, 2H), 7.30 (d, J=8.2, 2H), 7.10 (d, J=8.3, 2H), 6.91 (d, J=8.3, 2H), 4.21 (t, J=6.8, 2H), 2.94 (t, J=6.8, 2H), 2.45 (s, 3H). $^{13}$C NMR (75 MHz, CDCl$_3$) δ=144.66, 138.60, 132.96, 132.76, 130.19, 129.69, 127.72, 119.05, 70.34, 34.60, 21.55. NMR data was in accordance with literature values (26).

2-(4-Azidophenyl)-ethyl phthalimide

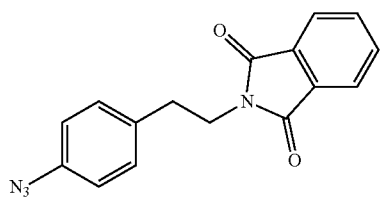 [SMILES: [N-]=[N+]=Nc1ccc(CCN2C(=O)c3ccccc3C2=O)cc1]

A 50-ml round-bottom flask was charged with 4.11 g of 2-(4-Azidophenyl)-ethyl-4-toluensulfonate (12.95 mmol, 1.00 eq.), together with 3.60 g potassium phthalimide (19.42 mmol, 1.50 eq.) and dissolved in 60 ml DMF (N,N-dimethylformamide). The brown solution was stirred over night at 100° C. All volatiles were removed under reduced pressure, 50 ml of water were added extracted three times with EtOAc, the combined organic fractions were washed two times with water, the organic layer was dried (MgSO$_4$) and all volatiles were removed under reduced pressure. The product was used in the next step without further purification. Pure product was obtained by flash column chromatography on silicagel (10% to 20% EtOAc in n-hexan) as a yellow solid (1.75 g, 5.99 mmol, 46.2%). $^1$H NMR (600 MHz, Chloroform-d) δ=7.85 (dd, J=5.4, 3.1, 2H), 7.73 (dd, J=5.4, 3.1, 2H), 7.25 (d, J=8.4, 2H), 6.96 (d, J=8.4, 2H), 3.93 (dd, J=8.3, 6.8, 2H), 3.00 (dd, J=8.3, 6.8, 2H). $^{13}$C NMR (151 MHz, CDCl$_3$) δ=168.12, 138.43, 134.76, 133.96, 132.00, 130.22, 123.26, 119.17, 39.14, 33.92.

2-(4-Azidophenyl)-ethylamine hydrochloride

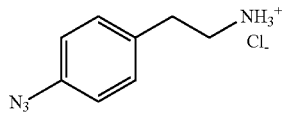 [SMILES: [N-]=[N+]=Nc1ccc(CC[NH3+])cc1]

A 100-ml round-bottom flask was charged with 722 mg of 2-(4-Azidophenyl)-ethyl phthalimide (2.47 mmol, 1.00 eq.), 144 µl hydrazine hydrate (2.96 mmol, 1.20 eq.), dissolved in 20 ml of dry ethanol under argon atmosphere and the solution was refluxed for 4 h. Most of the solvent was removed under reduced pressure, 50 ml water was added and the suspension was basified with 1 N NaOH. It was extracted three times with EtOAc, the combined organic fractions were washed two times with water, the organic layer was dried (MgSO$_4$) and all volatiles were removed under reduced pressure. Pure product was obtained by flash column chromatography on silicagel (10% MeOH (methanol) in DCM (dichloromethane)+0.5% N,N-ethyldimethylamine) and lyophilisation from HCl as yellowish solid (224 mg, 1.14 mmol, 46.2% over two steps). $^1$H NMR (600 MHz, Deuterium Oxide) δ=7.29 (d, J=7.6, 2H), 7.05 (d, J=7.6, 2H), 3.22 (t, J=7.2, 2H), 2.94 (t, J=7.2, 2H). $^{13}$C NMR (151 MHz, D$_2$O) δ=138.81, 133.24, 130.32, 119.40, 40.51, 32.13. NMR data was in accordance with literature values (27).

Ethyl-N-(4-(2-aminoethyl)phenyl)-P-ethynylphosphonamidate TFA Salt

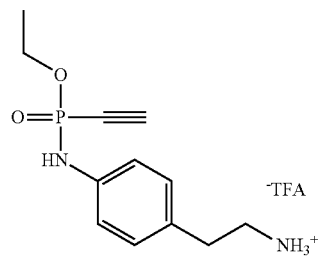

The compound was synthesized according to the general procedure 2 from 181 µl diethyl chlorophosphite (1.26 mmol, 1.20 eq.), 2.52 ml ethynylmagnesium bromide solution (0.5 M in THF, 1.26 mmol, 1.20 eq.) and 322 mg 2-(4-azidophenyl)ethyl amine hydrochloride (1.05 mmol, 1.00 eq.). The crude phosphonamidate was purified by preparative RP-HPLC (Method C described above) and obtained as brown oil. (209 mg, 0.57 mmol, 54.5%)

$^1$H NMR (300 MHz, Acetonitrile-d$_3$) δ=7.58 (s, 3H), 7.20-7.01 (m, 4H), 6.96 (d, J=8.5, 1H), 4.26-4.05 (m, 2H), 3.42 (d, J=12.8, 1H), 3.08 (d, J=7.8, 2H), 2.88 (dd, J=9.0, 6.4, 2H), 1.31 (t, J=7.1, 3H). $^{13}$C NMR (75 MHz, Acetonitrile-d$_3$) δ=161.38 (q, J=34.7), 139.20 (d, J=1.3), 131.75, 130.66, 119.63 (d, J=7.3), 90.09 (d, J=47.2), 77.02 (d, J=265.0), 63.54 (d, J=5.3), 41.92, 33.19, 16.41 (d, J=7.3). $^{31}$P NMR (122 MHz, Acetonitrile-d$_3$) δ=−9.71. HR-MS for C12H18N$_2$O2P$^+$ [M+H]$^+$ calcd: 253.1100. found 253.1095.

5-((2-(O-Ethyl-P-ethynyl-phosphonamidato-N-benzoyl)ethyl)amino)naphthalene-1-sulfonic acid

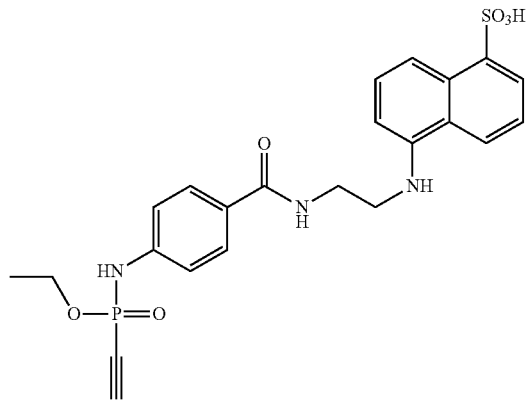 [SMILES: C#CP(=O)(Nc1ccc(C(=O)NCCNc2cccc3c(S(=O)(=O)O)cccc23)cc1)OCC]

The reaction was carried out in DMF. 265 μl of a 100 mM solution of Ethyl-N-(4-(2,5-dioxo-1-pyrrolidinyl)oxy-carbonyl-phenyl)-P-ethynyl phosphonamidate (0.0265 mmol, 1.00 eq.) and 1.06 ml of a 50 mM solution of 5-((2-Aminoethyl)aminonaphthalene-1-sulfonate (0.0530 mmol, 2.00 eq.) together with 795 μl DMF was premixed and 530 μl of a solution of 200 mM DIPEA (0.1060 mmol, 4.00 eq.) was added. The mixture was shaken for 2 hours at room-temperature, all volatiles were removed under reduced pressure, the crude mixture was purified by preparative HPLC using method C described above, and the desired compound obtained as a white solid after lyophilisation. (9.30 mg, 0.0186 mmol, 70.0%)

$^1$H NMR (600 MHz, DMSO-d$_6$) δ=8.78 (d, J=8.5, 1H), 8.57 (t, J=5.7, 1H), 8.36 (d, J=8.6, 1H), 8.11 (d, J=8.4, 1H), 7.99 (d, J=7.0, 1H), 7.80 (d, J=8.7, 2H), 7.43 (dd, J=8.5, 7.1, 1H), 7.38 (t, J=8.1, 1H), 7.14 (d, J=8.7, 2H), 6.92 (d, J=7.5, 1H), 4.43 (d, J=12.7, 1H), 4.21-4.05 (m, 2H), 3.62 (q, J=6.3, 2H), 3.46 (t, J=6.6, 2H), 1.31 (t, J=7.0, 3H). $^{13}$C NMR (151 MHz, DMSO-d$_6$) δ=167.03, 144.64, 143.48, 141.01, 130.59, 128.98, 127.65, 126.47, 125.13, 124.62, 123.86, 123.13, 119.62, 117.34 (d, J=7.8), 107.91, 91.69 (d, J=45.5), 77.26 (d, J=260.8), 62.31 (d, J=5.0), 45.51, 38.15, 16.42 (d, J=6.9). $^{31}$P NMR (243 MHz, DMSO) δ=-10.35. HR-MS for C23H25N3O6PS$^+$ [M+H]$^+$ calcd: 502.1196. found 502.1195.

Cy5-O-ethyl-P-alkynyl-phosphonamidate

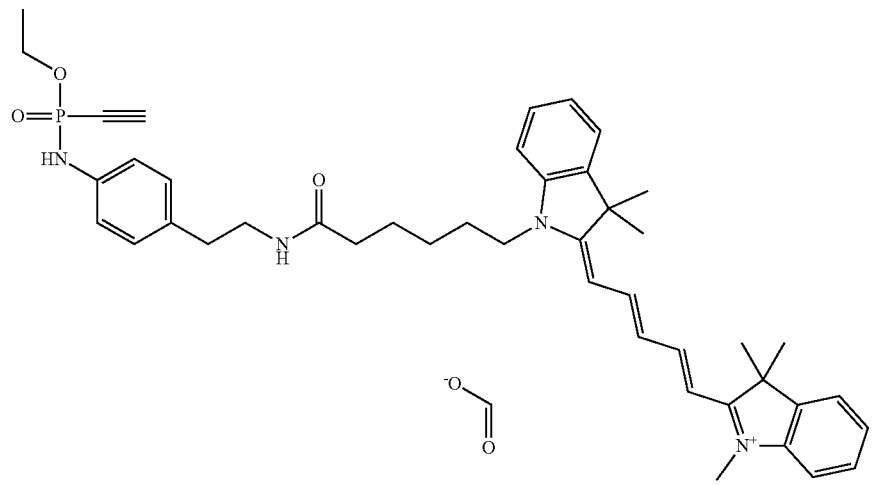

The Cy5-COOH was synthesized according to a procedure, previously published by our lab (28). A 5-ml-round bottom flask was charged with 33.2 mg Cy5-COOH (0.0628 mmol, 1.00 eq.), 35.8 mg HATU ((1-[Bis(dimethylamino)methylene]-1H-1,2,3-triazolo[4,5-b]pyridinium 3-oxid hexafluorophosphate), 0.0942 mmol, 1.5 eq.) and 200 μl DMF. The deep blue solution was cooled to 0° C. and 32 μl DIPEA (N,N-diisopropylethylamine, 0.1884 mmol, 3.0 eq.) were added. After 5 minutes a solution of 23 mg Ethyl-N-(4-(2-aminoethyl)phenyl)-P-ethynyl phosphonamidate TFA salt (0.0628 mmol, 1.00 eq.) in 300 μl DMF were added drop-wise. The solution was allowed to warm to room-temperature and stirred for 2 hours. All volatiles were removed under reduced pressure and the crude product was purified by flash column chromatography on silicagel (0% to 5% MeOH in DCM) and obtained as blue solid. (45 mg, 0.0590 mmol, 93.9%).

$^1$H NMR (600 MHz, Chloroform-d) δ=7.88 (td, J=13.0, 4.9, 2H), 7.43-7.33 (m, 4H), 7.23 (t, J=7.4, 2H), 7.15-7.07 (m, 4H), 7.01 (d, J=8.4, 2H), 6.72 (t, J=12.5, 1H), 6.46 (bs, 1H), 6.18 (dd, J=13.6, 8.5, 2H), 6.11 (q, J=7.6, 1H), 4.27-4.09 (m, 2H), 3.98 (t, J=7.6, 2H), 3.56 (s, 3H), 3.43 (q, J=6.9, 2H), 2.97 (d, J=12.8, 1H), 2.75 (t, J=7.5, 2H), 2.25 (t, J=7.3, 2H), 1.81 (p, J=8.0, 2H), 1.73-1.67 (m, 2H), 1.70 (s, 6H), 1.69 (s, 6H), 1.55-1.42 (m, 2H), 1.35 (t, J=7.1, 3H). $^{13}$C NMR (151 MHz, CDCl3) δ=173.64, 173.19, 173.11, 153.34, 152.99, 142.72, 141.90, 141.17, 140.89, 136.88, 133.32, 129.69, 128.78, 128.66, 126.32, 126.22, 125.34, 125.15, 122.21, 122.13, 118.60, 118.53, 110.83, 110.36, 103.77, 103.64, 88.54, 88.23, 75.27, 62.46, 49.40, 49.17, 44.22, 41.03, 35.94, 34.78, 27.96, 27.90, 27.84, 27.09, 26.32, 25.24, 16.17, 16.11, 16.04. $^{31}$P NMR (243 MHz, CDCl3) δ=-9.08.

Staudinger-Induced Thiol Addition with Alkynyl-Phosphonites for the Generation of Antibody Drug Conjugates (ADCs)

As set our herein above, we were able to show that a modification of full length igG antibodies with alkyne- and alkene-phosphonamidates is possible. In the above examples we used Cetuximab as a model antibody and modified the interchain-disulfides with a biotinylated phorsphonamidate via the reduction and alkylation protocol, previously described by Senter and coworkers (29). This concept was further developed towards a feasible system for the generation of ADCs by phosphonamidate mediated conjugation the highly potent tubulin binding cytotoxin MMAE and the Her2 binding antibody Trastuzumab.

Similar to our above studies with Cetuximab, we reduced the inter-chain disulfide bonds of Trastuzumab with dithiothreitol (DTT) and carried out Cys-conjugation reactions with different electrophilic biotin derivatives, including maleimide, iodoacetamide and alkyne-phosphonamidate (phosphonamidate-labelling), to have a direct comparison to state-of-the art techniques. The latter was synthesized by the Staudinger phosphonite reaction protocol in 72% overall yield. The antibody-labelling reactions were carried out with and without prior reduction of the disulfide bonds to probe the chemoselectivity of the Cys-conjugation reactions (FIGS. 16A-16B). Westernblot analysis revealed sufficient labelling for all of the tested biotin derivatives with reduced trastuzumab. Most strikingly, we observed high reactivity of maleimides with non-reduced trastuzumab, which was further confirmed by trypsin digestion and MS/MS analysis. In contrast, phosphonamidate-labelling demonstrated outstanding selectivity for Cys-residues (FIGS. 16A-16B).

FIGS. 16A-16B shows: FIG. 16A: Trastuzumab modification with three different Cys-reactive bitotin derivatives. Disulfide reduction was carried out with 1000 eq. DTT in 50 mM borate containing PBS for 30 minutes at 37° C. Excess DTT was removed by size exclusion chromatography. Labelling was conducted with 35 eq. biotin derivative with a final DMSO content of 1% in a Buffer containing 50 mM $NH_4HCO_3$ and 1 mM EDTA, pH 8.5 for the amidate and PBS containing 1 mM EDTA, pH 7.4 for the other two compounds. FIG. 16B: Western blot analysis. Lane 1 and 5: untreated antibody. Lane 2-4: reactions with prior DTT treatment. Lane 6-8: Control reactions without prior DTT treatment.

Phosphonamidate-linked ADCs were generated from the very efficient antimitotic toxin MMAF and the FDA approved Her2-addressing antiproliferative antibody trastuzumab (FIGS. 17A-17C). To investigate release of the toxic payload, ADCs with a cathepsin B cleavage side (Valine-Citruline linker VC) were prepared between the antibody and the toxin. Amidate-VC-PAB-MMAF constructs were synthesized based on a previously described procedure, as depicted in Scheme 27.

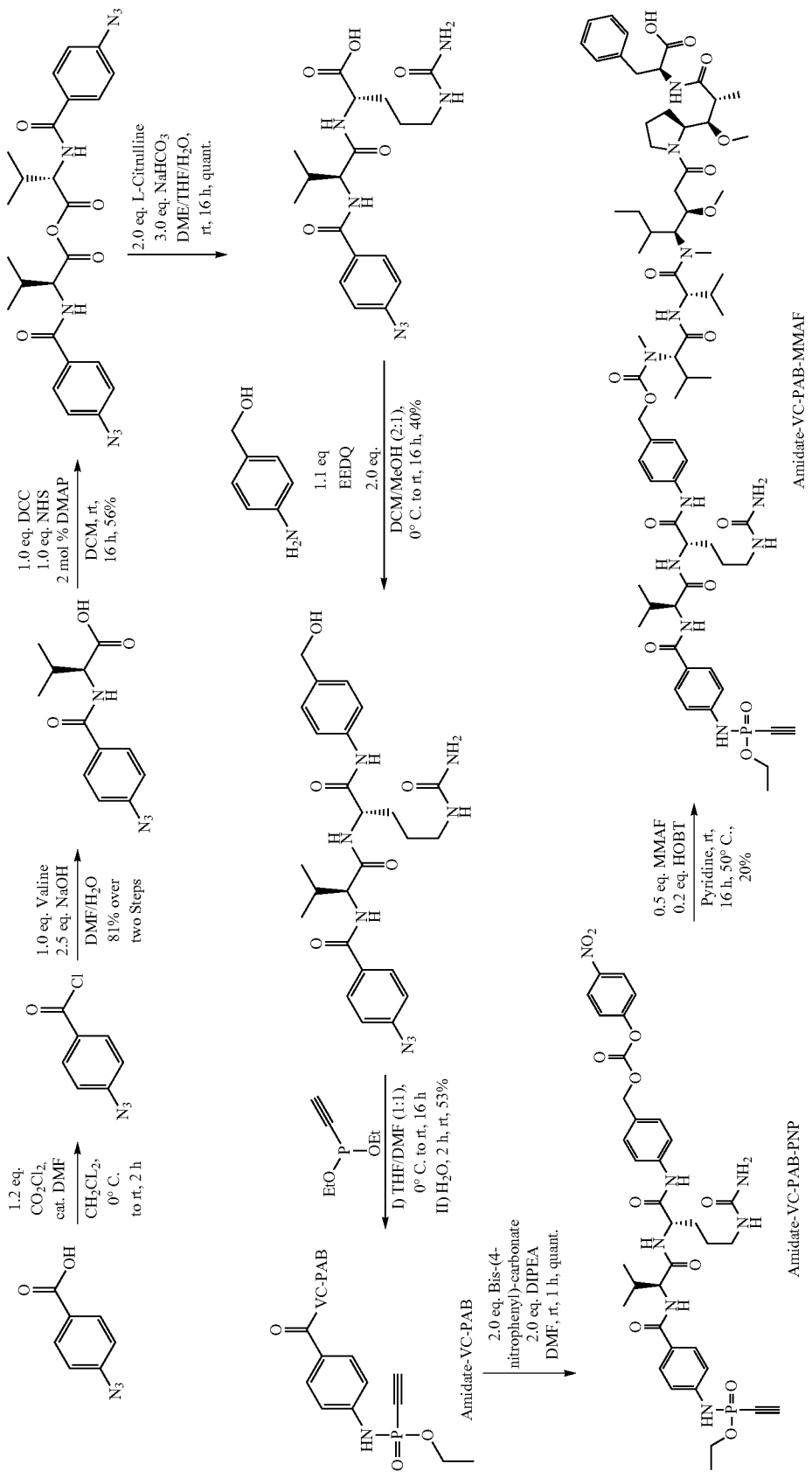

Conjugation to Trastuzumab was carried out in 50 mM ammoniumbicarbonate buffer at pH 8.5 for 16 hours at 14° C., after reduction of the interchain-disulfide bonds with DTT and removal of the excess reducing agent by Zeba™ Spin desalting columns.

FIGS. 17A-17C show: Trastuzumab modification with phosphonamidate modified, cathepsin cleavable MMAF (Amidate-VC-PAB-MMAF). FIG. 17A: Reaction scheme reduction and alkylation of interchain disulfides. FIG. 17B: SDS-PAGE analysis of the reaction. FIG. 17C. Deconvolutet MS spectra of the antibody fragments after deglaycosylation with PNGase F and reduction with DTT. LC: Light chain; HC: Heavy chain; mod: Amidate-VC-PAB-MMAF.

An average loading of 4.6 drug molecules per antibody was determined by ESI-MS after deglycosylation and reduction. We approximated the drug-to-antibody ratio (DAR) with the mass signal intensities of the heavy- and light-chain species bearing different degrees of modification.

The obtained Phosphonamidate-ADC conjugates were evaluated in a previously established Her2 based proliferation assay with two different Her2-overexpressing cell lines BT474 and SKBR3 (30). The Her2-non overexpressing cell line MDAMB468 was used as a control to proof Her2 selectivity. Phosphonamidate-linked conjugates were compared to a maleimide-linked cathepsin B-cleavable trastumzumab MMAF conjugate. These experiments clearly demonstrate that phosphonamidate-labelled MMAF-ADCs enable sufficient and selective killing of Her2 overexpressing cells. The measured $IC_{50}$-values were at least as good as the compared maleimide controls (FIG. 18). It is important to note, that it is not to be expected that the advantages of phosphonamidate-labelling have a positive effect on in vitro cell killing efficiency when compared to maleimide chemistry.

FIG. 18 shows: Increased antiproliferative potency of MMAF linked trastuzumab on two different Her2 overexpressing cell lines (BT474 and SKBR3) and one control (MDAMB468). Plots depict the number of proliferating cells after 4 days of antibody treatment in dependency of the antibody concentration. Trastuzumab alone (pink), trastuzumab-phosphonamidate-MMAF (blue) and trastuzumab-maleimide-MMAF (green).

Procedures for the Staudinger-Induced Thiol Addition with Alkynyl-Phosphonites for the Generation of Antibody Drug Conjugates (ADCs)

N-(4-azidobenzoyl)-L-valine

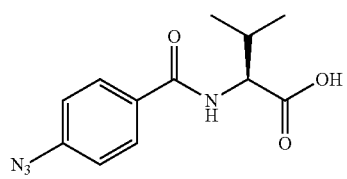 [SMILES: CC(C)[C@H](NC(=O)c1ccc(N=[N+]=[N-])cc1)C(=O)O]

A 50-ml Schlenk-flask was charged with 1.00 g of 4-azidobenzoic acid (6.13 mmol, 1.00 eq.) and suspended in 8.5 ml of dry DCM (dichloromethane) together with a drop of DMF (N,N-dimethylformamide) under argon. 630 μl of oxalylchloride were added drop-wise at 0° C. and the reaction mixture was stirred at room temperature for 2 h until the solution became clear. All volatiles were removed under reduced pressure and the corresponding solid was redissolved in 4 ml of DMF. The corresponding solution was added drop-wise at 0° C. to a solution of 720 mg L-valine (6.13 mmol, 1.00 eq.) and 612 mg sodium hydroxide (15.33 mmol, 2.50 eq.) in 8 ml water and stirred for 2 more hours. The solution was acidified with 1 N HCl and extracted three times with diethylether. The organic fractions were pooled, dried (MgSO$_4$) and the solvents were removed under reduced pressure. Pure product was obtained by flash column chromatography on silicagel (30% EtOAc, 0.5% formic acid in n-hexane) as colourless fume. (954 mg, 4.96 mmol, 80.9%)

$^1$H NMR (600 MHz, Chloroform-d) δ=10.12 (s, 1H), 7.79 (d, J=8.6, 2H), 7.05 (d, J=8.6, 2H), 6.79 (d, J=8.5, 1H), 4.76 (dd, J=8.5, 4.9, 1H), 2.33 (pd, J=6.9, 4.9, 1H), 1.03 (d, J=6.9, 3H), 1.01 (d, J=6.9, 3H). $^{13}$C NMR (151 MHz, CDCl$_3$) δ=175.82, 167.28, 144.03, 130.17, 129.13, 119.20, 77.16, 57.79, 31.40, 19.16, 17.99. HR-MS for C12H15N$_4$O3$^+$ [M+H]$^+$ calcd: 263.1139. found 263.1151.

N-(4-azidobenzoyl)-L-valine-anhydride

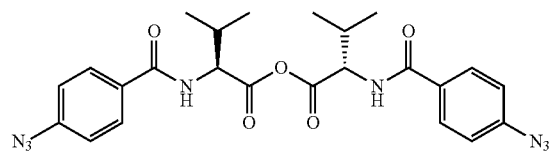 [SMILES: CC(C)[C@H](NC(=O)c1ccc(N=[N+]=[N-])cc1)C(=O)OC(=O)[C@@H](NC(=O)c1ccc(N=[N+]=[N-])cc1)C(C)C]

In a 100-ml round-bottom flask, 954 mg N-(4-azidobenzoyl)-L-valine (3.64 mmol, 1.00 eq.), 750 mg dicyclohexylcarbodiimide (3.64 mmol, 1.00 eq.), 418 mg N-hydroxysuccinimide (3.64 mmol, 1.00 eq.) and 9 mg 4-(dimethylamino)-pyridine (0.07 mmol, 0.02 eq.) were dissolved in 25 ml of THF and stirred over night at room temperature. The reaction mixture was filtered, the solids were washed several times with THF, the solvent was removed under reduced pressure and the crude product was purified by flash column chromatography on silicagel (20 to 40% EtOAc in n-hexane). The compound was isolated as white powder (513 mg, 1.01 mmol, 55.7%)

$^1$H NMR (600 MHz, Chloroform-d) δ=8.01 (d, J=8.7, 2H), 7.13 (d, J=8.7, 2H), 4.29 (d, J=4.6, 1H), 2.39 (heptd, J=6.9, 4.6, 1H), 1.16 (d, J=6.9, 3H), 1.03 (d, J=6.9, 3H). $^{13}$C NMR (151 MHz, CDCl$_3$) δ=177.52, 160.90, 144.51, 129.60, 122.43, 119.30, 70.68, 31.28, 18.76, 17.57.

N-(4-azidobenzoyl)-L-valine-L-citrulline

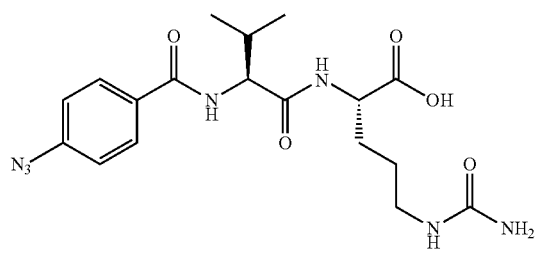 [SMILES: CC(C)[C@H](NC(=O)c1ccc(N=[N+]=[N-])cc1)C(=O)N[C@@H](CCCNC(N)=O)C(=O)O]

In a 50-ml round-bottom flask, 380 mg N-(4-azidobenzoyl)-L-valine-anhydride (0.75 mmol, 1.00 eq.) were dissolved in 2 ml of 1,2-Dimethoxyethane and cooled to 0° C. A solution of 351 mg L-citrulline (1.50 mmol, 2.00 eq.) and 144 mg sodium hydrogencarbonate (2.25 mmol, 3.00 eq.) in 4 ml H$_2$O and 2 ml THF (tetrahydrofuran) was added dropwise and stirred over night at room temperature. All volatiles were removed under reduced pressure and the crude product was purified by flash column chromatography on silicagel (10% MeOH, 0.5% formic acid in CH$_2$Cl$_2$). The compound was isolated as colourless oil (312 mg, 0.74 mmol, 99.0%).

$^1$H NMR (600 MHz, DMSO-d$_6$) δ=8.31 (d, J=8.8, 1H), 8.27-8.21 (m, 1H), 7.96 (d, J=8.6, 2H), 7.20 (d, J=8.6, 2H), 6.05 (t, J=5.5, 1H), 5.47 (s, 2H), 4.37 (t, J=8.3, 1H), 4.18 (td, J=8.1, 5.1, 1H), 2.98 (q, J=6.4, 2H), 2.15 (dq, J=13.6, 6.8, 1H), 1.78-1.68 (m, 1H), 1.68-1.56 (m, 1H), 1.51-1.35 (m, 2H), 0.96 (d, J=6.8, 3H), 0.94 (d, J=6.8, 3H). $^{13}$C NMR (151 MHz, DMSO) δ=174.09, 171.54, 165.99, 159.40, 142.77, 131.36, 129.93, 119.23, 59.31, 52.57, 49.07, 30.77, 29.01, 27.07, 19.75, 19.28. HR-MS for C18H26N$_7$O5$^+$ [M+H]$^+$ calcd: 420.1990. found 420.1990.

N-(4-azidobenzoyl)-L-valine-L-citrulline-4-aminobenzyl Alcohol

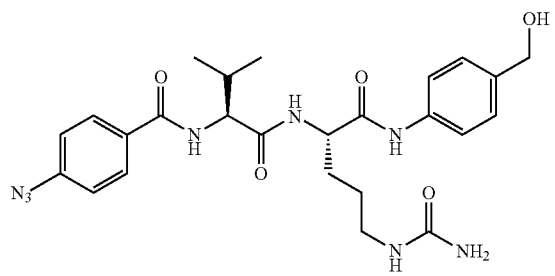 [SMILES: CC(C)[C@H](NC(=O)c1ccc(N=[N+]=[N-])cc1)C(=O)N[C@@H](CCCNC(N)=O)C(=O)Nc1ccc(CO)cc1]

In a 50-ml round-bottom flask, 330 mg N-(4-azidobenzoyl)-L-valine-L-citrulline (0.787 mmol, 1.0 eq.) and 107 mg 4-aminobenzyl alcohol (0.866 mmol, 1.10 eq.) were dissolved in 8 ml CH$_2$Cl$_2$ and 4 ml MeOH (methanol) under an argon atmosphere and cooled to 0° C. 390 mg N-Ethoxycarbonyl-2-ethoxy-1,2-dihydroquinoline (1.574 mmol, 2.00 eq.) were added portion-wise and the resulting solution was allowed to warm to room temperature overnight. All volatiles were removed under reduced pressure and the crude product was isolated by flash column chromatography on silicagel (10% to 15% MeOH in CH$_2$Cl$_2$) and obtained as white solid (164 mg, 0.313 mmol, 39.8%). Enantiomeric pure compound was isolated by preparative HPLC (Method D described above under "Procedures for the introduction of the alkyne-phosphonamidate moiety by generic building blocks via an amide bond") and obtained as a white solid after lyophilisation.

$^1$H NMR (600 MHz, DMSO-d$_6$) δ=9.93 (s, 1H), 8.32 (d, J=8.4, 1H), 8.21 (d, J=7.6, 1H), 7.96 (d, J=8.6, 2H), 7.55 (d, J=8.6, 2H), 7.24 (d, J=8.6, 2H), 7.21 (d, J=8.6, 2H), 6.12 (bs, 2H), 4.44 (s, 2H), 4.46-4.40 (m, 1H), 4.36 (t, J=8.1, 1H), 3.09-2.93 (m, 2H), 2.24-2.04 (m, J=6.7, 1H), 1.84-1.58 (m, 2H), 1.55-1.34 (m, 2H), 0.95 (d, J=6.7, 3H), 0.94 (d, J=6.7, 3H). $^{13}$C NMR (151 MHz, DMSO) δ=171.62, 170.79, 166.15, 159.46, 142.83, 137.95, 137.91, 131.29, 129.96, 127.38, 119.34, 119.26, 63.07, 59.56, 53.64, 39.20, 30.61, 29.88, 27.16, 19.79, 19.37. HR-MS for C25H33N$_8$O$_5^+$ [M+H]$^+$ calcd: 525.2568. found 525.2563. [α]$_D^{24}$=−49.6 (c=0.81; MeOH)

N-(4-(O-Ethyl-P-ethynyl-phosphonamidato-N-benzoyl)-L-valine-L-citrulline-4-aminobenzyl alcohol

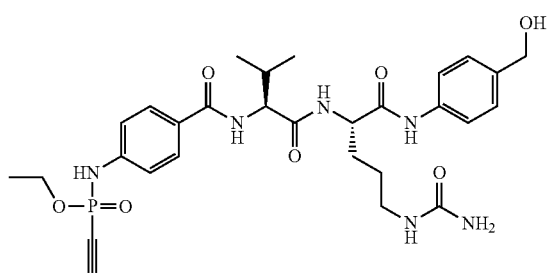 [SMILES: C#CP(=O)(Nc1ccc(C(=O)N[C@H](C(=O)N[C@@H](CCCNC(N)=O)C(=O)Nc2ccc(CO)cc2)C(C)C)cc1)OCC]

The compound was synthesized according to the general procedure from 230 μl diethyl chlorophosphite (0.925 mmol, 5.0 eq.), 1.85 ml ethynylmagnesium bromide solution (0.5 M in THF, 0.925 mmol, 5.0 eq.) and 97 mg N-(4-azidobenzoyl)-L-valine-L-citrulline-4-aminobenzyl alcohol (0.185 mmol, 1.0 eq.). The crude phosphonamidate was purified by preparative HPLC (method C described above under "Procedures for the introduction of the alkyne-phosphonamidate moiety by generic building blocks via an amide bond") and obtained as a white solid after lyophilisation. (60 mg, 0.098 mmol, 52.9%).

$^1$H NMR (600 MHz, DMSO-d$_6$) δ=9.96 (s, 1H), 8.80 (d, J=8.5, 1H), 8.22 (d, J=7.7, 1H), 8.11 (dd, J=8.6, 1.9, 1H), 7.82 (d, J=8.7, 2H), 7.56 (d, J=8.4, 2H), 7.24 (d, J=8.4, 2H), 7.14 (d, J=8.7, 2H), 4.39-4.46 (m, 4H), 4.33 (t, J=8.1, 1H), 4.20-4.03 (m, 2H), 3.02 (ddt, J=38.3, 13.4, 6.8, 2H), 2.20-2.09 (m, J=6.9, 1H), 1.79-1.57 (m, 2H), 1.53-1.35 (m, 2H), 1.31 (t, J=7.1, 3H), 0.95 (d, J=6.9, 3H), 0.93 (d, J=6.9, 3H). $^{13}$C NMR (151 MHz, DMSO-d$_6$) δ=171.74, 170.81, 166.59, 159.53, 143.51, 137.93 (d, J=9.0), 129.31, 127.57, 127.38, 119.34, 117.24 (d, J=7.7), 91.68 (d, J=45.5), 77.25 (d, J=261.1), 63.06, 62.29 (d, J=5.0), 59.45, 53.61, 39.27, 30.70, 29.82, 27.03, 19.82, 19.32, 16.42 (d, J=6.9). $^{31}$P NMR (243 MHz, DMSO-d$_6$) δ=−13.28, −13.32. HR-MS for C$_{29}$H$_{40}$N$_6$O$_7$P$^+$ [M+H]$^+$ calcd: 615.2691. found 615.2716.

N-(4-(O-Ethyl-P-ethynyl-phosphonamidato-N-ben-
zoyl)-L-valine-L-citrulline-4-aminobenzyl-4-nitrop-
henyl carbonate

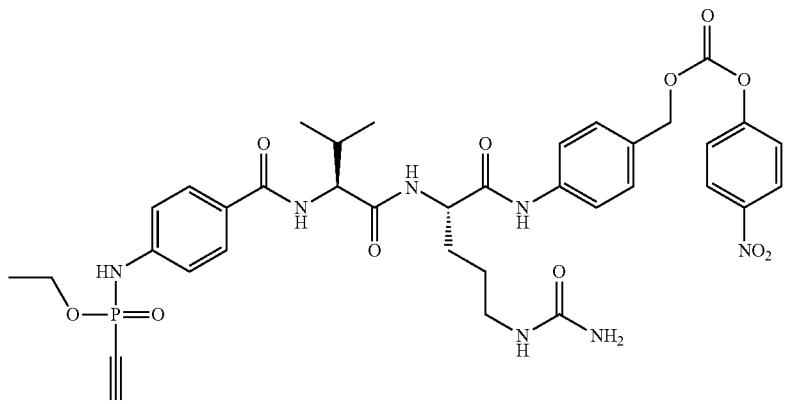 [SMILES: C#CP(=O)(Nc1ccc(C(=O)N[C@H](C(=O)N[C@@H](CCCNC(N)=O)C(=O)Nc2ccc(COC(=O)Oc3ccc([N+](=O)[O-])cc3)cc2)C(C)C)cc1)OCC]

A 5-ml round-bottom flask was charged with 31 mg N-(4-(O-Ethyl-P-ethynyl-phosphonamidato-N-benzoyl)-L-valine-L-citrulline-4-aminobenzyl alcohol (0.050 mmol, 1.00 eq.) and 31 mg Bis(4-nitrophenyl) carbonate (0.101 mmol, 2.00 eq.). The solids were dissolved in 140 µl of DMF (N,N-dimethylformamide) and 17.4 µl DIPEA (N,N-diiso-propylethylamine, 0.101 mmol, 2.00 eq.) were added. The yellow solution was stirred for 1 h at room temperature and the solution was added to 30 ml of ice-cold diethyl ether. The precipitate was collected by centrifugation, redissolved in DMF and again precipitated with ether. The procedure was conducted three times in total and finally the solid was dried under high vacuum conditions. The compound was isolated in quantitative yields and sufficiently pure for the next step. Analytical pure material was purified by preparative HPLC using method C described above under "Procedures for the introduction of the alkyne-phosphonamidate moiety by generic building blocks via an amide bond".

$^1$H NMR (600 MHz, DMSO-d$_6$) δ=10.10 (s, 1H), 8.79 (d, J=8.5, 1H), 8.32 (d, J=9.1, 1H), 8.23 (d, J=7.4, 1H), 8.07 (dd, J=8.5, 2.2, 1H), 7.81 (d, J=8.7, 2H), 7.66 (d, J=8.5, 2H), 7.57 (d, J=9.1, 1H), 7.42 (d, J=8.5, 2H), 7.13 (d, J=8.7, 2H), 5.25 (s, 2H), 4.47-4.40 (m, 2H), 4.34 (t, J=8.0, 1H), 4.20-4.05 (m, 2H), 3.01 (ddt, J=47.1, 13.4, 6.8, 2H), 2.20-2.09 (m, J=6.8, 1H), 1.80-1.59 (m, 2H), 1.55-1.35 (m, 2H), 1.30 (t, J=7.0, 3H), 0.95 (d, J=6.7, 3H), 0.93 (d, J=6.7, 3H). $^{13}$C NMR (151 MHz, DMSO-d$_6$) δ=171.79, 171.17, 166.58, 159.44, 155.75, 152.42, 145.63, 143.50, 139.83, 129.95, 129.77, 129.30, 127.59, 125.86, 123.08, 119.51, 117.24 (d, J=7.8), 91.67 (d, J=45.6), 77.26 (d, J=261.0), 70.71, 62.26 (d, J=5.0), 59.31, 53.68, 39.14, 30.71, 29.76, 27.19, 19.80, 19.30, 16.41 (d, J=6.9). $^{31}$P NMR (243 MHz, DMSO) δ=−10.39, −10.44. HR-MS for $C_{36}H_{43}N_7O_{11}P^+$ [M+H]$^-$ calcd: 780.2753. found 780.2744.

Amidate-Val-Cit-Pab-MMAF

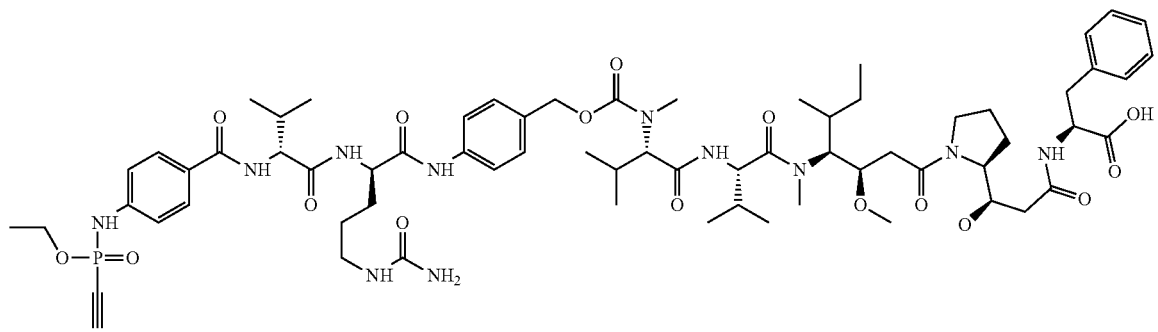 [SMILES: C#CP(=O)(Nc1ccc(C(=O)N[C@@H](C(=O)N[C@H](CCCNC(N)=O)C(=O)Nc2ccc(COC(=O)N(C)[C@H](C(=O)N[C@H](C(=O)N(C)[C@@H](C(C)CC)[C@@H](CC(=O)N3CCC[C@H]3[C@H](O)CC(=O)N[C@@H](Cc3ccccc3)C(=O)O)OC)C(C)C)C(C)C)cc2)C(C)C)cc1)OCC]

A 15-mL falcon-tube was charged with 14.35 mg N-(4-(O-Ethyl-P-ethynyl-phosphonamidato-N-benzoyl)-L-valine-L-citrulline-4-aminobenzyl-4-nitrophenyl carbonate (0.0184 mmol, 1.00 eq.), 0.50 mg 1-Hydroxybenzotriazol (0.0037 mmol, 0.20 eq.) and 13.15 mg MMAF (monomethylauristatin F, 0.0184 mmol, 1.00 eq.). The solids were dissolved in 250 ml dry DMF and 25 ml pyridine and heated to 60° C. over-night. All volatiles were removed under reduced pressure, the crude product was purified by semi-preparative HPLC using method E described above under "Procedures for the introduction of the alkyne-phosphonamidate moiety by generic building blocks via an amide bond", and the desired compound obtained as a white solid after lyophilisation. (4.84 mg, 0.0035 mmol, 19.2%). HR-MS for $C_{69}H_{104}N_{11}O_{16}P^{2+}$ [M+2H]$^{2+}$ calcd: 686.8695. found 686.8694.

FIG. 19 shows the UPLC-UV purity of phosphonamidate-Val-Cit-Pab-MMAF.

Trastuzumab Production

Trastuzumab expression and purification was executed as previously published with an additional final purification by gel filtration on a Superdex 200 Increase 10/300 from GE with phosphate-buffered saline (PBS) anf flow rate of 0.75 ml/min (30).

General Procedure for the Modification of Trastuzumab Via the Reduction/Alkylation Protocol The general procedure for the modification of Trastuzumab via the reduction/alkylation protocol is shown in FIG. 44.

Trastuzumab modification was carried out by incubating freshly expressed antibody (c=0.55 mg/ml) in a buffer containing 50 mM sodium borate and 4 mM DTT in PBS (pH 8.0) with a total volume of 80 µl at 37° C. for 40 min. Excess DTT removal and buffer exchange to a solution containing 50 mM $NH_4HCO_3$ and 1 mM EDTA (pH 8.5) was conducted afterwards using 0.5 mL Zeba™ Spin Desalting Columns with 7K MWCO (Thermo Fisher Scientific, Waltham, United States). 1.60 µl of a solution containing 13 mM amidate in DMSO was added quickly. And the mixture was shaken at 800 rpm and 14° C. for 16 hours. Excess amidate was again removed by buffer exchange to sterile PBS using 0.5 mL Zeba™ Spin Desalting Columns with 7K MWCO.

Cell Based Antiproliferation Assays

Antiproliferation assays were conducted as previously reported (30) with the following minor changes:

For MDAMB468 cells, a reduced amount of $2*10^3$ cells were seeded in each well of a 96-well optical cell culture plate supplemented with 100 µL culture media.

Images were acquired with an Operetta High-Content Imaging system (PerkinElmer, Waltham, MA, USA) equipped with a 20× high NA objective.

Cell counts were calculated from duplicates

Staudinger-Induced Thiol Addition with Alkynyl-Phosphonites for the Generation of Antibody Fluorophore Conjugates (AFCs)

In a similar manner, as described above under "Staudinger-induced thiol addition with alkynyl-phosphonites for the generation of Antibody Drug Conjugates (ADCs)" the fluorescent dye Cy5 was conjugated to Trastuzumab to generate an antibody-fluorophore conjugate. Synthesis of Cy5-O-ethyl-P-alkynyl-phosphonamidate was conducted as described above under "Introduction of the alkyne-phosphonamidate moiety by generic building blocks via an amide bond". The obtained Phosphonamidate-AFC conjugates were evaluated by immunostaining of two different Her2-overexpressing cell lines BT474 and SKBR3. The Her2-non overexpressing cell line MDAMB468 was used as a control to proof Her2 selectivity. Sufficient membrane staining after cell fixation was observed the two Her2-expressing cell lines, while the Her2-non expressing cell lines did not show increased fluorescence.

FIG. 20: Depicted are immunostainings of fixed cells over expressing the cell surface receptor Her2 (BT474 and SKBR3) or exhibiting low Her2 expression levels (MDAMB468). The AFC Trastuzumab-Amidate-Cy5 shows clear localization to the plasma membrane for Her2+ cell lines and no staining of Her2– cells. The merged images show the DAPI signal in blue and the Tras-phosphonamidate-Cy5 signal in red. Scale bar represents 10 µm.

Procedures for the Staudinger-Induced Thiol Addition with Alkynyl-Phosphonites for the Generation of Antibody Fluorophore Conjugates (AFCs).

The general procedures for the Staudinger-induced thiol addition with alkynyl-phosphonites for the generation of Antibody Fluorophore Conjugates (AFCs) are shown in FIG. 45.

Trastuzumab-Cy5 conjugates were synthesized according to the general procedure, described above under "Staudinger-induced thiol addition with alkynyl-phosphonites for the generation of Antibody Drug Conjugates (ADCs) with the following slight modifications: the amidate equivalents were raised to 130, and the DMSO (dimethylsulfoxide) content was raised to 5% (more precisely, from 2% to 5%) to solubilize the Cy5.

AFC Imaging Procedure

BT474, SKBR3 and MDAMB468 were seeded on sterile cover slips and incubated ON at 37° C., 5% CO2 for cell attachment. Cells were washed three times with 1×PBS prior to fixation for 10 min in 1×PBS/4% PFA (formaldehyde). Fixation was stopped by the addition of an equal volume 1×PBST (PBS+0.05% Tween20) followed by two more washes with PBST. AFCs were added to a final concentration of 5 µg/mL and incubated for 1 h at RT. Unbound AFC was removed by three washes with PBS.

Images were acquired on a Leica SP5 confocal microscopy system equipped with a 63×1.40 Oil immersion objective. Laserlines 405 nm and 594 nm were used in combination with standard DAPI and Cy5 filter settings. Image processing was carried out with ImageJ 1.5.1 h software extended by the Fiji processing package.

Stability Studies of the Phosphonamidate Linkage

To study the stability of the phosphonamidate bond in complex systems as cell lysate or serum, a dye-quencher pair was synthesized which generates a fluorescent signal upon cleavage of the phosphonamidate bond. Conjugates consist of the fluorescent dye EDANS, the quencher DABCYL and an attached peptide to ensure water solubility of the conjugates (FIGS. 21A-21E). A maleimide linked conjugate was synthesized for comparison experiments (FIG. 21B).

FIGS. 21A-21E show: FIG. 21A: Structure of the phosphonamidate linked FRET conjugate. FIG. 21B: Structure of the maleimide linked FRET conjugate. FIG. 21C: Principle of the fluorescence-quencher based readout. Conjugates were incubated at room temperature at a concentration of 10 µM. Measurements were performed at least in triplicates in a 96-well plate. FIG. 21D: Fluorescence increase was monitored over time. HCl samples were neutralized before the measurements. Lysate was freshly prepared from HeLa-cells, lysed in PBS. Serum originated from human blood. FIG. 21E: Comparison of a phosphonamidate- and a maleimide-linked dye-quencher pair during exposure to 1000 eq. glutathion in PBS.

As shown in FIGS. 21A-21E, the phosphonamidate adducts show a high stability in PBS, HeLA cell lysate and human serum, whereas only strong acidic conditions (1 N HCl) lead to phosphonamidate bond cleavage. The FRET-conjugates were also exposed to a high excess of glutathione. After 2 days of incubation with 1000 eq. of glutathione at physiological pH, 15% of the maleimide linkage was cleaved, while 99% of the phosphonamidate adducts were still intact (FIG. 21C).

In the next experiment, we probed whether the modification element of phosphonamidate-labelled or maleimide-labelled ADCs is transferred to serum proteins in the presence of thiols, as the stability of ADCs for several days is crucial during circulation in the blood stream. Trastuzumab modified with different biotin derivatives (FIGS. 22A-22B) was exposed to serum-like albumin concentrations of 0.5 mM, incubated at 37° C., and transfer of the modification from the antibody to the serum protein was monitored by western blotting (FIG. 22B). A significant transfer of the biotin to BSA (bovine serum albumin) at serum concentrations was observed for maleimide linkage while the phoshonamidate-linkage was stable under the tested conditions. Taken together, these stability experiments experiment clearly point to superior stability of the phoshonamidate-labelled ADCs as compared to maleimide-labelled ADCs potentially leading to a reduction of off-target toxicity when compared to conventional maleimide-linked conjugates.

FIGS. 22A-22B show: Transfer of the antibody modification to serum proteins. FIG. 22A: Tratuzumab-biotin conjugates were incubated at a concentration of 3 μM with 500 μM BSA in PBS at 37° C. FIG. 22B: Biotin transfer to albumin was monitored by western blot analysis. Lane 1: Untreated maleimide conjugate. Lane 2-5: Analysis of the BSA exposed maleimide adduct after 0, 1, 2 and 5 days. Lane 6: Untreated amidate conjugate. Lane 6-10: Analysis of the BSA exposed amidate adduct after 0, 1, 2 and 5 days.

Procedures for the Stability Studies of the Phosphonamidate Linkage

DABCYI-Cys Peptide

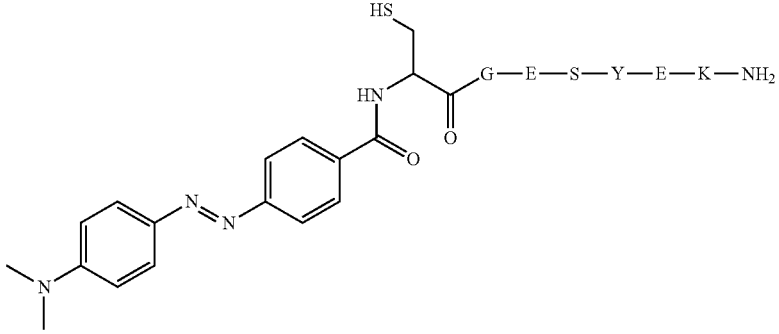

DABCYI-Cys peptide was synthesized by standard Fmoc-based chemistry in a linear synthesis by manual coupling. 0.1 mmol of Rink amide resin (subst: 0.4 mmol/g) was added to a reaction vessel and synthesis was performed with five-fold amino acid excess. Fmoc de-blocking was achieved by resin treatment with 20% piperidine in DMF twice for 5 minutes. Coupling was achieved by addition of HOBt/HBTU/DIPEA (5 eq./5 eq./10 eq) in DMF for 45 min. After the final Cys coupling, 5 eq. of the DABCYL acid was coupled with 5 eq. HATU and 10 eq. DIPEA in DMF for 45 min. The peptide was cleaved of the resin by addition of TFA/DTT/TIS (95/2.5/2.5, w,w,w) within 3 h. Subsequently, the peptide was precipitated by the addition of ice-cold diethyl ether. The precipitate was collected by centrifugation, dried and purified by preparative HPLC (method C described above under "Procedures for the introduction of the alkyne-phosphonamidate moiety by generic building blocks via an amide bond". The peptide was obtained as a red solid in a yield of 35.8% (38.2 mg, 35.8 μmol). ESI-MS for $C_{48}H_{66}N_{12}O14S^+$ $[M+2H]^+$ calcd: 533.23. found 533.34.

DABCYI-Cys peptide Phosphonamidate EDANS Adduct

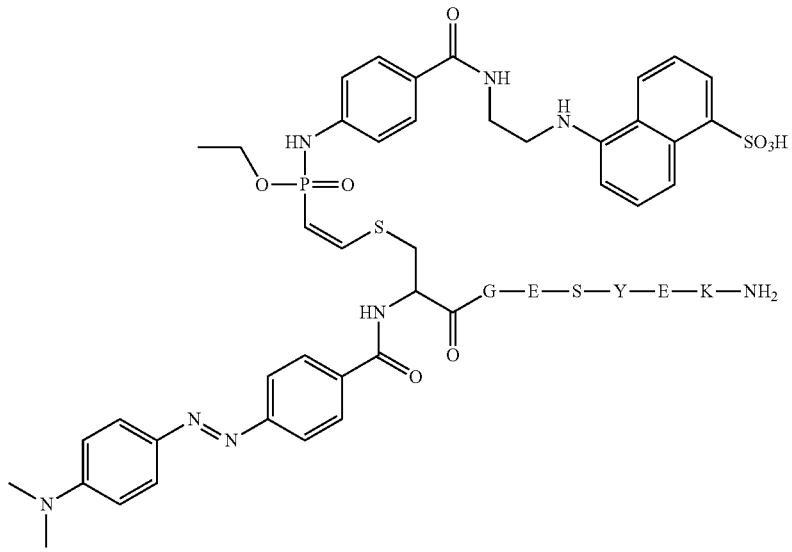

A 1.5-ml Eppendorf tube was charged with 263 µl of a solution of DABCYl-Cys peptide (20 mM) in 50 mM NH$_4$HCO$_3$ at a pH of 8.5. 158 µl 50 mM NH$_4$HCO$_3$ at a pH of 8.5 and 105 µl of a solution of EDANS amidate (100 mM) in DMF was added to give a final concentration of 20 mM peptide and 10 mM amidate in 20% DMF/Buffer. The tube was shaken at 800 rpm at room temperature for 3 h. All volatiles were removed under reduced pressure and the crude product purified by semi-preparative HPLC (method E described above under "Procedures for the introduction of the alkyne-phosphonamidate moiety by generic building blocks via an amide bond"). The peptide was obtained as a red solid ESI-MS for $C_{71}H_{90}N_{15}O_{20}PS_2^+$ [M+2H]$^+$ calcd: 783.78. found 784.47.

DABCYl-Cys Peptide Maleimide EDANS Adduct

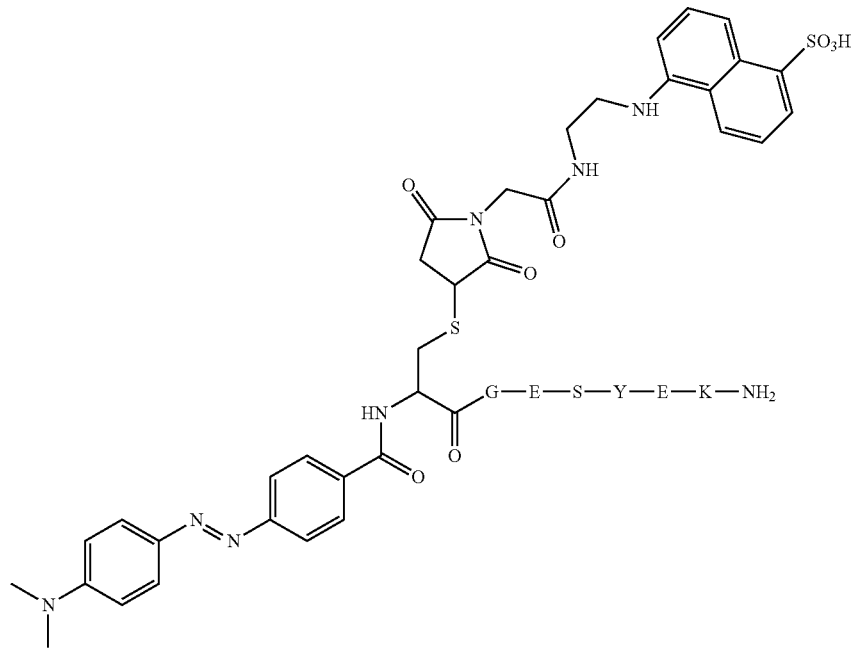

A 1.5-ml Eppendorf tube was charged with 188 µl of a solution of DABCYl-Cys peptide (20 mM) in PBS. 188 µl of a solution of EDANS maleimide (40 mM) in DMF was added to give a final concentration of 10 mM peptide and 20 mM maleimide in 50% DMF/Buffer. The tube was shaken at 800 rpm at room temperature for 3 h. All volatiles were removed under reduced pressure and the crude product purified by semi-preparative HPLC (method E described above under "Procedures for the introduction of the alkyne-phosphonamidate moiety by generic building blocks via an amide bond"). The peptide was obtained as a red solid. ESI-MS for $C_{66}H_{83}N_{15}O_{20}S_2^+$ [M+2H]$^+$ calcd 734.77. found. 734.79.

Stability Studies of the Dabcyl-EDANS Adducts

Stabilities studies were conducted in 96-well plate (Corning 3615, black with clear, flat bottom) at least in triplicates. 5 µl of a 200 µM Stock solution of the Dabcyl-EDANS adducts and 95 µl of the respective test solutions were added to each well.

HeLa cell lysate was generated from approximately 1*10$^7$ cells, lysed in 400 µl PBS by sonification. Cells were grown on a 75 cm$^2$ cell culture plate, washed twice with PBS and harvested with a cell scraper. Human serum was purchased from Sigma Aldrich. Glutathione was dissolved at a concentration of 10 mM in PBS and the pH was adjusted to 7.4. 1N HCl studies were conducted at 200 µM, neutralized to pH 7 and diluted to 10 µM before fluorescence measurements.

Fluorescence was measured on a Tecan Safire plate reader. Excitation: 336 nm, emission: 490 nm, bandwidth: 5 nm at 20° C.

Incubation of Trastuzumab-Biotin Conjugates with BSA

Trastuzumab-Biotin conjugates were incubated at a concentration of 3 µM in PBS with a final concentration of 0.5 mM BSA at 37° C. Samples were drawn after 0, 1, 2 and 5 days, deep frozen in liquid Nitrogen and finally subjected to SDS/Page and western blot analysis.

Further Kinetic Investigations of the Thiol Addition

To study the kinetics of the thiol addition to alkyne-phosphonamidates at low concentrations, a fluorescent EDANS-based phosphonamidate was synthesized as described in chapter 1.1. Addition of glutathione as a model substrate was probed over time by fluorescence HPLC. Peak integration and normalization to unconjugated EDANS as an internal standard was applied to determine the second order rate constant of the reaction. A second order rate constant of 37.32±0.41 l/mol*s was measured.

FIGS. 23A-D show: Determination of the second order rate constant of the thiol addition. FIG. 23A: Reaction of the EDANS phosphonamidate with glutathione. FIG. 23B: Fluorescence HPLC trace after 30 min reaction time. FIG. 23C: Monitoring of the phosphonamidate decrease over time. FIG. 23D: Plot of the inverse concentration against reaction time. Error bars represent the mean of three replicates (n=3).

Procedures for the Further Kinetic Investigations of the Thiol Addition

Glutathione addition to the EDANS-phosphonamidate was conducted at a final concentration of 0.1 mM amidate, 0.1 mM glutathione and 0.02 mM EDANS as an internal standard in 50 mM NH$_4$HCO$_3$-buffer containing 1 mM EDTA at pH 8.5 with 1% DMF. 2.5 µl of a 20 mM stock solution of EDANS-phosphonamidate in DMF was premixed with 488 µl buffer and 5 µl of a 2 mM stock solution of EDANS in a 1:1 mixture of DMF and buffer. The reaction was started by the addition of 5 µl of a 10 mM solution of glutathione in buffer. 10 µl samples were drawn at 0, 15, 30, 60, 120, 240 and 480 minutes and acidified with 190 µl 10 mM NaOAc-Buffer (pH 5.0) and subjected to fluorescence HPLC analysis.

Synthesis of Further Phosphonites

Further, the O-substituent of the alkyne phosphonites was varied as shown in Scheme E2, and electron-rich phosphonites E1 to E5 were synthesized:

Scheme 28
Phosphonite Synthesis from Bis-(diispropyl)-amino-chloro-phosphine.
Depicted are isolated yields for the respective phosphonites E1-E5.

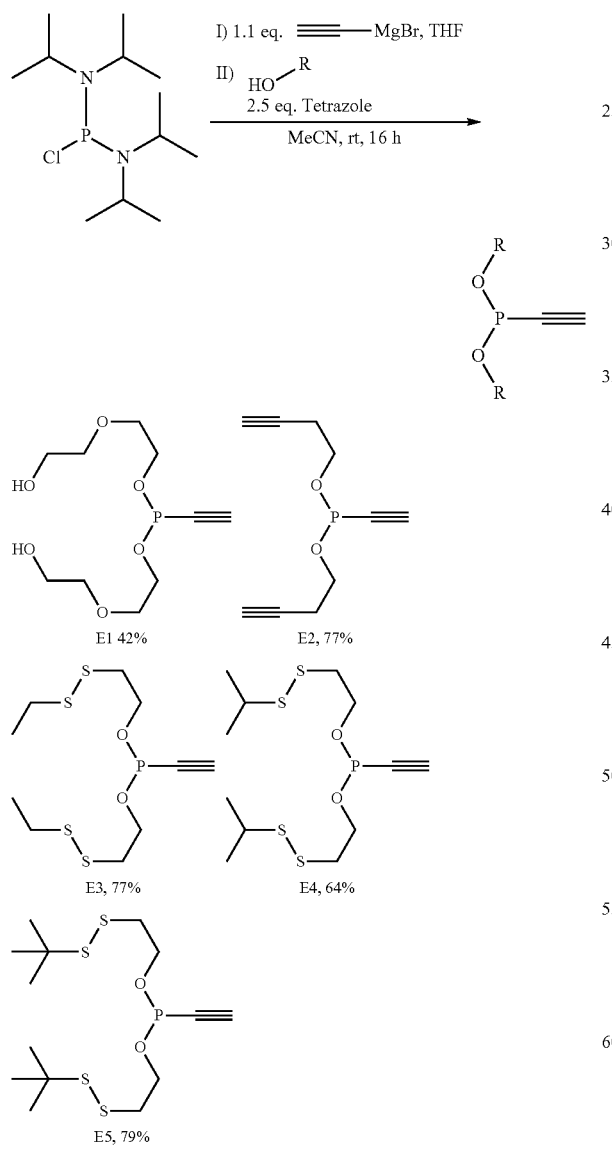

Procedures for the Synthesis of Further Phosphonites E1 to E5

General Procedure for the Synthesis of O-Substituted Alkynyl Phosphonamidates from Bis(Diisopropylamino)Chlorophosphine

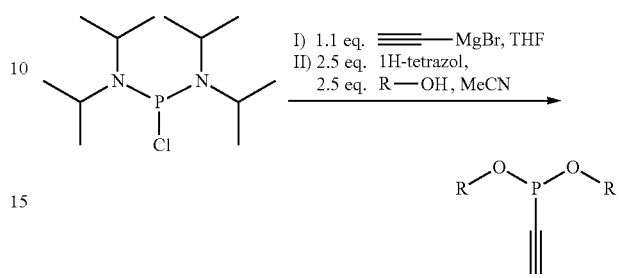

A 25-ml Schlenk flask was charged with 267 mg bis(diisopropylamino)chlorophosphine (1.00 mmol, 1.00 eq.) under an argon atmosphere, cooled to 0° C. and 2.20 ml ethynylmagnesium bromide solution (0.5 M in THF, 1.10 mmol, 1.10 eq.) was added drop wise. The yellowish solution was allowed to warm to room temperature and stirred for further 30 minutes. The respective alcohol, dissolved in 5.56 ml 1H-tetrazole solution (0.45 M in MeCN, 2.50 mmol) was added and the white suspension was stirred over night at room temperature. The reaction mixture was directly placed on a silica gel flash column.

Di-(2-(2-Hydroxyethoxy)ethyl) ethynylphosphonite (Compound E1)

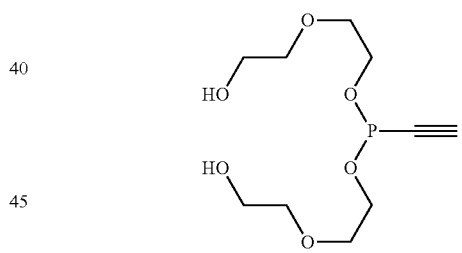

The compound was synthesized according to the above "General procedure for the synthesis of O-substituted alkynyl phosphonamidates from bis(diisopropylamino)chlorophosphine" from 267 mg bis(diisopropylamino)chlorophosphine (1.00 mmol, 1.00 eq.), 2.20 ml ethynylmagnesium bromide solution (0.5 M in THF, 1.10 mmol, 1.10 eq.), 1.06 g 2-(2-Hydroxyethoxy)ethan-1-ol (10.00 mmol, 10.00 eq.), 5.56 ml 1H-tetrazole solution (0.45 M in MeCN, 2.50 mmol) and purified by flash column chromatography on silicagel (5% MeOH in $CH_2Cl_2$). The compound was obtained as a yellowish oil. (112 mg, 0.421 mmol, 42.1%).

$^1$H NMR (300 MHz, Chloroform-d) δ=4.14-3.98 (m, 4H), 3.65-3.59 (m, 4H), 3.58-3.49 (m, 8H), 3.15 (d, J=2.4, 1H). $^{13}$C NMR (75 MHz, Chloroform-d) δ=92.52, 92.50, 84.61, 83.98, 72.60, 70.72 (d, J=4.0), 67.20 (d, J=6.0), 61.44. $^{13}$NMR (75 MHz, Chloroform-d) δ=92.51 (d, J=1.4), 84.30 (d, J=46.8), 72.60, 70.72 (d, J=4.0), 67.20 (d, J=6.0), 61.44. $^{31}$P NMR (122 MHz, $CDCl_3$) δ=131.97.

Di-(3-Butinyl) ethynylphosphonite (Compound E2)

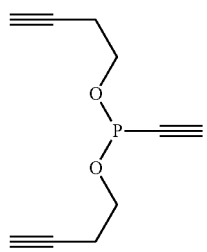

The compound was synthesized according to the above "General procedure for the synthesis of O-substituted alkynyl phosphonamidates from bis(diisopropylamino)chlorophosphine" from 267 mg bis(diisopropylamino)chlorophosphine (1.00 mmol, 1.00 eq.), 2.20 ml ethynylmagnesium bromide solution (0.5 M in THF, 1.10 mmol, 1.10 eq.), 189 µl 3-Butyn-1-ol (2.50 mmol, 2.50 eq.), 5.56 ml 1H-tetrazole solution (0.45 M in MeCN, 2.50 mmol) and purified by flash column chromatography on silicagel (10% EtOAC in n-hexane). The compound was obtained as a colourless oil. (152 mg, 0.774 mmol, 77.4%).

$^1$H NMR (300 MHz, Chloroform-d) δ=4.07 (dtd, J=8.1, 7.0, 1.5, 4H), 3.14 (d, J=2.3, 1H), 2.56 (tdd, J=7.0, 2.7, 0.6, 4H), 2.03 (t, J=2.7, 2H). $^{13}$C NMR (75 MHz, Chloroform-d) δ=92.42 (d, J=1.3), 83.92 (d, J=47.1), 80.24, 70.02, 65.81 (d, J=6.5), 21.28 (d, J=4.7). $^{31}$P NMR (122 MHz, CDCl$_3$) δ=130.15.

The procedures for the synthesis of compounds E3, E4 and E5 are provided herein below under "Procedures for the synthesis of compounds having a cleavable group on the O-substituent".

Staudinger Phosphonite Reaction with Phosphonite E1 and E2

The highly stable nature of electron rich phosphonites was further exploited by performing the Staudinger phosphonite reaction with alkyne-phosphonites in aqueous solvents. As depicted in FIG. 24, formation of the desired product from alkyne phosphonite E1 was observed in a pure aqueous system.

FIG. 24 shows: Reaction of an azido modified peptide with the water soluble phosphonite E1 in Tris buffer. A: Reaction scheme. B: HPLC-trace; orange: starting material; blue: reaction after 2 h.

Procedures for the Staudinger Phosphonite Reaction with Phosphonites E1 and E2

Peptide E9

Peptide E9 was synthesized by standard Fmoc-based chemistry in a linear synthesis by manual coupling. 0.1 mmol of Rink amide resin (subst: 0.4 mmol/g) was added to a reaction vessel and synthesis was performed with five-fold amino acid excess. Fmoc de-blocking was achieved by resin treatment with 20% piperidine in DMF twice for 5 minutes. Coupling was achieved by addition of HOBt/HBTU/DIPEA (5 eq./5 eq./10 eq) in DMF for 45 min. After the final Gly coupling, 5 eq. of the 4-azido benzoic acid was coupled with 5 eq. HATU and 10 eq. DIPEA in DMF for 45 min. The peptide was cleaved of the resin by addition of TFA/TIS/H$_2$O (95/2.5/2.5, w,w,w) within 3 h. Subsequently, the peptide was precipitated by the addition of ice-cold diethyl ether. The precipitate was collected by centrifugation, dried and purified by preparative HPLC (method C described above under "Procedures for the introduction of the alkyne-phosphonamidate moiety by generic building blocks via an amide bond"). ESI-MS for C37H50N$_{11}$O13$^+$ [M+H]$^+$ calcd: 856.36. found 856.36.

Staudinger Phosphonite Reaction of Peptide E9 with Amidate E1 in Basic Tris-Buffer 10 µl of a 50 mM stock solution of peptide E9 in 100 mM Tris buffer (pH 9.0) was added to 80 µl of 100 mM Tris buffer (pH 9.0). 10 µl of a solution of 500 mM phosphonite E1 in the same buffer was added and shaken at 37° C. for 2 hours at 800 RPM. A sample of 10 µl was drawn, diluted with 90 µl 1% TFA in H$_2$O and subjected to UPLC-MS-analysis.

Synthesis of E6

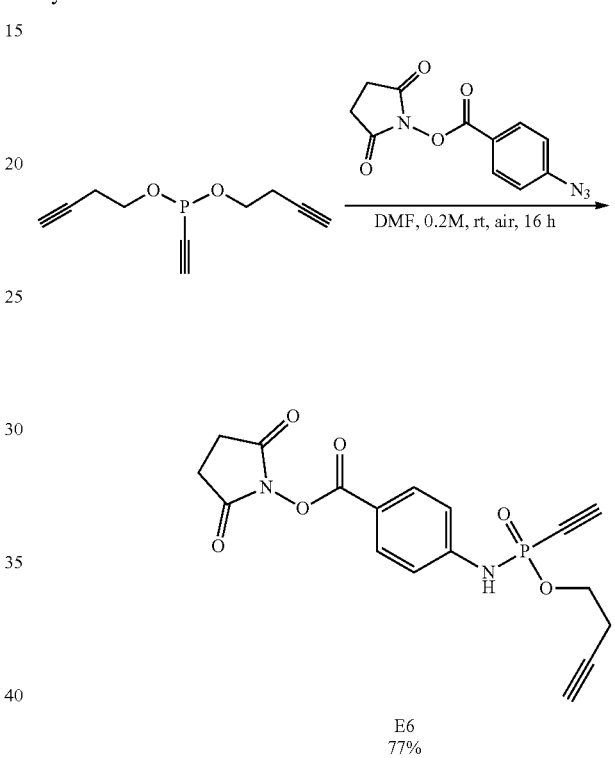

E6
77%

General procedure: 1.00 mmol of an organic azide (1.00 eq.) was stirred together with 1.00 mmol of an alkynyl phosphonite (1.00 eq.) in 5 ml DMF overnight. The organic solvent was removed under educed pressure and the residue purified by column chromatographite on silica. Following this general procedure, 37 mg Di-(3-Butinyl) ethynylphosphonite (compound E2) (0.192 mmol, 1.00 eq.) and 50 mg 4-azidobenzoic-acid-N-hydroxysuccinimide ester (0.162 mmol, 1.00 eq.) were mixed in 1 ml of DMF and purified by flash column chromatography on silicagel (70% EtOAc in hexane). The compound was obtained as colourless oil. (55 mg, 0.147 mmol, 76.6%).

$^1$H NMR (300 MHz, Chloroform-d) δ=8.33-7.93 (m, 3H), 7.21 (d, J=8.8, 2H), 4.47-3.94 (m, 2H), 3.06 (d, J=13.2, 1H), 2.89 (s, 4H), 2.65 (td, J=6.7, 2.7, 2H), 2.07 (t, J=2.7, 1H). $^{13}$C NMR (75 MHz, Chloroform-d) δ 169.61, 161.42, 145.52, 132.30, 118.19, 117.72 (d, J=8.1 Hz), 89.38 (d, J=50.0 Hz), 79.09, 70.94, 63.92 (d, J=5.0 Hz), 31.48, 25.69, 20.57 (d, J=8.2 Hz). $^{31}$P NMR (122 MHz, CDCl$_3$) δ=−9.74.

Synthesis of Compounds Having a Cleavable Group on the O-Substituent and Cleavage Experiments
Introduction of a Cleavable Group on the O-Substituent It has been described previously that cleavable disulfides can be used to liberate a specific payload under reducing conditions. For example, this approach has been applied to the specific release of a cytotoxic payload from an Antibody Drug Conjugate (ADC) within a cellular environment (31). In this context, it could be shown that disulfides that carry a leaving group in the beta position undergo cyclisation to a thiirane after disulfide cleavage and liberate a given payload (32).

For the purpose of the present invention, the synthesis of a conjugate having a cleavable disulfide-comprising O-substituent was envisaged as shown in Scheme 29.

Scheme 29, which is depicted in FIG. 46, shows the synthesis of a conjugate having a cleavable disulfide-comprising O-substituent via the Staudinger phosphonite reaction.

The following compounds having a cleavable group R on the O-substituent were synthesized and subjected to cleavage experiments:

wherein R is

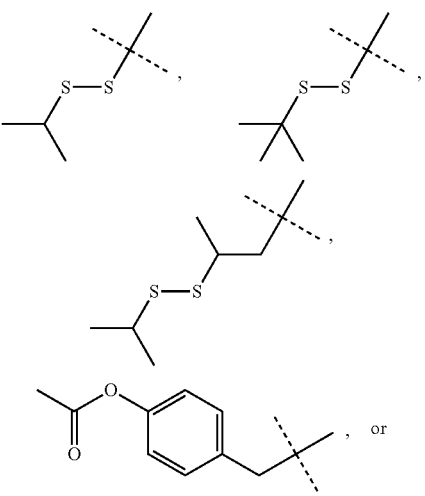

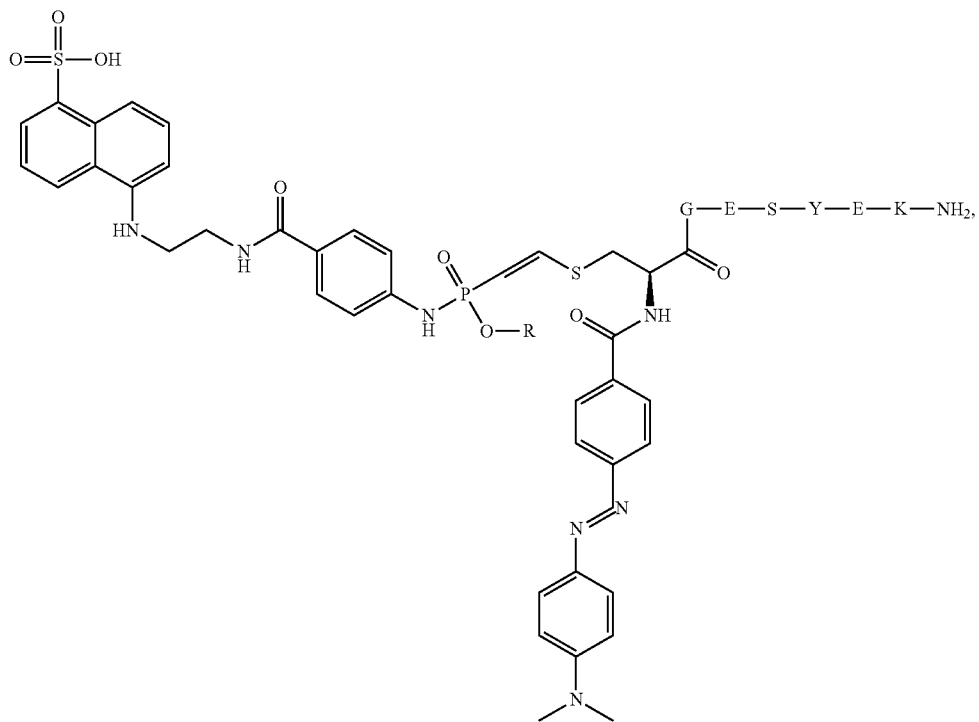

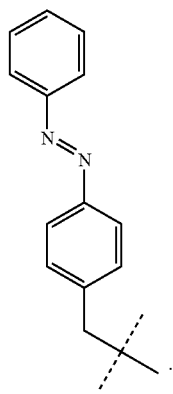

Procedures for the Synthesis of Compounds Having a Cleavable Croup on the O-Substituent General Procedure 1 for the Synthesis of 2-hydroxyethyl disulfides

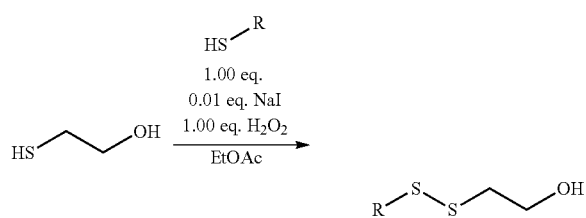

A 250 ml-round bottom flask was charged with 10 mmol (1.00 eq.) of the respective thiol, 10 mmol 2-mercaptoethanol (1.00 eq.), 0.1 mmol sodium iodide and 20 ml EtOAc. The mixture was rapidly stirred and 10 mmol of a solution of 30% $H_2O_2$ in water was added drop-wise. The mixture was stirred at room temperature for 1 h, volatiles were removed under reduced pressure and the disulfide was isolated by column chromatographie.

2-Hydroxyethyl ethyldisulfide

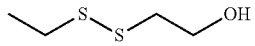

The compound was synthesized according to the above "General procedure 1 for the synthesis of 2-hydroxyethyl disulfides" from 2.00 ml Ethanethiol (27.74 mmol, 1.00 eq.), 1.96 ml 2-mercaptoethanol (27.74 mmol, 1.00 eq.), 41 mg sodium iodide (0.28 mmol, 0.01 eq.) and 3.14 ml hydrogen peroxide solution (aqueous, 30%) (27.74 mmol, 1.00 eq.). The disulfide was isolated by column chromatographie on silica (20% EtOAc in hexane) as colourless oil. Yield: 2.15 g (15.53 mmol, 56.0%).

$^1$H NMR (300 MHz, Chloroform-d) δ=3.91 (dd, J=5.7, 2H), 2.87 (t, J=5.7, 2H), 2.74 (q, J=7.3, 2H), 2.08 (s, 1H), 1.35 (t, J=7.3, 3H).

2-Hydroxyethyl isopropyldisulfide

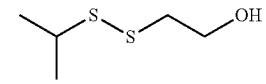

The compound was synthesized according to the above "General procedure 1 for the synthesis of 2-hydroxyethyl disulfides" from 2.00 ml isopropylthiol (21.53 mmol, 1.00 eq.), 1.52 ml 2-mercaptoethanol (21.53 mmol, 1.00 eq.), 32 mg sodium iodide (0.21 mmol, 0.01 eq.) and 2.44 ml hydrogen peroxide solution (aqueous, 30%) (21.53 mmol, 1.00 eq.). The disulfide was isolated by column chromatographie on silica (10% EtOAc in hexane) as colourless oil. Yield: 1.10 g (7.22 mmol, 33.6%)

$^1$H NMR (300 MHz, Chloroform-d) δ=3.88 (m, 2H), 3.02 (hept, J=6.7, 1H), 2.85 (t, J=5.9, 2H), 2.37 (m, 1H), 1.32 (d, J=6.7, 6H). $^{13}$C NMR (75 MHz, CDCl$_3$) δ=60.48, 41.94, 41.14, 22.54.

2-Hydroxyethyl tert-butyldisulfide

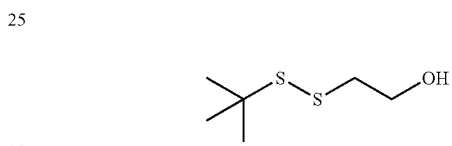

The compound was synthesized according to the above "General procedure 1 for the synthesis of 2-hydroxyethyl disulfides" from 2.00 ml tert-Butylthiol (17.74 mmol, 1.00 eq.), 1.24 ml 2-mercaptoethanol (17.74 mmol, 1.00 eq.), 26 mg sodium iodide (0.18 mmol, 0.01 eq.) and 2.04 ml hydrogen peroxide solution (aqueous, 30%) (17.74 mmol, 1.00 eq.). The disulfide was isolated by column chromatographie on silica (10% EtOAc in hexane) as colourless oil. Yield: 0.90 g (5.41 mmol, 30.5%).

$^1$H NMR (300 MHz, Chloroform-d) δ=3.87 (t, J=5.9, 2H), 2.86 (t, J=5.9, 2H), 2.33 (bs, 1H), 1.35 (s, 9H). NMR Data was in accordance with literature values (33).

2-(3-Hydroxypropyl) isopropyl disulfide

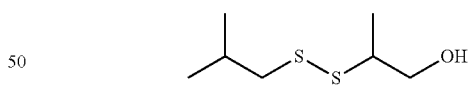

A 500-ml round-bottom flask was charged with 2.00 ml thiolactic acid (23.55 mmol, 1.00 eq.) and 150 ml dry THF. At 0° C., 1.60 g Lithium aluminium hydride (47.10, 2.0 eq.) were added portion-wise. The mixture was stirred at room temperature for 1 h, cooled again to 0° C. and quenched carefully with 6 N HCl. The aqueous phase was extracted with twice with 100 ml EtOAc, the organic fractions pooled, dried (MgSO$_4$) and all volatiles were removed under reduced pressure.

The resulting colourless oil was redissolved in 20 ml EtOH and 2.18 ml isobutyl thiol (23.55 mmol, 1.00 eq.), 55 mg sodium iodide (0.24 mmol, 0.01 eq.) and 2.70 ml hydrogen peroxide solution (aqueous, 30%) (23.55 mmol, 1.00 eq.) were added. The yellowish solution was stirred for another hour. Volatiles were removed under reduced pressure and the above stated disulfide isolated by column chromatographie on silica (20% EtOAc in hexane) as colourless oil. Yield: 1.15 g (6.928 mmol, 29.4%).

$^1$H NMR (300 MHz, Chloroform-d) δ=3.69 (dd, J=5.8, 3.2, 2H), 3.08-2.83 (m, 2H), 1.37-1.25 (m, 9H). $^{13}$C NMR (75 MHz, CDCl3) δ=65.49, 48.70, 41.66, 22.60, 22.51, 16.89.

1-(4-(hydroxymethyl)phenyl)-2-phenyldiazene

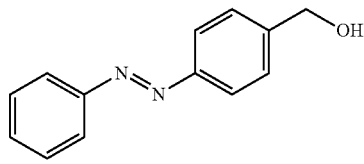 [SMILES: OCc1ccc(/N=N/c2ccccc2)cc1]

The compound was synthesized according to previously published procedure and isolated as orange solid (34).

$^1$H NMR (300 MHz, Chloroform-d) δ=8.03-7.86 (m, 4H), 7.68-7.42 (m, 5H), 4.81 (s, 2H). NMR Data was in accordance with literature values (34).

General Procedure 2 for the Synthesis of O-Substituted Alkynyl Phosphonites from bis(diisopropylamino)chlorophosphine

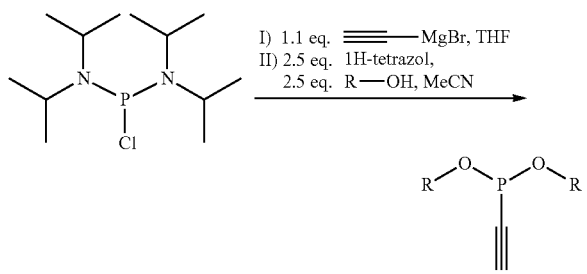

A 25-ml Schlenk flask was charged with 267 mg bis(diisopropylamino)chlorophosphine (1.00 mmol, 1.00 eq.) under an argon atmosphere, cooled to 0° C. and 2.20 ml ethynylmagnesium bromide solution (0.5 M in THF, 1.10 mmol, 1.10 eq.) was added drop wise. The yellowish solution was allowed to warm to room temperature and stirred for further 30 minutes. The respective alcohol, dissolved in 5.56 ml 1H-tetrazole solution (0.45 M in MeCN, 2.50 mmol) was added and the white suspension was stirred over night at room temperature. The reaction mixture was directly placed on a silica gel flash column.

Di-(ethyl disulfido)ethyl) ethynylphosphonite

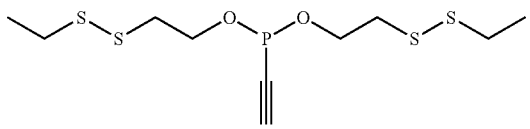 [SMILES: C#CP(OCCSSCC)OCCSSCC]

The compound was synthesized according to the above "General procedure 2 for the synthesis of O-substituted alkynyl phosphonites from bis(diisopropylamino)chlorophosphine" from 116 mg bis(diisopropylamino)chlorophosphine (0.44 mmol, 1.00 eq.), 0.96 ml ethynylmagnesium bromide solution (0.5 M in THF, 0.48 mmol, 1.10 eq.), 150 mg 2-Hydroxyethyl ethyldisulfide (1.10 mmol, 2.50 eq.), 2.42 ml 1H-tetrazole solution (0.45 M in MeCN, 1.10 mmol, 2.50 eq.) and purified by flash column chromatography on silicagel (10% to 20% EtOAc in hexane). The compound was obtained as yellowish oil. (112 mg, 0.34 mmol, 77.0%).

$^1$H NMR (300 MHz, Chloroform-d) δ=4.22 (dt, J=7.6, 6.8, 4H), 3.15 (d, J=2.3, 1H), 2.95 (t, J=6.8, 4H), 2.75 (q, J=7.3, 4H), 1.35 (t, J=7.3, 6H). $^{31}$P NMR (122 MHz, CDCl$_3$) δ=130.46.

Di-(2-isopropyl disulfido)ethyl) ethynylphosphonite

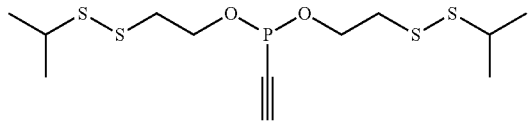 [SMILES: C#CP(OCCSSC(C)C)OCCSSC(C)C]

The compound was synthesized according to the above "General procedure 2 for the synthesis of O-substituted alkynyl phosphonites from bis(diisopropylamino)chlorophosphine" from 213 mg bis(diisopropylamino)chlorophosphine (0.80 mmol, 1.00 eq.), 1.76 ml ethynylmagnesium bromide solution (0.5 M in THF, 0.88 mmol, 1.10 eq.), 370 mg 2-Hydroxyethyl isopropyldisulfide (2.00 mmol, 2.50 eq.), 4.44 ml 1H-tetrazole solution (0.45 M in MeCN, 2.00 mmol, 2.50 eq.) and purified by flash column chromatography on silicagel (10% EtOAc in hexane). The compound was obtained as yellowish oil. (183 mg, 0.51 mmol, 63.9%).

$^1$H NMR (300 MHz, Chloroform-d) δ=4.21 (dt, J=8.0, 6.8, 4H), 3.15 (d, J=2.3, 1H), 3.04 (p, J=6.7, 2H), 2.94 (t, J=6.8, 4H), 1.33 (d, J=6.7, 12H). $^{31}$P NMR (122 MHz, CDCl$_3$) δ=130.40.

Di-(2-tert-butyl disulfido)ethyl) ethynylphosphonite

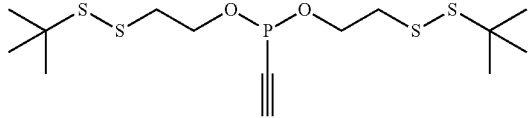 [SMILES: C#CP(OCCSSC(C)(C)C)OCCSSC(C)(C)C]

The compound was synthesized according to the above "General procedure 2 for the synthesis of O-substituted alkynyl phosphonites from bis(diisopropylamino)chlorophosphine" from 167 mg bis(diisopropylamino)chlorophosphine (0.63 mmol, 1.00 eq.), 1.38 ml ethynylmagnesium bromide solution (0.5 M in THF, 0.69 mmol, 1.10 eq.), 260 mg 2-Hydroxyethyl tert-butyldisulfide (1.57 mmol, 2.50 eq.), 3.48 ml 1H-tetrazole solution (0.45 M in MeCN, 1.57 mmol, 2.50 eq.) and purified by flash column chromatography on silicagel (10% EtOAc in hexane). The compound was obtained as yellowish oil. (190 mg, 0.49 mmol, 78.5%).

$^1$H NMR (300 MHz, Chloroform-d) δ=4.20 (dt, J=7.9, 6.9, 4H), 3.14 (d, J=2.2, 1H), 2.95 (t, J=6.9, 4H), 1.36 (s, 18H). $^{13}$C NMR (75 MHz, Chloroform-d) δ=92.35 (d, J=1.0), 84.21 (d, J=47.8), 66.37 (d, J=6.1), 47.98, 40.77 (d, J=4.3), 29.89. $^{31}$P NMR (122 MHz, CDCl$_3$) δ=130.28.

Di-((2-isopropyl disulfido)-3-propyl) ethynylphosphonite

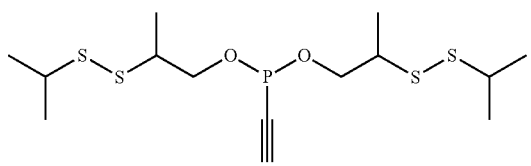 [SMILES: C#CP(OCC(C)SSC(C)C)OCC(C)SSC(C)C]

The compound was synthesized according to the above "General procedure 2 for the synthesis of O-substituted alkynyl phosphonites from bis(diisopropylamino)chlorophosphine" from 267 mg bis(diisopropylamino)chlorophosphine (1.00 mmol, 1.00 eq.), 2.20 ml ethynylmagnesium bromide solution (0.5 M in THF, 1.10 mmol, 1.10 eq.), 415 mg 2-(3-Hydroxypropyl) isopropyl disulfide (2.50 mmol, 2.50 eq.), 5.55 ml 1H-tetrazole solution (0.45 M in MeCN, 2.50 mmol, 2.50 eq.) and purified by flash column chromatography on silicagel (0-10% EtOAc in hexane). The compound was obtained as a diastereomeric mixture as yellowish oil. (91 mg, 0.235 mmol, 23.5%).

$^1$H NMR (300 MHz, Chloroform-d) δ=4.28-4.06 (m, 2H), 3.99-3.81 (m, 2H), 3.21-3.10 (m, 1H), 3.07-2.95 (m, 4H), 1.37-1.28 (m, 18H). $^{13}$C NMR (75 MHz, Chloroform-d) δ=92.39 (d, J=3.6), 84.32 (d, J=49.3), 71.18 (d, J=4.9), 48.18-44.79 (m), 41.65, 22.55 (d, J=6.5), 17.12. $^{31}$P NMR (122 MHz, CDCl$_3$) δ=130.56, 130.32, 130.10.

Di-(4-acetoxy benzyl) ethynylphosphonite

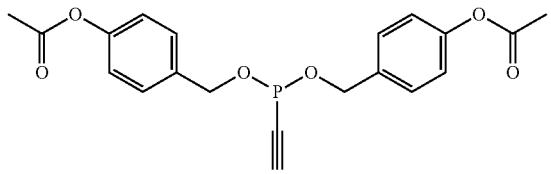 [SMILES: C#CP(OCc1ccc(OC(C)=O)cc1)OCc1ccc(OC(C)=O)cc1]

The compound was synthesized according to the above "General procedure 2 for the synthesis of O-substituted alkynyl phosphonites from bis(diisopropylamino)chlorophosphine" from 267 mg bis(diisopropylamino)chlorophosphine (1.00 mmol, 1.00 eq.), 2.20 ml ethynylmagnesium bromide solution (0.5 M in THF, 1.10 mmol, 1.10 eq.), 415 mg 2-(3-Hydroxypropyl) isopropyl disulfide (2.50 mmol, 2.50 eq.), 5.55 ml 1H-tetrazole solution (0.45 M in MeCN, 2.50 mmol, 2.50 eq.) and purified by flash column chromatography on silicagel (30% EtOAc in hexane). The compound was obtained as a as colourless oil. (118 mg, 0.306 mmol, 30.6%).

$^1$H NMR (300 MHz, Chloroform-d) δ=7.34 (d, J=8.5, 4H), 7.08 (d, J=8.5, 4H), 4.95 (dd, J=8.4, 1.7, 4H), 3.20 (d, J=2.3, 1H), 2.32 (s, 6H). $^{13}$C NMR (75 MHz, Chloroform-d) δ=169.44, 150.37, 135.31 (d, J=4.3), 128.89, 121.68, 92.68, 84.40 (d, J=47.6), 69.35 (d, J=6.8), 21.16. $^{31}$P NMR (122 MHz, CDCl$_3$) δ=131.09.

Di (4-(diazophenyl)-benzyl) ethynylphosphonite

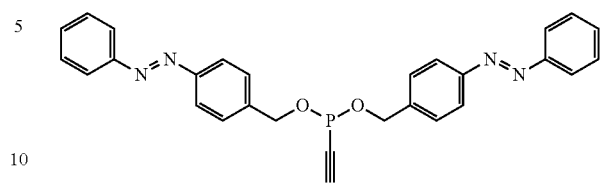

The compound was synthesized according to the above "General procedure 2 for the synthesis of O-substituted alkynyl phosphonites from bis(diisopropylamino)chlorophosphine" from 98 mg bis(diisopropylamino)chlorophosphine (0.37 mmol, 1.00 eq.), 0.80 ml ethynylmagnesium bromide solution (0.5 M in THF, 0.4 mmol, 1.10 eq.), 195 mg 1-(4-(hydroxymethyl)phenyl)-2-phenyldiazene (0.93 mmol, 2.50 eq.), 2.00 ml 1H-tetrazole solution (0.45 M in MeCN, 0.93 mmol, 2.50 eq.) and purified by flash column chromatography on silicagel (0-10% EtOAc in hexane). The compound was obtained as orange solid. (82 mg, 0.171 mmol, 46.3%).

$^1$H NMR (300 MHz, Chloroform-d) δ=7.98-7.86 (m, 8H), 7.59-7.44 (m, 10H), 5.08 (d, J=8.5, 4H), 3.24 (d, J=2.3, 1H). $^{13}$C NMR (75 MHz, Chloroform-d) δ=152.60, 152.27, 140.55 (d, J=4.3), 131.07, 129.09, 128.24, 123.03, 122.90, 92.89, 84.35 (d, J=47.2), 69.54 (d, J=6.9). $^{31}$P NMR (122 MHz, CDCl$_3$) δ=131.77.

General Procedure 3 for the Synthesis of O-Substituted Alkynyl Phosphonamidates from Alkynyl Phosphonites and Azides

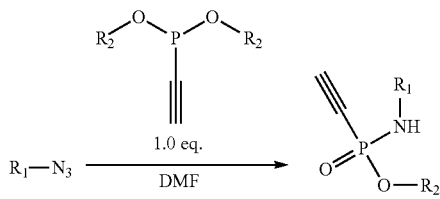

1.00 mmol of an organic azide (1.00 eq.) was stirred together with 1.00 mmol of an alkynyl phosphonite (1.00 eq.) in 5 ml DMF overnight. The organic solvent was removed under educed pressure and the residue purified by column chromatographie on silica.

2-Isopropyl-disulfido-ethyl-N-(4-benzoic-acid-N-hydroxysuccinimide ester)-P-ethynyl phosphonamidate

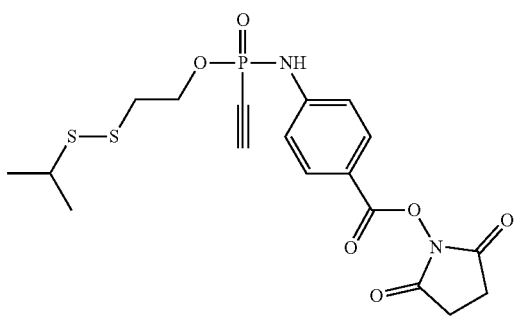 [SMILES: C#CP(=O)(Nc1ccc(C(=O)ON2C(=O)CCC2=O)cc1)OCCSSC(C)C]

The compound was synthesized according to the above "General procedure 3 for the synthesis of O-substituted alkynyl phosphonamidates from alkynyl phosphonites and azides" from 147 mg Di-(2-isopropyl disulfido)ethyl) ethynylphosphonite (0.411 mmol, 1.00 eq.) and 106 mg 4-azidobenzoic-acid-N-hydroxysuccinimide ester (0.411 mmol, 1.00 eq.) and purified by flash column chromatography on silicagel (60% EtOAc in hexane). The compound was obtained as colourless oil. (80 mg, 0.175 mmol, 42.6%).

$^1$H NMR (300 MHz, Chloroform-d) δ=8.08 (d, J=8.7, 2H), 7.20 (d, J=8.8, 2H), 7.13 (d, J=7.5, 1H), 4.63-4.18 (m, 2H), 3.23-2.76 (m, 8H), 1.31 (dd, J=6.7, 1.0, 6H). $^{31}$P NMR (122 MHz, CDCl$_3$) δ=−10.16.

2-tert-butyl-disulfido-ethyl-N-(4-benzoic-acid-N-hydroxysuccinimide ester)-P-ethynyl phosphonamidate

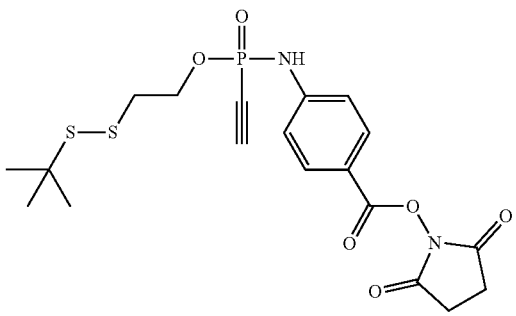

The compound was synthesized according to the above "General procedure 3 for the synthesis of O-substituted alkynyl phosphonamidates from alkynyl phosphonites and azides" from 50 mg Di-(2-tert-butyl disulfido)ethyl) ethynylphosphonite (0.129 mmol, 1.00 eq.) and 33 mg 4-azidobenzoic-acid-N-hydroxysuccinimide ester (0.129 mmol, 1.00 eq.) and purified by flash column chromatography on silicagel (70% EtOAc in hexane). The compound was obtained as colourless solid. (29 mg, 0.0638 mmol, 47.4%).

$^1$H NMR (300 MHz, Chloroform-d) δ=8.06 (d, J=8.7, 2H), 7.49 (d, J=7.5, 1H), 7.21 (d, J=8.7, 2H), 4.58-4.26 (m, 2H), 3.09-2.81 (m, 7H), 1.33 (s, 9H). $^{31}$P NMR (122 MHz, CDCl$_3$) δ=−9.98.

2-isopropyl disulfido-3-propyl-N-(4-benzoic-acid-N-hydroxysuccinimide ester)-P-ethynyl phosphonamidate

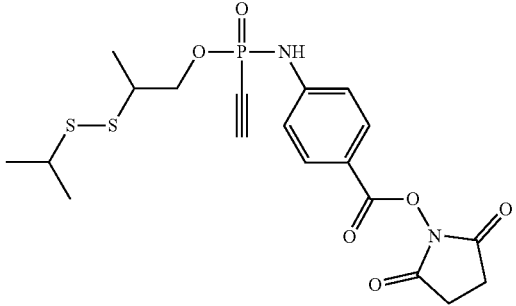 [SMILES: C#CP(=O)(Nc1ccc(C(=O)ON2C(=O)CCC2=O)cc1)OCC(C)SSC(C)C]

The compound was synthesized according to the above "General procedure 3 for the synthesis of O-substituted alkynyl phosphonamidates from alkynyl phosphonites and azides" from 61 mg Di-((2-isopropyl disulfido)-3-propyl) ethynylphosphonite (0.158 mmol, 1.00 eq.) and 40 mg 4-azidobenzoic-acid-N-hydroxysuccinimide ester (0.158 mmol, 1.00 eq.) and purified by flash column chromatography on silicagel (70% EtOAc in hexane). The compound was obtained as mixture of diastereomers as colourless oil. (32 mg, 0.068 mmol, 43.0%).

$^1$H NMR (300 MHz, Chloroform-d) δ=8.05 (d, J=8.7, 2H), 7.84-7.74 (m, 1H), 7.21 (d, J=8.8, 2H), 4.57-4.27 (m, 2H), 3.20-2.66 (m, 7H), 1.46-1.21 (m, 9H). $^{31}$P NMR (122 MHz, CDCl$_3$) δ=−9.87.

4-acetoxy-benzyl-N-(4-benzoic-acid-N-hydroxysuccinimide ester)-P-ethynylphosphonamidate

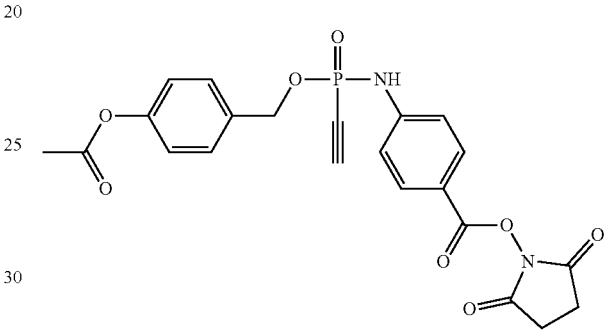

The compound was synthesized according to the above "General procedure 3 for the synthesis of O-substituted alkynyl phosphonamidates from alkynyl phosphonites and azides" from 103 mg Di-(4-acetoxy benzyl) ethynylphosphonite (0.267 mmol, 1.00 eq.) and 69 mg 4-azidobenzoic-acid-N-hydroxysuccinimide ester (0.267 mmol, 1.00 eq.) and purified by flash column chromatography on silicagel (70% EtOAc in hexane). The compound was obtained as colourless oil. (36 mg, 0.077 mmol, 28.7%).

$^1$H NMR (300 MHz, Chloroform-d) δ=7.53-7.34 (m, 2H), 7.20-6.99 (m, 7H), 5.14 (d, J=8.8, 2H), 3.01 (d, J=13.3, 1H), 2.91 (s, 4H), 2.32 (s, 3H). $^{31}$P NMR (122 MHz, CDCl$_3$) δ=−10.33.

4-Diazophenyl-benzyl-N-(4-benzoic-acid-N-hydroxysuccinimide ester)-P-ethynyl phosphonamidate

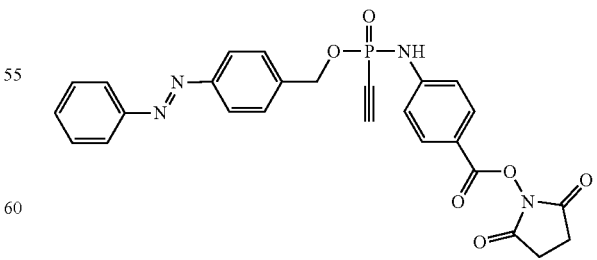

The compound was synthesized according to the above "General procedure 3 for the synthesis of O-substituted alkynyl phosphonamidates from alkynyl phosphonites and azides" from 71 mg Di (4-(diazophenyl)-benzyl) ethynylphosphonite (0.148 mmol, 1.00 eq.) and 39 mg 4-azido-benzoic-acid-N-hydroxysuccinimide ester (0.148 mmol, 1.00 eq.) and purified by flash column chromatography on silicagel (50% EtOAc in hexane). The compound was obtained as orange solid. (58 mg, 0.112 mmol, 75.8%).

$^1$H NMR (600 MHz, DMSO-d$_6$) δ=9.44 (d, J=8.6, 1H), 8.02 (d, J=8.8, 2H), 7.96-7.89 (m, 4H), 7.67 (d, J=8.5, 2H), 7.64-7.57 (m, 3H), 7.33 (d, J=8.8, 2H), 5.28 (ddd, J=45.1, 12.5, 8.7, 2H), 4.61 (d, J=13.0, 1H), 2.88 (s, 4H). $^{13}$C NMR (151 MHz, DMSO-d$_6$) δ=170.90, 161.75, 152.36, 152.23, 147.36, 139.31 (d, J=7.6), 132.33, 132.17, 129.97, 129.41, 123.14, 123.08, 118.17 (d, 5 J=8.1), 117.25, 93.06 (d, J=46.9), 76.49 (d, J=265.4), 66.88, 25.98. $^{31}$P NMR (243 MHz, DMSO) δ=−10.42.

General Procedure 4 for the Amide Bond Formation Between Phosphonamidate-NHS Esters and EDANS

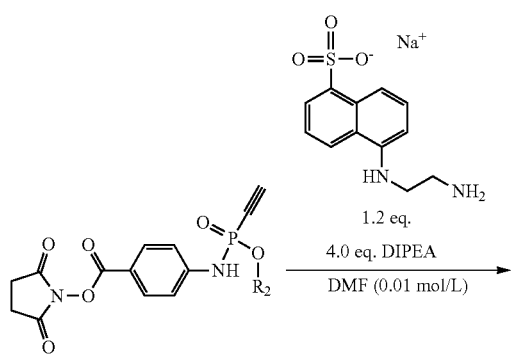

0.1 mmol NHS-phosphonamidate (1.00 eq.) and 0.12 mmol 5-((2-Aminoethyl)aminonaphthalene-1-sulfonate sodium salt (1.20 eq.) were dissolved in 10 mL DMF. 0.40 mmol of DIPEA (4.0 eq.) was added and the mixture stirred for 3 hours at room-temperature. All volatiles were removed under reduced pressure and the crude mixture was purified by preparative HPLC using method E described above under "Procedures for the introduction of the alkyne-phosphonamidate moiety by generic building blocks via an amide bond".

5-((2-(O-(2-Isopropyl-disulfido-ethyl)-P-ethynyl-phosphonamidato-N-benzoyl)ethyl)amino)naphthalene-1-sulfonic acid

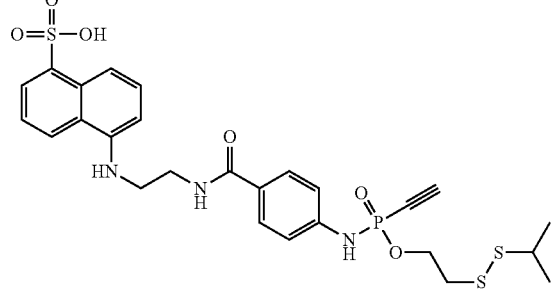

The compound was synthesized according to the above "General procedure 4 for the amide bond formation between phosphonamidate-NHS esters and EDANS" from 72 mg 2-Isopropyl-disulfido-ethyl-N-(4-benzoic-acid-N-hydroxysuccinimide ester)-P-ethynyl phosphonamidate (0.157 mmol, 1.00 eq.), 54 mg 5-((2-Aminoethyl)aminonaphthalene-1-sulfonate sodium salt (0.188 mmol, 1.20 eq.) and 109 µl DIPEA (0.628 mmol, 4.0 eq.) and purified by semi-preparative HPLC (method E described above under "Procedures for the introduction of the alkyne-phosphonamidate moiety by generic building blocks via an amide bond"). The compound was obtained as white solid. (62 mg, 0.102 mmol, 64.9%).

$^1$H NMR (600 MHz, DMSO-d$_6$) δ=8.90 (d, J=8.8, 1H), 8.61 (t, J=5.6, 1H), 8.56 (d, J=8.6, 1H), 8.13 (d, J=8.3, 1H), 8.04 (dd, J=7.2, 1.1, 1H), 7.82 (d, J=8.7, 2H), 7.60-7.31 (m, 2H), 7.17 (d, J=8.8, 2H), 4.51 (d, J=12.8, 1H), 4.37-4.17 (m, 2H), 3.65 (q, J=6.3, 2H), 3.52 (t, J=6.5, 2H), 3.07 (p, J=6.7, 1H), 3.03 (t, J=6.3, 2H), 1.24 (dd, J=6.7, 2.8, 6H). $^{13}$C NMR (151 MHz, DMSO-d$_6$) δ=167.03, 144.53, 143.31, 130.53, 129.02, 127.63, 126.33, 125.44, 125.15, 124.70, 123.21, 117.55, 117.50, 92.38 (d, J=45.7), 76.79 (d, J=262.5), 63.85 (d, J=4.7), 46.85, 40.77, 39.01 (d, J=7.7), 37.65, 22.72. $^{31}$P NMR (243 MHz, DMSO) δ=−9.84.

5-((2-(O-(2-tert-butyl-disulfido-ethyl)-P-ethynyl-phosphonamidato-N-benzoyl)ethyl)amino)naphthalene-1-sulfonic acid

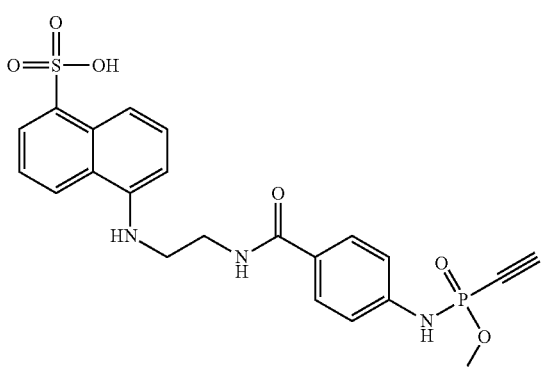

The compound was synthesized according to the above "General procedure 4 for the amide bond formation between phosphonamidate-NHS esters and EDANS" from 10 mg 2-tert-butyl-disulfido-ethyl-N-(4-benzoic-acid-N-hydroxysuccinimide ester)-P-ethynyl phosphonamidate (0.021 mmol, 1.00 eq.), 7 mg 5-((2-Aminoethyl)aminonaphthalene-1-sulfonate sodium salt (0.025 mmol, 1.20 eq.) and 15 μl DIPEA (0.084 mmol, 4.0 eq.) and purified by semi-preparative HPLC (method E described above under "Procedures for the introduction of the alkyne-phosphonamidate moiety by generic building blocks via an amide bond"). The compound was obtained as white solid. (8 mg, 0.013 mmol, 62.3%).

$^1$H NMR (600 MHz, DMSO-d$_6$) δ=8.87 (d, J=8.7, 1H), 8.57 (t, J=5.8, 1H), 8.21 (d, J=8.6, 1H), 8.10 (d, J=8.5, 1H), 7.94 (dd, J=7.1, 1.2, 1H), 7.80 (d, J=8.7, 2H), 7.36 (dd, J=8.5, 7.1, 1H), 7.31 (dd, J=8.7, 7.5, 1H), 7.14 (d, J=8.8, 2H), 6.74 (d, J=7.6, 1H), 4.49 (d, J=12.8, 1H), 4.37-4.11 (m, 2H), 3.60 (q, J=6.4, 2H), 3.40 (t, J=6.5, 2H), 3.03 (t, J=6.5, 2H), 1.29 (s, 9H). $^{31}$P NMR (243 MHz, DMSO) δ=−9.87.

5-((2-(O-2-isopropyl disulfido-3-propyl)-P-ethynyl-phosphonamidato-N-benzoyl)ethyl)amino)naphthalene-1-sulfonic acid

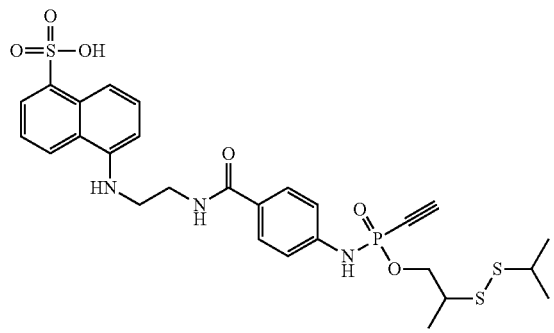 [SMILES: C#CP(=O)(Nc1ccc(C(=O)NCCNc2cccc3c(S(=O)(=O)O)cccc23)cc1)OCC(C)SSC(C)C]

The compound was synthesized according to the above "General procedure 4 for the amide bond formation between phosphonamidate-NHS esters and EDANS" from 29 mg 2-isopropyl disulfido-3-propyl-N-(4-benzoic-acid-N-hydroxysuccinimide ester)-P-ethynyl phosphonamidate (0.061 mmol, 1.00 eq.), 21 mg 5-((2-Aminoethyl)aminonaphthalene-1-sulfonate sodium salt (0.073 mmol, 1.20 eq.) and 42 μl DIPEA (0.244 mmol, 4.0 eq.) and purified by semi-preparative HPLC (method E described above under "Procedures for the introduction of the alkyne-phosphonamidate moiety by generic building blocks via an amide bond"). The compound was obtained as a mixture of diastereomers as white solid. (15 mg, 0.024 mmol, 39.5%).

$^1$H NMR (600 MHz, DMSO-d$_6$) δ=8.88 (d, J=8.8, 1H), 8.58 (t, J=5.7, 1H), 8.35 (d, J=8.6, 1H), 8.10 (dt, J=8.6, 1.1, 1H), 7.98 (dd, J=7.1, 1.1, 1H), 7.81 (d, J=8.7, 2H), 7.39 (ddd, J=31.3, 8.6, 7.3, 2H), 7.15 (d, J=8.8, 2H), 6.91 (d, J=7.5, 1H), 4.51 (dd, J=12.9, 1.8, 1H), 4.25-4.13 (m, 1H), 4.13-3.98 (m, 1H), 3.61 (q, J=6.4, 2H), 3.45 (t, J=6.6, 2H), 3.18 (dtd, J=10.6, 6.8, 5.2, 1H), 3.03 (h, J=6.7, 1H), 1.30-1.19 (m, 9H). $^{13}$C NMR (151 MHz, DMSO-d$_6$) δ=166.92, 144.74, 143.21, 130.61, 128.96, 127.79, 126.43, 125.10, 124.61, 123.82, 123.09, 117.50 (d, J=7.5), 92.58 (d, J=9.5), 92.28 (d, J=9.4), 76.76 (d, J=262.3), 68.10 (d, J=4.9), 45.48, 41.32 (d, J=8.6), 38.15, 22.74, 17.14 (d, J=4.1). $^{31}$P NMR (243 MHz, DMSO) δ=−9.76, −9.79.

5-((2-(O-(4-acetoxy benzyl)-P-ethynyl-phosphonamidato-N-benzoyl)ethyl)amino)naphthalene-1-sulfonic Acid

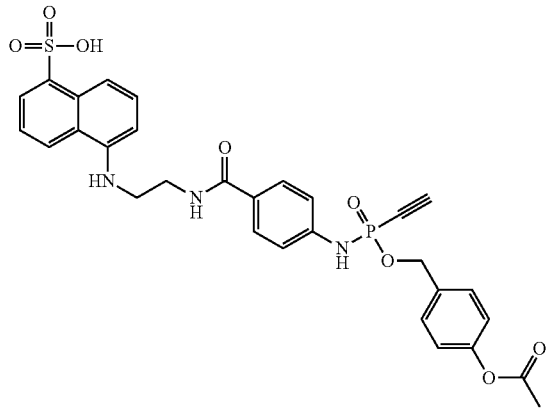 [SMILES: C#CP(=O)(Nc1ccc(C(=O)NCCNc2cccc3c(S(=O)(=O)O)cccc23)cc1)OCc1ccc(OC(C)=O)cc1]

The compound was synthesized according to the above "General procedure 4 for the amide bond formation between phosphonamidate-NHS esters and EDANS" from 36 mg 4-acetoxy-benzyl-N-(4-benzoic-acid-N-hydroxysuccinimide ester)-P-ethynyl phosphonamidate (0.076 mmol, 1.00 eq.), 22 mg 5-((2-Aminoethyl)aminonaphthalene-1-sulfonate sodium salt (0.095 mmol, 1.20 eq.) and 53 μl DIPEA (0.284 mmol, 4.0 eq.) and purified by semi-preparative HPLC (method E described above under "Procedures for the introduction of the alkyne-phosphonamidate moiety by generic building blocks via an amide bond"). The compound was obtained as white solid. (14 mg, 0.023 mmol, 30.4%).

$^1$H NMR (600 MHz, DMSO-d$_6$) δ=8.92 (d, J=8.6, 1H), 8.56 (t, J=5.7, 1H), 8.32 (d, J=8.7, 1H), 8.10 (d, J=8.5, 1H), 8.03-7.92 (m, 1H), 7.80 (d, J=8.6, 2H), 7.47 (d, J=8.5, 2H), 7.41 (dd, J=8.5, 7.2, 1H), 7.36 (t, J=8.1, 1H), 7.17 (d, J=6.7, 2H), 7.15 (d, J=6.7, 2H), 6.88 (d, J=7.5, 1H), 5.25-5.05 (m, 2H), 4.49 (d, J=12.8, 1H), 3.61 (q, J=6.3, 2H), 3.44 (t, J=6.6, 2H), 2.28 (s, 3H). $^{13}$C NMR (151 MHz, DMSO-d$_6$) δ=169.61, 166.95, 150.96, 144.73, 143.29, 133.66 (d, J=7.7), 130.61, 129.81, 128.99, 127.82, 126.47, 125.06, 124.53, 123.68, 123.10, 122.42, 117.44 (d, J=7.9), 92.28 (d, J=45.6), 77.01 (d, J=261.8), 66.59 (d, J=4.4), 45.26, 38.24, 21.31. $^{31}$P NMR (243 MHz, DMSO) δ=−9.87.

5-((2-(O-(4-Diazophenyl-benzyl)-P-ethynyl-phosphonamidato-N-benzoyl)ethyl)amino)naphthalene-1-sulfonic acid

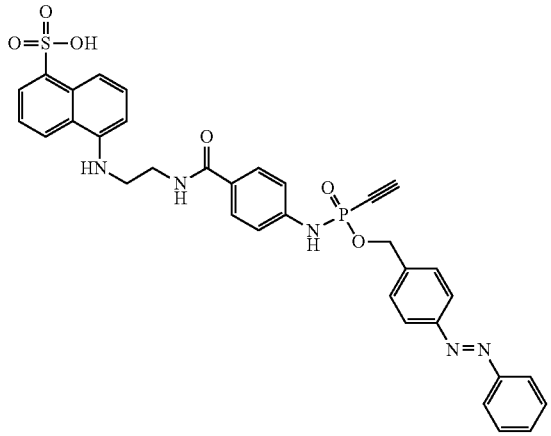 [SMILES: C#CP(=O)(Nc1ccc(C(=O)NCCNc2cccc3c(S(=O)(=O)O)cccc23)cc1)OCc1ccc(/N=N/c2ccccc2)cc1]

The compound was synthesized according to the above "General procedure 4 for the amide bond formation between phosphonamidate-NHS esters and EDANS" from 27 mg 4-Diazophenyl-benzyl-N-(4-benzoic-acid-N-hydroxysuccinimide ester)-P-ethynyl phosphonamidate (0.053 mmol, 1.00 eq.), 15 mg 5-((2-Aminoethyl)aminonaphthalene-1-sulfonate sodium salt (0.064 mmol, 1.20 eq.) and 37 µl DIPEA (0.212 mmol, 4.0 eq.) and purified by semi-preparative HPLC (method E described above under "Procedures for the introduction of the alkyne-phosphonamidate moiety by generic building blocks via an amide bond"). The compound was obtained as orange solid. (18 mg, 0.027 mmol, 50.9%).

$^1$H NMR (600 MHz, DMSO-d$_6$) δ=8.98 (d, J=8.7, 1H), 8.57 (t, J=5.7, 1H), 8.36 (d, J=8.6, 1H), 8.11 (d, J=8.5, 1H), 7.98 (d, J=7.1, 1H), 7.97-7.88 (m, 4H), 7.81 (d, J=8.8, 2H), 7.66 (d, J=8.5, 2H), 7.64-7.52 (m, 4H), 7.42 (dd, J=8.5, 7.1, 1H), 7.37 (t, J=8.1, 1H), 7.18 (d, J=8.7, 2H), 6.92 (d, J=7.5, 1H), 5.37-5.04 (m, 2H), 4.53 (d, J=12.8, 1H), 3.61 (q, J=6.4, 2H), 3.45 (t, J=6.6, 2H). $^{13}$C NMR (151 MHz, DMSO-d$_6$) δ=166.95, 152.36, 152.18, 144.75, 143.27, 139.56, 139.51, 132.15, 130.61, 129.97, 129.32, 129.01, 127.84, 126.44, 125.11, 124.62, 123.83, 123.13, 123.07, 117.49 (d, J=8.0), 92.47 (d, J=45.9), 76.95 (d, J=262.7), 66.56 (d, J=4.4), 45.47, 38.15. $^{31}$P NMR (243 MHz, DMSO) δ=−9.68.

General Procedure 5 for the Addition of a Cys-Model Peptide to Different O-Substituted EDANS Phosphonamidates The General procedure 5 for the addition of a Cys-model peptide to different O-substituted EDANS phosphonamidates is depicted in FIG. 47.

Equal volumes of a 5 mM solution of the respective EDANS-phosphonamidate in DMF and a 5 mM solution of the above stated DABCYL-Modified Cys-peptide in 100 mM NH$_4$HCO$_3$—Buffer (pH8.5) were freshly prepared, mixed and shaken at room temperature for 1 h. All volatiles were removed under reduced pressure and the thiol adducts isolated by semi-preparative HPLC (method E described above under "Procedures for the introduction of the alkyne-phosphonamidate moiety by generic building blocks via an amide bond"). Isolated conjugates were analyzed by HPLC-MS as set out in the following Table 5 and FIGS. 25A-25E:

TABLE 5

| R | HPLC trace | Mass analysis | Isolated Yield |
|---|---|---|---|
| ![S-S-iPr] | see FIG. 25A | C$_{74}$H$_{96}$N$_{15}$O$_{20}$PS$_4^{2+}$ [M + 2H]$^{2+}$ calcd: 836.78, found: 836.94 | 39.4% |
| ![S-S-nBu] | see FIG. 25B | C$_{75}$H$_{98}$N$_{15}$O$_{20}$PS$_4^{2+}$ [M + 2H]$^{2+}$ calcd: 843.77, found: 844.10 | 44.7% |
| ![S-S-iBu] | see FIG. 25C | C$_{75}$H$_{98}$N$_{15}$O$_{20}$PS$_4^{2+}$ [M + 2H]$^{2+}$ calcd: 843.77, found: 844.05 | 24.5% |
| ![OAc-Ph] | see FIG. 25D | C$_{78}$H$_{94}$N$_{15}$O$_{22}$PS$_2^{2+}$ [M + 2H]$^{2+}$ calcd: 843.79, found: 844.13 | 26.1% |
| ![diazo-Ph] | see FIG. 25E | C$_{82}$H$_{96}$N$_{17}$O$_{20}$PS$_2^{2+}$ [M + 2H]$^{2+}$ calcd: 866.81, found: 867.12 | Product not isolated |

Procedure for the Cleavage of the Disulfide Containing Amidate-Adducts with TCEP The procedure for the cleavage of the disulfide containing amidate-adducts with TCEP is depicted in FIG. 48.

10 µl of a 1 mM stock solution of the respective peptide (SM1-3) in phosphate buffered saline (PBS) was premixed with 80 µl of PBS. 10 µl of a 10 mM stock solution of Tris-(2-carboxyethyl)-phosphin (TCEP) in PBS was added and the solutions were shaken at 37° C. for one hour. 15 µl samples were drawn afterwards, diluted with 15 µl of 2% trifuloroacetic acid (TFA) solution in water and subjected to UPLC-MS analysis. The UPLC-MS analysis is depicted in FIGS. 26A-26C. Red line shows incubation with TCEP, black with PBS only. Peaks were identified by MS.

The results show that the disulfide-containing O-substituents are cleaved and the EDANS-containing part is liberated from the starting materials.

Procedure for the Cleavage of the Ester-Containing Amidate-Adducts with Cell Lysate The procedure for the cleavage of the ester-containing amidate-adducts with Cell lysate is depicted in FIG. 49.

10 µl of a 1 mM stock solution of the peptide SM4 in PBS was premixed with 90 µl of freshly prepared HeLa-lysate in PBS. The solutions was shaken at 37° C. for one hour. A 15 µl sample was drawn afterwards, diluted with 15 µl of 2% TFA solution in water and subjected to UPLC-MS analysis. The UPLC-MS analysis is depicted in FIG. 27. Red line shows incubation with cell lysate, black with PBS only. Peaks were identified by MS. The results show that the O-substituent on the phosphorus comprising an ester moiety is cleaved and the EDANS-containing part is liberated from the starting material.

Procedure for the Diazo-Containing Amidate-Adducts with Sodium Dithionite

The procedure for the cleavage of the diazo-containing amidate-adducts with sodium dithionite is depicted in FIG. 50.

10 µl of a 1 mM stock solution of the peptide SM5 in PBS was premixed with 80 µl of PBS. 10 µl of a 200 mM stock solution of TCEP in PBS was added and the solutions were shaken at 37° C. for one hour. 15 µl samples were drawn afterwards, diluted with 15 µl of 2% TFA solution in water and subjected to UPLC-MS analysis. The UPLC-MS analysis is depicted in FIG. 28. Red line shows incubation with TCEP, black with PBS only. Peaks were identified by MS. The results show that the O-substituent on the phosphorus comprising a diazo moiety is cleaved and the EDANS-containing part is liberated from the starting material.

Thus, it has been demonstrated that a cleavage of the amidates having various cleavable groups as O substituent on the phosphorus is possible.

Without wishing to be bound by any theory, for a disulfide-containing group on the phosphorus it is believed that the mechanism of the cleavage proceeds as exemplarily depicted in Scheme 31 (FIG. 52), i.e. through reductive cleavage of the disulfide, cyclisation to a thiirane to generate a free phosphonamidic acid which undergoes P—N-hydrolysis to liberate the payload as a free amine.

Scheme 30, which is depicted in FIG. 51, shows the reductive cleavage and elimination mechanism.

Disulfide Substituted Phosphonites for Protein Conjugation

The cyclic cell-penetrating peptide c(Tat) was conjugated to eGFP via the Staudinger induced thiol addition with a disulfide substituted phosphonite.

First, we synthesized the cyclic Tat-peptide via solid phase peptide synthesis (SPPS) (see Scheme 32). By capping the N-terminus with 4-azidobenzoic acid we obtained compound E11 having an azide moiety. After purification by preparative HPLC the Staudinger phosphonite reaction of E11 with the disulfide containing alkyne phosphonites was carried out in DMF to give compounds E12 and E13, which were purified again by preparative HPLC.

Scheme 31, which is depicted in FIG. 52, shows the SPPS of alkyne functionalized cyclic Tat.

With the alkyne functionalized peptides in hand we further tested the thiol addition towards a cysteine containing eGFP as shown in FIG. 29. The eGFP C70M S147C is a mutant, which exhibits only two cysteines of which only one is addressable.

For the tert-butyl-disulfide substituent (E13) the thiol addition reaction went to completion after incubating eGFP with 6 equivalents phosphonite in PBS at 37° C. for 16 hours at a protein concentration of 63 µM. When applying the same reaction conditions with the isopropyldisulfide substituent (E12) the product was obtained in about 50% conversion according to MALDI analysis as shown in FIG. 29.

FIG. 29 shows: Thiol addition of alkyne-c(Tat) to eGFP C70M S147C.

Procedures for the Disulfide Substituted Phosphonites for Protein Conjugation

Synthesis of c(Tat)-Azide

The c(Tat) was synthesized in a 0.1 mmol scale on a Rink Amide Resin with a loading of 0.78 mm/g. The synthesis was carried out on a PTI synthesizer with single couplings of each amino acid (10 eq. amino acid for 40 min) in DMF. After the final building block coupling the peptide, still Fmoc protected, was treated with Pd(PPh$_3$)$_4$ (24 mg, 20 µmol, 20 mol %) and Phenylsilane (308 µl, 2.5 mmol, 2.5 eq.) in 4 ml dry DCM for 1 hour in order to cleave the alloc and allyl protecting groups in one step. After confirmation of full deprotection by test cleavage, cyclization with 2 eq. HATU 4 eq. DIPEA was carried out over night in DMF.

The peptide was then Fmoc-deprotected using 20% Piperidine in DMF and the 4-azidobenzoic acid (81.6 mg, 0.5 mmol, 5 eq.) was coupled to the N-terminus with HATU (190.1 mg, 0.5 mmol, 5 eq.) and DIPEA (170 µl, 1.0 mmol, 10 eq.) for 1 hour. Finally the peptide was cleaved from the resin by treatment with 4 ml of a TFA:TIS:H$_2$O (95:2.5:2.5) for 3 hours and precipitated in cold diethylether. The crude peptide was purified by preparative reverse phase C18 HPLC (0-5 min 95/5, water (0.1% TFA)/MeCN (0.1% TFA); 5-60 min 10/90, water (0.1% TFA)/MeCN (0.1% TFA)). The product was gained as white powder (30.0 mg, 11.4 µmol, 11.4% yield) and was analyzed by analytical UPLC (5 to 95% of acetonitrile in water containing 0.1% TFA on a RP-C18 column). LRMS: m/z: 648.49 [M+3H]$^{3+}$ (calcd. m/z: 648.0569).

Synthesis of c(Tat)-Phosphonamidate Alkyne: Staudinger Reaction on c(Tat)-Azide

The purified c(Tat)-azido peptide (5 mg, 1.9 µmol, 1 eq.) was reacted with both disulfide substituted phosphonites according to the general protocol. The crude peptide was purified by preparative reverse phase C18 HPLC. The product was gained as white powder and was analyzed by MALDI-TOF.

Hydrothiolation of Electron-Deficient c(Tat)-Phosphonamidate Alkyne: Reaction with GFP C70M S147C The hydrothiolation reaction of the electron-deficient c(Tat)-phosphonamidate alkyne with GFP C70M S147C is depicted in FIG. 53.

eGFP C70M S147C (2.7 nmol, 1 eq) in PBS was concentrated to 40 µl and c(Tat)-phosphonamidate alkyne (0.05 mg, 16.2 nmol, 6 eq.) was added. After the reaction mixture was shaken at 37° C. and 800 rpm over night it was purified by ZebaSpin filters with a MWCO of 7 kDa. The product was analyzed by MALDI-TOF. For the conjugation of peptide E12 an approximately 50% conversion to the product was observed, while in contrast the conjugation of peptide E13 gave a full conversion.

MALDI TOF for E14: expected Product (in Da): 29919 (M+H$^+$), 14960 (M+2H$^+$). found (in Da): 29933 (M+H$^+$), 14967 (M+2H$^+$)

MALDI TOF for E15: expected Product (in Da): 29933 (M+H$^+$), 14967 (M+2H$^+$). found (in Da): 29940 (M+H$^+$), 14965 (M+2H$^+$)

Intramolecular Staudinger Induced Thiol Addition for Peptide Cyclization

The incorporation of an azide as well as a thiol into a complex molecule, e.g. a peptide, leads the way for the intramolecular staudinger induced thiol addition, that can realize an intramolecular cyclization as shown in FIG. 38.

Without wishing to be bound by any theory, it is assumed that first the azide is reacting with the electron-rich alkyne/alkene-phosphonite upon which the phosphonamidate is formed and an electron-poor alkyne/alkene-phosphonamidate is formed that undergoes a fast intramolecular thiol addition with the cysteine in the peptide structure.

First we synthesized a peptide taken from the protein sequence of BCL-9 and we incorporated an azidohomoalanine and a cysteine distanced by three amino acids into the peptide by standard solid phase peptide synthesis. After cleavage from the solid phase and purification by preparative HPLC we gained the peptide. With this in hand we could probe the intramolecular cyclization by staudinger induced thiol addition.

We reacted the in dry DMSO solubilized peptide with either diethyl-ethynylphosphonite or diethyl-vinylphosphonite for 24 hours. After preparative HPLC the cyclized peptide was gained, which was confirmed by Ellman's test.

Procedures for the Intramolecular Staudinger Induced Thiol Addition for Peptide Cyclization Synthesis of BCL9-Azide The structure of the BCL9-azide is depicted in FIG. 54. The BCL9-azide was synthesized in a 0.1 mmol scale on a Rink Amide Resin with a loading of 0.78 mm/g. The synthesis was carried out on a PTI synthesizer with single couplings of each amino acid (5 eq. amino acid for 40 min) in DMF. Finally the peptide was cleaved from the resin by treatment with 4 ml of a TFA:TIS:H$_2$O (95:2.5:2.5) for 2 hours and precipitated in cold diethylether. The crude peptide was purified by preparative reverse phase C18 HPLC (0-5 min 95/5, water (0.1% TFA)/MeCN (0.1% TFA); 5-60 min 10/90, water (0.1% TFA)/MeCN (0.1% TFA)). The product was gained as white powder (35.0 mg, 11.5 μmol, 11.5% yield) and was analyzed by analytical UPLC (5 to 95% of acetonitrile in water containing 0.1% TFA on a RP-C18 column). LRMS: m/z: [M+3H]$^{3+}$ 759.86 (calcd. m/z: 759.6590).

Intramolecular Staudinger induced Thiol Addition
Alkyne-Phosphonamidate

The Staudinger reaction of the BCL-9azide with an alkyne-phosphonamidate is depicted in FIG. 55.

Staudinger Reaction on BCL9-Azide

The peptide 1 (20 mg, 6.55 μmol, 1 eq.) was dissolved in dry DMSO (1.5 ml, 4.4 mM). After drying under high vacuum in a previously flame dried flask the Bisethoxy-alkyne-phosphonite was given to the reaction mixture (volume according to percentage of product determined by NMR, 39.3 μmol, 6 eq.). The reaction mixture was heated to 50° C. and stirred for 24 hours. After addition of water, the reaction mixture was purified via basic (10 mM ammonium acetate buffer pH 9.0/MeCN) semi-preparative reverse phase C18 Nucleodur HPLC (0-5 min 95/5, Buffer/MeCN; 5-70 min 10/90, Buffer/MeCN) and gave the cyclized product as a white powder (3.82 mg, 1.22 μmol, 18.7% overall yield). The product was further analyzed with an Ellman's test which showed that 97% of the cysteine was reacted. The final product 2 was analyzed by LC-UV: rt. 5.0 min (0-1 min 95/5, water (0.1% TFA)/MeCN (0.1% TFA); 1-16.5 min 5/95, water (0.1% TFA)/MeCN (0.1% TFA) on RP-C18 column) and mass. LRMS: m/z: [M+3H]$^{3+}$ 1049.19 (calcd. m/z: 1048.5349).

Alkene-Phosphonamidate

The Staudinger reaction of the BCL-9azide with an alkene-phosphonamidate is depicted in FIG. 56.

Staudinger Reaction on BCL9-Azide

The peptide 3 (34 mg, 11.55 μmol, 1 eq.) was dissolved in dry DMSO (4 ml, 2.9 mM). After drying under high vacuum in a previously flame dried flask the Bisethoxyvinyl-phosphonite was given to the reaction mixture (volume according to percentage of product determined by NMR, 39.3 μmol, 6 eq.). The reaction mixture stirred for 24 hours at room temperature. After addition of water, the reaction mixture was purified by preparative reverse phase C18 HPLC (0-5 min 95/5, water (0.1% TFA)/MeCN (0.1% TFA); 5-60 min 10/90, water (0.1% TFA)/MeCN (0.1% TFA)). The product was gained as white powder (14.9 mg, 4.8 μmol, 41.3% yield) and was analyzed by analytical UPLC (5 to 95% of acetonitrile in water containing 0.1% TFA on a RP-C18 column). LRMS: m/z: [M+4H]$^{4+}$+782.89 (calcd. m/z: 782.6660). The product 4 was further analyzed with an Ellman's test which showed that 99% of the cysteine was reacted.

REFERENCES (1) Hackenberger, C. P. R.; Schwarzer, D. *Angew. Chemie-Int. Ed.* 2008, 47 (52), 10030.
(2) Spicer, C. D.; Davis, B. G. *Nat. Commun.* 2014, 5, 4740.
(3) Sletten, E. M.; Bertozzi, C. R. *Angew. Chemie-Int. Ed.* 2009, 48 (38), 6974.
(4) Patterson, D. M.; Nazarova, L. A.; Prescher, J. A. *ACS Chem. Biol.* 2014, 9 (3), 592.
(5) Lang, K.; Chin, J. W. *ACS Chem. Biol.* 2014, 9 (1), 16.
(6) Nikic, I.; Plass, T.; Schraidt, O.; Szymaski, J.; Briggs, J. A. G.; Schultz, C.; Lemke, E. A. *Angew. Chemie-Int. Ed.* 2014, 53 (8), 2245.
(7) Agard, N. J.; Prescher, J. A.; Bertozzi, C. R. *J. Am. Chem. Soc.* 2004, 126 (46), 15046.
(8) Chalker, J. M.; Bernardes, G. J. L.; Lin, Y. A.; Davis, B. G. *Chem.—An Asian J.* 2009, 4 (5), 630.
(9) Hoesl, M. G.; Budisa, N. *Angew. Chemie-Int. Ed.* 2011, 50 (13), 2896.
(10) Artner, L. M.; Merkel, L.; Bohlke, N.; Beceren-Braun, F.; Weise, C.; Dernedde, J.; Budisa, N.; Hackenberger, C. P. R. *Chem. Commun.* 2012, 48 (4), 522.
(11) van Kasteren, S. I.; Kramer, H. B.; Jensen, H. H.; Campbell, S. J.; Kirkpatrick, J.; Oldham, N. J.; Anthony, D. C.; Davis, B. G. *Nature* 2007, 446 (7139), 1105.
(12) Witte, C.; Martos, V.; Rose, H. M.; Reinke, S.; Klippel, S.; Schröder, L.; Hackenberger, C. P. R. *Angew. Chemie-Int. Ed.* 2015, 54 (9), 2806.
(13) Vallée, M. R. J.; Artner, L. M.; Dernedde, J.; Hackenberger, C. P. R. *Angew. Chemie-Int. Ed.* 2013, 52 (36), 9504.
(14) Vallée, M. R. J.; Majkut, P.; Wilkening, I.; Weise, C.; Müller, G.; Hackenberger, C. P. R. *Org. Lett.* 2011, 13 (20), 5440.
(15) Vallée, M. R. J.; Majkut, P.; Krause, D.; Gerrits, M.; Hackenberger, C. P. R. *Chemistry* 2015, 21 (3), 970.
(16) Pfaff, M.; Tangemann, K.; Müller, B.; Gurrath, M.; Müller, G.; Kessler, H.; Timpl, R.; Engel, J. *J. Biol. Chem.* 1994, 269 (32), 20233.
(17) Doronina, S. O.; Toki, B. E.; Torgov, M. Y.; Mendelsohn, B. a; Cerveny, C. G.; Chace, D. F.; DeBlanc, R. L.; Gearing, R. P.; Bovee, T. D.; Siegall, C. B.; Francisco, J. a; Wahl, A. F.; Meyer, D. L.; Senter, P. D. *Nat. Biotech.* 2003, 21 (7), 778.

(18) Ortial, S.; Montchamp, J. L. *Org. Lett.* 2011, 13 (12), 3134.
(19) Park, C.; Lee, K.; Kim, C. *Angew. Chemie-Int. Ed.* 2009, 48 (7), 1275.
(20) Barltrop, J. A.; Plant, P. J.; Schofield, P. *Chem. Commun.* (London) 1966, 822.
(21) Khorev, O.; Stokmaier, D.; Schwardt, O.; Cutting, B.; Ernst, B. *Bioorganic Med. Chem.* 2008, 16 (9), 5216
(22) Gunnoo, S. B.; Madder, A.; *ChemBioChem.* 2016, 17, 529-553
(23) T. K. Claus, S. Telitel, A. Welle, M. Bastmeyer, A. P. Vogt, G. Delaittre, C. Barner-Kowollik, *Chem. Commun.* (Cambridge, U. K.) 2017, 53, 1599-1602.
(24) M. M. Dcona, D. Mitra, R. W. Goehe, D. A. Gewirtz, D. A. Lebman, M. C. T. Hartman, *Chem. Commun.* (Cambridge, U. K.) 2012, 48, 4755-4757.
(25) Y. Chen, A. S. Kamlet, J. B. Steinman, D. R. Liu, *Nat Chem* 2011, 3, 146-153.
(26) J. I. Degraw, J. S. Engstrom, *Journal of Labelled Compounds* 1975, 11, 233-239.
(27) A. J. Perez, F. Wesche, H. Adihou, H. B. Bode, *Chemistry—A European Journal* 2016, 22, 639-645.
(28) H. D. Herce, D. Schumacher, A. F. L. Schneider, A. K. Ludwig, F. A. Mann, M. Fillies, M.-A. Kasper, S. Reinke, E. Krause, H. Leonhardt, M. C. Cardoso, C. P. R. Hackenberger, *Nat Chem* 2017, advance online publication.
(29) S. O. Doronina, B. E. Toki, M. Y. Torgov, B. A. Mendelsohn, C. G. Cerveny, D. F. Chace, R. L. DeBlanc, R. P. Gearing, T. D. Bovee, C. B. Siegall, J. A. Francisco, A. F. Wahl, D. L. Meyer, P. D. Senter, *Nat Biotech* 2003, 21, 778-784.
(30) A. Stengl, D. Hörl, H. Leonhardt, J. Helma, *Slas Discovery* 2017, 22, 309-315.
(31) a) T. H. Pillow, J. D. Sadowsky, D. Zhang, S.-F. Yu, G. Del Rosario, K. Xu, J. He, S. Bhakta, R. Ohri, K. R. Kozak, E. Ha, J. R. Junutula, J. A. Flygare, *Chemical Science* 2017, 8, 366-370; b) L. R. Staben, S. G. Koenig, S. M. Lehar, R. Vandlen, D. Zhang, J. Chuh, S.-F. Yu, C. Ng, J. Guo, Y. Liu, A. Fourie-O'Donohue, M. Go, X. Linghu, N. L. Segraves, T. Wang, J. Chen, B. Wei, G. D. L. Phillips, K. Xu, K. R. Kozak, S. Mariathasan, J. A. Flygare, T. H. Pillow, *Nat Chem* 2016, 8, 1112-1119.
(32) a) A. Satyam, *Bioorg. Med. Chem. Lett.* 2008, 18, 3196-3199; b) L. W. C. Miles, L. N. Owen, *Journal of the Chemical Society (Resumed)* 1952, 817-826.
(33) G.-M. Fang, J.-X. Wang, L. Liu, *Angew. Chem., Int. Ed.* 2012, 51, 10347-10350.
(34) P. Fatás, E. Longo, F. Rastrelli, M. Crisma, C. Toniolo, A. I. Jiménez, C. Cativiela, A. Moretto, *Chemistry—A European Journal* 2011, 17, 12606-12611.

The invention claimed is:

1. A compound of formula (V*)

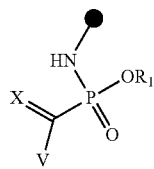

wherein:

X represents $CR_3(R_4)$;

R independently represents an optionally substituted aliphatic or aromatic residue;

optionally, $R_1$ represents $C_1$-$C_8$-alkyl optionally substituted with at least one of $(C_1$-$C_8$-alkoxy$)_n$ wherein n is 1, 2, 3, 4, 5 or 6, F, Cl, Br, I, —$NO_2$, —$N(C_1$-$C_8$-alkyl)H, —$NH_2$, —$N(C_1$-$C_8$-alkyl$)_2$, =O, $C_3$-$C_8$-cycloalkyl, —S—S—$(C_1$-$C_8$-alkyl), hydroxy-$(C_1$-$C_8$-alkoxy$)_n$ wherein n is 1, 2, 3, 4, 5 or 6, $C_2$-$C_8$-alkynyl or optionally substituted phenyl; or optionally, $R_1$ represents phenyl optionally independently substituted with at least one of $C_1$-$C_8$-alkyl, $(C_1$-$C_8$-alkoxy$)_n$ wherein n is 1, 2, 3, 4, 5 or 6, F, Cl, I, Br, —$NO_2$, —$N(C_1$-$C_8$-alkyl)H, —$NH_2$ or —$N(C_1$-$C_8$-alkyl$)_2$; or optionally, $R_1$ represents a 5- or 6-membered heteroaromatic system;

$R_3$ represents H or $C_1$-$C_8$-alkyl;

$R_4$ represents H or $C_1$-$C_8$-alkyl;

V represents ethyl or propyl; and

● represents an aliphatic or aromatic residue.

2. The compound according to claim 1, wherein $R_1$ independently represents methyl, ethyl, propyl or butyl.

3. The compound according to claim 1, wherein $R_1$ represents

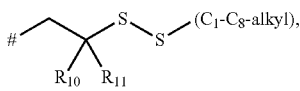

wherein $R_{10}$ and $R_{11}$ independently represent hydrogen or $C_1$-$C_8$-alkyl;

and #represents the position of O.

4. The compound according to claim 1, wherein $R_1$ represents $C_1$-$C_8$-alkyl substituted with phenyl, said phenyl being further substituted with

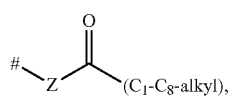

wherein Z is O or NH, and wherein #represents the position of said phenyl.

5. The compound according to claim 1, wherein $R_1$ represents hydroxyethyl or homopropargyl.

6. The compound according to claim 1, wherein $R_1$ represents $C_1$-$C_8$-alkyl substituted with $(C_1$-$C_8$-alkoxy$)_n$ wherein n is 1, 2, 3, 4, 5 or 6.

7. The compound according to claim 1, wherein $R_1$ represents $C_1$-$C_8$-alkyl substituted with hydroxy-$(C_1$-$C_8$-alkoxy$)_n$ wherein n is 1, 2, 3, 4, 5 or 6.

8. The compound according to claim 1, wherein $R_1$ represents —$(CH_2)_2$—O—$(CH_2)_2$—OH.

9. The compound according to claim 1, wherein $R_1$ represents an aliphatic residue, wherein the aliphatic residue is a polymer.

10. The compound according to claim 1, wherein $R_1$ represents an aliphatic residue, wherein the aliphatic residue is a polyethyleneglycol.

11. The compound according to claim 1, wherein ● represents an optionally substituted $C_1$-$C_8$-alkyl;
an optionally substituted phenyl; or
an optionally substituted 5- or 6-membered heteroaromatic system.

12. The compound according to claim 1, wherein ● represents a radioactive or non-radioactive nuclide, biotin, a reporter enzyme, a nucleotide, an oligonucleotide, a fluorophore, an amino acid, or a peptide.

13. The compound according to claim 1, wherein ● represents a linker, a drug, or a linker-drug conjugate.

14. A process for the preparation of a compound of formula (V*), said process comprising the steps of:
reacting a compound of formula (III*)

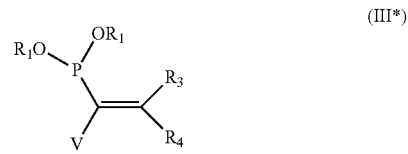

wherein $R_1$ INDEPENDENTLY REPRESENTS AN OPTIONALLY SUBSTITUTED ALIPHATIC OR AROMATIC residue;

optionally, $R_1$ represents $C_1$-$C_8$-alkyl optionally substituted with at least one of $(C_1$-$C_8$-alkoxy$)_n$ wherein n is 1, 2, 3, 4, 5 or 6, F, Cl, Br, I, —$NO_2$, —$N(C_1$-$C_8$-alkyl)H, —$NH_2$, —$N(C_1$-$C_8$-alkyl$)_2$, —O, $C_3$-$C_8$-cycloalkyl, —S—S—$(C_1$-$C_8$-alkyl), hydroxy-$(C_1$-$C_8$-alkoxy$)_n$ wherein n is 1, 2, 3, 4, 5 or 6, $C_2$-$C_8$-alkynyl or optionally substituted phenyl; or optionally, $R_1$ represents phenyl optionally independently substituted with at least one of $C_1$-$C_8$-alkyl, $(C_1$-$C_8$-alkoxy$)_n$ wherein n is 1, 2, 3, 4, 5 or 6, F, Cl, I, Br, —$NO_2$, —$N(C_1$-$C_8$-alkyl) H, —$NH_2$ or —$N(C_1$-$C_8$-alkyl$)_2$; or optionally, $R_1$ represents a 5- or 6-membered heteroaromatic system;
$R_3$ represents H or $C_1$-$C_8$-alkyl;
$R_4$ represents H or $C_1$-$C_8$-alkyl; and
V represents $C_1$-$C_8$-alkyl;
with an azide of formula (IV)

(IV)

wherein:
● represents an aliphatic or aromatic residue;
to prepare a compound of formula (V*)

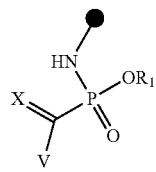
(V*)

●, wherein, $R_1$, and V are as defined above;
X represents $CR_3$ ($R_4$); and
$R_3$ and $R_4$ are as defined above.

15. The process according to claim 14, wherein $R_1$ independently represents methyl, ethyl, propyl or butyl.

16. The process according to claim 14, wherein $R_1$ represents hydroxyethyl or homopropargyl.

17. The process according to claim 14, wherein $R_1$ represents $C_1$-$C_8$-alkyl substituted with hydroxy-($C_1$-$C_8$-alkoxy)$_n$, wherein n is 1, 2, 3, 4, 5 or 6.

18. The process according to claim 14, wherein $R_1$ represents an aliphatic residue, wherein the aliphatic residue is a polymer.

19. The process according to claim 14, wherein ● represents an optionally substituted $C_1$-$C_8$-alkyl;
an optionally substituted phenyl; or
an optionally substituted 5- or 6-membered heteroaromatic system.

20. The process according to claim 14, wherein ● represents a linker, a drug, or a linker-drug conjugate.

* * * * *

UNITED STATES PATENT AND TRADEMARK OFFICE
CERTIFICATE OF CORRECTION

PATENT NO. : 12,171,837 B2
APPLICATION NO. : 18/349727
DATED : December 24, 2024
INVENTOR(S) : Christian Hackenberger et al.

Page 1 of 1

It is certified that error appears in the above-identified patent and that said Letters Patent is hereby corrected as shown below:

In the Claims

Column 139, Claim 1, Line 24:
"R independently" should read: --$R_1$ independently--.

Column 140, Claim 14, Lines 53-54:
"$R_1$ INDEPENDENTLY REPRESENTS AN OPTIONALLY SUBSTITUTED ALIPHATIC OR AROMATIC" should read: --$R_1$ independently represents an optionally substituted aliphatic or aromatic--.

Column 140, Claim 14, Line 59:
"-O," should read: --=O,--.

Column 142, Claim 14, Line 1:
"●, wherein," should read: --wherein ●,--.

Signed and Sealed this
Twenty-fifth Day of February, 2025

Coke Morgan Stewart
*Acting Director of the United States Patent and Trademark Office*

SEQUENCE LISTING

```
Sequence total quantity: 21
SEQ ID NO: 1            moltype = AA  length = 15
FEATURE                 Location/Qualifiers
REGION                  1..15
                        note = AviTag
source                  1..15
                        mol_type = protein
                        organism = synthetic construct
SEQUENCE: 1
GLNDIFEAQK IEWHE                                                        15

SEQ ID NO: 2            moltype = AA  length = 26
FEATURE                 Location/Qualifiers
REGION                  1..26
                        note = Calmodulin-tag
source                  1..26
                        mol_type = protein
                        organism = synthetic construct
SEQUENCE: 2
KRRWKKNFIA VSAANRFKKI SSSGAL                                            26

SEQ ID NO: 3            moltype = AA  length = 6
FEATURE                 Location/Qualifiers
REGION                  1..6
                        note = polyglutamate tag
source                  1..6
                        mol_type = protein
                        organism = synthetic construct
SEQUENCE: 3
EEEEEE                                                                   6

SEQ ID NO: 4            moltype = AA  length = 13
FEATURE                 Location/Qualifiers
REGION                  1..13
                        note = E-tag
source                  1..13
                        mol_type = protein
                        organism = synthetic construct
SEQUENCE: 4
GAPVPYPDPL EPR                                                          13

SEQ ID NO: 5            moltype = AA  length = 8
FEATURE                 Location/Qualifiers
REGION                  1..8
                        note = FLAG-tag
source                  1..8
```

```
                            mol_type = protein
                            organism = synthetic construct
SEQUENCE: 5
DYKDDDDK                                                                        8

SEQ ID NO: 6                moltype = AA   length = 9
FEATURE                     Location/Qualifiers
REGION                      1..9
                            note = HA-tag
source                      1..9
                            mol_type = protein
                            organism = synthetic construct
SEQUENCE: 6
YPYDVPDYA                                                                       9

SEQ ID NO: 7                moltype = AA   length = 6
FEATURE                     Location/Qualifiers
REGION                      1..6
                            note = His-tag
source                      1..6
                            mol_type = protein
                            organism = synthetic construct
SEQUENCE: 7
HHHHHH                                                                          6

SEQ ID NO: 8                moltype = AA   length = 10
FEATURE                     Location/Qualifiers
REGION                      1..10
                            note = Myc-tag
source                      1..10
                            mol_type = protein
                            organism = synthetic construct
SEQUENCE: 8
EQKLISEEDL                                                                     10

SEQ ID NO: 9                moltype = AA   length = 18
FEATURE                     Location/Qualifiers
REGION                      1..18
                            note = NE-tag
source                      1..18
                            mol_type = protein
                            organism = synthetic construct
SEQUENCE: 9
TKENPRSNQE ESYDDNES                                                            18

SEQ ID NO: 10               moltype = AA   length = 15
FEATURE                     Location/Qualifiers
REGION                      1..15
                            note = S-tag
source                      1..15
                            mol_type = protein
                            organism = synthetic construct
SEQUENCE: 10
KETAAAKFER QHMDS                                                               15

SEQ ID NO: 11               moltype = AA   length = 38
FEATURE                     Location/Qualifiers
REGION                      1..38
                            note = SBP-tag
source                      1..38
                            mol_type = protein
                            organism = synthetic construct
SEQUENCE: 11
MDEKTTGWRG GHVVEGLAGE LEQLRARLEH HPQGQREP                                       38

SEQ ID NO: 12               moltype = AA   length = 13
FEATURE                     Location/Qualifiers
REGION                      1..13
                            note = Softag 1
source                      1..13
                            mol_type = protein
                            organism = synthetic construct
SEQUENCE: 12
SLAELLNAGL GGS                                                                 13

SEQ ID NO: 13               moltype = AA   length = 8
FEATURE                     Location/Qualifiers
REGION                      1..8
                            note = Softag 3
```

```
source                        1..8
                              mol_type = protein
                              organism = synthetic construct
SEQUENCE: 13
TQDPSRVG                                                                    8

SEQ ID NO: 14                 moltype = AA   length = 8
FEATURE                       Location/Qualifiers
REGION                        1..8
                              note = streptag
source                        1..8
                              mol_type = protein
                              organism = synthetic construct
SEQUENCE: 14
WSHPQFEK                                                                    8

SEQ ID NO: 15                 moltype = AA   length = 6
FEATURE                       Location/Qualifiers
REGION                        1..6
                              note = TC tag
source                        1..6
                              mol_type = protein
                              organism = synthetic construct
SEQUENCE: 15
CCPGCC                                                                      6

SEQ ID NO: 16                 moltype = AA   length = 14
FEATURE                       Location/Qualifiers
REGION                        1..14
                              note = V5 tag
source                        1..14
                              mol_type = protein
                              organism = synthetic construct
SEQUENCE: 16
GKPIPNPLLG LDST                                                            14

SEQ ID NO: 17                 moltype = AA   length = 11
FEATURE                       Location/Qualifiers
REGION                        1..11
                              note = VSV-tag
source                        1..11
                              mol_type = protein
                              organism = synthetic construct
SEQUENCE: 17
YTDIEMNRLG K                                                               11

SEQ ID NO: 18                 moltype = AA   length = 8
FEATURE                       Location/Qualifiers
REGION                        1..8
                              note = Xpress tag
source                        1..8
                              mol_type = protein
                              organism = synthetic construct
SEQUENCE: 18
DLYDDDDK                                                                    8

SEQ ID NO: 19                 moltype = AA   length = 16
FEATURE                       Location/Qualifiers
REGION                        1..16
                              note = Isopeptag
source                        1..16
                              mol_type = protein
                              organism = synthetic construct
SEQUENCE: 19
TDKDMTITFT NKKDAE                                                          16

SEQ ID NO: 20                 moltype = AA   length = 13
FEATURE                       Location/Qualifiers
REGION                        1..13
                              note = SpyTag
source                        1..13
                              mol_type = protein
                              organism = synthetic construct
SEQUENCE: 20
AHIVMVDAYK PTK                                                             13

SEQ ID NO: 21                 moltype = AA   length = 12
FEATURE                       Location/Qualifiers
REGION                        1..12
```

```
                    note = SnoopTag
source              1..12
                    mol_type = protein
                    organism = synthetic construct
SEQUENCE: 21
KLGDIEFIKV NK                                              12
```